United States Patent
Keillor et al.

(10) Patent No.: US 10,894,777 B2
(45) Date of Patent: Jan. 19, 2021

(54) TG2 INHIBITOR PIPERAZINE COMPOUNDS AND USES THEREOF

(71) Applicants: UNIVERSITY OF OTTAWA, Ottawa (CA); UNIVERSITY OF MARYLAND, BALTIMORE, Baltimore, MD (US); UNIVERSITY OF ROCHESTER, Rochester, NY (US)

(72) Inventors: Jeffrey W. Keillor, Ottawa (CA); Abdullah Akbar, Ottawa (CA); Richard L. Eckert, Baltimore, MD (US); Matthew Fisher, Baltimore, MD (US); Gail V. W. Johnson, Rochester, NY (US)

(73) Assignees: UNIVERSITY OF OTTAWA, Ottawa (CA); UNIVERSITY OF MARYLAND, BALTIMORE, Baltimore, MD (US); UNIVERSITY OF ROCHESTER, Rochester, NY (US)

( * ) Notice: Subject to any disclaimer, the term of this patent is extended or adjusted under 35 U.S.C. 154(b) by 33 days.

(21) Appl. No.: 16/093,751

(22) PCT Filed: Apr. 13, 2017

(86) PCT No.: PCT/IB2017/052162
§ 371 (c)(1),
(2) Date: Oct. 15, 2018

(87) PCT Pub. No.: WO2017/179018
PCT Pub. Date: Oct. 19, 2017

(65) Prior Publication Data
US 2019/0389814 A1    Dec. 26, 2019

Related U.S. Application Data

(60) Provisional application No. 62/323,135, filed on Apr. 15, 2016, provisional application No. 62/360,417, filed on Jul. 10, 2016.

(51) Int. Cl.
| | |
|---|---|
| *A61K 31/4965* | (2006.01) |
| *C07D 295/10* | (2006.01) |
| *C07D 241/04* | (2006.01) |
| *C07C 317/36* | (2006.01) |
| *C07D 405/06* | (2006.01) |

(52) U.S. Cl.
CPC .......... *C07D 241/04* (2013.01); *C07C 317/36* (2013.01); *C07D 405/06* (2013.01)

(58) Field of Classification Search
CPC .......... A61K 31/4965; C07D 295/10
USPC ............. 514/255.01; 544/386
See application file for complete search history.

(56) References Cited

U.S. PATENT DOCUMENTS

| | | |
|---|---|---|
| 2009/0220554 A1 | 9/2009 | Griffin et al. |
| 2010/0105726 A1 | 4/2010 | Shin et al. |
| 2015/0232420 A1 | 8/2015 | Dominguez et al. |

FOREIGN PATENT DOCUMENTS

WO    2014047288 A2    3/2014

OTHER PUBLICATIONS

International Search Report and Written Opinion issued in International application PCT/IB2017/052162 dated Jul. 10, 2017.
Fisher, M.L. et al., Transglutaminase Is Required for Epidermal Squamous Cell Carcinoma Stem Cell Survival, Mol. Cancer Res., vol. 13, No. 7, pp. 1083-1094, Jul. 2015.
Fisher, M.L. et al., Type II Transglutaminase Stimulates Epidermal Cancer Stem Cell Epithelial-Mesenchymal Transition, Oncotarget, vol. 6, No. 24, pp. 20525-20239, Aug. 21, 2015.
Fisher, M.L. et al., Transglutaminase Interaction With Alpha6/Beta4-Integrin Stimulates YAP1-Dependent Deltanp63alpha Stabilization and Leads to Enhanced Cancer Stem Cell Survival and Tumor Formation, Cancer Res., vol. 76, No. 24, pp. 7265-7276, Dec. 15, 2016.

*Primary Examiner* — Douglas M Willis
(74) *Attorney, Agent, or Firm* — BCF LLP

(57) ABSTRACT

There are provided Tissue Transglutaminase (TG2) inhibitor compounds, and compositions and methods of use thereof for the prevention or treatment of a cancer. Compounds of Formula I, and pharmaceutically acceptable salts thereof, are provided:

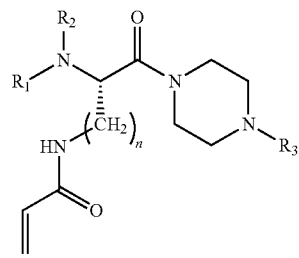

Formula I

12 Claims, 49 Drawing Sheets

A

B

C

D

A

B

C

A

B

C

D

A

B

C

A

B

A

B

TG2 INHIBITOR PIPERAZINE COMPOUNDS AND USES THEREOF

CROSS-REFERENCE TO RELATED APPLICATIONS

This application is a national phase filing, under 35 U.S.C. § 371 of International Application No. PCT/IB2017/052162 filed Apr. 13, 2017, which claims the benefit of U.S. Provisional Patent Application No. 62/323,135 filed Apr. 15, 2016 and of U.S. Provisional Patent Application No. 62/360,417 filed Jul. 10, 2016, both of which are hereby incorporated by reference in their entirety.

GOVERNMENT INTEREST

This invention was made with government support under Grant Numbers CA131074, CA184027, and NS065825 awarded by the National Institutes of Health. The government has certain rights in the invention.

FIELD

The present disclosure relates to Tissue Transglutaminase 2 inhibitor compounds, and compositions and methods of use thereof for treating cancer.

BACKGROUND

Tissue transglutaminase 2 (TG2) is a multifunctional protein that plays a role in many different cellular processes including differentiation, neuronal growth, inflammation, development and wound healing. TG2 is the most frequently occurring transglutaminase in eukaryotes and is present in almost all mammalian cells. TG2 can act as a scaffold or linker protein to mediate protein-protein interactions both extracellularly and intracellularly. TG2 is known to catalyze protein cross-linking in the extracellular matrix (ECM) and to participate in GTP-binding inside the cell.

In addition to catalyzing calcium-dependent transamidation reactions, TG2 binds and hydrolyzes GTP, and GTP binding inhibits the transamidation activity. Under normal physiological conditions, due to low calcium levels and high GTP levels, intracellular TG2 is likely a latent enzyme with respect to transamidation activity. However, in pathological conditions with high intracellular calcium and decreased GTP reserves, increases in TG2 transamidation activity likely occur. A significant outcome of calcium binding is that concurrent with activation, TG2 undergoes an extraordinary conformational change that results in an extended structure. In contrast, in the GTP bound state, TG2 exists in a compact and closed structure that decreases the accessibility of the active site. Therefore, calcium binding and GTP binding inversely regulate the conformational state of TG2, as well as the transamidation activity.

Despite intensive research, cancer remains one of the leading causes of mortality in North America, with metastasis and drug resistance accounting for the majority of cancer related deaths. Recent evidence has suggested a few reasons for the ineffectiveness of some chemotherapeutic approaches: 1) An increasing body of evidence has demonstrated the existence of cancer stem cells (CSCs) in many of the most common and most lethal tumours. CSCs have been identified in human blood cell-derived cancers as well as solid organ tumours of the colon, breast, lung, prostate, brain, pancreas and skin. These stem cells may not be removed by excision of the tumour, and fewer than 100 CSCs are capable of re-generating a tumour. 2) Some tumour cells can undergo epithelial to mesenchymal transition (EMT), taking on the properties of stem cells and initiating metastasis. 3) Most anti-cancer drugs target the rapidly dividing cells of epithelial tumours. However, CSCs and cells undergoing EMT proliferate slowly, and alternative pathways for inducing EMT have been discovered, such that these refractory cancer cells are resistant to most chemotherapeutic agents. Drug resistance has also been linked to cells undergoing EMT, particularly for drugs that target cell growth pathways, such as doxorubicin and the most common chemotherapeutics. Novel approaches for anti-cancer therapies are therefore needed, particularly to target CSCs and cells undergoing EMT, both of which have proven refractory to current inhibitors.

Recent studies have shown that TG2 likely plays a significant role in tumor cell biology. For example, TG2 expression has been correlated with various types of malignancies, including glioblastomas, lung and breast cancers, suggesting an important role for TG2 in tumor proliferation and survival. TG2 is markedly overexpressed in some cancer cells, and has been implicated in maintaining and enhancing EMT in breast and ovarian cancer. Two different TG2 inhibitors (monodansylcadaverine (MDC), a non-specific competitive inhibitor, and the active site directed inhibitor, Z-DON) have been shown to reduce proliferation in two out of three glioblastoma multiforme (GBM) cell lines tested (Zhang, J. et al., Cell Reports 3(6): 2008-2020, 2013). TG2 has also been implicated in epidermal cancer stem (ECS) cell survival and EMT regulation. It has been shown that TG2 expression is upregulated in drug resistant cells and that TG2 inhibitors may increase sensitivity of certain GBM cells to chemotherapy. TG2 is thus a promising target for addressing cancer recurrence, metastasis, and chemoresistance.

Gliomas are intrinsic tumors of the central nervous system and are classified by the type of cell from which they arise, as well as their potential for growth and spread. Astrocytomas develop from astrocytes, and grade IV astrocytomas, which are often referred to as glioblastoma multiforme (GBM), are the most common and aggressive type of primary brain tumor. More than half of the patients diagnosed with malignant primary brain tumors in the United States each year have GBM (Landi, D. et al., Front. Oncol. 4: 1-7, 2014). The prognosis for individuals with GBM is very poor even with multimodal treatment strategies, which usually involve removal of the primary tumor followed by radiotherapy and/or chemotherapy. Almost all the tumors invariably reoccur since there are no effective therapeutics to prevent the relapse, and the median survival time for patients with GBM is ~12-14 months (Brennan, C. W. et al., Cell 155(2):462-477, 2013). Further, although GBM does not undergo metastasis, it frequently develops chemoresistance by other mechanisms.

Epidermal squamous cell carcinoma (SCC) is among the most common cancers, being the second most prevalent type of non-melanoma skin cancer, and its incidence is increasing at a rapid rate due to the aging of the population and increased exposure to ultraviolet light. SCC-derived CSCs express stem cell markers characteristic of normal epidermal stem cells and embryonic stem cells, the CSCs show enhanced migration and invasive abilities in vitro, and subcutaneous injection of as few as 100 CSCs can result in the generation of tumors in mice (Adhikary, G. et al., PLoS ONE 8: e84324, 2013). SCC is typically treated by surgical excision, but the rate of recurrence approaches 10% and the recurrent tumors are aggressive and difficult to treat.

International PCT Application Publication No. WO 2014/047288 teaches transglutaminase TG2 inhibitors, pharmaceutical compositions, and methods of use thereof for treating patients suffering from certain disease states responsive to the inhibition of transglutaminase TG2 activity. These disease states include neurodegenerative disorders such as Huntington's disease and gluten sensitivity disease such as Celiac disease, although the described TG2 inhibitor compounds are shown to possess a high P-glycoprotein efflux rate and therefore be unsuitable candidates for treatments of disease where BBB permeability is desired. Methods of treatment including administering at least one compound or pharmaceutically acceptable salt thereof as a single active agent or administering at least one compound or pharmaceutically acceptable salt thereof in combination with one or more other therapeutic agents are also described.

There is a need for more potent TG2 inhibitors and for novel anti-cancer therapies.

SUMMARY

It is an object of the present invention to ameliorate at least some of the deficiencies present in the prior art. Embodiments of the present technology have been developed based on the inventors' appreciation that there is a need for improved Tissue Transglutaminase 2 (TG2) inhibitor compounds.

In a first broad aspect there are provided compounds of Formula I, or pharmaceutically acceptable salts thereof:

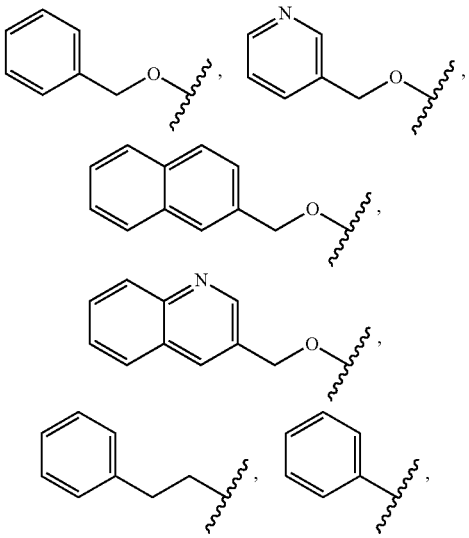

Formula I wherein:
$R_1$ is carbonyl-$R^a$, where $R^a$ is selected from:

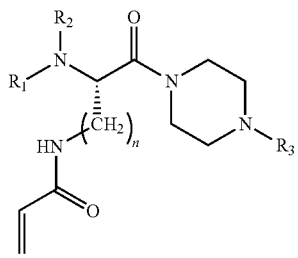

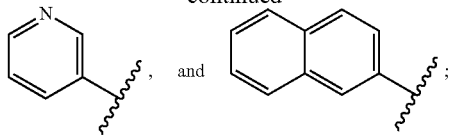

$R_2$ is hydrogen or substituted or unsubstituted $C_{1-6}$ alkyl;
$R_3$ is carbonyl-$R^b$ or sulfonyl-$R^b$, where $R^b$ is selected from:

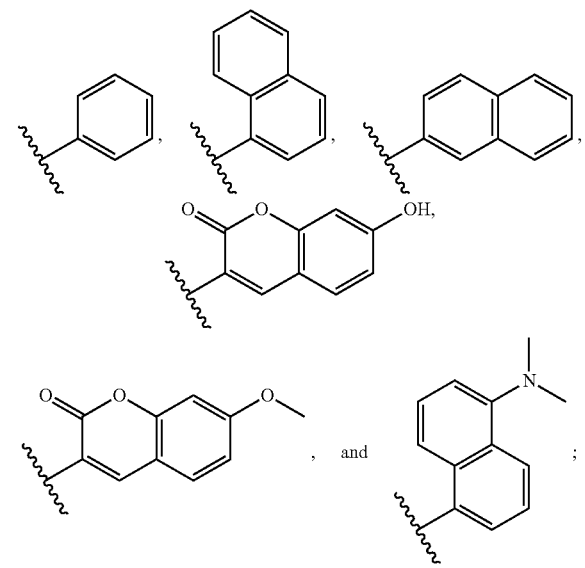

and n is 1, 2, 3, or 4.

In some embodiments of Formula I, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic are unsubstituted. In other embodiments of Formula I, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic may be substituted by hydroxyl, amino, carboxyl, sulfonate, carboxylic ester, amide, carbamate, or aminoalkyl.

In some embodiments of Formula I, $R_1$ is benzyloxy (i.e., carbonyl-$R^a$ where $R^a$ is

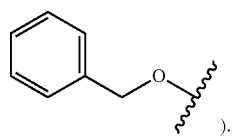 [SMILES: *OCc1ccccc1]

).

In some embodiments of Formula I, $R_2$ is hydrogen. In some embodiments, of Formula I, $R_2$ is substituted $C_{1-6}$ alkyl, e.g., substituted methyl. In some embodiments of Formula I, $R_2$ is unsubstituted $C_{1-6}$ alkyl, e.g., unsubstituted methyl.

In some embodiments of Formula I, $R_3$ is carbonyl-$R^b$. In some embodiments of Formula I, $R_3$ is sulfonyl-$R^b$.

In some embodiments of Formula I, $R^b$ is

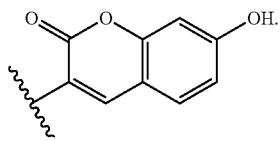 [SMILES: *c1cc2ccc(O)cc2oc1=O]

In some embodiments of Formula I, $R^b$ is

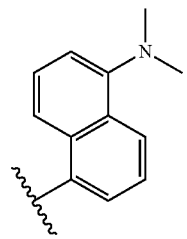

In some embodiments of Formula I, n is 1. In some embodiments of Formula I, n is 2. In some embodiments of Formula I, n is 3. In some embodiments of Formula I, n is 4.

In some embodiments of Formula I, $R_1$ is benzyloxy; $R_2$ is hydrogen; and n is 4.

In some embodiments of Formula I, the compound is VA4, VA5, or a pharmaceutically acceptable salt thereof:

VA4

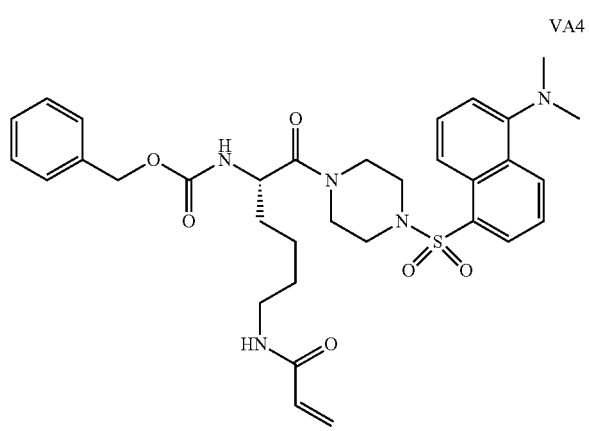

VA5

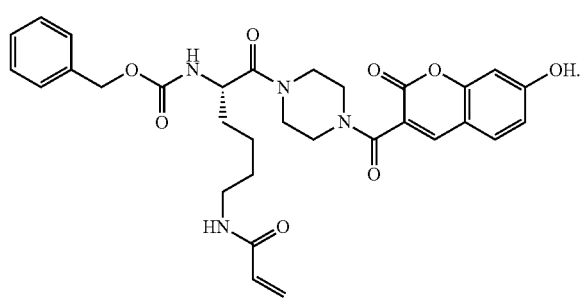

In some embodiments of Formula I, the compound is not VA5.

In some embodiments of Formula I, the compound is AA9, AA10, or a pharmaceutically acceptable salt thereof:

AA9

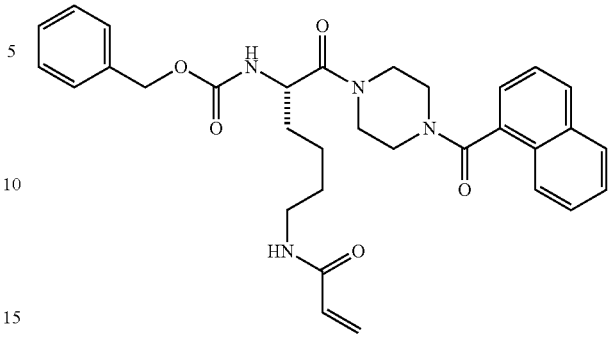

AA10

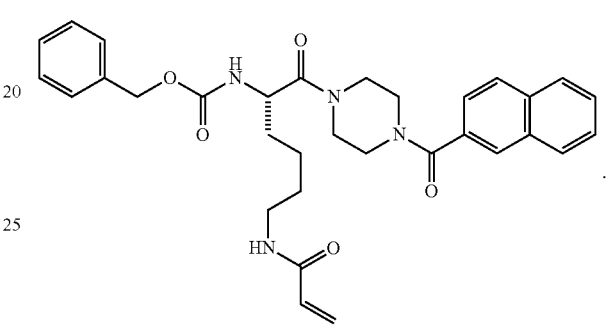

In some embodiments of Formula I, the compound is a compound shown in Table 2, or a pharmaceutically acceptable salt thereof.

In some embodiments of Formula I, the compound is a compound shown in Table 3, or a pharmaceutically acceptable salt thereof.

In some embodiments, a TG2 inhibitor compound provided herein is a compound shown in Table 5, or a pharmaceutically acceptable salt thereof.

In some embodiments, a TG2 inhibitor compound provided herein is a compound shown in Table 6, or a pharmaceutically acceptable salt thereof.

In some embodiments, a TG2 inhibitor compound provided herein is a compound shown in Table 7, or a pharmaceutically acceptable salt thereof.

In some embodiments, a TG2 inhibitor compound provided herein is a compound shown in Table 8, or a pharmaceutically acceptable salt thereof.

In some embodiments, compounds of Formula I are TG2 inhibitor compounds. In an embodiment, compounds provided herein inhibit one or more activity of TG2, e.g., GTP binding, GTPase activity, and/or transamidation activity. In some embodiments, compounds provided herein act as conformational modulators of TG2, holding the TG2 in an open conformation that does not bind GTP, in addition to abrogating transamidation activity through covalent binding to the active site. In some embodiments, compounds provided herein are irreversible TG2 inhibitors.

In another broad aspect, there are provided pharmaceutical compositions comprising a compound described herein, or a pharmaceutically acceptable salt thereof, and a pharmaceutically acceptable carrier. In some embodiments, there are provided pharmaceutical compositions comprising a compound of Formula I, or a pharmaceutically acceptable salt thereof, and a pharmaceutically acceptable carrier. In some embodiments, there are provided pharmaceutical compositions comprising a compound of Formula II, or a pharmaceutically acceptable salt thereof, and a pharmaceutically acceptable carrier. In some embodiments, there are provided pharmaceutical compositions comprising a compound of Formula I, or a pharmaceutically acceptable salt thereof, and a pharmaceutically acceptable carrier, wherein the compound is not VA5.

In yet another aspect, there are provided methods of inhibiting TG2, comprising contacting the TG2 in vitro with a compound described herein, or a pharmaceutically acceptable salt thereof, in an amount sufficient to inhibit one or more activity of the TG2. For example, GTPase, GTP binding, and/or transamidation activity of TG2 may be inhibited or reduced, and/or TG2 may be held in an open conformation by the compound or the pharmaceutically acceptable salt. The compound may be, e.g., a compound of Formula I or a pharmaceutically acceptable salt thereof.

In another broad aspect, there are provided methods of inhibiting TG2 in a subject, comprising administering to the subject an effective amount of a compound described herein, or a pharmaceutically acceptable salt thereof, so as to inhibit one or more activity of TG2 in the subject. For example, GTPase activity, GTP binding activity, and/or transamidation activity of TG2 may be inhibited or reduced in the subject, and/or TG2 may be held in an open conformation.

In some embodiments of methods provided herein, the compound is a compound of Formula I, as described above, or a pharmaceutically acceptable salt thereof. In some embodiments of methods provided herein, the compound is a compound of Formula I, as described above, or a pharmaceutically acceptable salt thereof, wherein the compound is not VA5.

In some embodiments of methods provided herein, the compound is a compound shown in Table 2, 3, 5, 6, 7, or 8, or a pharmaceutically acceptable salt thereof.

In some embodiments of methods provided herein, the compound is VA4, VA5, NC9, AA9, AA10, or a pharmaceutically acceptable salt thereof.

In other embodiments of methods provided herein, the compound is a compound of Formula II, or a pharmaceutically acceptable salt thereof:

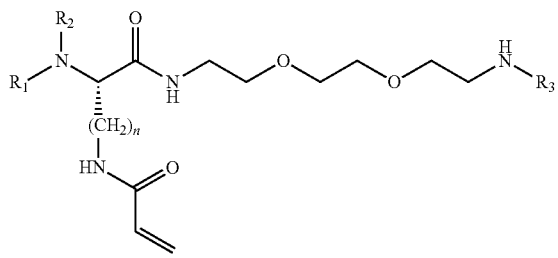

Formula II wherein:

$R_1$ is carbonyl-$R^a$, where $R^a$ is selected from:

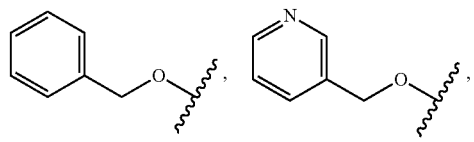

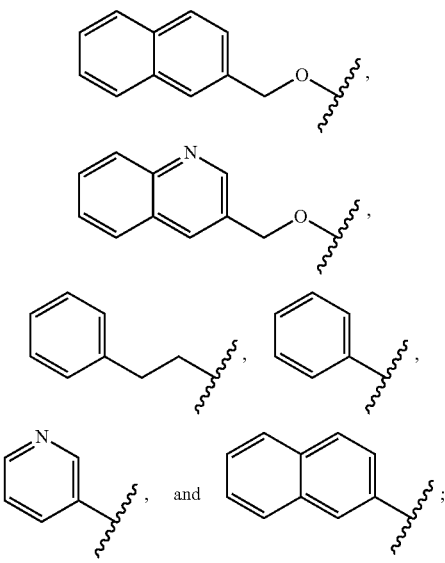

$R_2$ is hydrogen or substituted or unsubstituted $C_{1-6}$ alkyl;

$R_3$ is carbonyl-$R^b$ or sulfonyl-$R^b$, where $R^b$ is selected from:

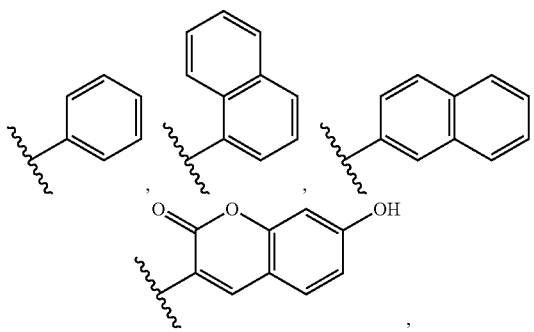

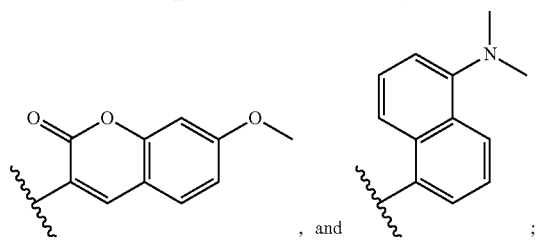

and n is 1, 2, 3, or 4.

In some embodiments of Formula II, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic are unsubstituted. In other embodiments of Formula II, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic may be substituted by hydroxyl, amino, carboxyl, sulfonate, carboxylic ester, amide, carbamate, or aminoalkyl.

In some embodiments of Formula II, $R_1$ is benzyloxy (i.e., carbonyl-$R^a$ where $R^a$ is

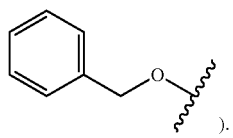).

In some embodiments of Formula II, $R_2$ is hydrogen. In some embodiments, of Formula II, $R_2$ is substituted $C_{1-6}$ alkyl, e.g., substituted methyl. In some embodiments of Formula II, $R_2$ is unsubstituted $C_{1-6}$ alkyl, e.g., unsubstituted methyl.

In some embodiments of Formula II, $R_3$ is carbonyl-$R^b$. In some embodiments of Formula II, $R_3$ is sulfonyl-$R^b$.

In some embodiments of Formula II, $R^b$ is

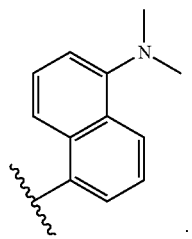 [SMILES: *c1cccc2c(N(C)C)cccc12].

In some embodiments of Formula II, n is 1. In some embodiments of Formula II, n is 2. In some embodiments of Formula II, n is 3. In some embodiments of Formula II, n is 4.

In some embodiments of Formula II, $R_1$ is benzyloxy; $R_2$ is hydrogen; and n is 4.

In some embodiments of Formula II, the compound is NC9, or a pharmaceutically acceptable salt thereof:

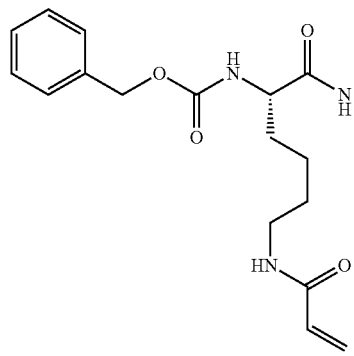

NC9

In some embodiments, compounds of Formula II inhibit one or more activity of TG2, e.g., GTPase activity, GTP binding activity, and/or transamidation activity. In some embodiments, compounds of Formula II hold the TG2 in an open conformation.

In another broad aspect, therapeutic methods of use of the compounds and compositions described herein for the prevention and treatment of cancer are provided. In an embodiment, there are provided methods of treating a cancer in a subject in need thereof, comprising administering to the subject an effective amount of a compound described herein, or a pharmaceutically acceptable salt thereof, so as to treat the cancer in the subject. In some embodiments, the compound is a compound of Formula I or Formula II as described above, or a compound of Table 2, 3, 5, 6, 7, or 8, or a pharmaceutically acceptable salt thereof. In some embodiments, one or more activity of TG2 activity is inhibited in the subject, e.g., GTPase activity, GTP binding, and/or transglutaminase activity are inhibited or reduced in the subject.

In some embodiments, the cancer is a blood-cell derived cancer such as, without limitation, a lymphoma, a leukemia, or a myeloma. In some embodiments, the cancer is a solid organ tumor such as, without limitation, a tumor of the colon, breast, lung, prostate, brain, pancreas, ovary, or skin. In an embodiment, the cancer is an epidermal squamous cell carcinoma (SCC). In another embodiment, the cancer is a glioma, such as a malignant glioma or a glioblastoma, e.g., glioblastoma multiforme (GBM).

In some embodiments, the cancer is drug- or chemoresistant. In some embodiments, the cancer is drug- or chemo-resistant and the compound or pharmaceutically acceptable salt acts to sensitize or re-sensitize the cancer to the drug or chemotherapy, e.g., the compound or pharmaceutically acceptable salt acts to increase the sensitivity of refractory cancer cells to chemotoxic agents or to overcome resistance to chemotherapy.

In some embodiments, cancer recurrence is prevented or inhibited in the subject, e.g., recurrence after surgical removal of a tumor is prevented or inhibited.

In some embodiments, metastasis is prevented or inhibited in the subject. EMT is the first critical step in metastasis, which is the most important feature of malignant tumors. During the morphogenetic process of EMT, epithelial cells lose epithelial characteristics and take on invasive mesenchymal properties. In some embodiments, therefore, the EMT transition is prevented or inhibited.

In some embodiments, cancer stem cell (CSC) survival or proliferation is prevented or inhibited. In an embodiment, epidermal cancer stem (ECS) cell survival or proliferation is prevented or inhibited. In an embodiment, CSC or ECS spheroid formation is prevented or inhibited.

In some embodiments, cancer (e.g., tumor) progression, growth, migration, and/or invasion is prevented or inhibited. For example, migration of cancer cells, e.g., GBM cells, may be prevented or inhibited by the compound or pharmaceutically acceptable salt. Cancer invasion, e.g., malignant glial cell (MGC) invasion, may be inhibited. In an embodiment, progression of a cancer is delayed.

In another embodiment, there is provided a method for enhancing the efficacy of a cancer therapy for the treatment of a cancer, comprising administering a compound described herein, or a pharmaceutically acceptable salt thereof, to a subject in need thereof, and simultaneously, separately or sequentially administering the cancer therapy. Non-limiting examples of the cancer therapy include surgical resection, chemotherapy, radiation therapy, immunotherapy, and gene therapy.

In a further aspect, there are provided kits for treating a cancer in a subject in need thereof, comprising a compound (or a pharmaceutically acceptable salt thereof) or a pharmaceutical composition, as described herein; optionally one or more additional component such as acids, bases, buffering agents, inorganic salts, solvents, antioxidants, preservatives, or metal chelators; and instructions for use thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the invention and to show more clearly how it may be carried into effect, reference will now be made by way of example to the accompanying drawings, which illustrate aspects and features according to embodiments of the present invention, and in which.

Figure 21:
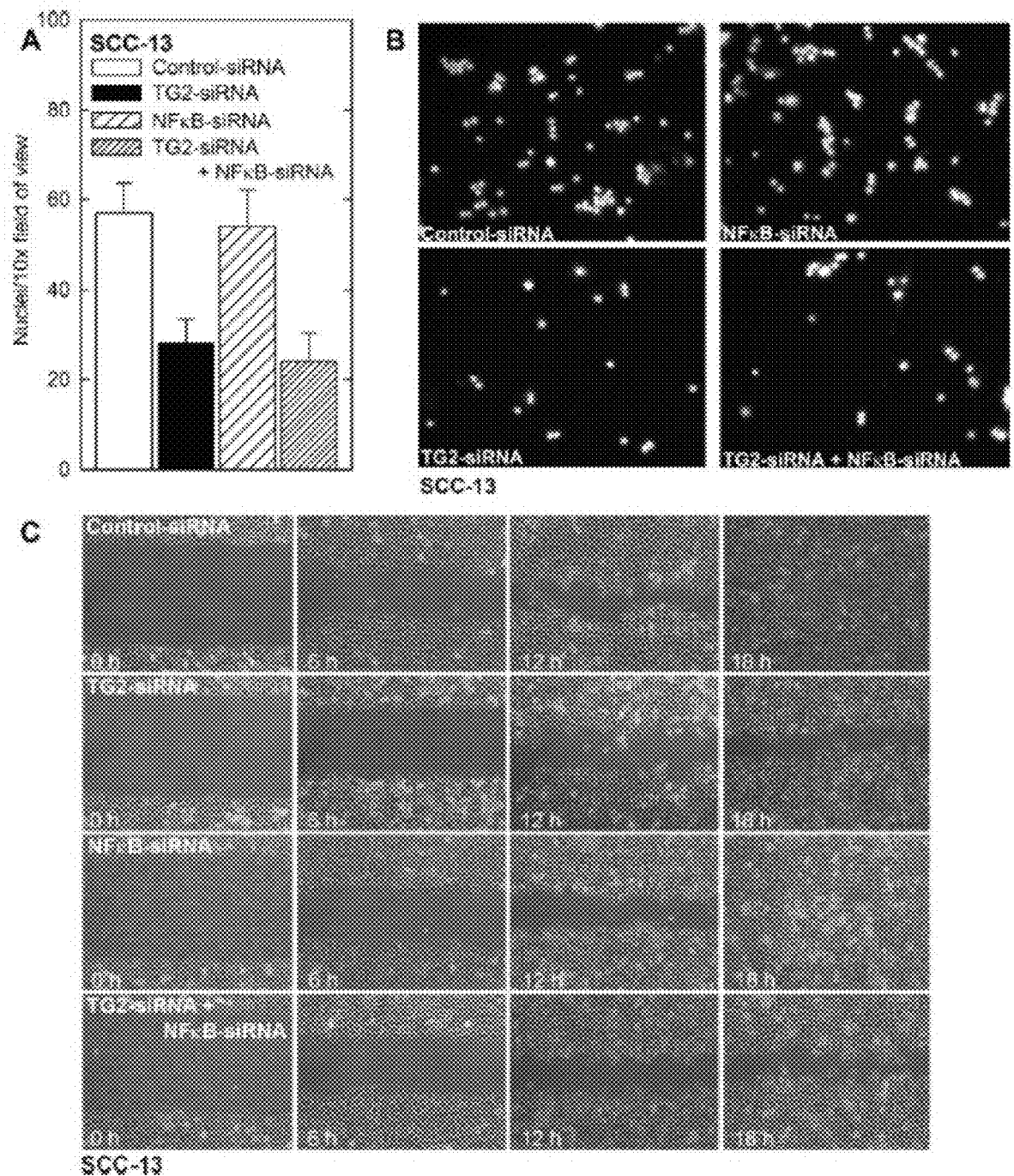

FIG. 21 shows NFκB is not required for ECS cell migration and invasion. In (A) and (B), it is shown that NFκB-knockdown does not suppress ECS cell matrigel invasion. SCC-13 cells were treated with Control-, TG2-, NFκB- or a combination of siRNA and then seeded in the upper chamber above a matrigel-coated membrane in 1 mL of growth medium containing 1% FCS in a Millicell chamber. The lower chamber was filled with growth medium containing 10% FCS. After 30 h, the membrane was removed, washed and stained with DAPI, and an inverted fluorescent microscope was used to count the nuclei of migrated cells. In (C), it is shown that NFκB-knockdown does not impede ECS cell migration. SCC-13 cells (2 million) cells were plated in spheroid media on 100 mm dishes and grown as monolayers. Confluent monolayers were then scratched with a 10-μL pipette tip, rinsed, and width of the wound was monitored for 0-18 h. Similar results were observed in each of three experiments.

Figure 22:
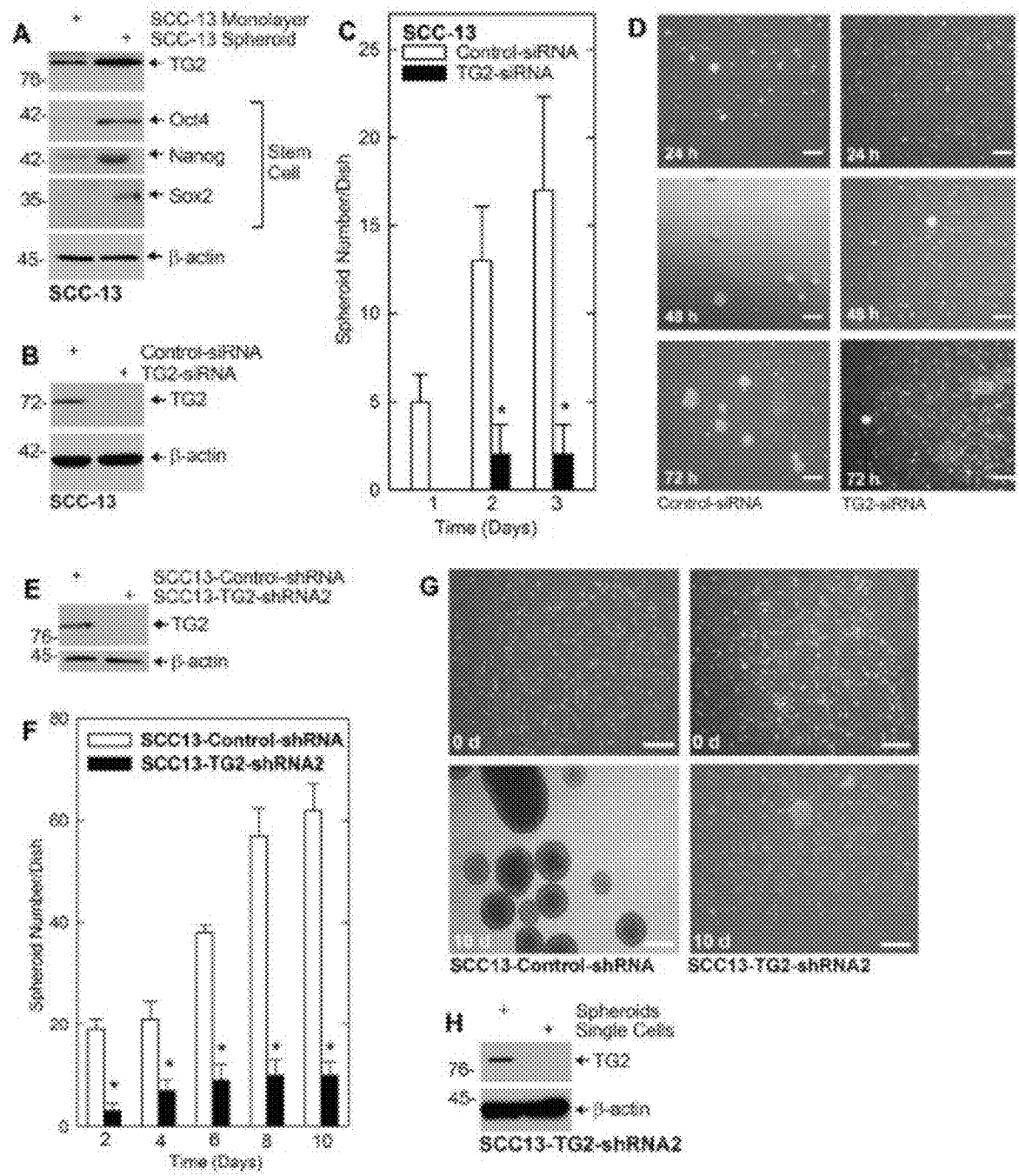

FIG. 22 shows TG2 is enriched in ECS cells and is required for spheroid formation. In (A), it is shown that ECS cells are enriched for expression of TG2. SCC-13 cells (40,000 per well) were grown as monolayers (non-stem cells) or as unattached spheroids (ECS cells) in spheroid medium for 10 days before extracts were prepared. In (B), ECS cells were electroporated with control- or TG2-shRNA and after 72 hours extracts were prepared to assay TG2 level. In (C), it is shown that TG2 is required for spheroid formation. SCC-13 cells were electroporated with 3 μg of control- or TG2-siRNA, and then plated at 40,000 cells per well in 35-mm dishes and grown as spheroids and then counted. In (D), there are shown photos of cells photographed at 24, 48, and 72 hours after plating. In (E), SCC13-Control-shRNA and SCC13-TG2-shRNA2 cells were harvested, and extracts were prepared for immunoblot detection of TG2 and β-actin. In (F), it is shown that TG2 is required for spheroid growth. Cells were plated at 40,000 per 35-mm dish in spheroid medium, and spheroid formation was monitored. In (G), cells from B were photographed at 0 and 10 days after plating. In (H), SCC13-TG2-shRNA2 cell spheroids and non-spheroids (single cells) were collected at 10 days and assayed for TG2 level. Spheroid formation was associated with restoration of TG2 expression. In all plots, the values are mean±SEM, n=3, p<0.05, and the bars=125 μm.

Figure 23:
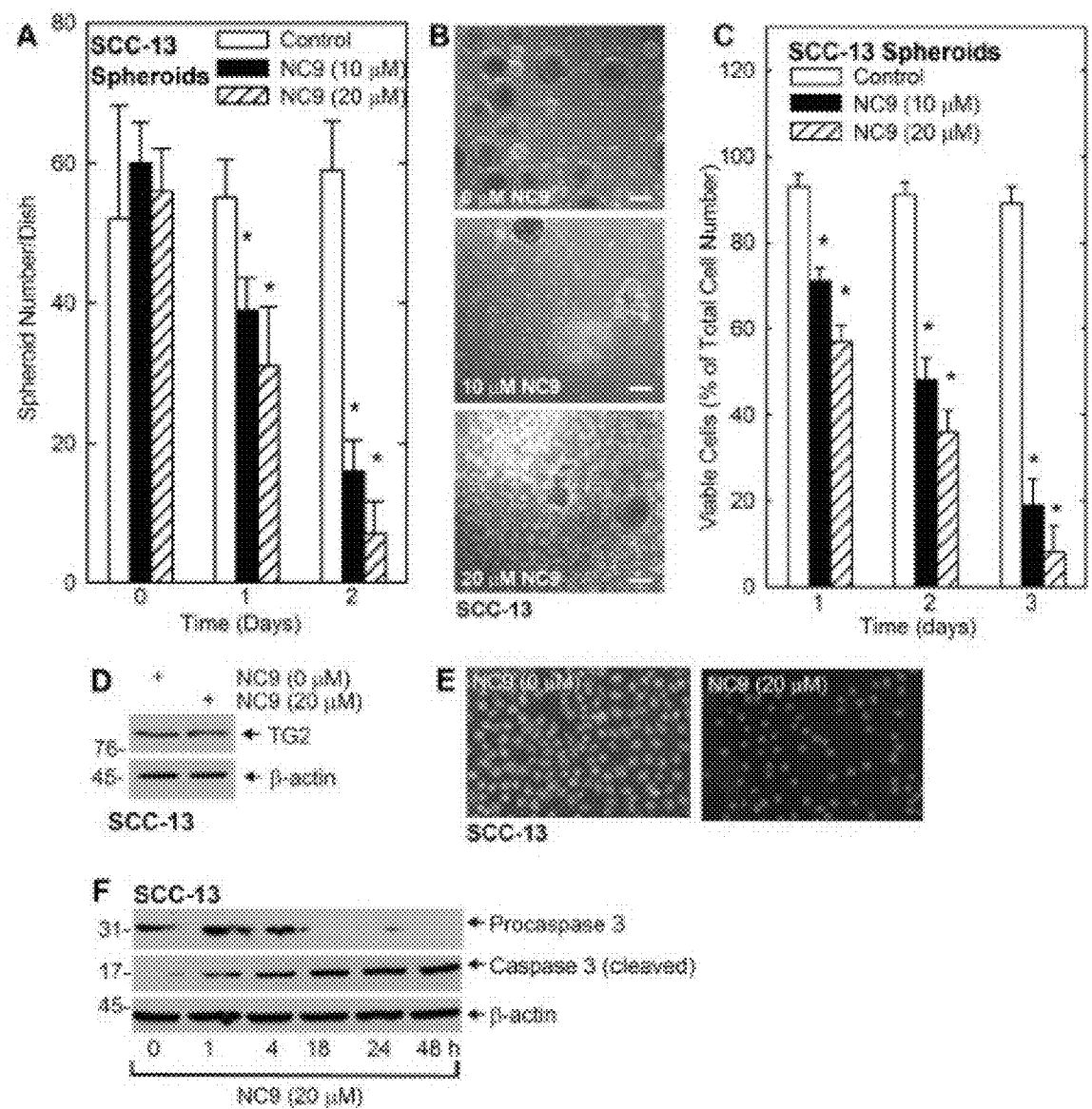

FIG. 23 shows that NC9 causes fragmentation of preformed spheroids. In (A), SCC-13 cells (40,000) were plated in non-adherent six well dishes, grown for 8 days in spheroid medium, and then NC9 was added and spheroid number was monitored at 0-48 hours. In (B), spheroids were grown for 10 days, treated for 48 hours with indicated level of NC9 and photographed. In (C), SCC-13 cells were plated at 40,000 cells per well in non-adherent six well dishes and after 10 days the spheroids were treated with 0-20 μM NC9 for 0-72 hours before trypan blue exclusion viability assay. In (D), SCC-13 spheroids were grown for 10 days, treated with 0 or 20 μM NC9 for 48 hours, and TG2 level was assayed by immunoblot. In (E), SCC-13 cells were grown as monolayers in spheroid medium and TG2 activity was monitored by FC incorporation assay as outlined in the Materials and Methods for Example 7. In (F), SCC-13 cell 8 day spheroids were treated with 20 NM NC9 and cells were harvested at the indicated times for immunoblot detection of procaspase 3 and cleaved caspase 3. In all panels, the values are mean±SEM, n=3, p<0.05.

Figure 24:
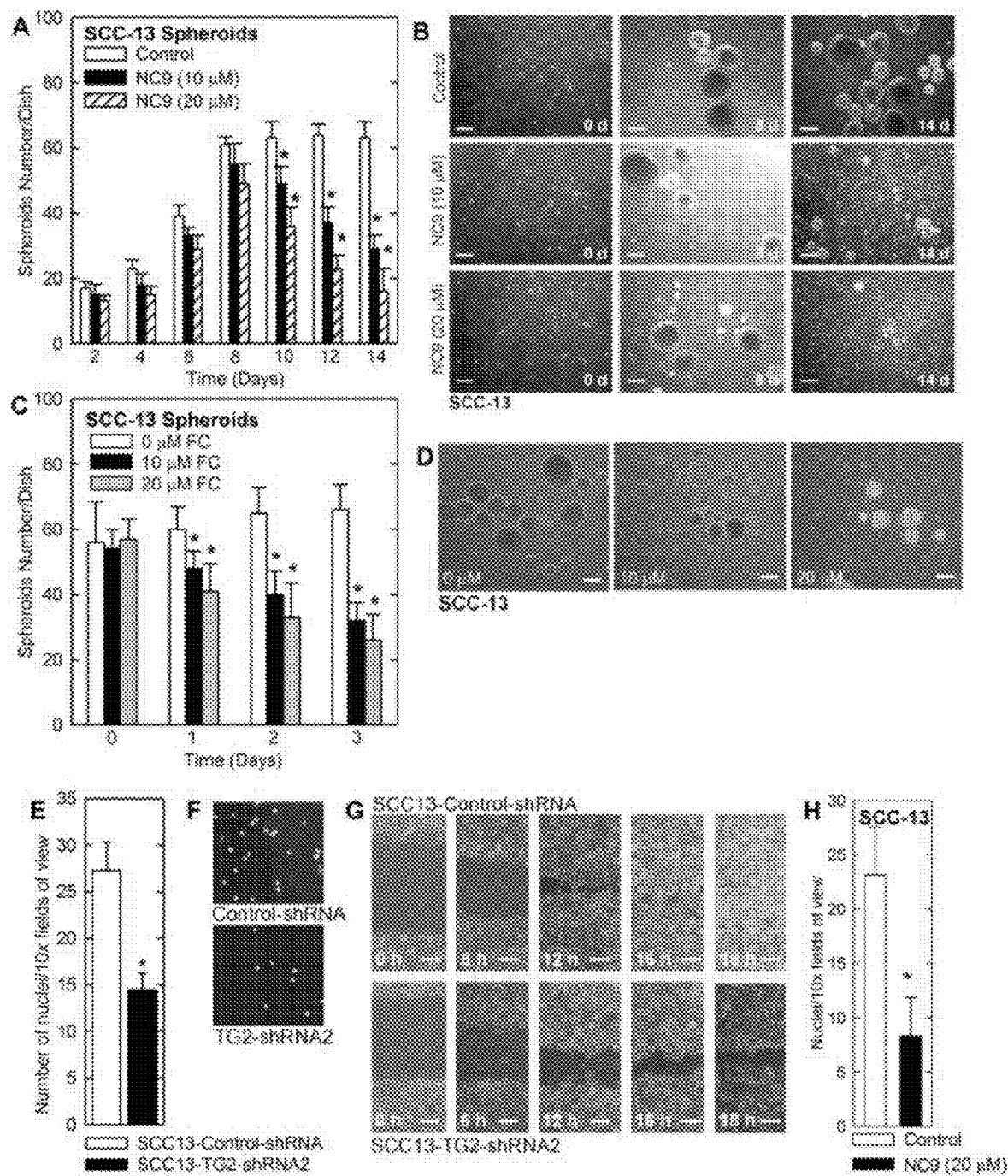

FIG. 24 shows impact of NC9 and TG2 knockdown on spheroid formation, invasion and wound closure. In (A), SCC-13 cells (40,000) were plated in spheroid growth conditions and after 18 hours, 0, 10 or 20 μM NC9 was added. Incubation was continued for 0-14 days without addition of fresh NC9 or medium, and spheroid number was counted at each time point. In (B), cells were treated as in panel A and images were captured at 0, 8 and 14 days. Similar results were observed in each of three experiments. In (C), SCC-13 cells were seeded in six well non-attachment plates and after 8 days spheroids were treated with 0-20 NM FC for 72 hours. In (D), there are shown images of spheroids following 2 days treatment with various concentrations of FC. In all panels, the values are mean±SEM, n=3, p<0.05. In (E), SCC13-Control-shRNA and SCC13-TG2-shRNA2 cells (25,000) were seeded on top of matrigel in 1 mL of growth medium in a Millicell chamber. After 24 hours, the membrane was rinsed with phosphate buffered saline and fixed in 4% paraformaldehyde and then stained with DAPI. The underside of chambers were viewed with an inverted fluorescent microscope and nuclei counted. In (F), images of the DAPI-stained membrane are shown. In (G), SCC13-Control-shRNA and SCC13-TG2-shRNA2 cells (2 million) were plated on 100 mm dishes in growth medium in monolayer conditions and confluent monolayers were "wounded" with a 10-μL pipette. Images were collected at 0-18 hours after wounding to assess closure. Cell proliferation did not account for the difference in wound closure rate (not shown). In (H), SCC-13 cells were pretreated for 1 hour with 0 or 20 μM NC9 and then 25,000 cells were seeded on Matrigel in six Millicell chambers per treatment. After 24 hours, the chambers were harvested, cleaned and cells that had migrated through to the membrane inner surface were visualized using DAPI. The values are mean±SEM, n=6, p<0.05.

Figure 25:
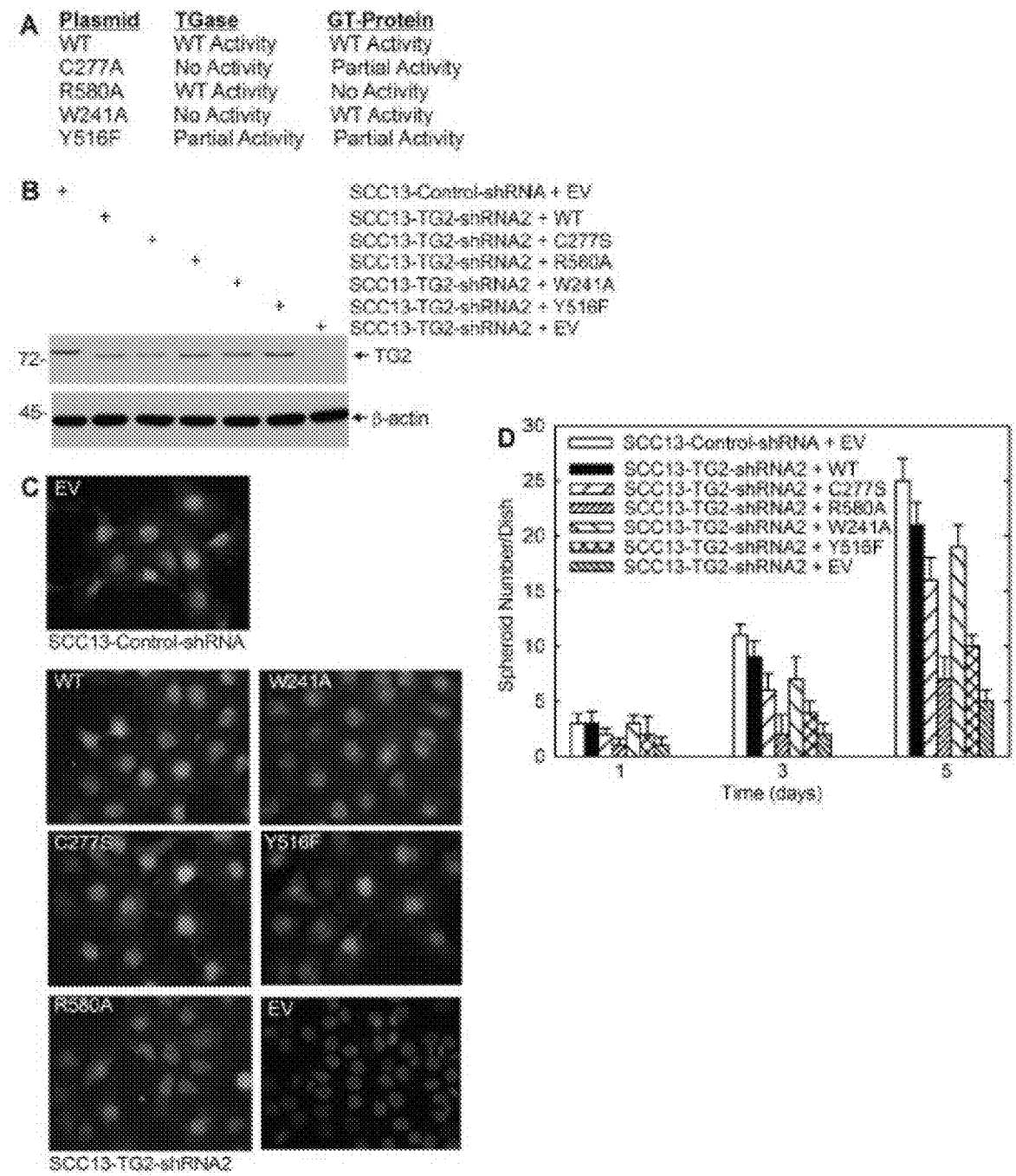

FIG. 25 shows expression of TG2 mutants in SCC13-TG2-shRNA cells. In (A), TG2 mutants and impact on TGase and GTP-binding/G-protein-related activity are shown. In (B), SCC13-TG2-shRNA2 cells (TG2 knockdown) were electroporated with plasmids encoding wild-type or mutant TG2, or empty vector (EV) and grown as monolayers in spheroid growth medium. After three days, the cells were harvested for immunoblot with anti-TG2. In (C), SCC13-TG2-shRNA2 cells were electroporated with plasmids encoding the indicated plasmids, plated on attachment plates in spheroid medium and after 3 days the cells were fixed, permeabilized and stained with anti-TG2. As a control, SCC13-Control-shRNA cells were electroporated with empty vector and stained in parallel. TG2 detected in these cells was endogenous. Similar findings were observed in each of three repeated experiments. In (D), SCC13-Control-shRNA cells were electroporated with 3 μg of empty vector (EV) and SCC13-TG2-shRNA2 cells were electroporated with plasmid encoding TG2-wt, TG2 mutants (C277S, R580A, Y526F or W241A) or empty vector. After electroporation, the cells were seeded at 40,000 cells in each of six low-attachment wells in 2.5 mL of spheroid media. Spheroids were counted on days 1, 3 and 5.

Figure 26:
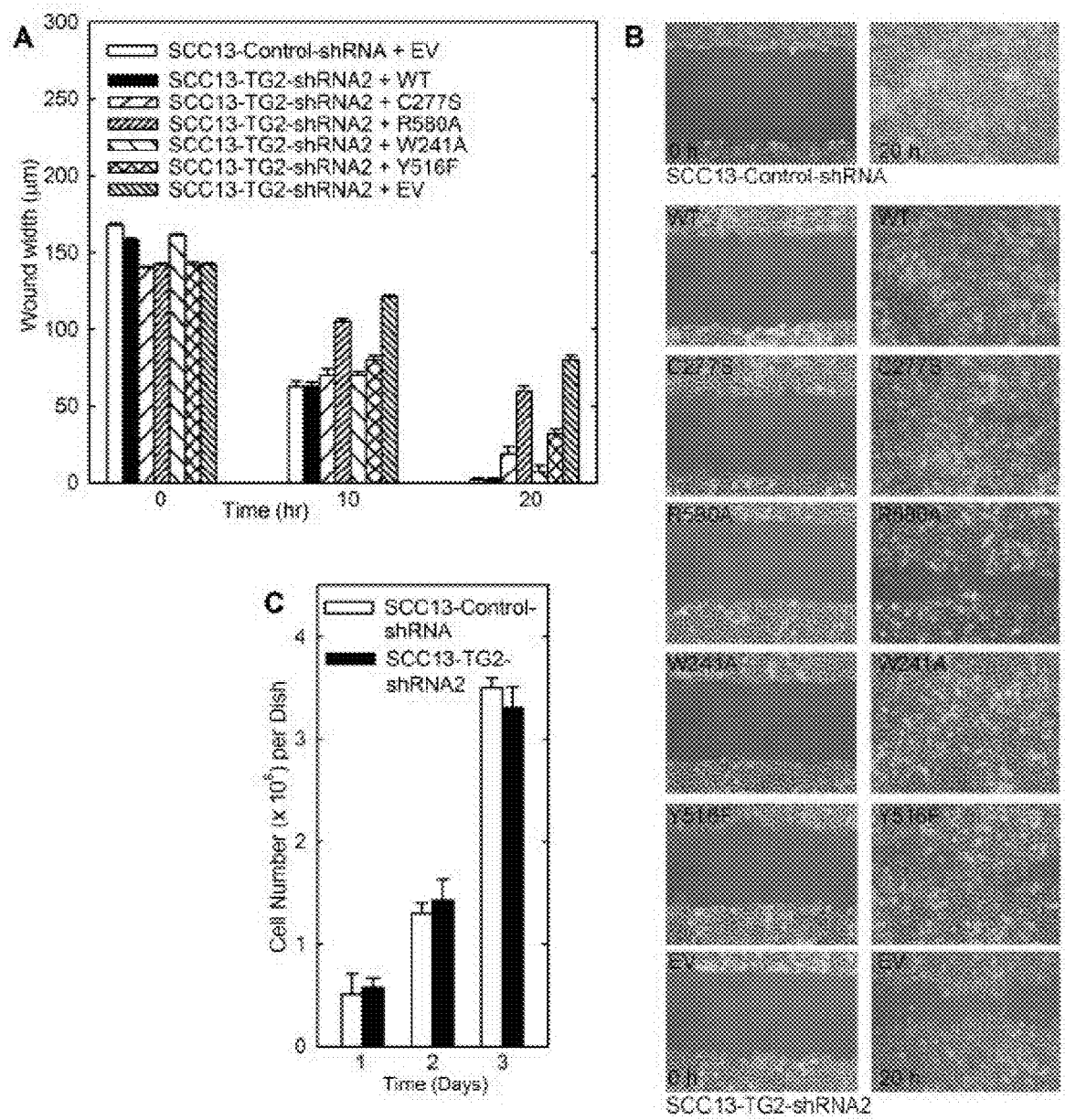

FIG. 26 shows TG2 mutant impact on migration and proliferation in SCC13-TG2-shRNA2 cells. In (A), SCC13-Control-shRNA cells were electroporated with 3 µg of empty vector (EV) and SCC13-TG2-shRNA2 cells were electroporated with plasmid encoding TG2-wt, TG2 mutants (C277S, R580A, Y526F or W241A) or empty vector. After electroporation, the cells were seeded at high density in 6-well cluster conventional attachment plates in 2.5 mL of spheroid media. Uniform wounds were created using a pipette and wound width was monitored at 0, 10 and 20 h. An immunoblot confirming mutant expression is shown in (B), which shows wound images at 20 hours. In (C), it is shown that TG2 knockdown does not alter SCC-13 cell proliferation. SCC13-Control-shRNA and SCC13-TG2-shRNA cells were plated at equal density in attachment plates in spheroid medium and growth was monitored over a period of three days. Values are mean±SEM, n=3, p<0.05.

Figure 27:
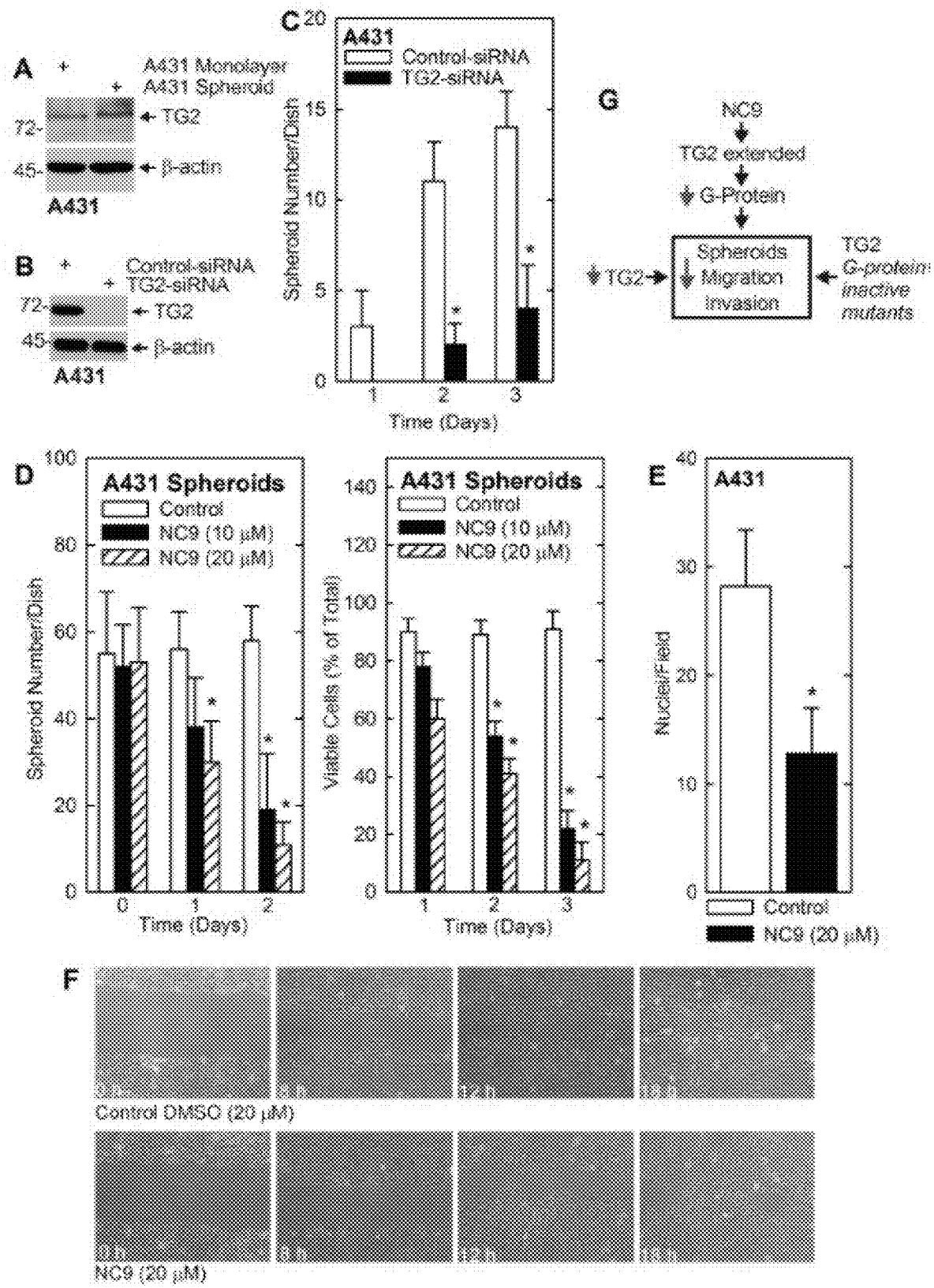

FIG. 27 shows role of TG2 in A431 cells. In (A), A431 cells were grown as monolayers or in ultralow attachment plates (spheroids) in spheroid medium. After 8 days, extracts were prepared and assayed for expression of TG2 by immunoblot. Similar results were observed in four separate experiments. In (B), A431 cells were electroporated with control- or TG2-siRNA and after 72 hours cell extracts were prepared to detect TG2. In (C), A431 cells were electroporated with the indicated siRNA and 40,000 cells were seeded into low-attachment six well dishes at time zero. Spheroid number was counted on days 1, 2 and 3. In (D), A431 cells were seeded at 40,000 cells per six well cluster dish and after 12 hours NC9 was added at time zero. Spheroid number and trypan-blue viable cell number were determined at the indicated times following NC9 addition. The values are mean±SEM, n=3, p<0.05. In (E), A431 cells, maintained as spheroids, were treated with 0 (Control) or 20 µM NC9 for 1 hour and then plated atop Matrigel in 1 mL of spheroid medium in a Millicell chamber. After 24 hours, the chambers were collected and stained with DAPI to detect cells that had migrated through the Matrigel to the inner surface of the membrane. The values are mean±SEM, n=6, p<0.05. In (F), A431-derived ECS cells were seeded at confluence as monolayer cultures. A wound was created and ability of the cells to close the wound was monitored with time. In (G), a model describing regulation of spheroid formation, migration and invasion by TG2 is shown, in which reduction in TG2 level, or loss of TG2 GTP binding/G-protein function, reduces ECS cell function (survival, spheroid formation, invasion and migration), and NC9 inactivates TG2 TGase activity forcing it into an extended conformation to indirectly reduce GTP binding activity.

Figure 28:
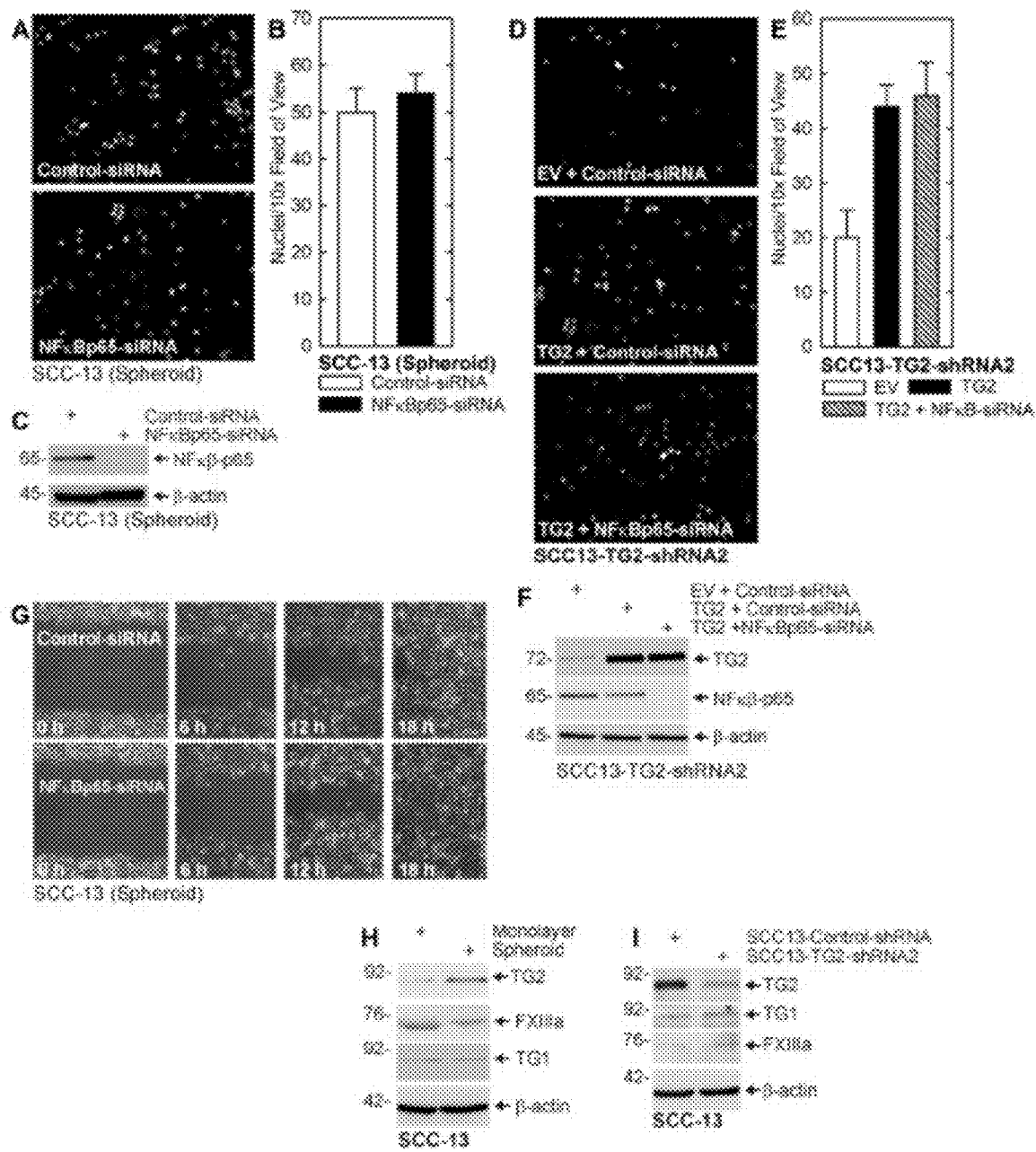

FIG. 28 shows NFκB does not mediate TG2-dependent invasion or migration. In (A) and (B), ECS cells were electroporated with the indicated siRNA and permitted to recover for 24 hours. The cells (25,000 per well) were seeded on top a matrigel-coated membrane in 1 mL of spheroid growth medium in a Millicell chamber. After 24 hours, the membrane was rinsed with phosphate buffered saline, fixed in 4% paraformaldehyde and stained with DAPI. The undersides of the membranes were viewed with an inverted fluorescent microscope and nuclei counted. In (C), ECS cells were harvested at the end of migration to assay NFκB level. In (D) and (E), ECS cells were electroporated with empty vector (EV) or TG2-encoding (TG2) expression plasmid in the presence of control- or NFκB-siRNA. After 24 hours, the membranes were process to visualize the nuclei of migrated cells. In (F), ECS cells were harvested at the end of migration to assay TG2 and NFκB levels. In (G), ECS cells were electroporated with control- or NFκB-siRNA, seeded at confluent density. After attachment, uniform wounds were prepared, and cell migration to fill the wound was monitored from 0-18 hours. Cell division did not significantly contribute to wound closure under these conditions (not shown). In (H), extracts were prepared from ECS cells (8 day spheroids) and non-stem cancer cells derived from monolayer cultures. Extracts were electrophoresed for immunoblot detection of the indicated epitopes. In (I), ECS cells were treated with control- or TG2-siRNA and maintained in spheroid medium in non-attachment plates. After 48 hours extracts were prepared for assay of the indicated epitopes. Similar results were observed in each of three experiments.

Figure 29:
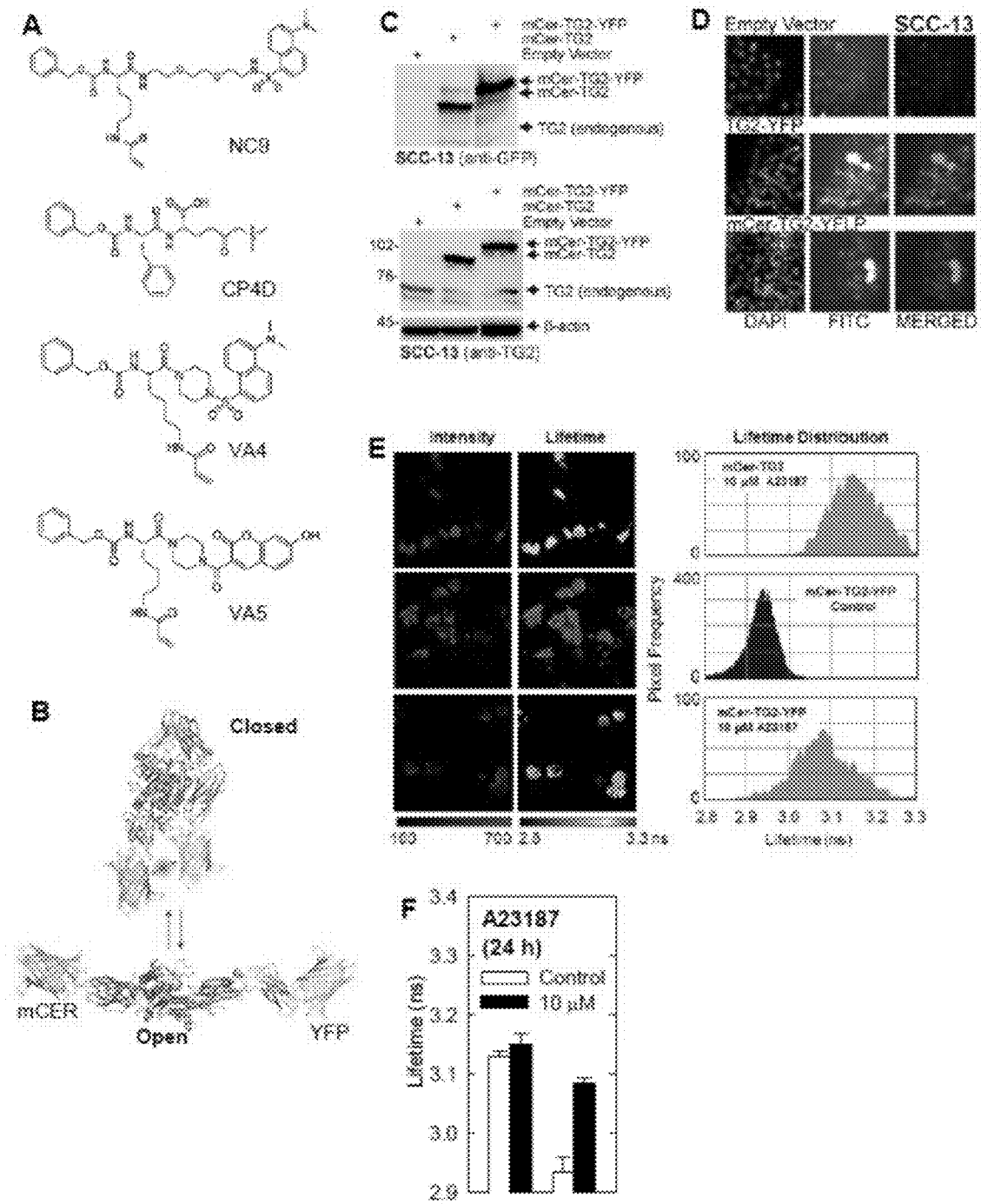

FIG. 29 shows calcium regulation of TG2 conformation detected by FRET/FLIM microscopy. In (A), structures of TG2 transamidase site-specific substrate competitive (Cp4d) and irreversible (NC9, VA4, VA5) inhibitors are shown. In (B), a schematic showing closed and extended TG2 conformations and the position of the mCer (donor) and YAP (acceptor) fluorescence probes is shown. When TG2 is in the closed/folded conformation, the mCer/YFP probes are closely juxtaposed resulting in short energy transfer lifetimes. In the TG2 open/extended conformation separation of the probes results in longer lifetimes. In (C) and (D), it is shown that mCer-TG2 and mCer-TG2-YFP are expressed in SCC-13 cells. Cells were electroporated with 3 µg of each expression plasmid and after 48 h cell extracts were prepared for anti-YFP immunoblot and cells were fixed for anti-YFP cell staining. Note that anti-YFP detects both mCer and YFP. In (E), there are shown FLIM images of SCC-13 electroporated with mCer-TG2 or mCer-TG2-YFP and then treated for 24 h with 10 µM calcium ionophore (A23187). The left panel is intensity and the right panel is fluorescent lifetime for a representative experiment. The plot indicates the distribution of lifetimes determined for a single experiment. In (F), the average lifetime in nanoseconds was determined for mCer-TG2 or mCer-TG2-YFP expressing cells treated for 24 h with 0 or 10 µM A23187. The values are mean+SEM, n=4 (p<0.001).

Figure 30:
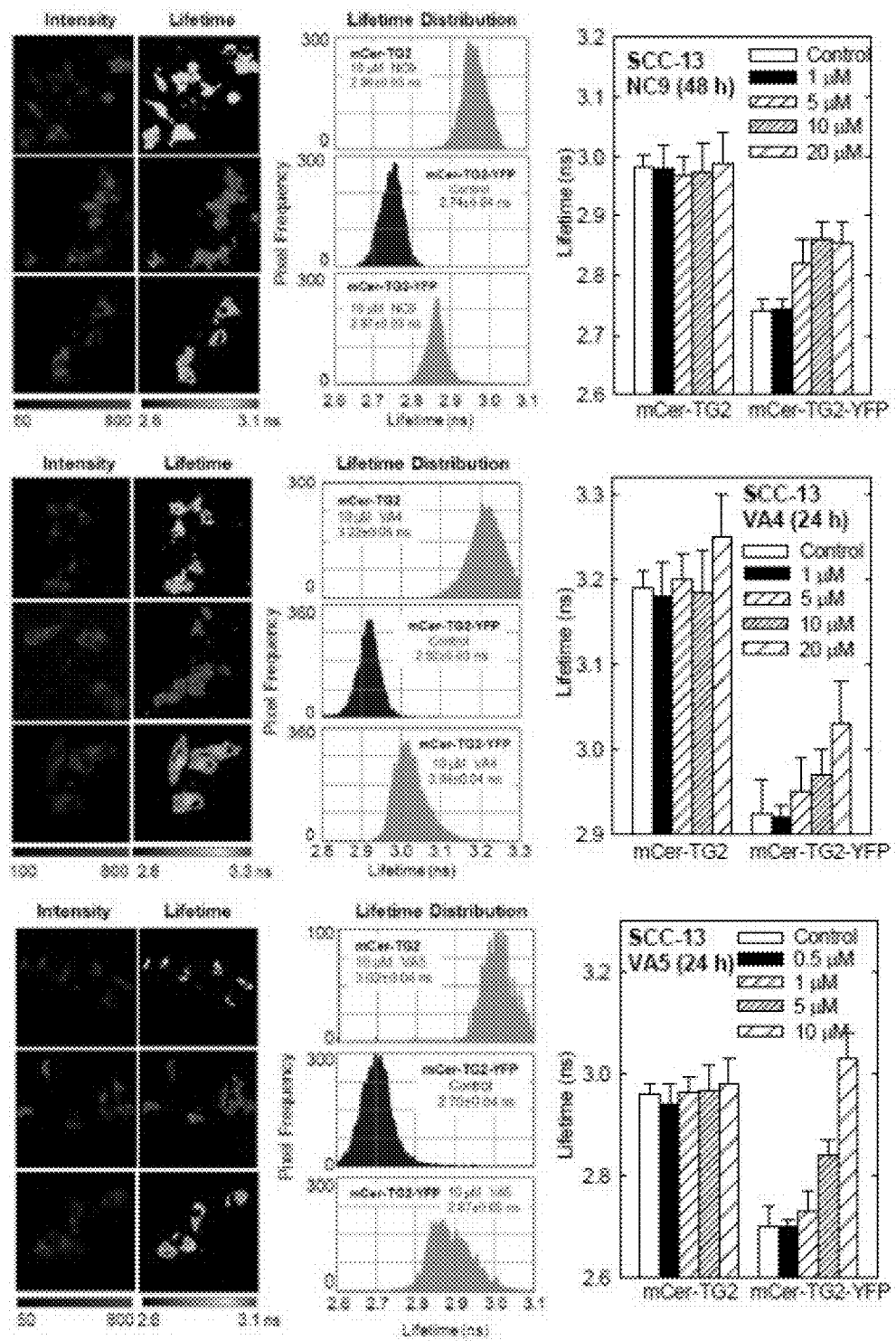

FIG. 30 shows irreversible TG2 transamidase site-selective inhibitors shift TG2 from a closed to open conformation. SCC-13 were electroporated with 3 µg of mCer-TG2 or mCer-TG2-YFP and then incubated with 0-20 µM of NC9, VA4 or VA5 (irreversible TG2 inhibitors) for 24 or 48 h prior to microscopic determination of fluorescence lifetime. Fluorescent images (left) and lifetime distributions (middle) are shown for each compound. The plots show the mean lifetime+SEM, n=4 (p<0.001).

Figure 31:
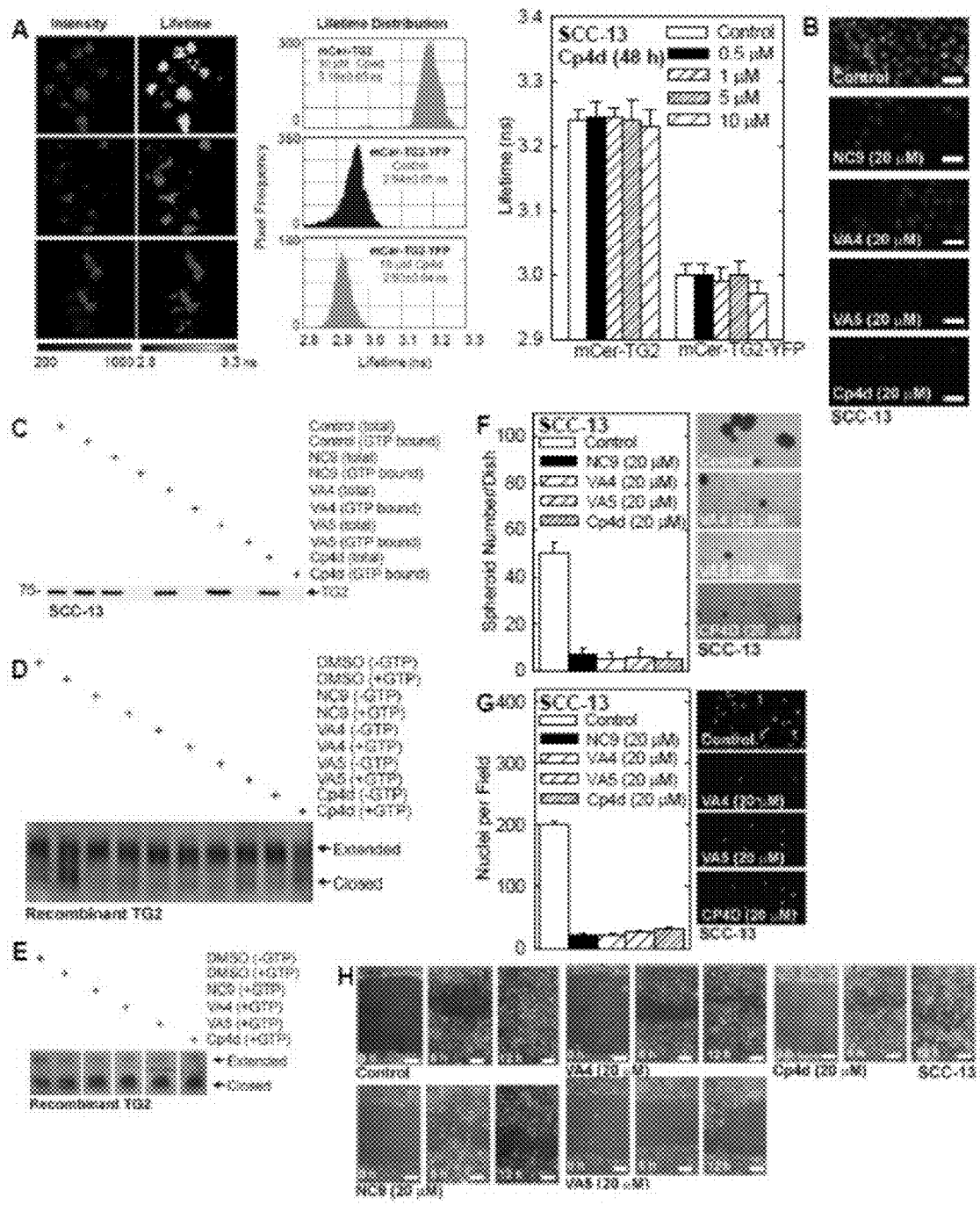

FIG. 31 shows impact of Cp4d on TG2 structure, and impact of inhibitors on TG2 transamidase/GTP binding activity and biological responses. In (A), Cp4d impact on TG2 structure is shown. SCC-13 cells were electroporated with 3 µg of mCer-TG2 or mCer-TG2-YFP and then incubated for 48 h with 0-10 µM Cp4d. Fluorescent intensity and distributions are shown on the left and middle panels. The right panel is a plot showing the average lifetime+SEM, n=4 (p<0.001). In (B), inhibitor treatment suppressed TG2 transamidase activity. SCC-13 cells were pre-loaded with fluorescein cadaverine (FC) and then challenged with calcium ionophore to increase intracellular calcium and TG2 transamidase activity. The images, which are representative of three separate experiments, show that the inhibitors reduced TG2 transamidase activity as measured by reduced FC crosslinking. In (C), transamidase inhibitors reduced GTP binding to endogenous TG2. SCC-13 cells were incubated for 48 h with the indicated inhibitor and extracts were prepared and incubated with GTP-agarose beads. The beads were then washed, boiled in Laemmli buffer and electrophoresed for immunoblot detection of TG2. Cell equivalent amounts of total extract and pulldown samples were electrophoresed in parallel to facilitate comparison of TG2 bound versus total. In (D), evidence for a direct impact of inhibitors on TG2 structure is shown. Recombinant TG2 was pre-incubated for 1 h with the indicated inhibitor and then challenged with 0 or 500 µM GTP prior to native gel electrophoresis and coomassie staining. The arrows show migration of the closed and extended forms of TG2. In (E), recombinant TG2 was treated by simultaneous addition of the indicated inhibitor and 500 µM GTP prior to native gel electrophoresis and coomassie staining. Migration of the closed and extended form is shown. In (F), TG2 inhibitors suppressed cancer stem cell survival. SCC-13 cells (20,000 cells) were plated in spheroid growth conditions and permitted to form spheroids for 8 d (Adhikary, G. et al., PLoS One 8:e84324 (2013); Fisher, M. L. et al., Oncotarget 6:20525-39 (2015)). They were then treated for 48 h with 0 or 20 µM of the indicated inhibitor and surviving spheroids were counted. The values are mean±SEM, n=6 (p<0.001). In (G), TG2 inhibitors reduced SCC-13 cell matrigel invasion. SCC-13 cells were plated on a matrigel-coated membrane in the presence of 0 or 20 µM of the indicated inhibitor and after 24 h the cells migrating to the internal side of the membrane were counted. The values are mean±SEM, n=6 (p<0.001). In (H), inhibitors reduced SCC-13 cell migration. Confluent cultures were scratched to generate a wound and closure of this wound was monitored from 0-12 h.

Figure 32:
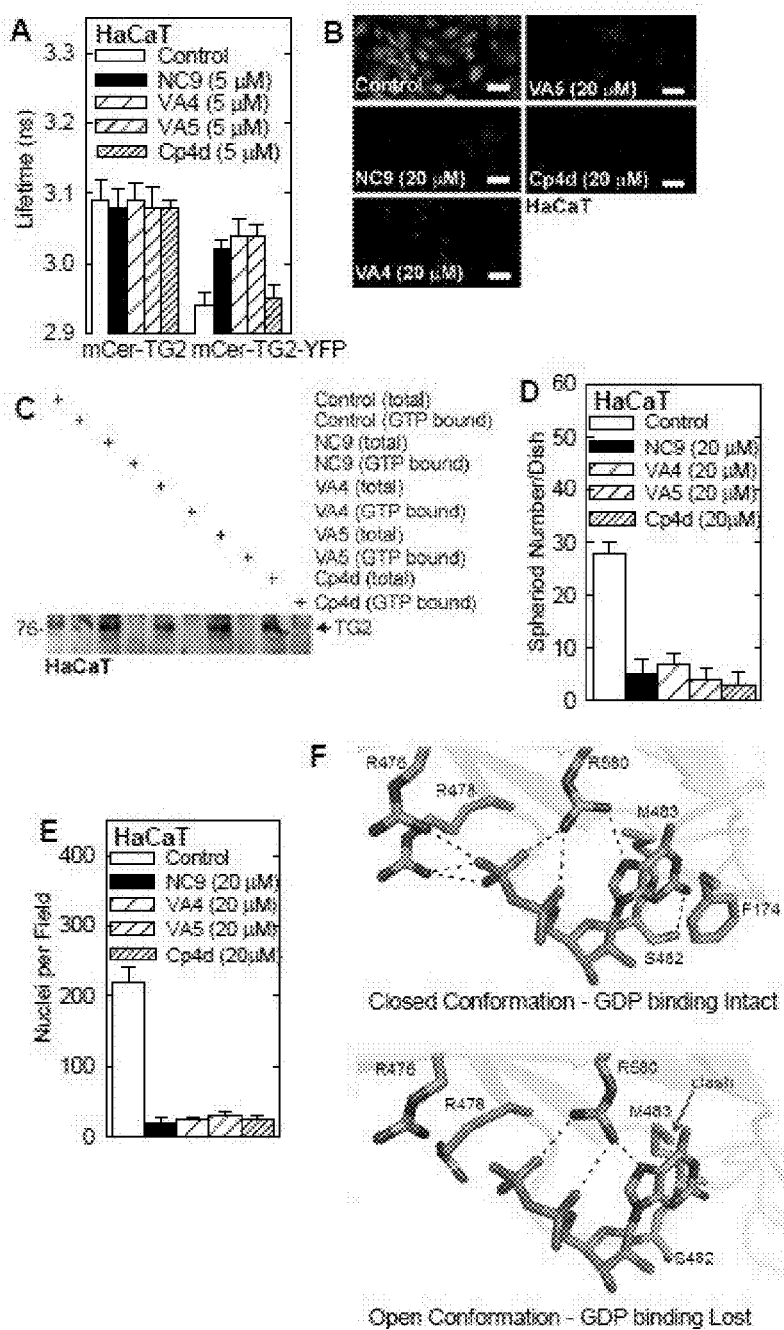

FIG. 32 shows impact of inhibitors on HaCaT cell biology. In (A), inhibitors catalyzed TG2 conformation change in HaCaT cells. HaCaT cells were electroporated with mCer-TG2 or mCer-TG2-YAP and then treated with 0 or 5 µM of the indicated inhibitor and fluorescent lifetime was monitored. The values are mean±SEM, n=4 (p<0.001). In (B), inhibitors suppressed TG2 transamidase activity. HaCaT cells were preloaded with fluorescein cadaverine, treated with the indicated inhibitor and then challenged with calcium ionophore, washed and assayed for FC incorporation. In (C), transamidase inhibitors reduced GTP binding to endogenous TG2. HaCaT were incubated for 48 h with the indicated inhibitor and extracts were prepared and incubated with GTP-agarose beads to measure TG2 binding to GTP agarose. The beads were then washed, boiled in Laemmli buffer and electrophoresed for immunoblot detection of TG2. Cell equivalent quantities of total and bound samples were electrophoresed to facilitate comparison of GTP bound versus total. In (D) and (E), inhibitors suppressed HaCaT cell spheroid formation and matrigel invasion. Experiments were performed as described in FIGS. 31 (F) and (G). In (F), structural analysis of GDP binding at nucleotide binding site in TG2 closed and open conformations is shown (details in Example 8).

Figure 33:
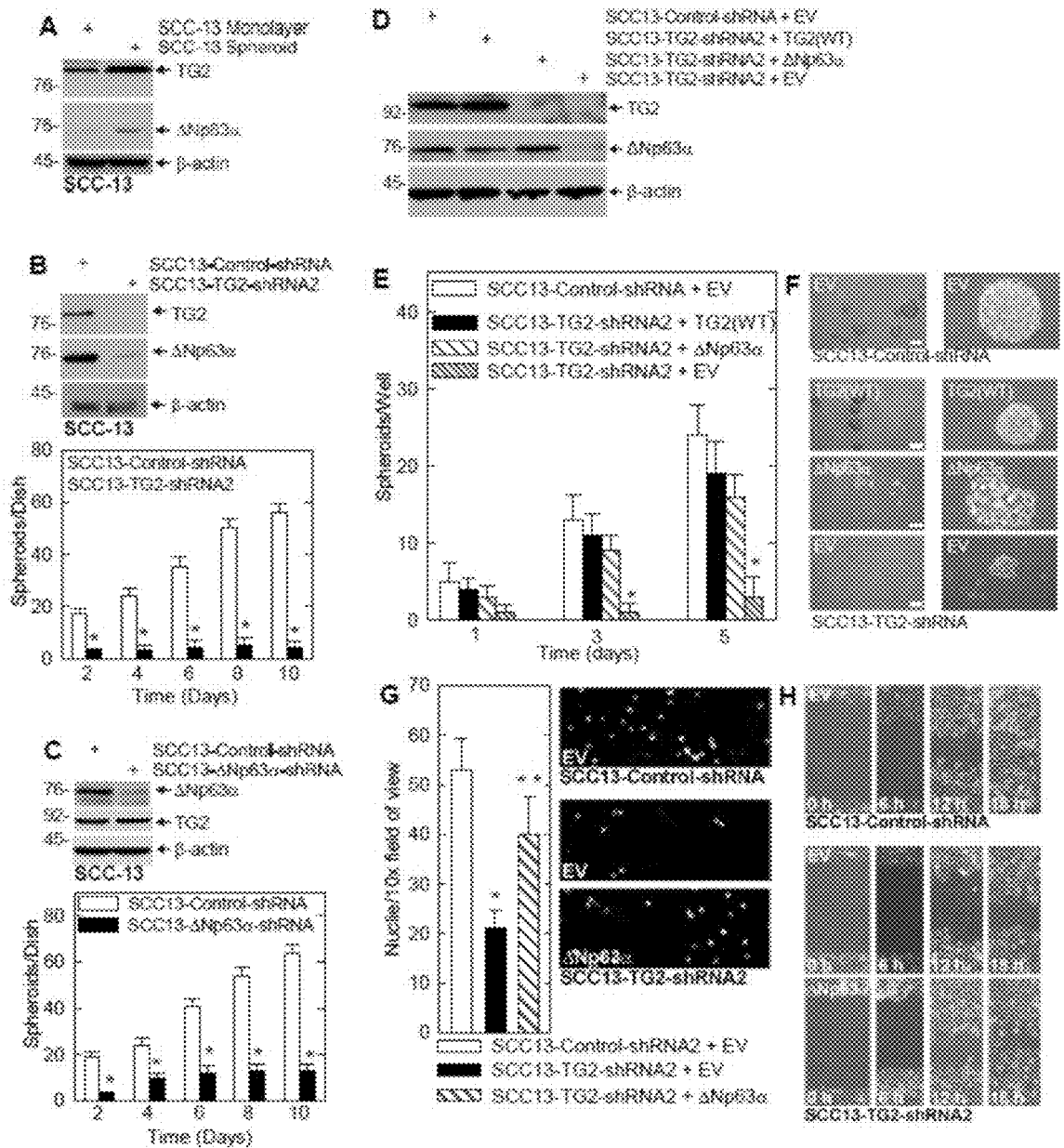

FIG. 33 shows TG2 and ΔNp63α are enriched in ECS cells, and required for ECS cell survival. In (A), ECS cells have elevated TG2 and ΔNp63α. SCC-13 cells (40,000 per well) were grown in spheroid medium in attached (monolayer) or non-attached (spheroid, ECS cell) conditions. At 10 d lysates were electrophoresed for detection of the indicated epitopes. In (B), SCC13-Control-shRNA and SCC13-TG2-shRNA2 cells were grown in spheroid culture for 10 d prior to counting of spheroid number and extract preparation for detection of TG2 and ΔNp63α. In (C), SCC13-Control-shRNA and SCC13-ΔNp63α-shRNA were grown in spheroid culture for 10 d prior to counting of spheroid number and extract preparation for detection of TG2 and ΔNp63α. In (D), SCC13-Control-shRNA or SCC13-TG2-shRNA2 cells were double electroporated with empty vector (EV) or expression vectors encoding TG2 or ΔNp63α and after 5 d the indicated proteins were detected. In (E) and (F), the indicated cell lines were electroporated with EV, TG2 or ΔNp63α and grown as spheroids for 5 d prior to counting of spheroids and recording of images. In (G), the indicated cell lines were electroporated with the indicated plasmid and after 48 h seeded onto a matrigel-coated membrane in a Millicell chamber for invasion assay. After 20 h the membrane was removed, fixed, and DAPI-stained for nuclei counting. In (H), cells were electroporated with the indicated plasmid, plated at high density to form confluent monolayers, the monolayers were scratched with a 10 µl pipette tip to create a wound and wound closure was monitored with time. The plotted values are mean±SEM and asterisks indicate significant change compared to control, n=3, p<0.005. The double asterisk in panel G indicates a significant change compared to the single asterisk group, n=3, p<0.005.

Figure 34:
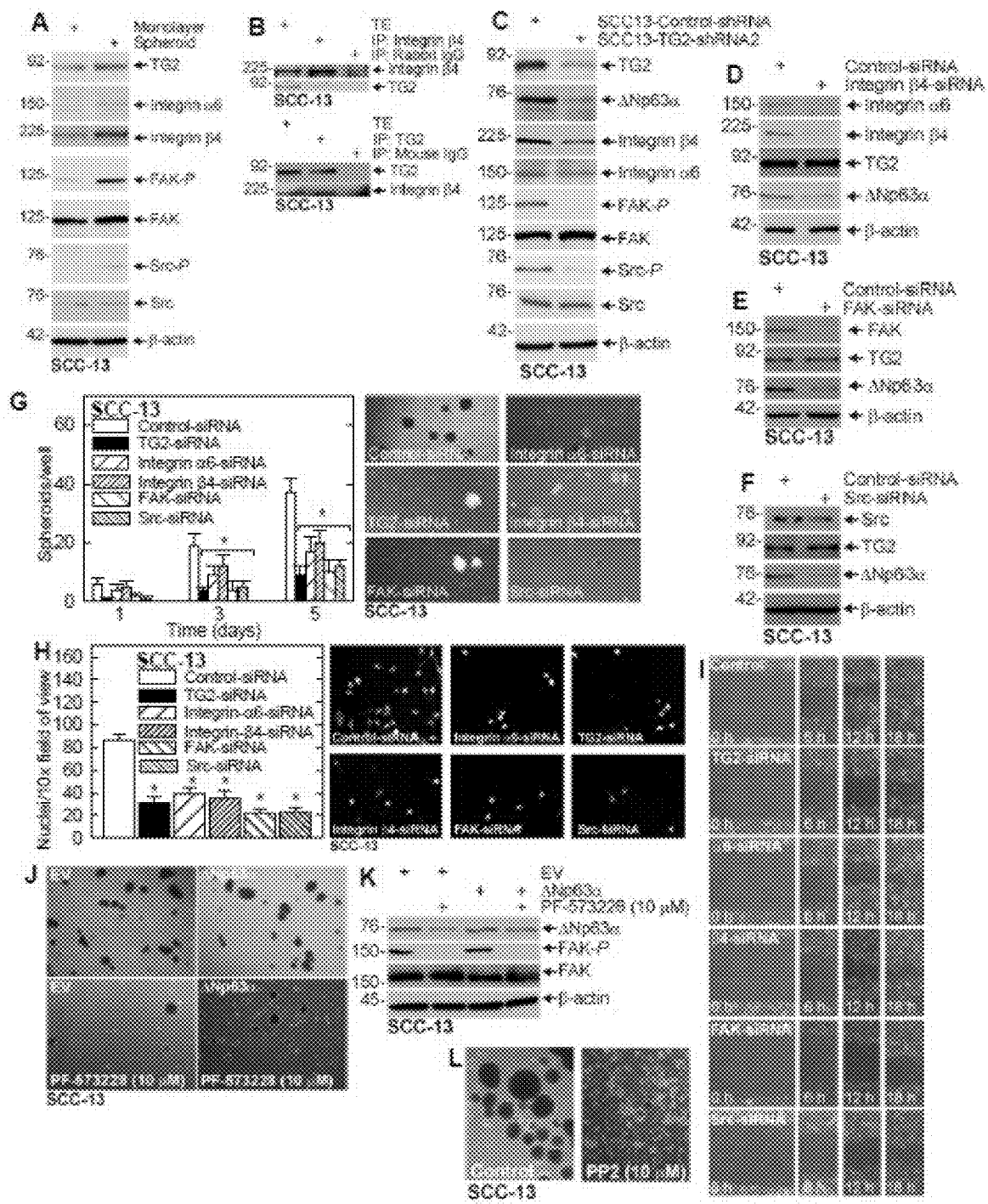

FIG. 34 shows α6/β4-Integrin signaling is essential for ΔNp63α expression. In (A), ECS cells display elevated 6α4 integrin levels and elevated FAK/Src signaling. SCC-13 cells (40,000 per well) were grown in spheroid medium in attached (monolayer) or non-attached (spheroid, ECS cell). Cells were collected after 10 d and lysates were prepared for immunoblot. In (B), SCC-13 cells spheroid were grown for 8 d and extracts were immunoprecipitated as indicated prior to immunoblot. In (C), integrin signaling is reduced in SCC13-TG2-shRNA2 cells. Cells were grown in spheroid medium in monolayer culture for 10 d prior to collection of lysates for immunoblot. In (D), (E), and (F), SCC-13 cells were double-electroporated with Control- or Integrin β4-, FAK-, or Src-siRNA and 48 h later extracts were prepared for immunoblot. In (G), (H), and (I), SCC-13 cells were double-electroporated with the indicated siRNA and 24 h later plated for growth as spheroids and for invasion and migration assays. In (J), (K), and (L), cells were double-electroporated with indicated siRNA and 24 h later plated for spheroid formation in the presence of the indicated inhibitor. Spheroids were grown for 5 d and then photographed and extracts prepared for immunoblot. The plotted values are mean±SEM and asterisks indicate significant change compared to control, n=3, p<0.005.

Figure 35:
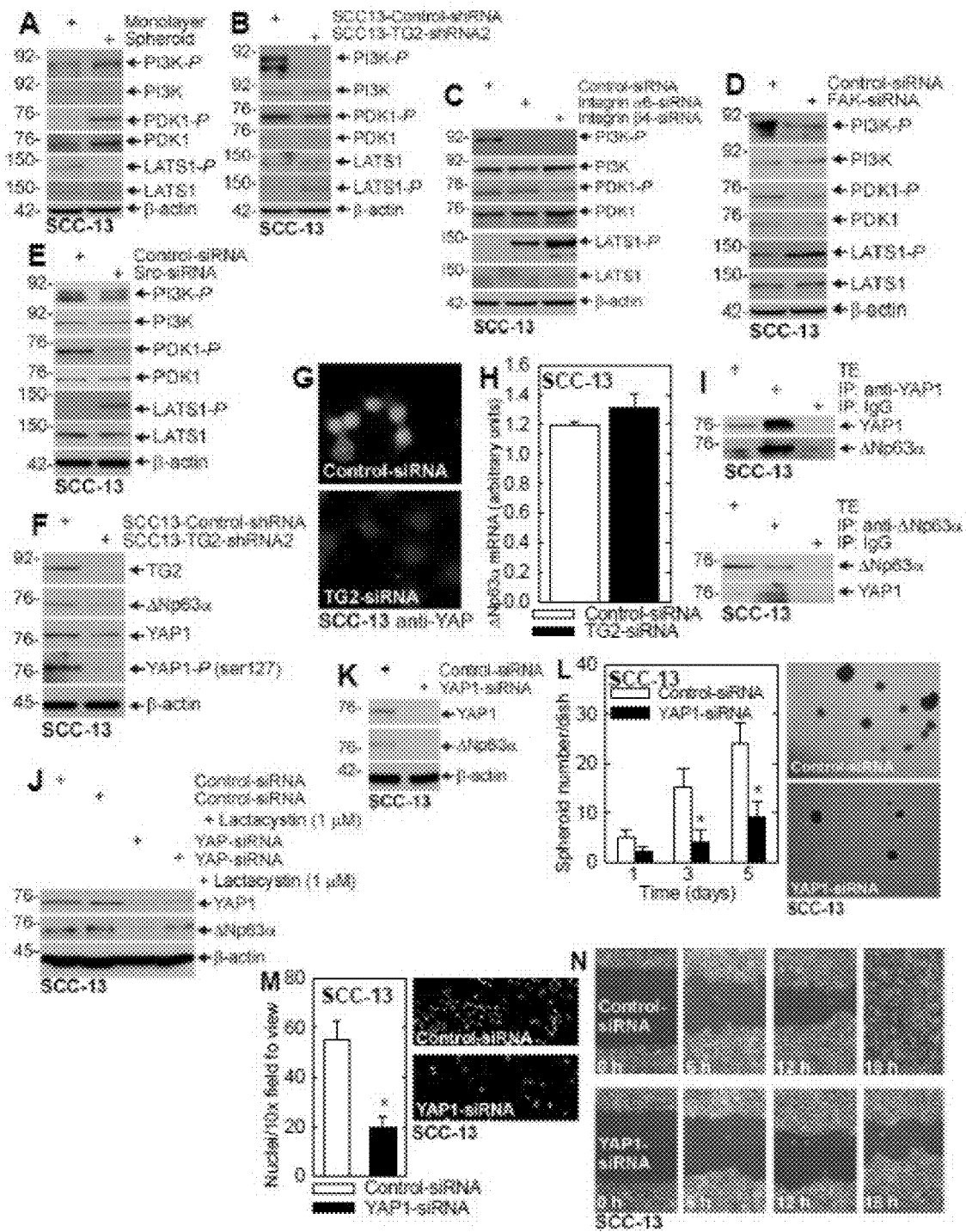

FIG. 35 shows that TG2 suppresses Hippo signaling to increase ΔNp63α level. In (A), cells were grown in spheroid medium in monolayer or spheroid culture and after 10 d harvested for immunoblot. In (B), SCC13-Control-shRNA and SCC13-TG2-shRNA2 cells were grown in monolayer culture in spheroid medium and lysates were collected for immunoblot detection of the indicated epitopes. In (C), (D), and (E), SCC-13 cells were double electroporated with the indicated siRNA, grown as monolayer cultures for 2 d and lysates were collected for immunoblot. In (F), SCC13-Control-shRNA and SCC13-TG2-shRNA2 cells were grown as monolayers in spheroid medium and lysates collected at 6 d for marker detection. In (G), SCC-13 cells were double-electroporated with Control- or TG2-siRNA and given 24 h to recover before being seeded on chamber slides. The following day, cells were fixed in 4% paraformaldehyde, stained with anti-YAP1 and appropriate secondary antibody, and co-stained with DAPI. In (H), SCC-13 cells, double-electroporated with Control- or TG2-siRNA, were grown in spheroid medium for 48 h prior to extracts being prepared for assay of ΔNp63α mRNA by qRT-PCR. In (I), SCC-13 cells were grown as spheroids and at day 8 lysates were collected for immunoprecipitation/immunoblot. In (J), SCC-13 cells were double-electroporated with Control- or YAP-siRNA followed by treatment with 1 μM lactacystin in monolayer culture. Extracts were prepared after an additional 24 h. In (K), SCC-13 cells were double-electroporated with Control- or YAPsiRNA and after 2 d in monolayer culture extracts were prepared for immunoblot. In (L), (M), and (N), SCC-13 cells were electroporated with Control- or YAP1-siRNA and then seeded for spheroid formation, invasion and migration assay. The plotted values are mean±SEM and asterisks indicate significant change compared to control, n=3, p<0.005.

Figure 36:
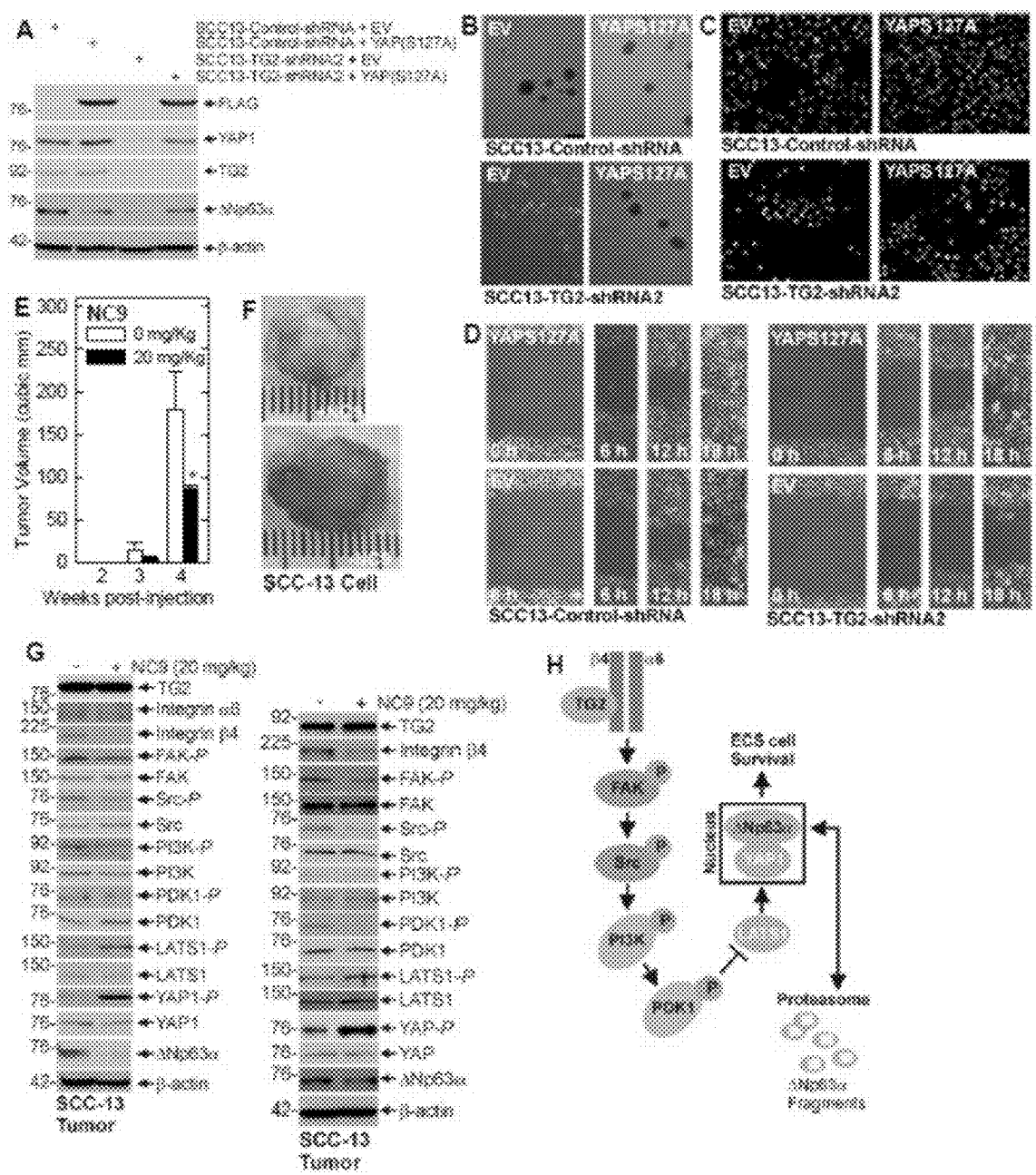

FIG. 36 shows YAP enhances ECS cell survival and TG2 inhibitor suppresses tumor formation. In (A), SCC13-Control-shRNA and SCC13-TG2-shRNA2 cells were double electroporated with empty vector (EV) or YAP(S127A)-encoding vector and at 48 h post-electroporation lysates were collected for immunoblot. In (B), (C), and (D), the indicated cell lines were electroporated with EV or YAP (S127A)-encoding vector and then plated for spheroid formation, invasion and migration assay. In (E) and (F), ECS cells (100,000 cells derived from SCC-13) were injected into each front flank in NSG mice. At 1 d post injection, the mice were treated with 0 or 20 mg NC9 per kg body weight delivered in 200 μl by gavage three times per week. Images represent appearance and size of typical control and NC9 treated tumors harvested on week four. In (G), tumors were harvested at 4 wk and extracts were prepared for assay of indicated proteins. Blots from two representative tumors are shown. In (H), a proposed TG2 signaling scheme is shown. TG2 interacts with α6/β4 integrin to enhance integrin (FAK/Src) signaling which increases PI3K/PDK1 activity and PDK suppresses activity in the Hippo signaling cascade (LATS1). This leads to reduced LATS1 phosphorylation of YAP1 which then interacts with and stabilizes ΔNp63α. This signaling pathway enhances ECS cell survival, invasion and migration. Loss of TG2 function reduces YAP1 which leads to degradation of ΔNp63α and reduced ECS cell survival, invasion and migration. The plotted values are mean±SEM and asterisks indicate significant change compared to control, n=3, p<0.005.

Figure 37:
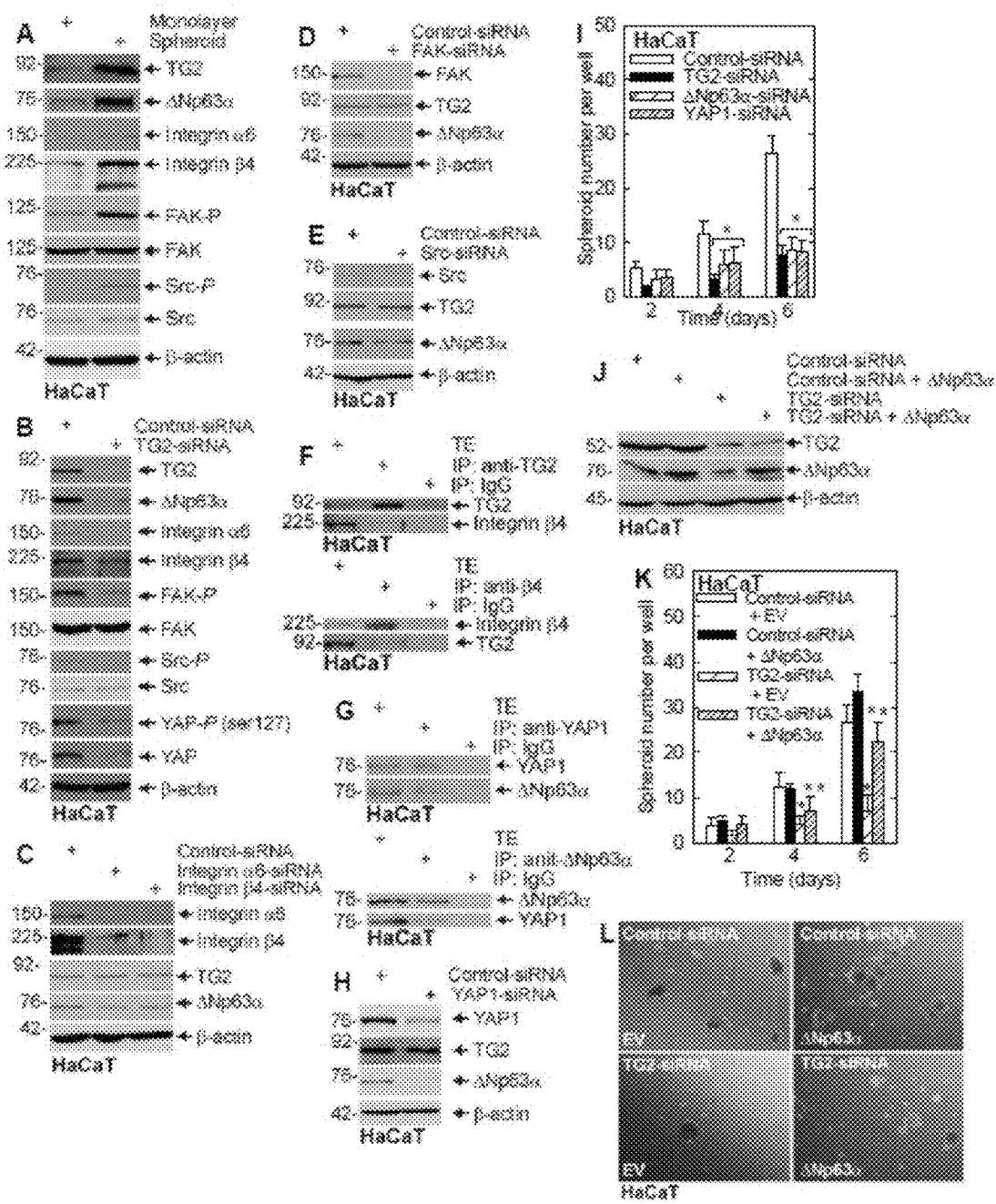

FIG. 37 shows TG2 stimulated signaling in HaCaT cells. In (A), HaCaT cell-derived ECS cells display elevated integrin signaling and ΔNp63α level. HaCaT cells (40,000 per well) were grown in spheroid medium in monolayer or spheroid culture and at 10 d lysates were prepared for immunoblot. In (B), (C), (D), and (E), HaCaT cells were double-electroporated with the indicated siRNA and then maintained in spheroid medium in monolayer culture for 48 h before extracts were prepared for detection of the indicated proteins. In (F) and (G), HaCaT cells were grown in non-attached conditions as spheroids for 8 d. After day 8, lysates were prepared for immunoprecipitation and immunoblot. In (H), HaCaT cells were double-electroporated with the indicated siRNA and then maintained in spheroid medium in monolayer culture for 48 h before extracts were prepared for detection of the indicated proteins. In (I), cells were double-electroporated with the indicated siRNA and then seeded to monitor for spheroid formation. In (J), (K), and (L), HaCaT cells were double-electroporated with the indicated siRNA or expression vector and at 48 h extracts were prepared for immunoblot. In parallel, cells were plated to assess ability to form spheroids and images were recorded. The plotted values are mean±SEM and asterisks indicate significant change compared to control, n=3, p<0.005. The double asterisk in panel K indicate a significant change compared to the single asterisk group, n=3, p<0.005.

Figure 38:
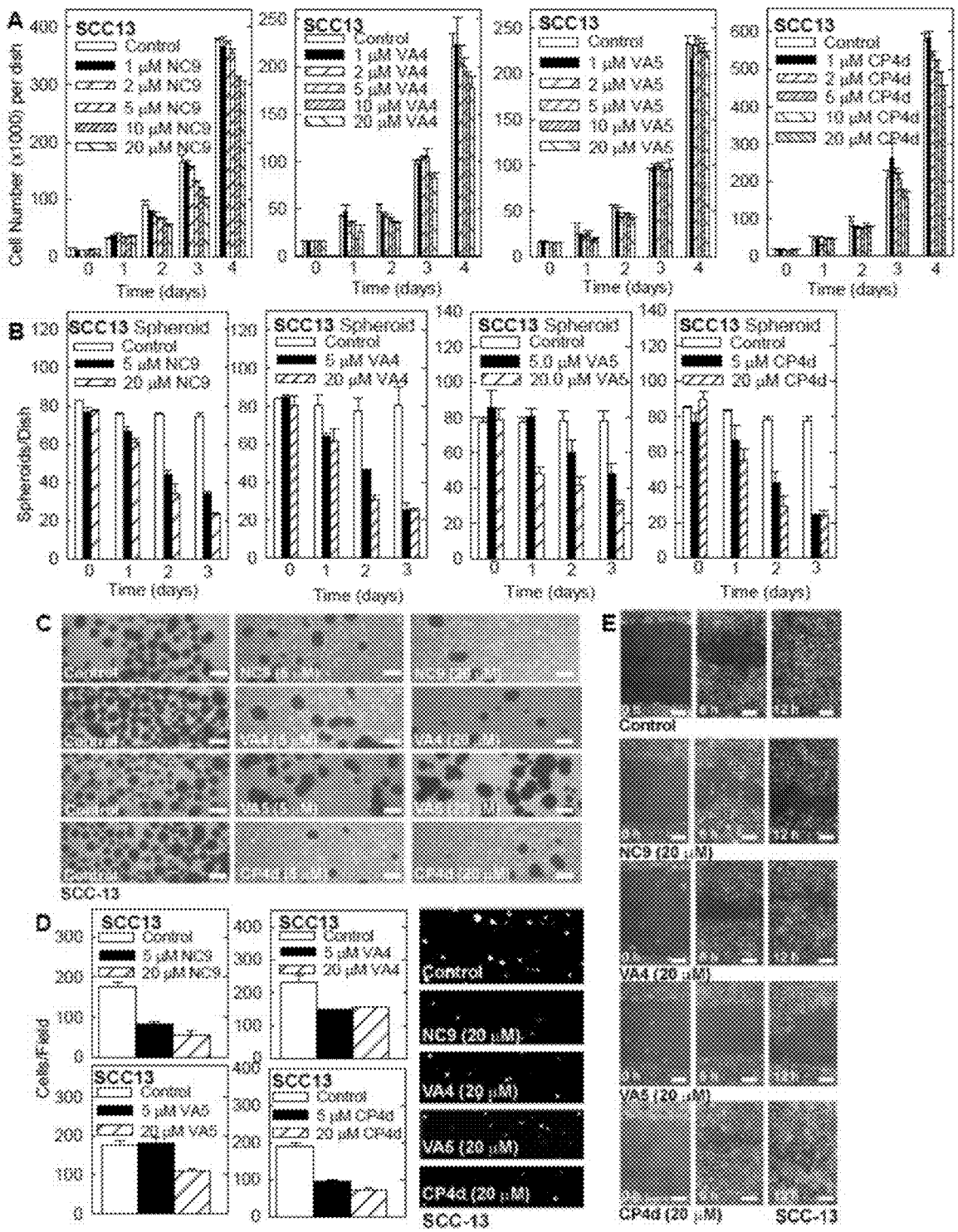

FIG. 38 shows testing of NC9, VA4, VA5 and CP4d compounds as indicated in skin squamous cell carcinoma cells (SCC13 or SCC-13) in assays for spheroid formation, matrigel invasion, and migration as indicated (A-E). SCC13 cells were grown for one week as monolayer in spheroid media; cells were harvested with 0.25% trypsin and plated with 2 mL of spheroid media at 15,000 cells per well in a 6-well dish. Cells were counted on day 0 and then treated with the indicated concentration of the indicated compound. Control was 0.1% DMSO. Cells were counted using a cell counter, 2 wells per treatment on each day. Values shown are mean±SEM, n=1.

Figure 39:
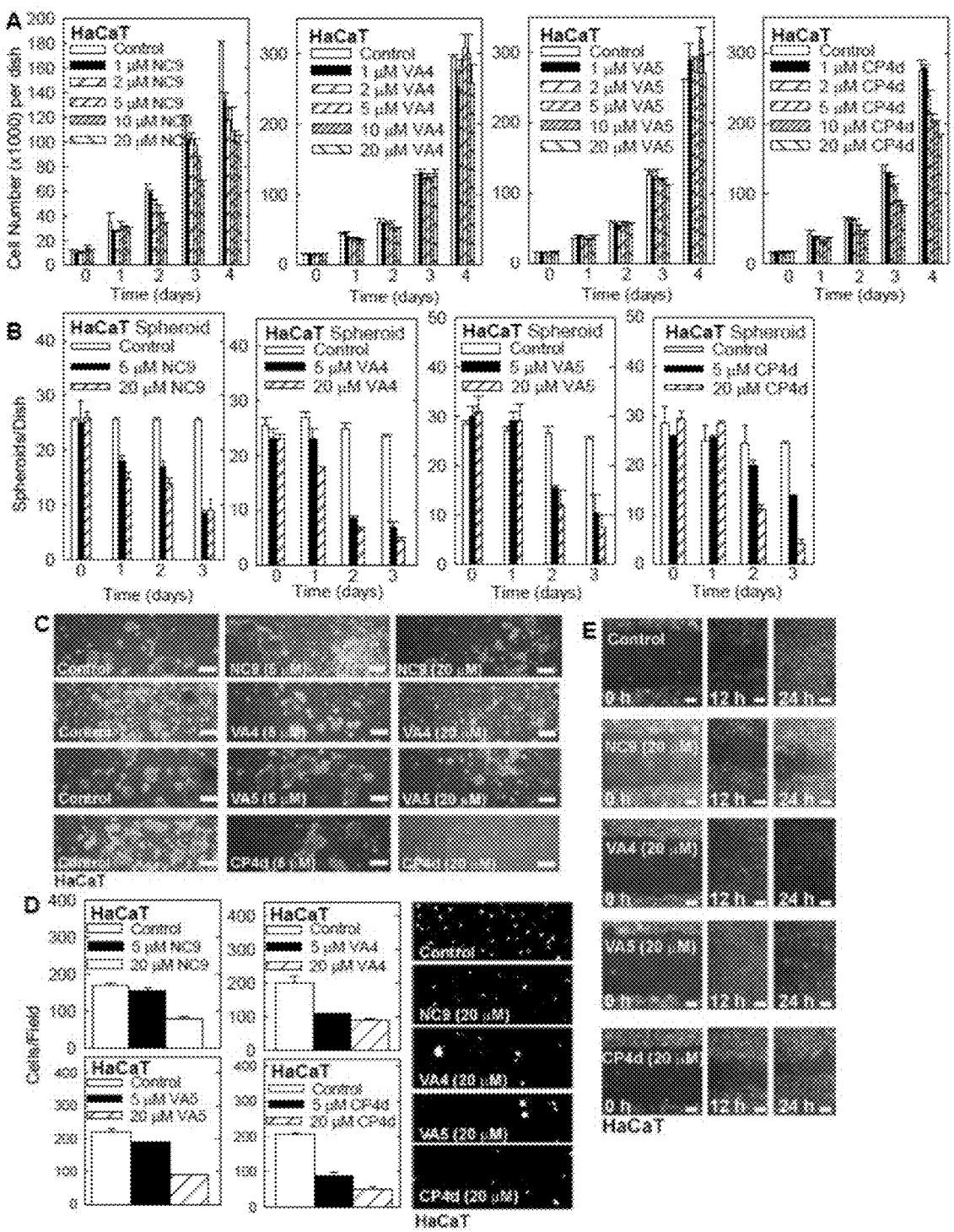

FIG. 39 shows testing of NC9, VA4, VA5 and CP4d compounds as indicated in epidermis derived immortalized keratinocytes (HaCaT) in assays for spheroid formation, matrigel invasion, and migration as indicated (A-E). HaCaT cells were grown for one week as a monolayer in spheroid media. Cells were harvested with 0.25% trypsin and plated with 2 mL of spheroid media at 15,000 cells per well in a 6-well dish. Cells were counted on day 0 and then treated with the indicated concentration of the indicated compound. Control was 0.1% DMSO. Cells were counted using a cell counter, 2 wells per treatment on each day. Values shown are mean±SEM, n=1.

Figure 40:
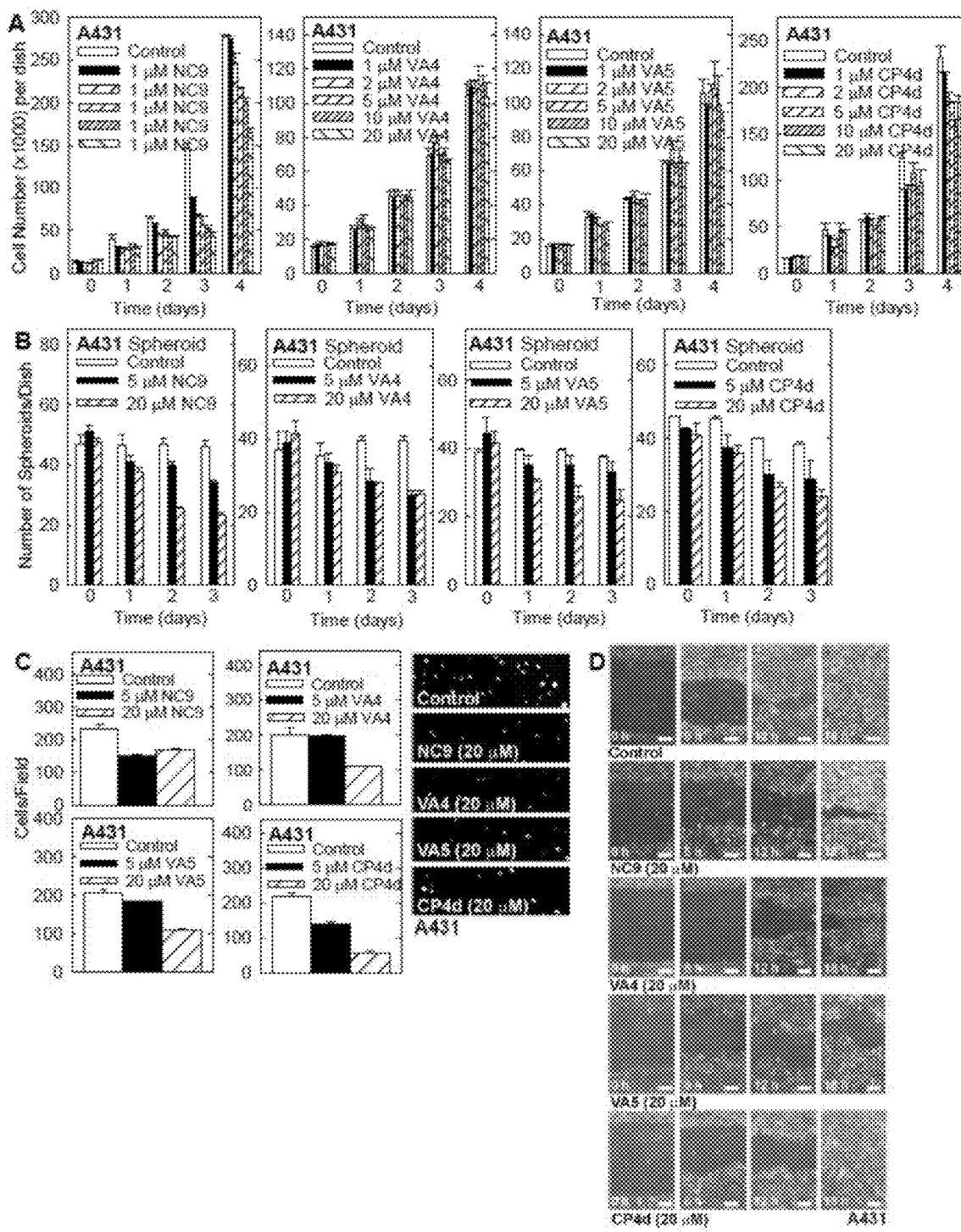

FIG. 40 shows testing of NC9, VA4, VA5 and CP4d compounds as indicated in epidermoid carcinoma (A431) cells in assays for spheroid formation, matrigel invasion, and migration as indicated (A-D). A431 cells were grown for one week as a monolayer in spheroid media. Cells were harvested with 0.25% trypsin and plated with 2 mL of spheroid media at 15,000 cells per well in a 6-well dish. Cells were counted on day 0 and then treated with the indicated concentration of the indicated compound. Control was 0.1% DMSO. Cells were counted using a cell counter, 2 wells per treatment on each day. Values shown are mean±SEM, n=1.

Figure 41:
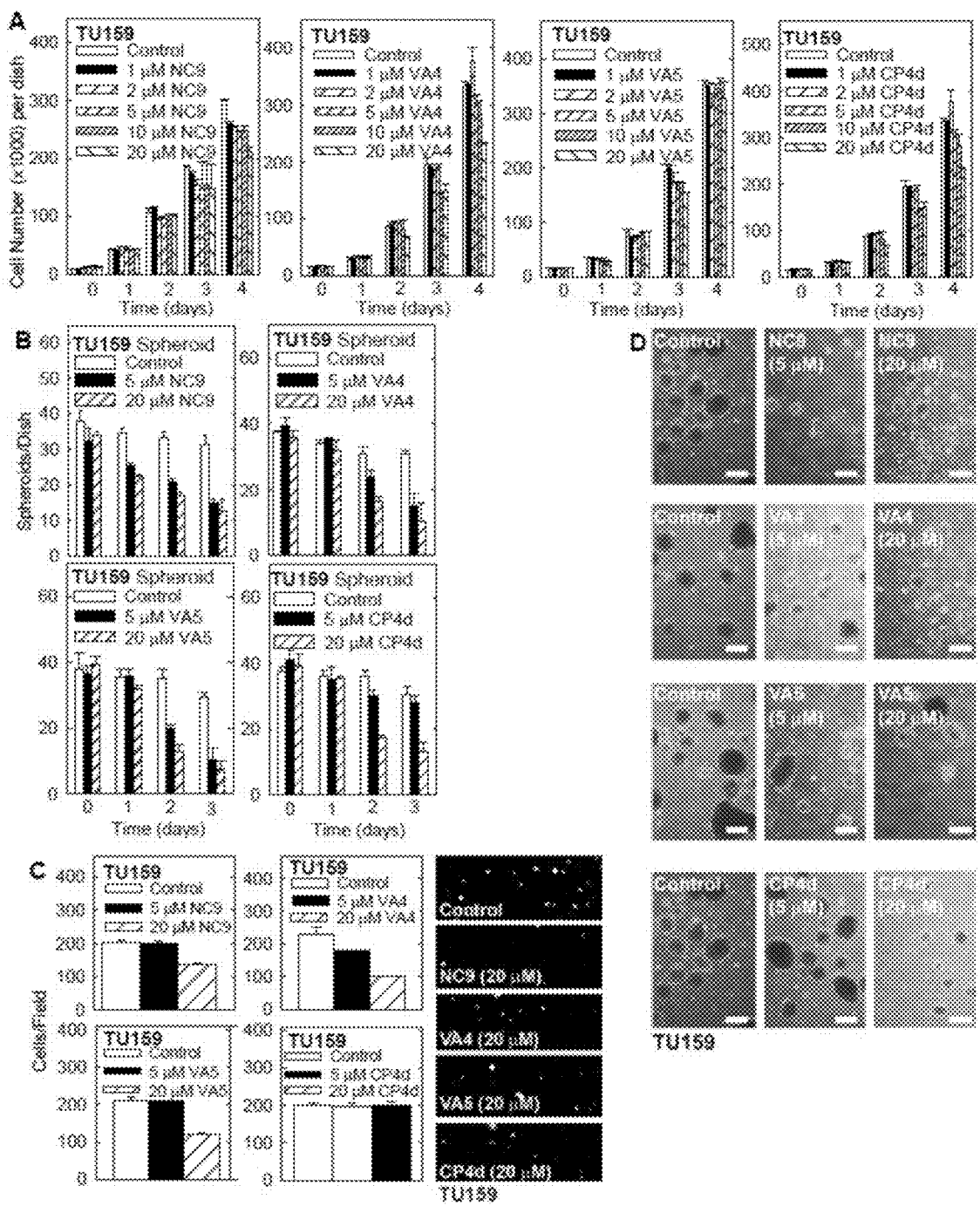

FIG. 41 shows testing of NC9, VA4, VA5 and CP4d compounds as indicated in the head and neck (TU159) cancer cell line in assays for spheroid formation, matrigel invasion, and migration as indicated (A-D). TU159 cells were harvested with 0.25% trypsin and plated with 2 mL of spheroid media at 40,000 cells per well in a 6 well low-attachment plate. The cells were grown as spheroids for 8 days. On day 8 the spheroids were treated with the indicated concentration of the indicated compound. Control was 0.1% DMSO. The same 2 wells per treatment were counted on each day. Values shown are mean±SEM, n=1.

Figure 42:
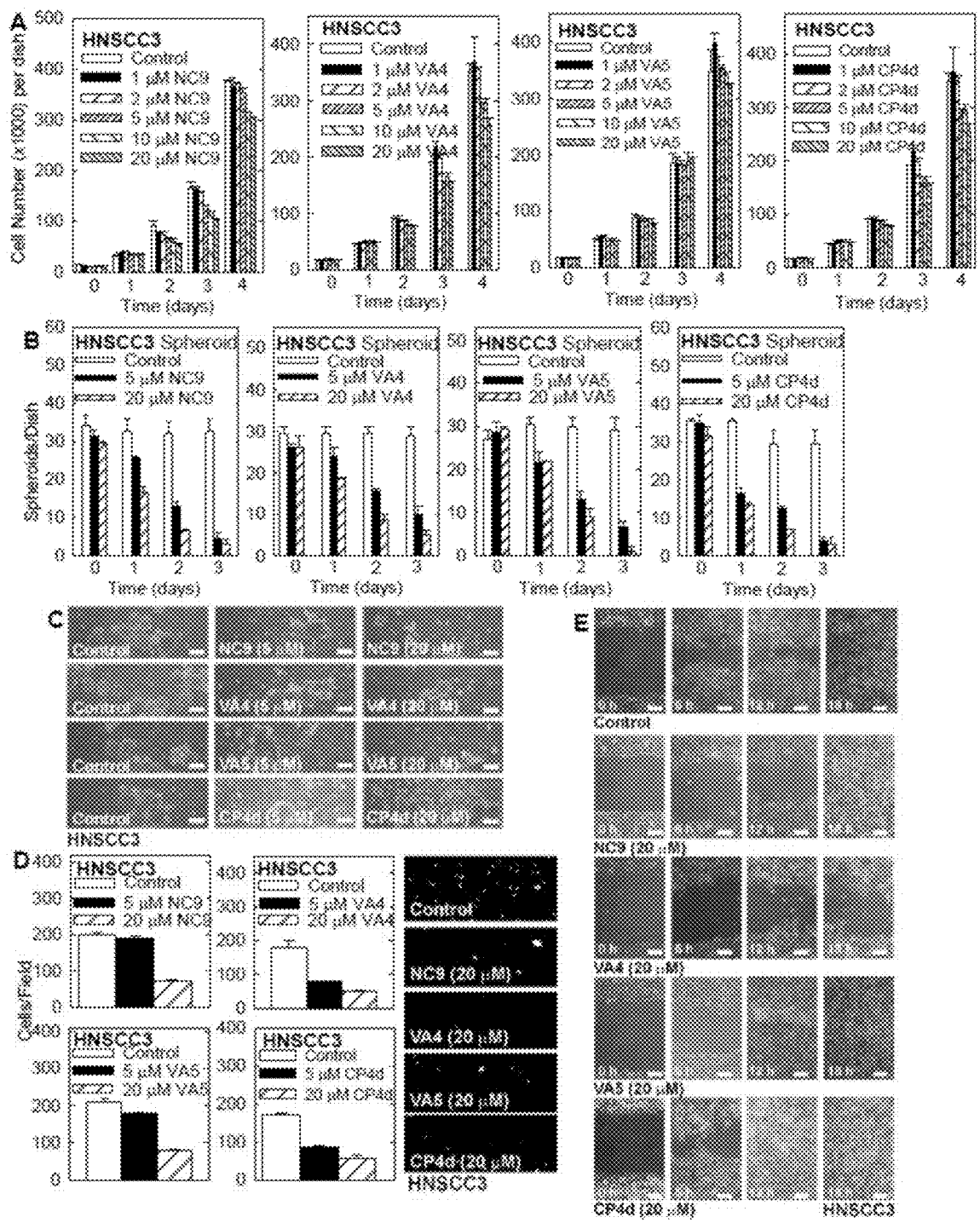

FIG. 42 shows testing of NC9, VA4, VA5 and CP4d compounds as indicated in the head and neck (HNSCC3) cancer cell line in assays for spheroid formation, matrigel invasion, and migration as indicated (A-E). HNSCC3 cells were grown for one week as a monolayer in spheroid media. Cells were harvested with 0.25% trypsin and plated with 2 mL of spheroid media at 15,000 cells per well in a 6-well dish. Cells were counted on day 0 and then treated with the indicated concentration of the indicated compound. Control was 0.1% DMSO. The same 2 wells per treatment were counted on each day. Values shown are mean±SEM, n=1.

Figure 43:
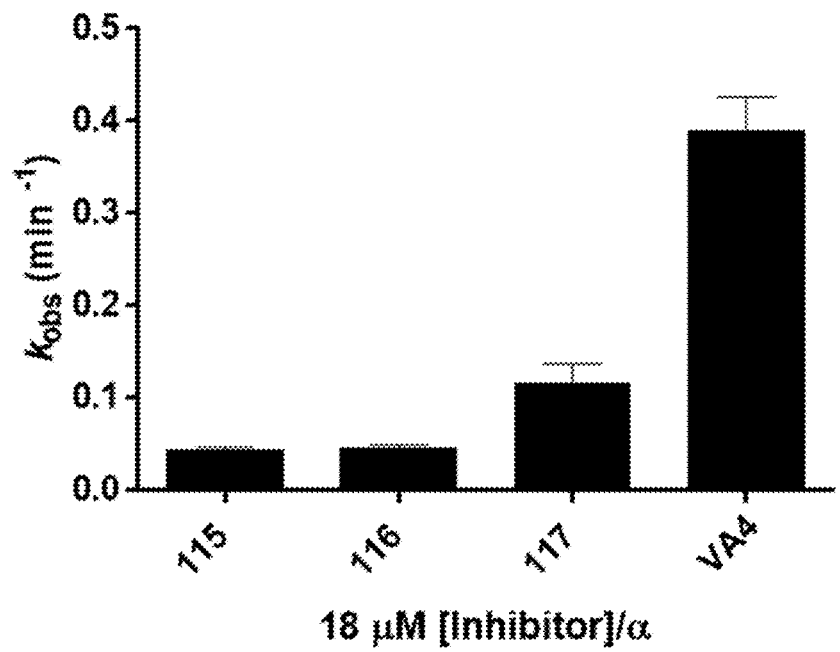

FIG. 43 shows observed rate constants ($k_{obs}$) of inactivation of human transglutaminase 2 (hTG2) with 18 μM of inhibitors 115-117 and VA4, as indicated.

Figure 44:
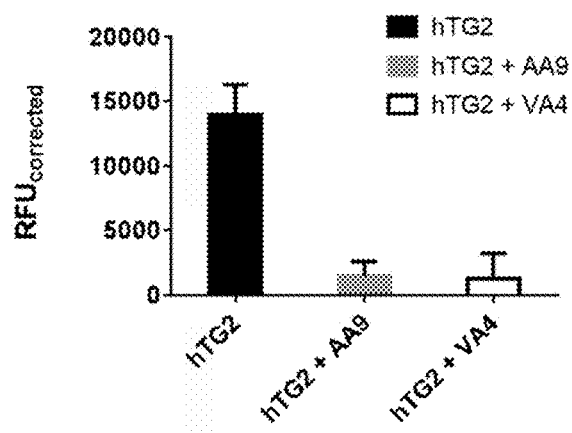

FIG. 44 shows suppression of GTP binding activity using 3 μM of GTP-γ-S FL BODIPY after inhibition of hTG2 with VA4 and AA9.

DETAILED DESCRIPTION

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "derivative" as used herein, is understood as being a substance similar in structure to another compound but differing in some slight structural detail.

The present description refers to a number of chemical terms and abbreviations used by those skilled in the art. Nevertheless, definitions of selected terms are provided for clarity and consistency.

As used herein, the terms "alkyl" and "$C_{1-6}$ alkyl" can be straight-chain or branched. Examples of alkyl residues containing from 1 to 6 carbon atoms are methyl, ethyl, propyl, butyl, pentyl, hexyl, the n-isomers of all these residues, isopropyl, isobutyl, isopentyl, neopentyl, isohexyl, 3-methylpentyl, sec-butyl, tert-butyl, or tert-pentyl. Alkyl residues may be substituted or unsubstituted. In some embodiments, for example, alkyl may be substituted by hydroxyl, amino, carboxyl, carboxylic ester, amide, carbamate, or aminoalkyl.

As used herein, the term "cycloalkyl" can be monocyclic or polycyclic, for example monocyclic, bicyclic or tricyclic, i.e., they can for example be monocycloalkyl residues, bicycloalkyl residues and tricycloalkyl residues, provided they have a suitable number of carbon atoms and the parent hydrocarbon systems are stable. A bicyclic or tricyclic cycloalkyl residue has to contain at least 4 carbon atoms. In an embodiment, a bicyclic or tricyclic cycloalkyl residue contains at least 5 carbon atoms. In a further embodiment, a bicyclic or tricyclic cycloalkyl residue contains at least 6 carbon atoms and up to the number of carbon atoms specified in the respective definition. Cycloalkyl residues can be saturated or contain one or more double bonds within the ring system. In particular they can be saturated or contain one double bond within the ring system. In unsaturated cycloalkyl residues the double bonds can be present in any suitable positions. Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl, which can also be substituted, for example by $C_{1-4}$ alkyl. Examples of substituted cycloalkyl residues are 4-methylcyclohexyl and 2,3-dimethylcyclopentyl. Examples of parent structures of bicyclic ring systems are norbornane, bicyclo[2.2.1]heptane, bicyclo[2.2.2]octane and bicyclo[3.2.1]octane.

As used herein, the term "aryl" means an aromatic substituent that is a single ring or multiple rings fused together. When formed of multiple rings, at least one of the constituent rings is aromatic. In an embodiment, aryl substituents include phenyl, naphthyl and anthracyl groups.

The term "heteroaryl", as used herein, is understood as being unsaturated rings of five or six atoms containing one or two O- and/or S-atoms and/or one to four N-atoms, provided that the total number of hetero-atoms in the ring is 4 or less. The heteroaryl ring is attached by way of an available carbon or nitrogen atom. Non-limiting examples of heteroaryl groups include 2-, 3-, or 4-pyridyl, 4-imidazolyl, 4-thiazolyl, 2- and 3-thienyl, and 2- and 3-furyl. The term "heteroaryl", as used herein, is understood as also including bicyclic rings wherein the five or six membered ring containing O, S and N-atoms as defined above is fused to a benzene or pyridyl ring. Non-limiting examples of bicyclic rings include but are not limited to 2- and 3-indolyl as well as 4- and 5-quinolinyl.

TG2 Inhibitor Compounds

In a broad aspect, the present disclosure relates to TG2 inhibitor compounds, and their use as cancer therapeutics. It is noted that the TG2 enzyme catalyzes a transamidation reaction between protein-bound glutamine and lysine residues, resulting in the cross-linking of proteins. This acyl-transfer reaction is mediated by a catalytic triad that resembles that of the calpain-type cysteine proteases. TG2 transamidation activity is important among other things for stabilizing the extracellular matrix (ECM). TG2 also binds GTP in the cytosol and modulates signal transduction by participating in G protein signaling.

TG2 transamidation and GTP-binding activities are mutually exclusive and ligand dependent; calcium is required for transamidation activity, whereas the presence of guanosine nucleotides suppresses it. Early spectroscopic studies suggested this was due to significant conformational changes, for which crystallographic studies have since provided direct structural evidence. TG2 has been crystallized in two strikingly different forms, both of which comprise four structurally distinct domains. In the presence of GDP, the enzyme adopts a "closed" conformation, wherein these four domains are arranged in a compact tertiary structure. In contrast, after reaction with an irreversible inhibitor in the presence of calcium, the enzyme was crystallized in an "open" conformation, where the same four domains are arranged in an extended linear tertiary structure (Pinkas, D. M. et al., *PLoS Biol.* 5: e327, 2007).

Without wishing to be limited by theory, it is believed that TG2 inhibitor compounds described herein may act as active site directed irreversible inhibitors of TG2 that lock the enzyme in its "open" conformation which does not bind GTP. Thus, TG2 inhibitor compounds described herein may exploit the reactivity of the active site residues to covalently attach to the enzyme, and upon binding they lock the enzyme in a conformation that cannot bind GTP, thereby abolishing that activity in addition to transglutaminase activity. TG2 inhibitor compounds described herein are thus distinct from previously known inhibitors of TG2 that may bind the catalytic active site, blocking transamidation activity, but do not inhibit GTP binding.

In an embodiment, there is provided a compound of Formula I, or a pharmaceutically acceptable salt thereof:

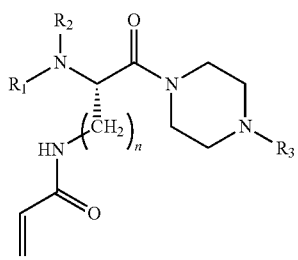

Formula I wherein:

$R_1$ is carbonyl-$R^a$, where $R^a$ is selected from:

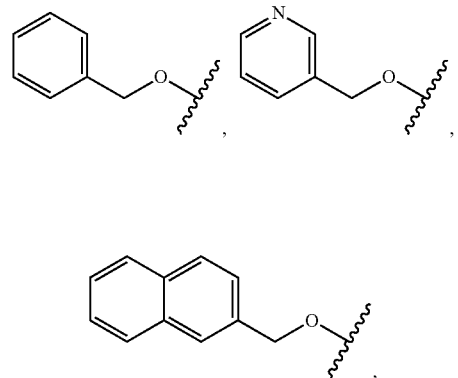

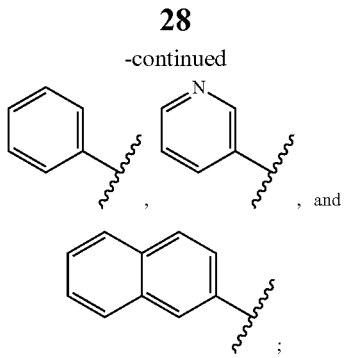

, and $R_2$ is hydrogen or substituted or unsubstituted $C_{1-6}$ alkyl;

$R_3$ is carbonyl-$R^b$ or sulfonyl-$R^b$, where $R^b$ is selected from:

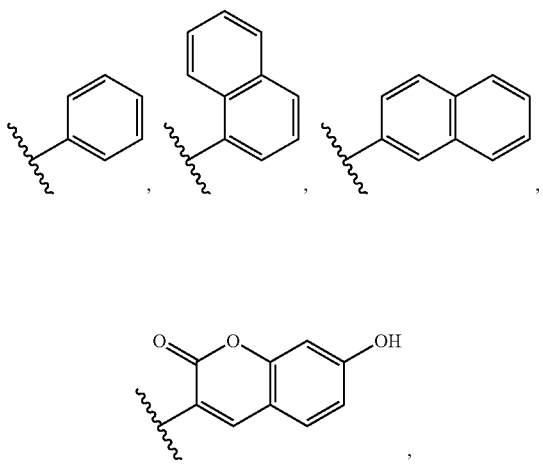

, and and n is 1, 2, 3, or 4.

In some embodiments of Formula I, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic are unsubstituted. In other embodiments of Formula I, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic may be substituted by hydroxyl, amino, carboxyl, sulfonate, carboxylic ester, amide, carbamate, or aminoalkyl.

In some embodiments of Formula I, R$_1$ is benzyloxy (i.e., carbonyl-R$^a$ where R$^a$ is

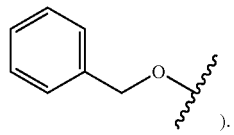 [SMILES: *OCc1ccccc1]
).

In some embodiments of Formula I, R$_2$ is hydrogen. In some embodiments, of Formula I, R$_2$ is substituted C$_{1-6}$ alkyl, e.g., substituted methyl. In some embodiments of Formula I, R$_2$ is unsubstituted C$_{1-6}$ alkyl, e.g., unsubstituted methyl.

In some embodiments of Formula I, R$_3$ is carbonyl-R$^b$. In some embodiments of Formula I, R$_3$ is sulfonyl-R$^b$.

In some embodiments of Formula I, R$^b$ is

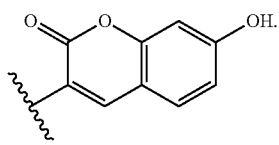 [SMILES: *c1cc2ccc(O)cc2oc1=O]

In some embodiments of Formula I, R$^b$ is

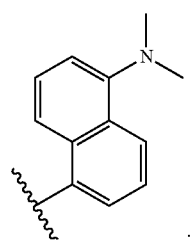 [SMILES: *c1cccc2c(N(C)C)cccc12]

In some embodiments of Formula I, n is 1. In some embodiments of Formula I, n is 2. In some embodiments of Formula I, n is 3. In some embodiments of Formula I, n is 4.

In some embodiments of Formula I, R$_1$ is benzyloxy; R$_2$ is hydrogen; and n is 4.

In some embodiments of Formula I, the compound is VA4, VA5, or a pharmaceutically acceptable salt thereof:

VA4
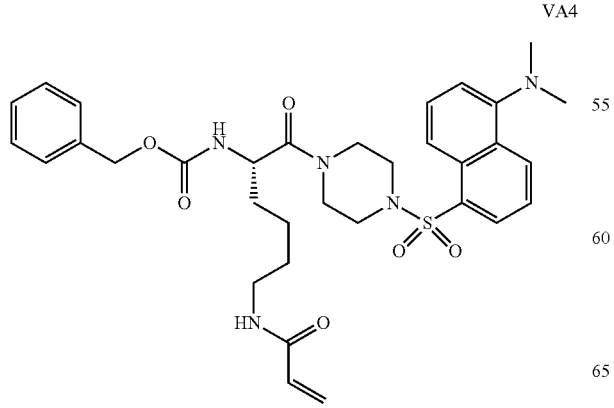

VA5
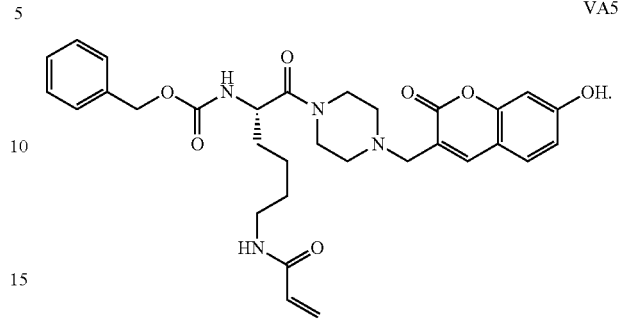

In some embodiments of Formula I, the compound is not VA5.

In some embodiments, compounds of Formula I inhibit one or more activity of TG2, e.g., GTPase activity, GTP binding activity, and/or transamidation activity. In some embodiments, compounds of Formula I hold the TG2 in an open conformation, e.g., in a conformation that does not bind GTP.

In some embodiments of the pharmaceutical compositions and therapeutic methods provided herein, there is provided a compound of Formula II, or a pharmaceutically acceptable salt thereof:

Formula II
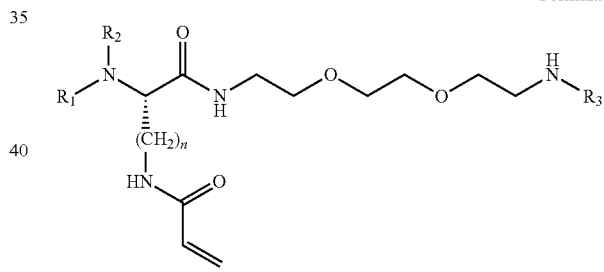

wherein:

R$_1$ is carbonyl-R$^a$, where R$^a$ is selected from:

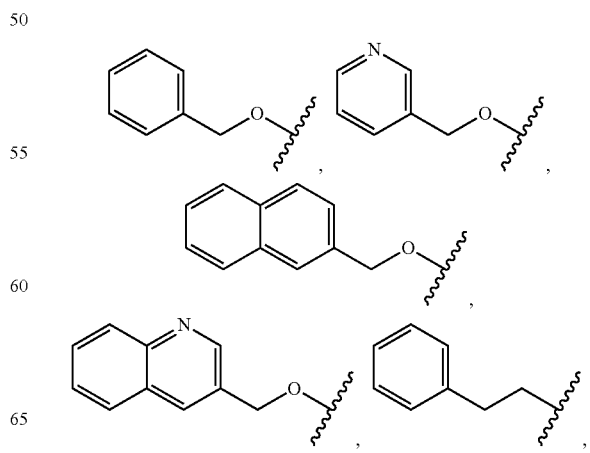

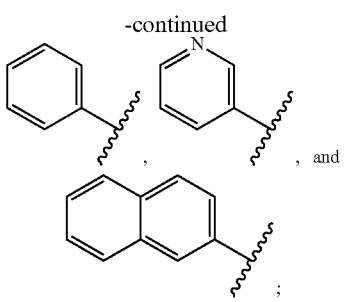

$R_2$ is hydrogen or substituted or unsubstituted $C_{1-6}$ alkyl;
$R_3$ is carbonyl-$R^b$ or sulfonyl-$R^b$, where $R^b$ is selected from:

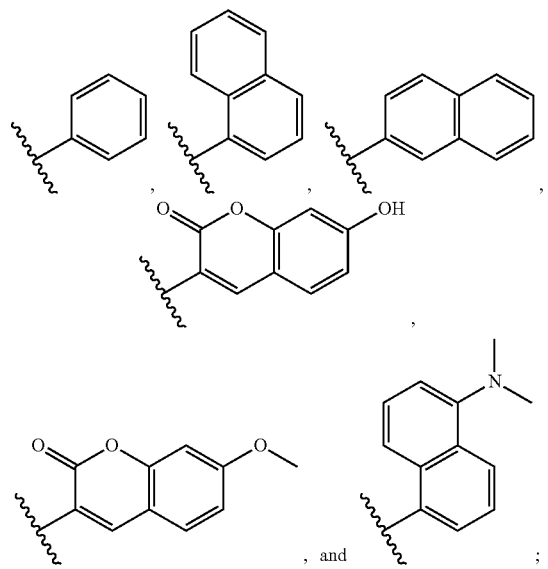

and
n is 1, 2, 3, or 4.

In some embodiments of Formula II, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic are unsubstituted. In other embodiments of Formula II, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic may be substituted by hydroxyl, amino, carboxyl, sulfonate, carboxylic ester, amide, carbamate, or aminoalkyl.

In some embodiments of Formula II, $R_1$ is benzyloxy (i.e., carbonyl-$R^a$ where $R^a$ is

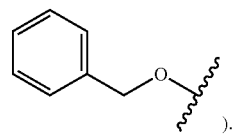 [SMILES: *OCc1ccccc1]

).

In some embodiments of Formula II, $R_2$ is hydrogen. In some embodiments, of Formula II, $R_2$ is substituted $C_{1-6}$ alkyl, e.g., substituted methyl. In some embodiments of Formula II, $R_2$ is unsubstituted $C_{1-6}$ alkyl, e.g., unsubstituted methyl.

In some embodiments of Formula II, $R_3$ is carbonyl-$R^b$. In some embodiments of Formula II, $R_3$ is sulfonyl-$R^b$.

In some embodiments of Formula II, $R^b$ is

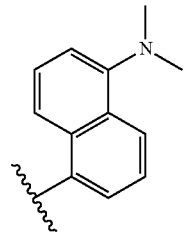

In some embodiments of Formula II, n is 1. In some embodiments of Formula II, n is 2. In some embodiments of Formula II, n is 3. In some embodiments of Formula II, n is 4.

In some embodiments of Formula II, $R_1$ is benzyloxy; $R_2$ is hydrogen; and n is 4.

In some embodiments of Formula II, the compound is NC9, or a pharmaceutically acceptable salt thereof:

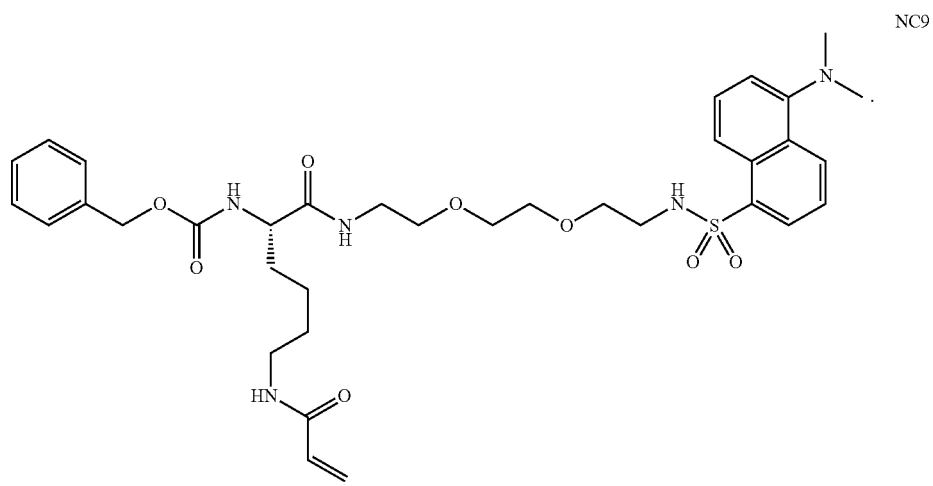 [SMILES: C=CC(=O)NCCCC[C@H](NC(=O)OCc1ccccc1)C(=O)NCCOCCOCCNS(=O)(=O)c1cccc2c(N(C)C)cccc12]

NC9

In some embodiments, compounds of Formula II inhibit one or more activity of TG2, e.g., GTPase activity, GTP binding activity, and/or transamidation activity. In some embodiments, compounds of Formula II hold the TG2 in an open conformation, e.g., in a conformation that does not bind to TG2.

In some embodiments, one or more of the compounds shown in Table 2 and pharmaceutically acceptable salts thereof are provided:

TABLE 2

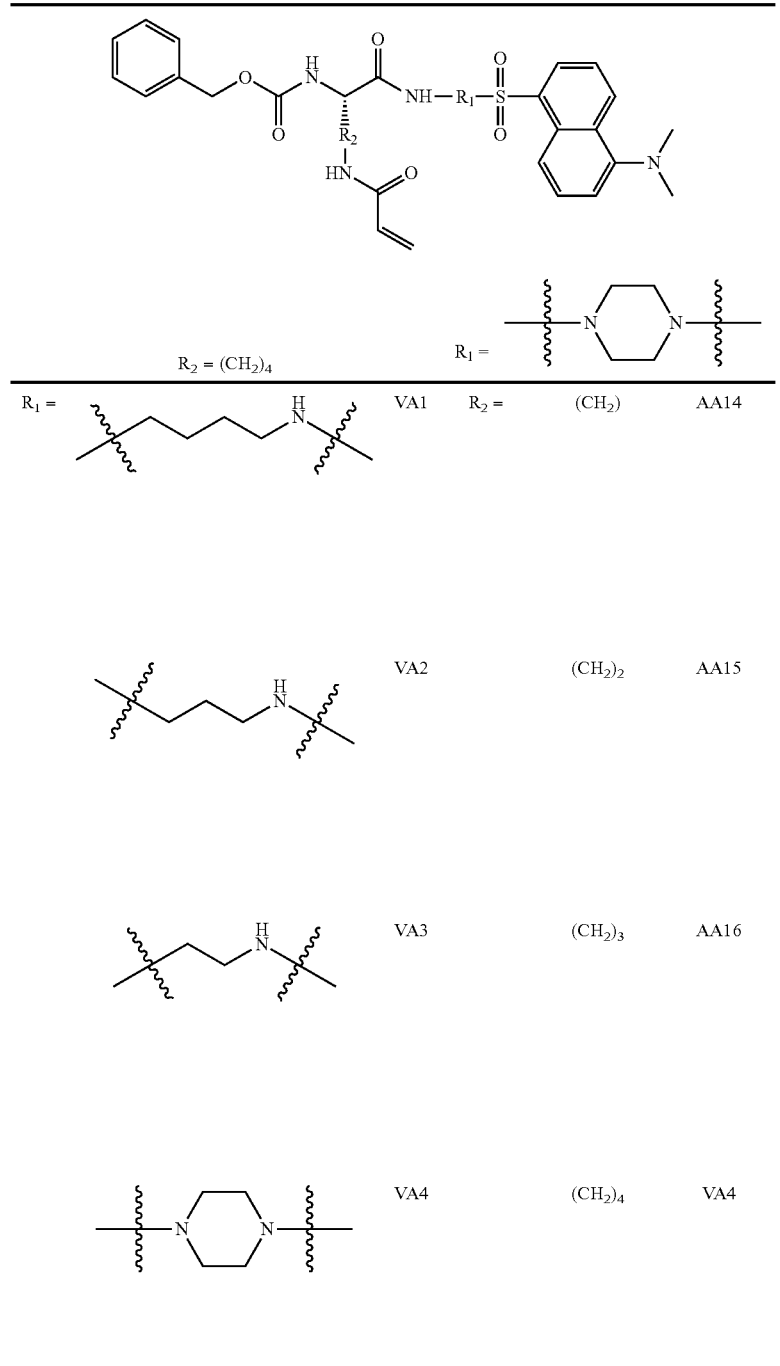

In some embodiments, one or more of the compounds shown in Table 3 and pharmaceutically acceptable salts thereof are provided:

TABLE 3

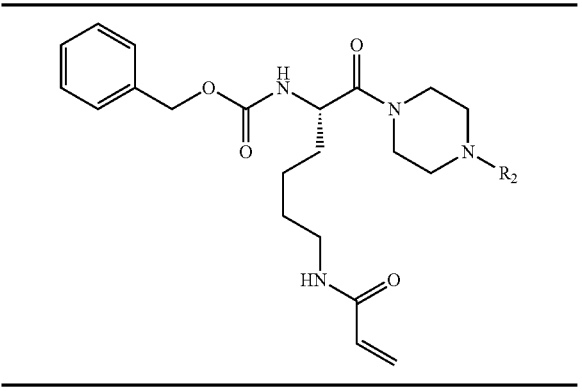

R₂ =

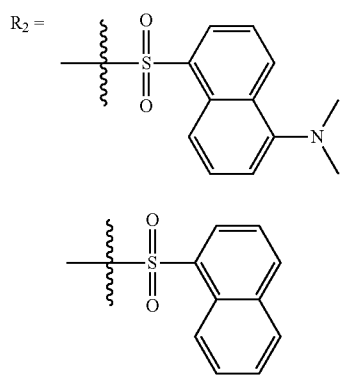  VA4

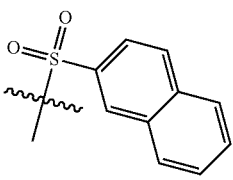 [SMILES: *S(=O)(=O)c1ccc2ccccc2c1]  NMI18

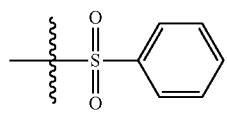  NMI17

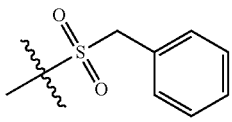 [SMILES: *S(=O)(=O)Cc1ccccc1]  NMI14

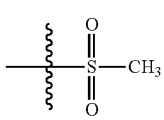  NMI16

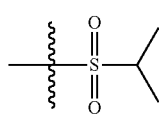  MAI23

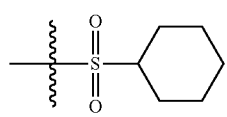 [SMILES: *S(=O)(=O)C1CCCCC1]  NMI26

TABLE 3-continued

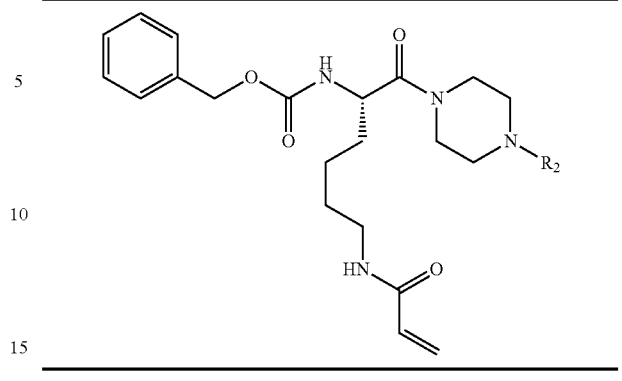

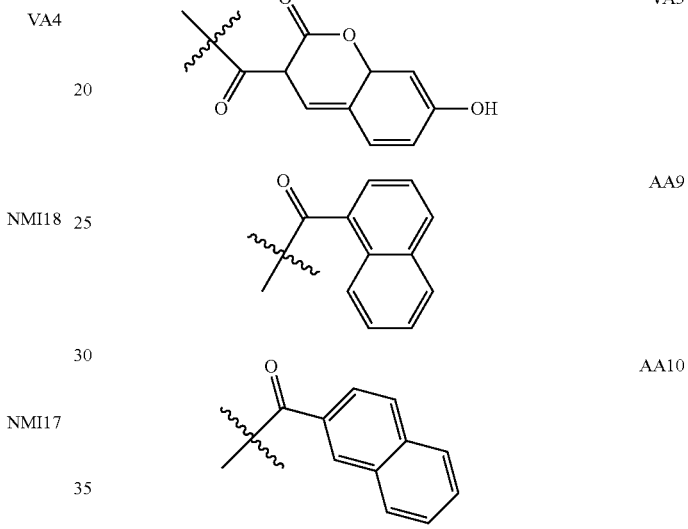

NMI27

In some embodiments, one or more of the compounds shown in Table 5 and pharmaceutically acceptable salts thereof are provided.

In some embodiments, one or more of the compounds shown in Table 6 and pharmaceutically acceptable salts thereof are provided.

In some embodiments, one or more of the compounds shown in Table 7 and pharmaceutically acceptable salts thereof are provided.

In some embodiments, one or more of the compounds shown in Table 8 and pharmaceutically acceptable salts thereof are provided.

In some embodiments, compounds of Tables 2, 3, 5, 6, 7, and 8 are irreversible inhibitors of TG2. Pharmaceutical compositions and therapeutic methods comprising the compounds in Tables 2, 3, 5, 6, 7, and 8, or pharmaceutically acceptable salts thereof, are also encompassed.

As would be understood by a person of ordinary skill in the art, the recitation of "a compound" is intended to include salts, solvates, oxides, and inclusion complexes of that compound as well as any stereoisomeric form, or a mixture of any such forms of that compound in any ratio. Thus, in accordance with some embodiments of the invention, a compound as described herein, including in the contexts of pharmaceutical compositions and methods of treatment is provided as the salt form.

Compounds described herein include, but are not limited to, their optical isomers, racemates, and other mixtures thereof. In those situations, the single enantiomers or diastereomer, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

The term "solvate" refers to a compound in the solid state, where molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

For compounds provided herein, it is intended that, in some embodiments, salts thereof are also encompassed, including pharmaceutically acceptable salts. Those skilled in the art will appreciate that many salt forms (e.g., TFA salt, tetrazolium salt, sodium salt, potassium salt, etc,) are possible; appropriate salts are selected based on considerations known in the art. The term "pharmaceutically acceptable salt" refers to salts prepared from pharmaceutically acceptable non-toxic acids or bases including inorganic acids and bases and organic acids and bases. For example, for compounds that contain a basic nitrogen, salts may be prepared from pharmaceutically acceptable non-toxic acids including inorganic and organic acids. Suitable pharmaceutically acceptable acid addition salts for the compounds of the present invention include without limitation acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include without limitation metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

Compositions

In another broad aspect, there are provided pharmaceutical compositions comprising a compound described herein, or a pharmaceutically acceptable salt thereof, and a pharmaceutically acceptable carrier.

In an embodiment, there is provided a pharmaceutical composition comprising a compound of Formula I or Formula II, or a pharmaceutically acceptable salt thereof, and a pharmaceutically acceptable carrier. In an embodiment, there is provided a pharmaceutical composition comprising NC9, VA4, VA5, AA9, AA10, or a pharmaceutically acceptable salt thereof, and a pharmaceutically acceptable carrier. In another embodiment, there is provided a pharmaceutical composition comprising a compound of Formula I or Formula II, or a pharmaceutically acceptable salt thereof, and a pharmaceutically acceptable carrier, with the proviso that the compound is not VA5.

The preparation of pharmaceutical compositions can be carried out as known in the art (see, for example, Remington: The Science and Practice of Pharmacy, $20^{th}$ Edition, 2000). For example, a therapeutic compound and/or composition, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine. Pharmaceutical preparations can also contain additives, of which many are known in the art, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The term "pharmaceutical composition" means a composition comprising a compound as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of a subject, e.g., humans and animals, without undue toxicity, irritation, allergic response, and the like, and are commensurate with a reasonable benefit/risk ratio.

A pharmaceutically acceptable carrier may include any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier may be suitable for intravenous, intraperitoneal, intramuscular, sublingual or oral administration. In other embodiments, the carrier is suitable for topical administration or for administration via inhalation. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions provided herein is contemplated. Supplementary active compounds can also be incorporated into the compositions. For example, a pharmaceutical composition provided herein may further comprise at least one additional cancer therapeutic, as discussed below.

A pharmaceutical composition provided herein can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, creams, tinctures, sprays or transdermal therapeutic systems, or the inhalative administration in the form of nasal sprays or aerosol mixtures, or, for example, microcapsules, implants or wafers.

Pharmaceutical compositions typically must be sterile and stable under the conditions of manufacture and storage. A composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin. Moreover, a compound can be administered in a time release formulation, for example in a composition which includes a slow release polymer. The compound can be prepared with carriers that will protect against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG).

Many methods for the preparation of such formulations are generally known to those skilled in the art. Sterile injectable solutions can be prepared by incorporating an active compound, such as a TG2 inhibitor compound provided herein, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, common methods of preparation are vacuum drying and freeze-drying which yields a powder of the active ingredient plus any additional desired ingredient from a previously sterile-filtered solution thereof. Compounds may also be formulated with one or more additional compounds that enhance their solubility.

It is often advantageous to formulate compositions (such as parenteral compositions) in dosage unit form for ease of administration and uniformity of dosage. The term "unit dosage form" refers to a physically discrete unit suitable as unitary dosages for human subjects and other animals, each unit containing a predetermined quantity of active material calculated to produce the desired therapeutic effect, in association with a suitable pharmaceutical carrier. The specification for the dosage unit forms of the invention may vary and are dictated by and directly dependent on (a) the unique characteristics of the therapeutic compound and the particular therapeutic effect to be achieved, and (b) the limitations inherent in the art of compounding such a therapeutic compound for the prevention or treatment of cancer. Dosages are discussed further below.

In some embodiments, there are provided pharmaceutical compositions that comprise an effective amount of a compound and/or composition described herein, and a pharmaceutically acceptable carrier. In an embodiment, there are provided pharmaceutical compositions for the treatment or prevention of a cancer, comprising a compound described herein, or a pharmaceutically acceptable salt thereof, and a pharmaceutically acceptable carrier. In another embodiment, there is provided a pharmaceutical composition for the delay of progression of a cancer, for the inhibition of cancer invasion, e.g., malignant glial cell (MGC) invasion, for inhibition of cancer stem cell growth, survival, spheroid formation and/or proliferation, for inhibition of metastasis, for inhibition of cancer recurrence, and/or for overcoming chemoresistance of a cancer, the composition comprising a compound described herein, or a pharmaceutically acceptable salt thereof, and a pharmaceutically acceptable carrier.

Methods of Use of Compounds and Compositions

In another aspect, there are provided methods for prevention or treatment of a cancer in a subject by administering an effective amount of a compound or composition described herein.

In some embodiments, there are provided methods for inhibition of TG2 in a subject by administering an effective amount of a compound or composition described herein.

The term "subject" includes living organisms with cancer, or who are susceptible to or at risk of cancer, e.g., due to a genetic predisposition, environmental exposure to carcinogens, and the like. Examples of subjects include humans, monkeys, cows, rabbits, sheep, goats, pigs, dogs, cats, rats, mice, and transgenic species thereof. The term "subject" generally includes animals susceptible to states characterized by cancer and/or tumor growth, e.g., mammals, e.g. primates, e.g. humans. The animal can also be an animal model for a disorder, e.g., a cancer mouse model, a xenograft recipient, and the like.

In some embodiments, a subject is in need of treatment by the methods provided herein, and is selected for treatment based on this need. A subject in need of treatment is art-recognized, and includes subjects that have been identified as having a disease or condition (e.g., cancer, e.g., having a tumor or a cancerous growth), or having a symptom of such a disease or condition, or being at risk of such a disease or condition, and would be expected, based on diagnosis, e.g., medical diagnosis, to benefit from treatment (e.g., curing, healing, preventing, alleviating, relieving, altering, remedying, ameliorating, improving, or affecting the disease or disorder, the symptom of the disease or disorder, or the risk of the disease or disorder).

As used herein, "treating" or "treatment" of a disease or condition refers, in some embodiments, to ameliorating at least one disease or condition (i.e., arresting or reducing the development of a disease or condition or at least one of the clinical symptoms thereof). In certain embodiments "treating" or "treatment" refers to ameliorating at least one physical parameter, such as tumor size, growth, or migration. In certain embodiments, "treating" or "treatment" refers to inhibiting or improving a disease or condition, either physically (e.g., stabilization of a discernible symptom), physiologically (e.g., stabilization of a physical parameter), or both. In certain embodiments, "treating" or "treatment" refers to delaying the onset (or recurrence) of a disease or condition. The term "treating" or "treatment" may refer to any indicia of success in the treatment or amelioration of a disease or condition, including any objective or subjective parameter such as abatement; remission; diminishing of symptoms or making the disease or condition more tolerable to the subject; improving a subject's physical or mental well-being, such as reducing pain experienced by the patient; and, in some situations additionally improving at least one parameter of a disease or condition, such as without limitation reducing tumor growth rate, reducing tumor volume, reducing or slowing tumor migration, invasion, and/or metastasis, overcoming chemoresistance, increasing sensitivity to chemotherapies, slowing migration, reducing cancer stem cell proliferation, and the like.

As used herein, "preventing" or "prevention" is intended to refer at least to the reduction of the likelihood of, or the risk of, or susceptibility to acquiring a disease or disorder (i.e., causing at least one of the clinical symptoms of the disease not to develop in a patient that may be exposed to or predisposed to or at risk of the disease but does not yet experience or display symptoms of the disease). The term "prevention" or "preventing" is also used to describe the administration of a compound or composition described herein to a subject who is at risk of (or susceptible to) such a disease or condition. Subjects amenable to treatment for prevention of a disease or condition include individuals at risk of the disease or condition but not showing symptoms, as well as patients presently showing symptoms. In some embodiments, "prevention" or "preventing" is used to described the administration of a compound or composition described herein to a subject who has been diagnosed with or treated for a disease or condition and is at risk of recurrence of the disease or condition.

In some embodiments, treatment or prevention are within the context of the present invention if there is a measurable difference between the performances of subjects treated using the compounds and methods provided herein as compared to members of a placebo group, historical control, or between subsequent tests given to the same subject.

The term "inhibition" or "inhibiting" is used herein to refer generally to reducing, slowing, restricting, delaying, suppressing, blocking, hindering, or preventing a process, such as without limitation reducing or slowing growth, spread or survival of a cancer, e.g., a tumor.

The term "effective amount" as used herein means that amount or dose of a compound or composition, upon single or multiple dose administration to a subject, which provides the desired effect (e.g., the desired biological or medicinal response, e.g., to ameliorate, lessen or prevent a disease, disorder or condition) in the subject being treated. In some embodiments, an effective amount is an amount or dose of a compound or composition that prevents or treats cancer in a subject, as described herein. In some embodiments, an effective amount is an amount or dose of a compound or composition that inhibits one or more activity of TG2 in a subject, as described herein.

It should be understood that the dosage or amount of a compound and/or composition used, alone or in combination with one or more active compounds to be administered, depends on the individual case and is, as is customary, to be adapted to the individual circumstances to achieve an optimum effect. Dosing and administration regimens are within the purview of the skilled artisan, and appropriate doses depend upon a number of factors within the knowledge of the ordinarily skilled physician, veterinarian, or researcher (e.g., see Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)). For example, dosing and administration regimens depend on the nature and the severity of the disorder to be treated, and also on the sex, age, weight and individual responsiveness of the human or animal to be treated, on the efficacy and duration of action of the compounds used, on whether the therapy is acute or chronic or prophylactic, and/or on whether other active compounds are administered in addition to the therapeutic molecule(s).

Thus the dose(s) of a compound or composition will vary depending upon a variety of factors including, but not limited to: the activity, biological and pharmacokinetic properties and/or side effects of the compound being used; the age, body weight, general health, gender, and diet of the subject; the time of administration, the route of administration, the rate of excretion, and any drug combination, if applicable; the effect which the practitioner desires the compound to have upon the subject; and the properties of the compound being administered (e.g. bioavailability, stability, potency, toxicity, etc). Such appropriate doses may be determined as known in the art. When one or more of the compounds of the invention is to be administered to humans, a physician may for example, prescribe a relatively low dose at first, subsequently increasing the dose until an appropriate response is obtained.

There are no particular limitations on the dose of each of the compounds for use in compositions provided herein. Exemplary doses include milligram or microgram amounts of the compound per kilogram of subject or sample weight (e.g., about 50 micrograms per kilogram to about 500 milligrams per kilogram, about 1 milligram per kilogram to about 100 milligrams per kilogram, about 1 milligram per kilogram to about 50 milligram per kilogram, about 1 milligram per kilogram to about 10 milligrams per kilogram, or about 3 milligrams per kilogram to about 5 milligrams per kilogram). Additional exemplary doses include doses of about 5 to about 500 mg, about 25 to about 300 mg, about 25 to about 200 mg, about 50 to about 150 mg, or about 50, about 100, about 150 mg, about 200 mg or about 250 mg, and, for example, daily or twice daily, or lower or higher amounts.

In some embodiments, the dose range for adult humans is generally from 0.005 mg to 10 g/day orally. Tablets or other forms of presentation provided in discrete units may conveniently contain an amount of a compound (e.g., of Formula I or Formula II) which is effective at such dosage or as a multiple of the same, for instance, units containing 5 mg to 500 mg, usually around 10 mg to 200 mg. A dosage unit (e.g., an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, or 500 mg) of a compound described herein.

Administration of compounds and compositions provided herein can be carried out using known procedures, at dosages and for periods of time effective to achieved a desired purpose. Dosage regimens can be adjusted to provide the optimum therapeutic response. For example, several divided doses may be administered daily or the dose may be proportionally reduced as indicated by the exigencies of the therapeutic situation. In some embodiments, a compound or composition is administered at an effective dosage sufficient to prevent or treat cancer in a subject. Further, a compound or composition may be administered using any suitable route or means, such as without limitation via oral, parenteral, intravenous, intraperitoneal, intramuscular, sublingual, topical, or nasal administration, via inhalation, or via such other routes as are known in the art.

Without intending to be limited by theory, the present inventors contemplate that the therapeutic benefits of inhibiting one or more activity of TG2 including without limitation GTP binding, GTPase activity, and/or transamidation activity, may be mediated by: sensitizing refractory cancer cells to chemotoxic agents; overcoming cancer cell resistance to chemotherapy; preventing or inhibiting cancer stem cell (CSC) survival and/or proliferation; preventing or inhibiting CSC spheroid formation; preventing or inhibiting cancer recurrence, e.g., recurrence after a therapy such as surgical excision; and/or preventing or inhibiting metastasis, e.g., the EMT transition. In some embodiments, cancer (e.g., tumor) progression, growth, migration, and/or invasion is prevented or inhibited. In some embodiments, invasion of cancer cells, e.g., malignant glial cells or GBM cells, is prevented or inhibited. In an embodiment, recurrence of a cancer after treatment, e.g., after surgical excision, is inhibited. For example, malignant glioma invasion is a primary cause of brain cancer treatment failure. In some embodiments malignant glial cell (MGC) invasion is inhibited, thereby reducing or delaying the cancer invasion into adjacent healthy tissues, such as the brain in the case of glioma. In an embodiment, progression of a cancer is inhibited.

A cancer may be a blood-cell derived cancer such as, without limitation, a lymphoma, a leukemia, or a myeloma, or a solid organ tumor such as, without limitation, a tumor of the colon, breast, lung, prostate, brain, pancreas, ovary, or skin. In an embodiment, the cancer is an epidermal squamous cell carcinoma (SCC). In another embodiment, the cancer is a glioma, such as a malignant glioma or a glioblastoma, e.g., glioblastoma multiforme (GBM).

There are provided therefore methods for treating cancer, such as glioma, e.g., glioblastoma or GBM, or SCC, in a subject in need thereof, comprising administering a compound or a composition as described herein to the subject. In some embodiments, there is provided a method for delaying the progression of cancer, such as glioma, e.g., glioblastoma or GBM, or SCC, in a subject in need thereof, comprising administering a compound or a composition as described herein to a subject. In some embodiments, there are further provided methods for inhibiting or reducing the migration or invasiveness of tumor cells, e.g., cells of glioma such as glioblastoma, comprising administering a compound or composition provided herein to a subject in need thereof. In other embodiments, there are provided methods for sensitizing refractory cancer cells to chemotoxic agents; preventing or inhibiting cancer stem cell (CSC) growth, survival and/or proliferation; preventing or inhibiting CSC spheroid formation; and/or preventing or inhibiting metastasis, e.g., the EMT transition. In some embodiments, there are provided methods for preventing or inhibiting a cancer (e.g., tumor) progression, growth, migration, and/or invasion.

In some embodiments, there are provided methods for preventing or inhibiting recurrence of a cancer after treatment, e.g., after drug treatment or surgical excision. In some embodiments, there are provided methods for delaying the progression of a cancer, wherein cancer re-growth is delayed by more than 30%, or by more than 50%, or by more than 70%, and/or wherein the survival periods of affected subjects is increased. In one embodiment, there is provided a method for inhibiting brain cancer invasion, for example MGC invasion. In another embodiment, there is provided a method for inhibiting progression of SCC.

There is further provided a method for enhancing the efficacy of cancer therapies for the treatment of cancer, selected from the group comprising resection, chemotherapy, radiation therapy, immunotherapy, and/or gene therapy, comprising administering a TG2 inhibitor compound or composition as described herein, and simultaneously, separately or sequentially administrating said cancer therapy. The term "enhancing the efficacy of a cancer therapy", as used herein, refers to an improvement of conventional cancer treatments and includes reduction of the amount of the anti-cancer composition which is applied during the conventional cancer treatment, e.g. amount of radiation in radiotherapy, of chemotherapeutics in chemotherapy, of immunotherapeutics in immunotherapy or of vectors in gene based therapies, and/or to an increase in efficacy of the conventional therapy and the anti-cancer composition when applied at conventional doses or amounts during the conventional cancer therapy. In one embodiment, enhancing the efficacy of a cancer therapy refers to prolonging the survival rate of subjects receiving the therapy.

It should be understood that compounds and/or compositions provided herein may be used alone or in combination with other cancer therapies. Non-limiting examples of other cancer therapies include resection of the cancer, chemotherapy, radiation therapy, immunotherapy, and/or gene-based therapy. The term "resection" refers to the surgical removal or excision of part or all of a tumor. The term "radiation therapy" refers to the treatment of cancer using radiation. The term "chemotherapy" refers to the treatment of cancer with chemical substances, so-called chemotherapeutics. The term "immunotherapy" as used herein refers to the stimulation of the reactivity of the immune system towards eliminating the cancer cells by using immunotherapeutics. The term "gene-based therapy" refers to the treatment of cancer based upon the transfer of genetic material (DNA, or possibly RNA) into an individual. Non-limiting examples of such other cancer therapies include: chemotherapeutics including but not limited to temozolomide, doxorubicin, vincristine, vinorelbine, procarbazine, carmustine, lomustine, taxol, taxotere, tamoxifen, retinoic acid, 5-fluorouracil, cyclophosphamide and thalidomide; immunotherapeutics such as but not limited to activated T cells and pulsed dendritic cells; gene transfer of CD3, CD7 and CD45 in glioma cells, concomitantly with the delivery of a compound or composition as defined herein.

Thus, compounds and/or compositions described herein may be administered alone or in combination with one or more additional cancer therapy. The latter can be administered before, after or simultaneously with the administration of the compounds and/or compositions described herein.

Kits

Compound and compositions provided herein may be packaged as part of a kit, optionally including a container (e.g. packaging, a box, a vial, etc). The kit may be commercially used according to the methods described herein and may include instructions for use in such methods. Additional kit components may include acids, bases, buffering agents, inorganic salts, solvents, antioxidants, preservatives, or metal chelators. The additional kit components may be present as pure compositions, or as aqueous or organic solutions that incorporate one or more additional kit components. Any or all of the kit components optionally further comprise buffers.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1. Characterization of TG2 Expression in GBM Cell Models

Glioblastoma multiforme (GBM) are a heterogeneous group of primary brain tumors that are very aggressive, resistant to therapeutic interventions such as radiation and chemotherapy, and invariably reoccur following surgical resection. TG2 has been shown to promote cell survival in a number of different tumors, and there is evidence that TG2 may also be a pro-survival factor in GBMs, however, the role(s) that TG2 plays in facilitating GBM survival and proliferation have not been clearly delineated. Further, the functions of TG2 are often cell and context specific.

We report herein studies to examine the ability of TG2 to facilitate GBM proliferation in several different GBM cell lines, as well as neurospheres derived from patient tumors and maintained in the absence of serum. The neurospheres represented the three major subtypes of GBM tumors: mesenchymal, proneural and classical. By using genetic and pharmacological manipulations of TG2, we showed that TG2 plays differential roles in the proliferative process depending on the cell type. In most GBM models TG2 played a crucial role in the proliferative process. We also found that some TG2 inhibitors were highly effective in reducing proliferation in a large subset of the GBM models. Overall, our results clearly show that TG2 plays an important, but context specific, role in GBM cell biology.

Figure 1:
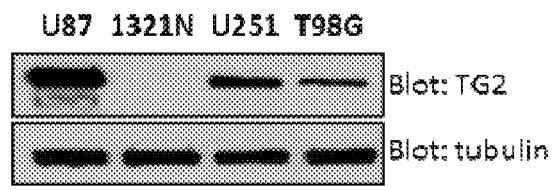
FIG. 1 shows effects of the TG2 inhibitor NC9 on colony formation capacity of GBM cells. In (A), it is shown that TG2 expression levels vary among glioblastoma cell lines. Lysates (20 μg) from the cell lines U87, 1321N, U251 and T98G were blotted for TG2 and tubulin. In (B), it is shown that transamidating activity correlates with TG2 protein levels. Cells were pretreated with NC9 for 1 h and TG2 was activated by 1 μM ionomycin treatment for 3 h in the presence of 10 μM NC9. DMSO was used as control. Transglutaminase activity was detected by an in situ transamidating assay. Results are shown as a percent of U87 transglutaminase activity (±SEM) (N=3). In (C) it is shown that TG2 mRNA levels correlate with TG2 protein levels and NC9 does not significantly affect TG2 mRNA expression. Cells were treated with 10 μM NC9 for 24 or 48 h and TG2 mRNA expression was measured by qRT-PCR following this treatment. DMSO was used as control. Results were normalized to actin mRNA and are shown as a percent of U87 24 h DMSO control (±SEM) (N=3). In (D) it is shown that NC9 significantly reduces the average colony size of the TG2-expressing glioblastoma cells. Cells were seeded in 0.35% agarose and treated with 10 μM NC9 for 2 weeks. DMSO was used as control. At the end of the treatment, the colonies were fixed and stained; and 20 random microscopic images were captured for each group. The average volume of each colony image was determined using Image J by a person blinded for cell lines and treatments and volumes were calculated from the area data and used for comparison. For each experiment, NC9 group was normalized to DMSO control. Results are shown as a percent of DMSO control (±SEM) (N=3). Statistical significance compared to control was tested using Dunnett's test; $*p<0.05$, $p<0.01$, $*p<0.005$.
Figure 1:
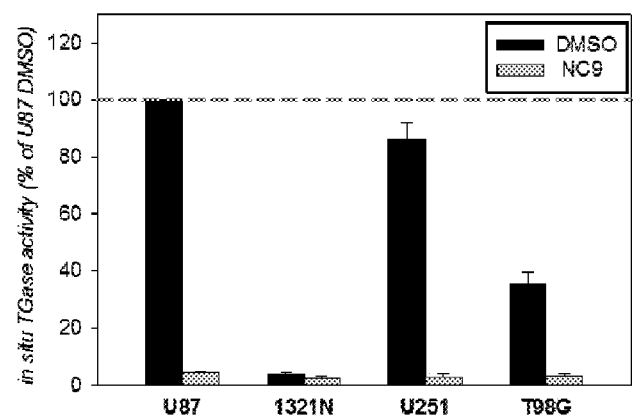
Figure 1:
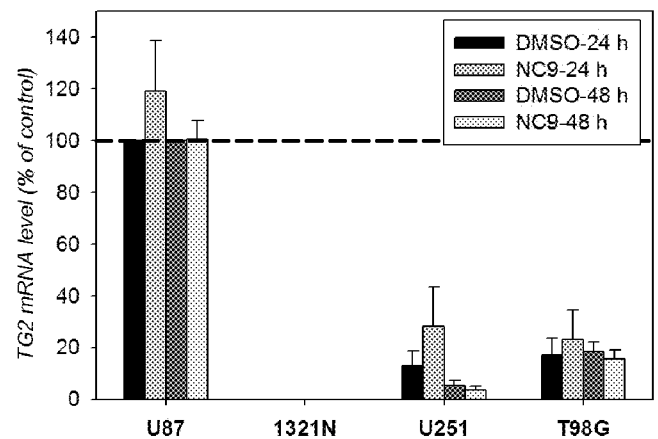
Figure 1:
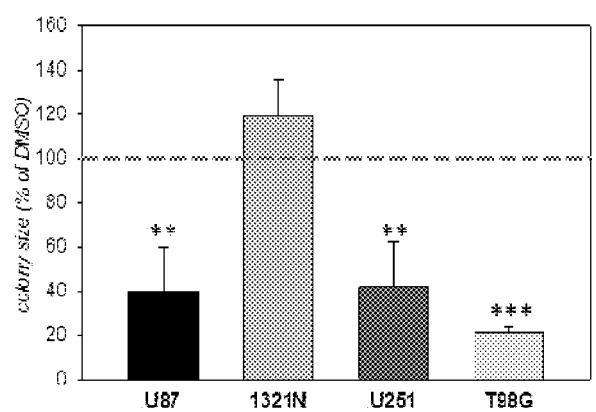
Figure 7:
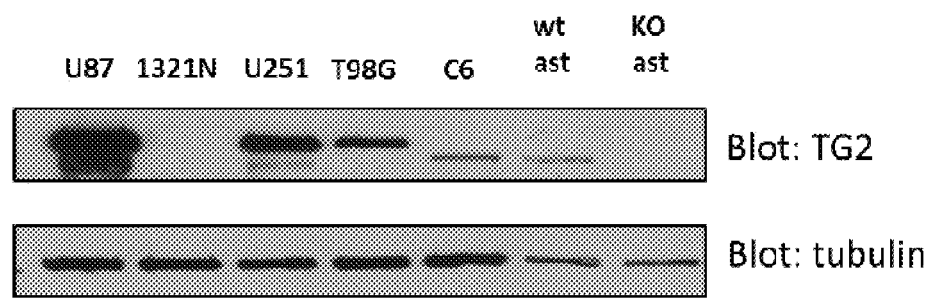
FIG. 7 shows TG2 expression in transformed and untransformed astrocytes. It is shown that GBM cells tend to express higher levels of TG2 compared to non-transformed astrocytes. Lysates (20 µg) from four human cell lines (U87, 1321N, U251 and T98G), a rat glioma cell line (C6), wild-type mouse astrocytes (wt ast) as well as TG2 knockout mouse astrocytes (KO ast) were blotted for TG2 and tubulin. Rat and mouse TG2 exhibit a faster electrophoretic mobility than human TG2. Note that the first 4 lanes of this blot are presented in FIG. 1.

To better understand the role of TG2 in GBM proliferation and survival, we used various model systems and experimental approaches. To initiate our studies we used 4 astrocytoma cell lines, 1321N, U87, U251 and T98G. These cell lines, except for the 1321N cells, have been used previously as GBM cell models. We characterized these cell lines in terms of their TG2 expression and found that there was considerable variation in the expression levels of TG2 in these cell lines (FIG. 1A). We could not detect TG2 expression in 1321N cells, whereas U87 cells expressed extremely high levels of TG2 (FIG. 1A). U251 and T98G cells expressed relatively moderate levels of TG2 (FIG. 1A); however, these expression levels are higher compared to untransformed astrocytes (FIG. 7). In situ transamidating activities (FIG. 1B) and mRNA levels of TG2 (FIG. 1C) in these cell lines correlated well with TG2 protein levels.

Figure 8:
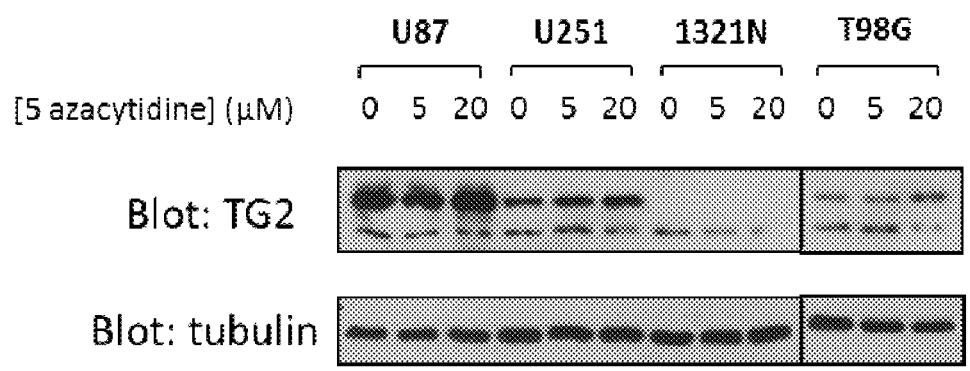
FIG. 8 shows methylation of TG2 gene is not the reason for the lack of TG2 expression in 1321N cells. It is shown that inhibition of DNA methylation increases the expression of TG2 in U87, U251 and T98G cells but not in 1321N cells. Cells were treated with 0, 5 or 20 µM of 5-azacytidine, which is a DNA methylation inhibitor, for 72 hours. Cell medium was changed every 24 h and fresh 5-azacytidine was added to the medium. At the end of the treatments, cells were lysed and 20 µg of lysates from the cells were blotted for TG2 and tubulin.

The complete lack of TG2 in 1321N cells was quite unexpected given that TG2 is detectable, albeit sometimes at very low levels, in almost all cell types (Gundemir, S. et al., Biochimica et Biophysica Acta. 1823(2):406-419, 2012). Although it is possible that the expression of TG2 can be regulated epigenetically, through methylation (Dyer, L. M. et al., Journal of Neuro-oncology 101(3):429-440, 2011), complete epigenetic silencing has not been reported to the best of our knowledge. Nonetheless, we wanted to determine if methylation of the TG2 gene could be responsible for the lack of TG2 in 1321N cells. To this end, we used a methylation inhibitor, 5'-azacytidine, to minimize DNA methylation. Intriguingly, 5'-azacytidine treatment increased TG2 expression in U251 and T98G cells, but not in 1321N cells (FIG. 8). This suggests that TG2 was not silenced through DNA methylation in 1321N cells, and the reason why there is no expression remains unknown. However, this TG2-negative cell line proved to be useful as it provided important insights about the TG2-dependence of our treatment paradigms.

Example 2. Characterization of TG2 Inhibition in GBM Cell Models

Figure 10:
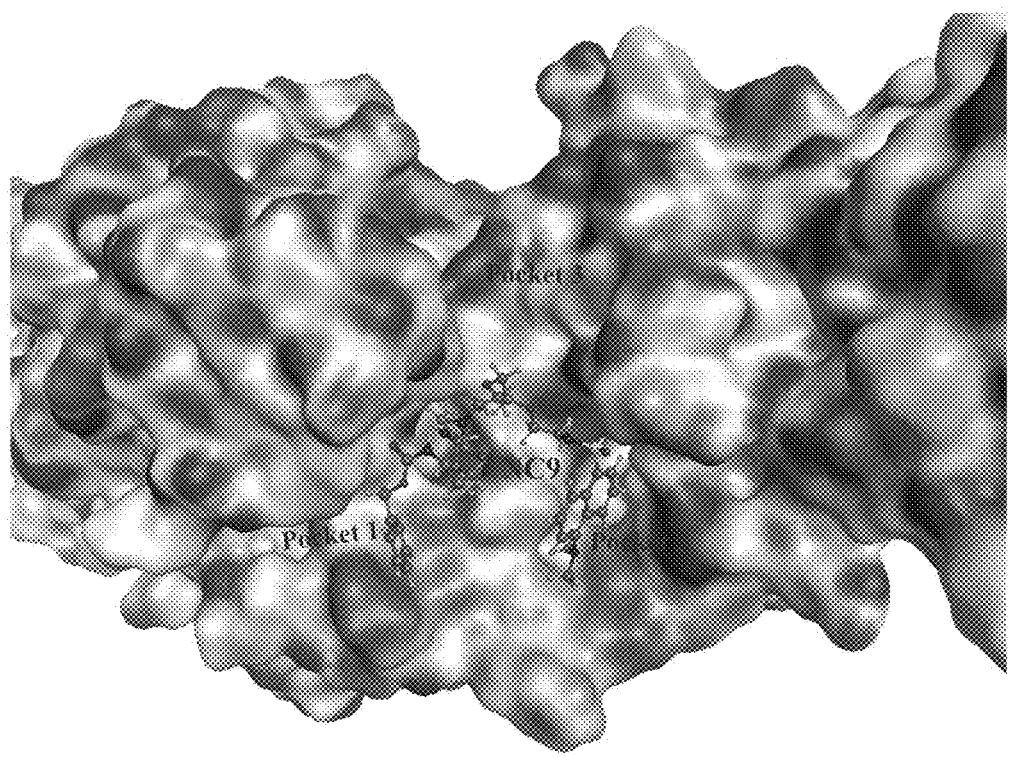
FIG. 10 shows a schematic drawing of inhibitor NC9 docked into the active site of "open" TG2. Competitive irreversible inhibitor NC9 is shown docked into the TG2 active site, placing warhead adjacent to active site nucleophile. Relevant binding pockets 1 & 2 on the surface of the open conformation of TG2 are indicated. Presumably, once these pockets are filled, TG2 cannot adopt its closed conformation that binds GTP.

First, we tested the inhibitory effect of NC9 on the transamidating activity of TG2 in the cell lines. NC9 is an effective irreversible TG inhibitor that locks TG2 in its open conformation (Caron, N. S. et al., PLoS ONE 7: e44159, 2012; Clouthier, C. M. et al., Angew. Chem. Int. Ed. Engl. 51: 12464-12468, 2012). To examine the inhibitory effect of NC9 on the transamidating activity of TG2, the calcium ionophore ionomycin was used. As shown in FIG. 1B, 10 µM of NC9 completely inhibited the in situ transamidation activity of TG2 induced by ionomycin-induced calcium influx. We also tested if NC9 had an effect on mRNA levels of TG2; however, no significant effects of NC9 treatment for 24 or 48 h were observed (FIG. 1C).

Figure 9:
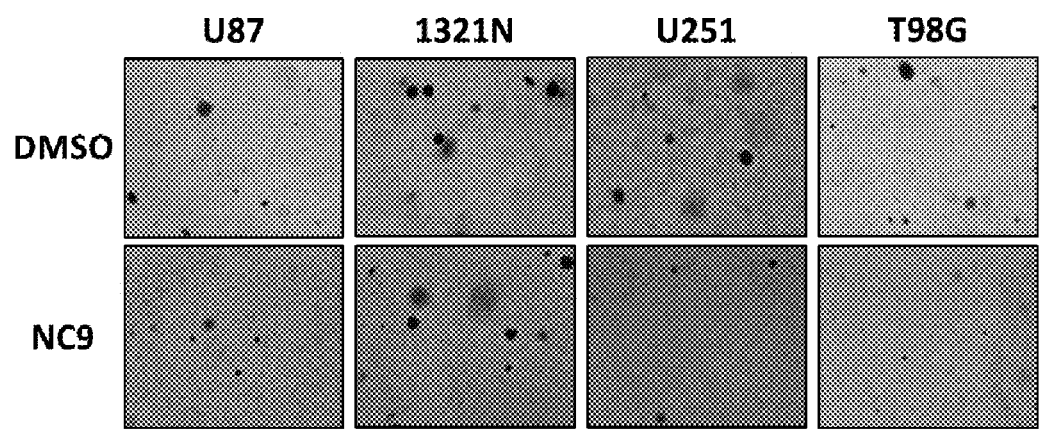
FIG. 9 shows NC9 significantly reduces the average colony size of the TG2-expressing glioblastoma cells. Representative images for Results shown in FIG. 1D are shown. Cells were seeded in 0.35% agarose and treated with 10 µM NC9 for 2 weeks. DMSO was used as control. At the end of the treatment, the colonies were fixed and stained. Random microscopic images were captured under 10× magnification.

To determine the effect of TG2 inhibition on the growth of GBM cells, we carried out a well-established agarose colony-formation assay. NC9 treatment (10 µM) significantly reduced the growth of U87, U251 and T98G colonies, but not 1321N colonies (FIG. 1D and FIG. 9). The fact that NC9 had no effect on the growth of TG2-null 1321N colonies strongly suggests that the reduction in colony growth was not due to a general NC9 toxicity, but due to its effect on TG2. Although TG2 expression was necessary for NC9 to inhibit colony growth, the expression level was not a direct determinant, as the growth of all TG2-expressing cell lines was inhibited regardless of the expression level (FIG. 1D and FIG. 7). Indeed, NC9 seemed to most effectively reduce colony growth in T98G cells, which express more modest amounts of TG2 (FIG. 1D).

Given that TG2 is a complex, multifunctional protein with several activities and different conformations (Gundemir, S.

et al., Biochimica et Biophysica Acta. 1823(2): 406-419, 2012), it is important to carry out knockdown experiments, in addition to using TG2 inhibitors, to more fully understand the role of TG2 in GBM biology. Previously we have efficiently knocked down TG2 using a lentiviral shRNA construct in other cell types (Gundemir, S. et al., Biochimica et Biophysica Acta. 1833(1): 1-10, 2013). Using this approach, we were also able to efficiently knockdown TG2 expression in the GBM cell lines shown in FIG. 2A. TG2 knockdown was maximal by approximately 1 week after lentiviral transduction and TG2 levels remained very low even after several passages and for up to a month (data not shown). Furthermore, we were able to visualize transduced cells and colonies by fluorescence microscopy as the lentiviral vector carrying the shRNA or scrambledRNA (scrRNA) constructs also expressed GFP (FIG. 2C).

The colony-formation assay was carried out using shRNA- or scrRNA-transduced cells. As expected, there was no difference between any treatment groups in 1321N cells, since these cells do not express TG2 (FIGS. 2A and 2B). Furthermore, the response to NC9 in scrRNA-transduced cells was very similar to that in untransduced cells: NC9 reduced colony growth in scrRNA transduced U87, U251 and T98G cells (FIG. 2B). Interestingly, knockdown of TG2 in U87 cells markedly reduced colony growth, modestly reduced colony growth in T98G cells and did not change colony growth in U251 cells (FIG. 2B). These data suggest that it is the NC9-TG2 complex in the U251 and T98G cells that inhibit proliferation, i.e., the mechanism may involve a toxic gain of function. Indeed, the growth-retarding effect of NC9 was completely lost in shRNA-transduced U87, U251 and T98G cells (FIG. 2B). This observation, in addition to the lack of effect on TG2-null 1321N cells, strongly suggests that TG2 is the target of NC9's anti-proliferative effect in GBM cells.

Figure 3:
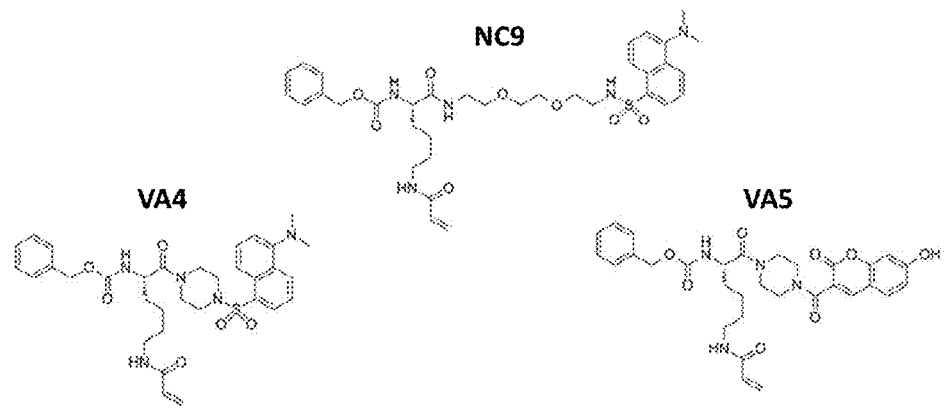
FIG. 3 shows the TG2 inhibitors NC9, VA4 and VA5 have similar effects on the transamidating and GTPase activities of TG2. In (A) there is shown the molecular structures of NC9, VA4 and VA5. In (B) it is shown that NC9, VA4 and VA5 inhibit ionomycin-activated transamidating activity of TG2 in U87 cells. U87 cells were pretreated with the inhibitors for 1 h and TG2 was activated by 1 μM ionomycin treatment for 3 h in the presence of the inhibitors (10 μM). DMSO was used as control. Transglutaminase activity was detected by an in situ transamidating assay. Results are shown as a percent of DMSO control (±SEM) (N=3). Statistical significance compared to control was tested using Dunnett's test; $*p<0.005$. In (C) it is shown that NC9, VA4 and VA5 inhibit resting transamidating activity of R580A-TG2 in SHSY5Y cells. SHSY5Y cells that stably overexpress R580A-TG2 were treated with the inhibitors (10 μM) for 16-20 h. DMSO was used as control. Transglutaminase activity was detected by an in situ transamidating assay. Results are shown as a percent of DMSO control (N=3). Statistical significance compared to control was tested using Dunnett's test; $*p<0.005$. In (D) it is shown that NC9, VA4 and VA5 inhibit GTP binding to TG2 almost completely. TG2 was preincubated with 1 μM GTP-γ-S FL BODIPY in 100 mM MOPS (pH=7.0) and 5 mM $MgCl_2$ for 10 min followed by addition of $H_2O$ (first column), inhibitor alone (second column) or inhibitor plus 0.5 mM $CaCl_2$ (third column). The concentrations for the inhibitors used were 120 μM, 40 μM and 40 μM for NC9, VA4 and VA5, respectively. Fluorescence (ex: 490 nm, em: 520 nm) was measured after 45 min on a microplate reader. Results are shown as corrected RFU values (±SEM) (N=3). Statistical significance compared to control was tested using Dunnett's test; $***p<0.005$.
Figure 3:
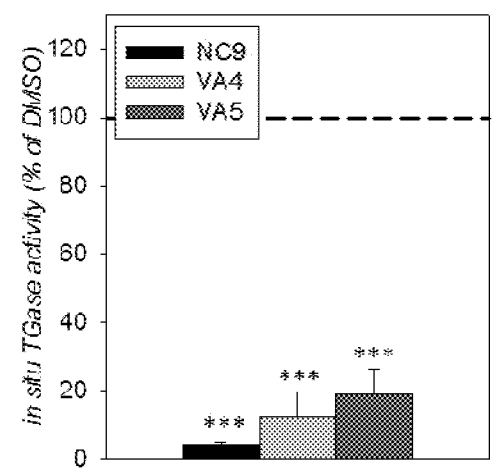
Figure 3:
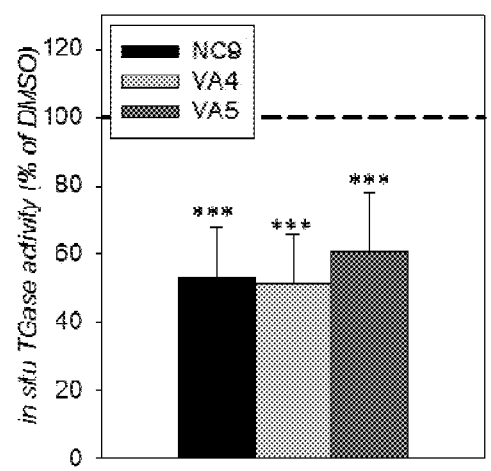
Figure 3:
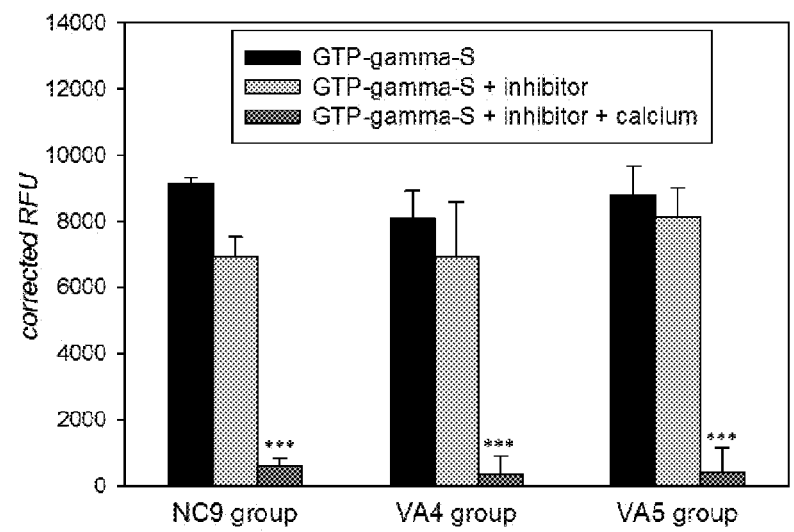

Example 3. Design, Synthesis and Characterization of TG2 Inhibitors in GBM Cells As the NC9-TG2 complex decreased proliferation in all cell lines that expressed TG2, we next examined how different TG2 inhibitors, based on the NC9 structure, affected GBM proliferation. Molecular modelling was performed to mimic the covalent binding of NC9 to the active site of TG2. Although NC9 effectively inhibits TG2 and maintains the protein in a more open conformation, the binding model from this docking experiment (FIG. 10) suggested that the length and flexibility of the polyethylene glycol (PEG) linker of NC9 was not ideal for its binding affinity. Several derivative inhibitors were therefore designed in which this linker was replaced with functional groups that are shorter and more conformationally rigid. The structures of two of these derivatives, VA4 and VA5, as well as NC9, are shown in FIG. 3A and their syntheses are described in further detail below.

Figure 11:
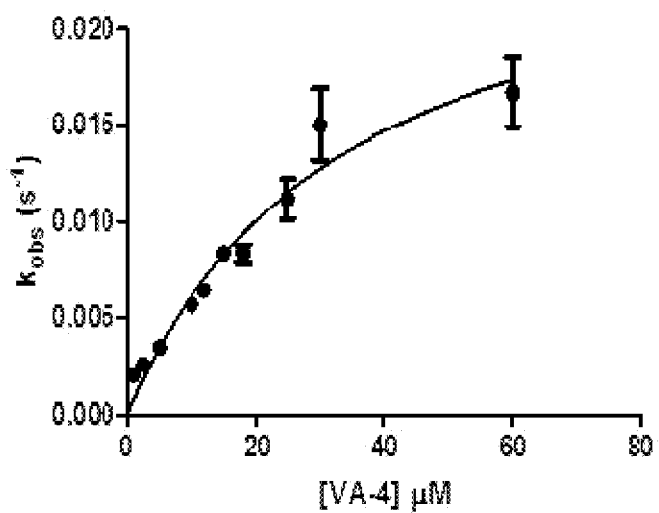
FIG. 11 shows non-linear regression of inactivation rate constant versus concentration of TG2 for irreversible inhibitors VA4 (A) and VA5 (B).
Figure 11:
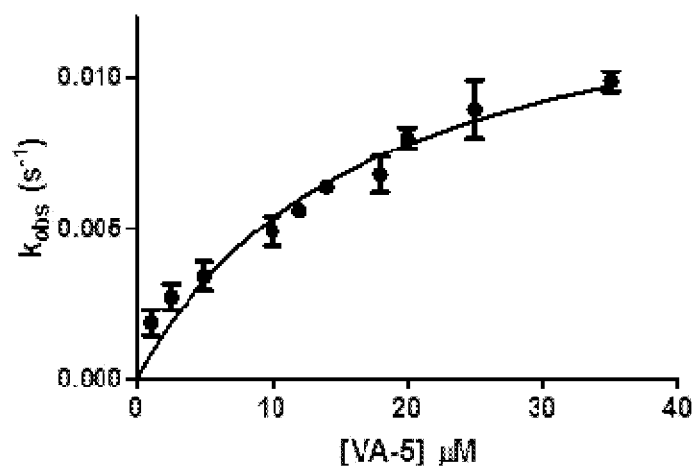

Kinetic studies were carried out in vitro, using purified recombinant human TG2 (Roy, I. et al., Protein Expr. Purif. 87: 41-46, 2013) and a direct, continuous spectrophotometric activity assay (Leblanc, A. et al., Biochemistry 40: 8335-8342, 2001). The time-dependent, irreversible inhibition observed by this kinetic method was characterized as described previously (Pardin, C. et al., Bioorg. Med. Chem. 14: 8379-8385, 2006). These data revealed the kinetic inactivation parameters for VA4 ($k_{inact}$=1.6 min$^{-1}$, $K_I$=9.0 µM) and for VA5 ($k_{inact}$=2.2 min$^{-1}$, $K_I$=10 µM) (FIG. 11 and Table 1).

TABLE 1

Kinetic inactivation parameters for VA4 and VA5.

| Compound | $k_{inact}$ (min$^{-1}$) | $K_I$ (?M) | $k_{inact}/K_I$ (?M$^{-1}$min$^{-1}$) |
|---|---|---|---|
| VA4 | 1.63 (±0.23) | 9.00 (±2.30) | 0.18 (±0.05) |
| VA5 | 0.86 (±0.11) | 6.26 (±1.60) | 0.13 (±0.04) |

These inhibitors were then tested in cell culture models for their efficiency in inhibiting in situ transamidating activity. U87 cells were used for these studies since they express relatively high levels of TG2. All compounds tested were observed to inhibit ionomycin-induced in situ transamidating activity almost completely (FIG. 3B), however since ionomycin is an ionophore, it could compromise membrane integrity. Therefore, we also used another approach to confirm that the inhibitors can pass uncompromised through plasma membranes. For these studies we used SH-SY5Y neuroblastoma cells stably overexpressing R580A-TG2. R580 has been shown to be crucial for binding of guanine nucleotides to TG2 (Begg, G. E. et al., J. Biol. Chem. 281(18): 12603-12609, 2006). Since guanine nucleotide binding allosterically inhibits transamidating activity, the R580A mutant has a higher resting-state activity than wild-type TG2, which allows us to measure activity in intact cells. Using this experimental paradigm we showed that the inhibition without calcium stimulation was incomplete, yet there was no difference between the inhibitors. Indeed, all inhibitors significantly inhibited basal transamidating activities in the R580A-TG2 cells (FIG. 3C), which suggests that they are all capable of passing through an intact plasma membrane.

Figure 12:
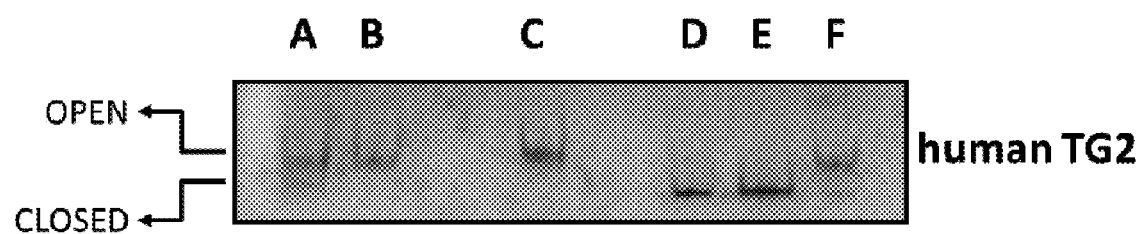
FIG. 12 shows NC9, VA4 and VA5 have similar effects on the conformation of TG2. It is shown that NC9, VA4 or VA5-bound TG2 is in an open conformation. 1.5 µg of purified human TG2 was incubated for 90 min with calcium and NC9 (lane A), calcium and VA4 (lane B), calcium and VA5 (lane C), DMSO (lane D), magnesium and GTP (lane E) or calcium (lane F). The concentrations for the inhibitors used were 120 µM, 40 µM and 40 µM for NC9, VA4 and VA5, respectively. Following this incubation, samples were run on polyacrylamide gel under non-denaturing conditions and in the presence of GDP and magnesium. The gel was Coomassie stained and a picture of the gel is shown.

TG2 has been shown to exist in two distinct conformations: a guanine nucleotide-bound 'closed' form and an 'open' form that binds calcium. We therefore examined the effects of the inhibitors on both GTP-binding and conformation using two independent approaches, although guanine nucleotide binding and conformation are interrelated. Based on results obtained from native PAGE, all of the tested inhibitors stabilized TG2 in the open conformation (FIG. 12). Similarly, using a BODIPY FL GTP-γ-S binding assay, we determined that the inhibitors completely abolished binding of GTP to TG2, when the protein was activated with calcium (FIG. 3D). These data strongly suggest that the inhibitors are very similar in terms of their effect on protein structure, the inhibited enzymes all being classed among the family of 'open' conformers.

Having thus characterized the inhibitors in terms of their inhibitory efficacy in in situ conditions and their effect on TG2 structure, we next tested their effect on GBM growth. For these studies we used the U87 and T98G cell lines. In the agarose colony formation assay, VA4 inhibited colony growth in a manner similar to NC9, whereas VA5 had a completely different effect (FIG. 4A). VA5 either did not suppress colony growth (T98G cells), or promoted it (U87 cells) (FIG. 4A). Because this result was unexpected we carried out additional studies. In most cases, chemical agents suppress colony growth by promoting cell death and/or slowing proliferation. In a SYTOX-orange assay, we observed minimal toxicity with these inhibitors at the concentrations used (data not shown); therefore, we focused on the possibility of slower proliferation. EdU incorporation into DNA is widely used as a proxy for DNA replication, and hence proliferation rate. In an EdU-incorporation assay, we observed that NC9 and VA4 slowed down the proliferation of GBM cells; however, VA5 had no effect (FIGS. 4B and 4C). These results indicate that NC9 and VA4 both suppressed colony growth via slowing down cell cycle in GBM cells. VA5, despite being structurally similar to NC9 and VA4, did not have the same suppressive effect.

Figure 13:
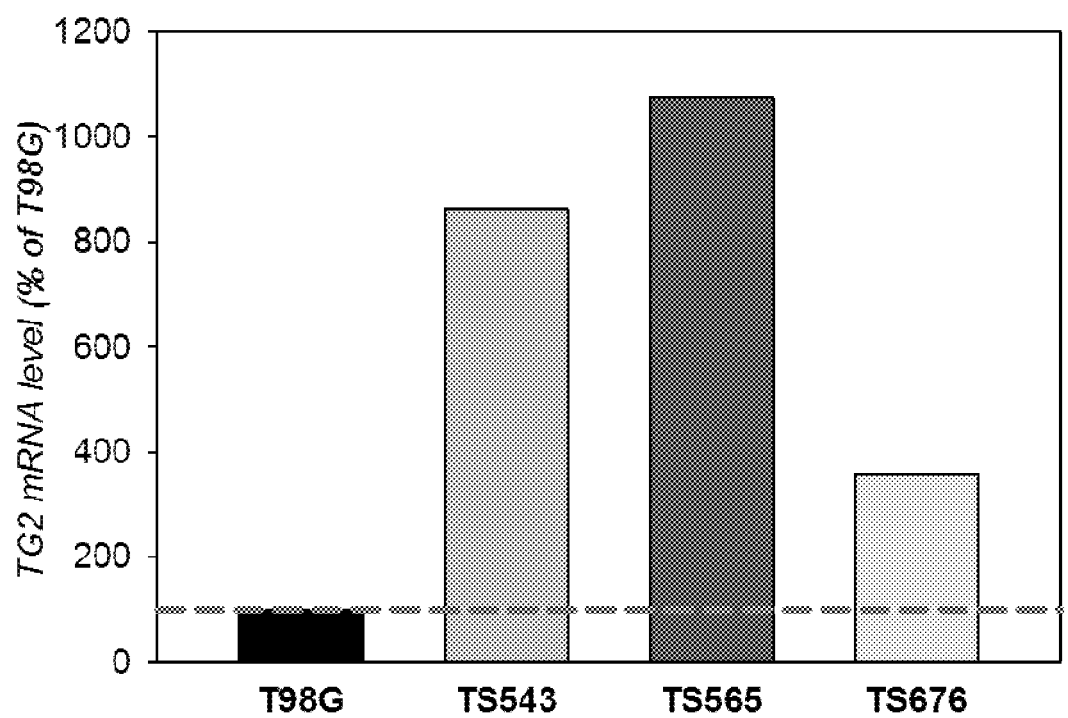
FIG. 13 shows all neurosphere lines tested express TG2. It is shown that TG2 mRNA levels in neurosphere varies, but are higher compared to T98G cells. Total RNA was isolated from the neurospheres or T98G cells. TG2 mRNA expression was measured by qRT-PCR. Results were normalized to actin mRNA and are shown as fold increase over T98G levels (N=2).

Although cell lines have been used extensively in GBM research, recent reports suggest that they may not reflect all the characteristics of the tumor from which they are derived. Neurospheres that are grown in a strictly defined medium, on the other hand, have almost the same gene expression profiles as the original tumor (Lee, J. et al., Cancer cell 9(5):391-403, 2006). Each tumor is unique, but a recent comprehensive study concluded that GBM tumors (and the neurospheres derived from them) can be divided into three general subtypes: classical, mesenchymal and proneural (Brennan, C. et al., PloS one, 4(11): e7752, 2009). Therefore, we next examined the effects of the inhibitors on the growth of neurospheres using 3 different lines: TS543, TS565 and TS676, which represent the mesenchymal, proneural and classical glioblastoma subtypes, respectively. TG2 expression in these cells lines varied considerably, but was overall much higher than that observed in T98G cells (FIG. 13). The lowest expression level was observed in the classical, TS676 line, and spheroid formation in this cell line was not affected by the inhibitors (FIG. 5). The responses of the mesenchymal TS543 and proneural TS565 cell lines to TG2 inhibitors were curiously similar to those of U87 and T98G cells, respectively (FIGS. 4A and 5A). NC9 and VA4 suppressed sphere growth in TS543 and TS565 lines, whereas VA5 actually promoted growth in the TS543 line and was only mildly suppressive in the TS565 line (FIG. 5).

Figure 6:
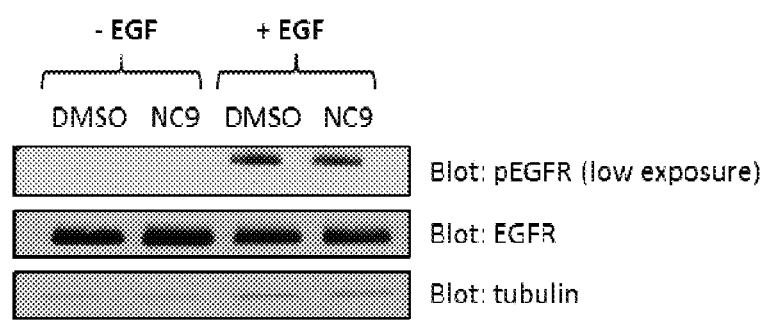
FIG. 6 shows TG2 mediation of EGFR pathway is cell type, inhibitor and condition specific. In (A) it is shown that shorter treatments with NC9 had no effect on EGF-stimulated EGFR phosphorylation in U87 cells. U87 cells were treated with 10 µM NC9 or DMSO control for 24 h followed by 10 min of 100 ng/mL EGF treatment. At the end of the treatments, cells were lysed and 20 µg of lysates from U87 cells were blotted for phospho-EGFR, EGFR and tubulin. In (B) it is shown that longer treatments with NC9, but not VA5, decrease phospho-EGFR and EGFR levels in U87 cells, but not T98G cells. U87 and T98G cells were treated with NC9 (10 µM), VA5 (10 µM) or DMSO control for 48-72 h. Cell medium was changed every 24 h and fresh inhibitors or DMSO was added to the medium. At the end of the treatment, cells were lysed and 20 µg of lysates from cells U87 and T98G were blotted for phospho-EGFR, EGFR and actin.

In a recent study, TG2 inhibitors were reported to suppress GBM cell growth, and it was suggested that TG2 conformation was an important contributing factor (Zhang, J. et al., Cell Reports 3(6):2008-2020, 2013). These studies were carried out primarily with U87 cells and suggested that TG2 inhibitors cause TG2 to maintain its open conformation, thereby preventing it from interacting with the E3 ligase c-cb1 and thus allowing it to ubiquitylate and promote the degradation of EGFR. These findings suggested that treatment of U87, but not T98G cells, with MDC or Z-DON for 24 hrs reduced the levels of EGFR. It was also shown that a 30 min pretreatment with MDC greatly reduced the extent of EGFR phosphorylation (activation) in response to EGF treatment in U87 cells. We tested this model in the same cell line (U87) with the inhibitor NC9, which favors open conformation (Caron, N. S. et al., PLoS ONE 7: e44159, 2012; Clouthier, C. M. et al., Angew. Chem. Int. Ed. Engl. 51: 12464-12468, 2012). In contrast to what was previously reported, NC9 treatment did not result in a decrease in EGFR or phospho-EGFR levels (FIG. 6A). Our results suggest that the effects of TG2 inhibitors on EGFR levels may be cell line, condition, and inhibitor specific, and that the proposed role of TG2 in the EGFR-dependent pathway in GBM proliferation may be a contributing event in certain situations, but is unlikely to be the most prominent mechanism through which TG2 regulates GBM proliferation. Results also indicate that the role of TG2 in the proliferation of GBMs is not the same in all cell lines, and the variability is likely due to specific gene profiles of the cells underlying the differential responses to the TG2 inhibitors. Indeed, TG2 plays a paradoxical role in cancer, as it has been reported to function both as an oncogene and a tumor suppressor (Dyer, L. M. et al., Journal of neuro-oncology 101(3):429-440, 2011; Eckert, R. L. et al., Mol. Carcinog. 54: 947-958, 2015), most likely due to its multifunctionality.

Figure 14:
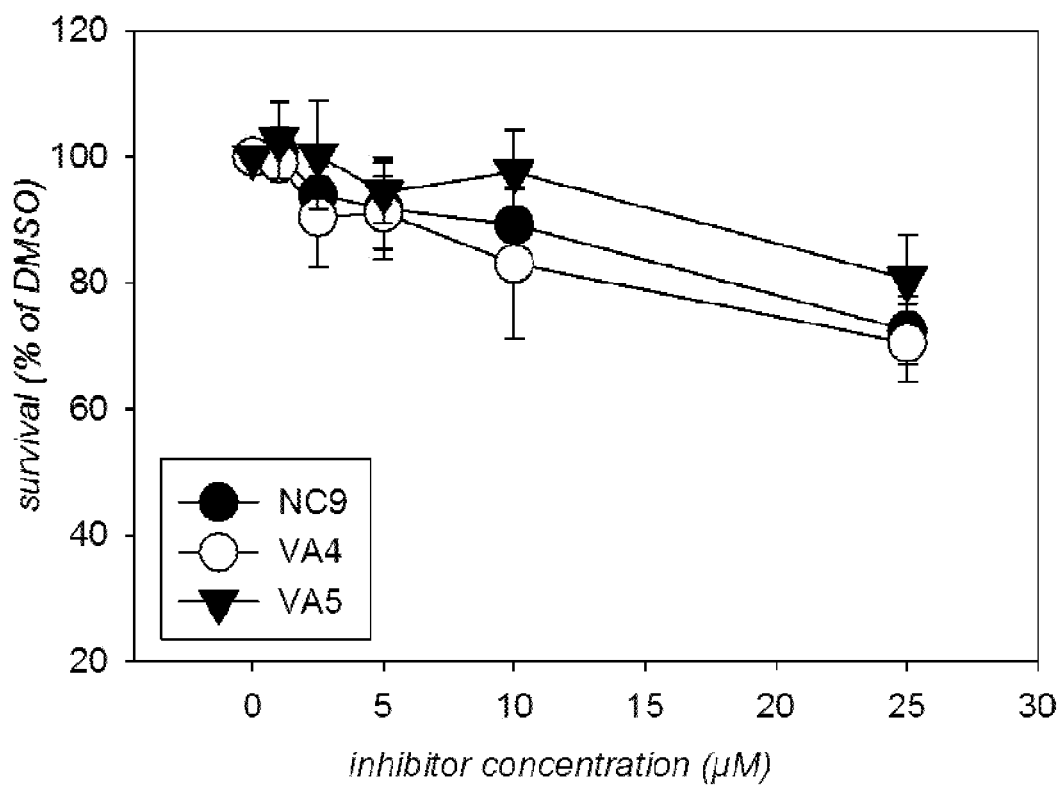
FIG. 14 shows NC9, VA4 and VA5 have minimal toxicity on neurons. It is shown that NC9, VA4 and VA5 are well tolerated up to 10 µM concentration by rat primary cortical neurons. Rat primary cortical neurons were cultured in neurobasal media for a week and treated with different concentrations of NC9, VA4 and VA5 for 24 h. DMSO was used as a control. At the end of the treatment, neuronal viability was measured by resazurin assay. Results are shown as a percent of DMSO control (±SEM) (N=3).

In summary, the above experiments have elucidated the role of TG2 in GBM cell proliferation. We used two different approaches to modulate TG2 (knockdown and inhibitor) in several GBM models (3 monolayer cell lines and 3 neurosphere lines), and showed that 3 inhibitors with the same reactive group had similar effects on TG2 activity and structure, yet remarkably different effects on GBM proliferation. These results also suggest that previously postulated pathways describing the role of TG2 in GBM proliferation are context and cell type specific. Overall, our results confirm that TG2 plays an important, albeit context specific, role in GBM cell biology, and that small molecules targeting TG2 are likely to be effective in at least a subset of GBM patients. Further the TG2 inhibitors (NC9 and VA4) were very efficacious in reducing GBM proliferation in most cell types and did not cause toxicity in neurons (FIG. 14). TG2 inhibitors thus demonstrate strong therapeutic potential.

Figure 2:
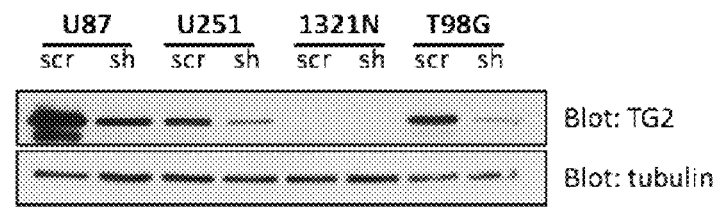
FIG. 2 shows the suppressive effect of NC9 on the colony formation capacity of GBM cells is TG2 dependent. In (A) there is shown knockdown of TG2 using lentiviral delivery of an shRNA construct for TG2. GBM cell lines were transduced with an shRNA construct for TG2 (sh) or a scrambled RNA control (scr). Six to eight days later, the cells were collected and 10 μg of lysates were blotted for TG2 and tubulin. In (B) it is shown that silencing TG2 expression decreases colony growth in some cell lines and NC9 loses its suppressive effect on colony growth when TG2 expression is silenced. Glioblastoma cell lines were transduced with sh or scr lentiviruses expressing GFP and 6-8 days later cells were seeded in 0.35% agarose and treated with 10 μM NC9 for 2 weeks. DMSO was used as control. At the end of the treatment, the colonies were visualized using fluorescent microscopy for GFP (ex: 490 nm, em: 520 nm) and 20 random microscopic images were captured for each group. The average volume of each colony image was determined using Image J by a person blinded for cell lines and treatments and volumes were calculated from the area data and used for comparison. For each experiment, NC9 group was normalized to DMSO control. Results are shown as a percent of DMSO control (±SEM) (N=3). Statistical significance compared to control was tested using Dunnett's test; $*p<0.05$, $p<0.01$, $*p<0.005$, n.s. (not significant). In (C) there are shown representative images showing the effect of TG2 knockdown and/or NC9 treatment in T98G cells.
Figure 2:
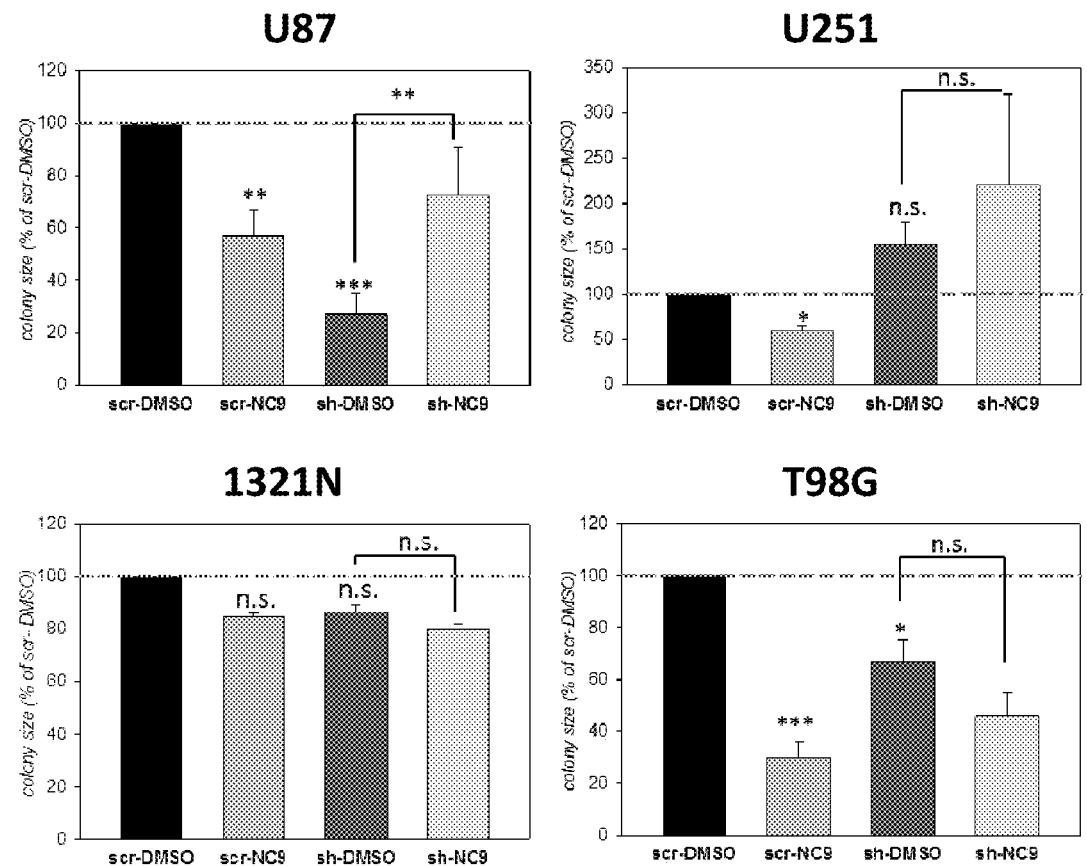
Figure 2:
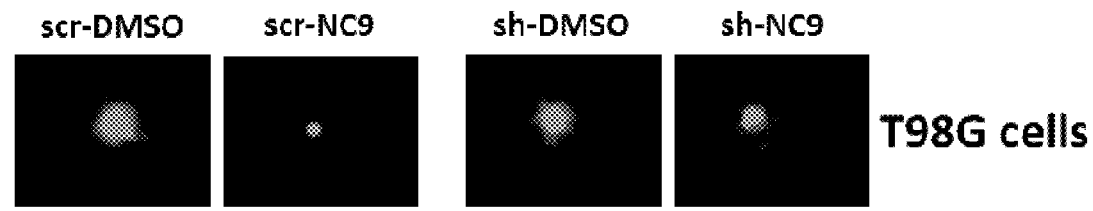
Figure 4:
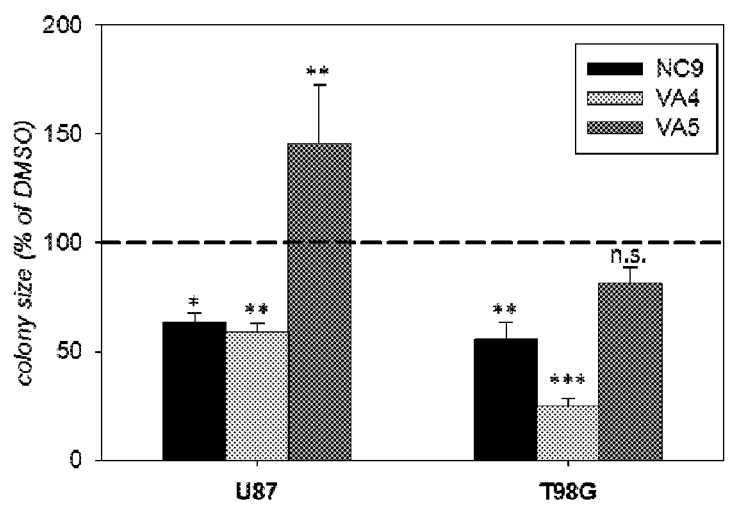
FIG. 4 shows NC9 and VA4, but not VA5, decrease the growth rate of GBM cell lines. In (A) it is shown that NC9 and VA4, but not VA5, significantly reduce the average colony size of U87 and T98G cells. Cells were seeded in 0.35% agarose and treated with the inhibitors (10 µM) or DMSO control for 2 weeks. At the end of the treatment, the colonies were fixed and stained; and 20 random microscopic images were captured for each group. The average volume of each colony image was determined using Image J by a person blinded for cell lines and treatments and volumes were calculated from the area data and used for comparison. For each experiment, inhibitor groups were normalized to DMSO control. Results are shown as a percent of DMSO control (±SEM) (N=3). Statistical significance compared to control was tested using Dunnett's test; *p<0.05, p<0.01, *p<0.005, n.s. (not significant). In (B) it is shown that NC9 and VA4, but not VA5, significantly reduce the proliferation rate of U87 and T98G cells. Cells were treated with NC9, VA4, VA5 or DMSO control for 24 h. At the end of the treatment, cells were pulsed with EdU, fixed and EdU-positive nuclei were detected by microscopy. The ratio of EdU-positive nuclei number to DAPI-stained total nuclei number was calculated for each individual experiment. Results are shown as a percent of DMSO control (±SEM) (N=3). Statistical significance compared to control was tested using Dunnett's test; *p<0.05, p<0.01, *p<0.005, n.s. (not significant). In (C) representative images for EdU incorporation assay are shown. Green represents proliferating EdU-positive cells and blue represents the DAPI counterstain for total number of nuclei.
Figure 4:
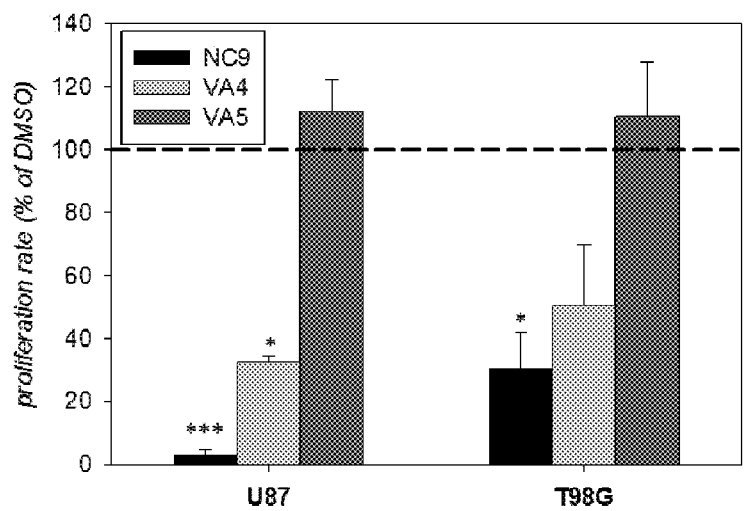
Figure 4:
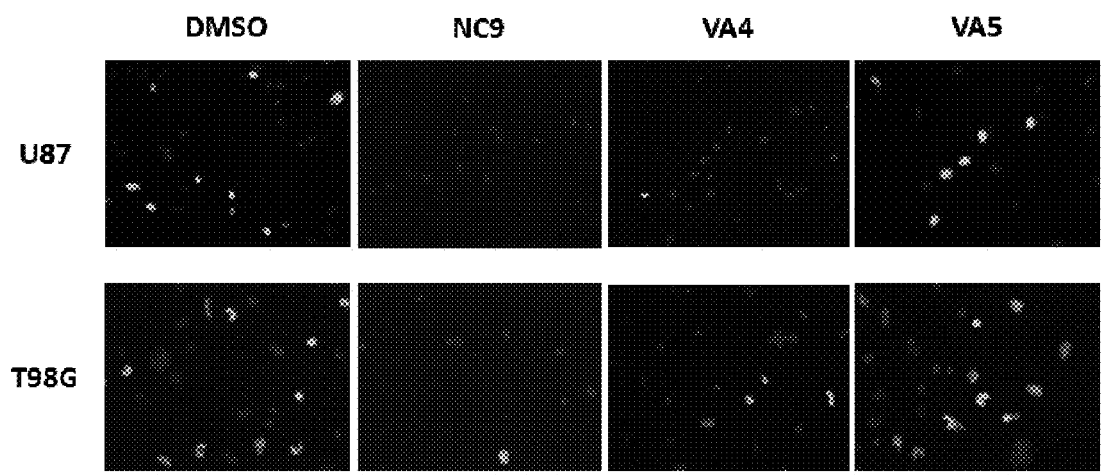
Figure 5:
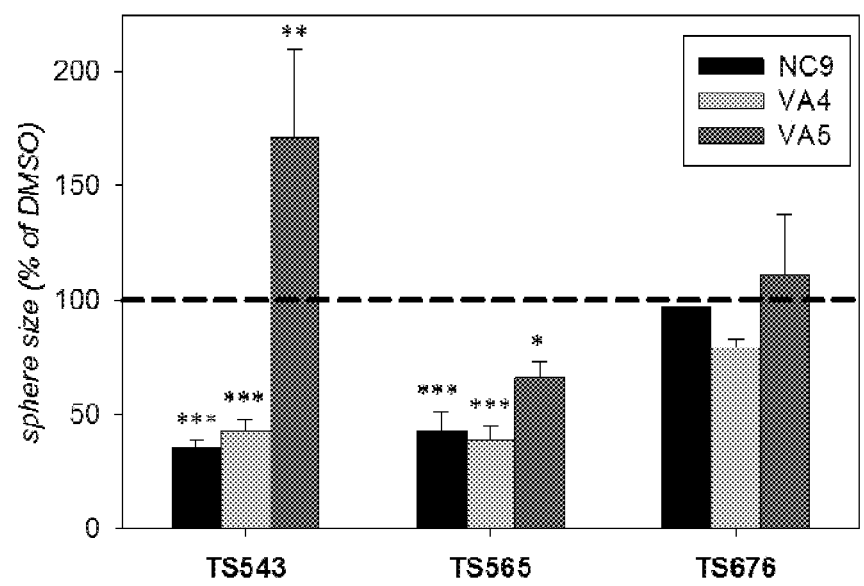
FIG. 5 shows NC9 and VA4, but not VA5, decrease neurosphere growth in a subtype-specific manner. In (A) it is shown that NC9 and VA4, but not VA5, significantly reduce the growth rate of some, but not all, glioblastoma-derived neurospheres. Neurospheres were grown in the presence of the inhibitors for 2 weeks and at the end 20-50 random microscopic images were captured for each group. The average volume of each sphere image was determined using Image J by a person blinded for cell lines and treatments and volumes were calculated from the area data and used for comparison. For each experiment, inhibitor groups were normalized to DMSO control. Results are shown as a percent of DMSO control (±SEM) (N=4-7). Statistical significance compared to control was tested using Dunnett's test; *p<0.05, p<0.01, *p<0.005. In (B) representative images showing the effect of the inhibitors on the growth of glioblastoma spheres are shown.
Figure 5:
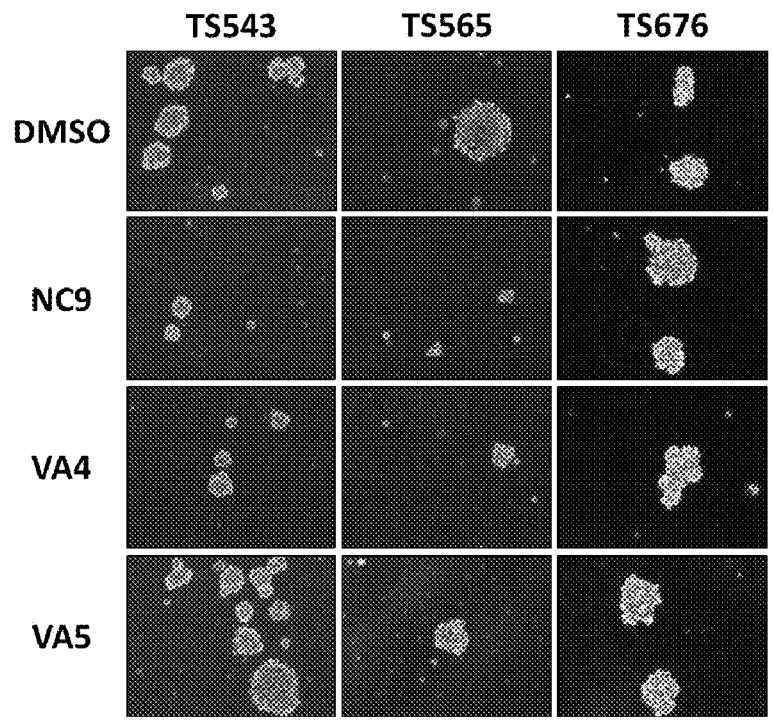

It is noted that the inhibitors were all similar in terms of their inhibition profile or their effect on TG2 conformation, however NC9 and VA4, generally speaking, inhibited GBM proliferation to similar extents, but VA5 did not (FIGS. 4, 5). The most straightforward explanation would have been that NC9 and VA4 have other targets and they suppress GBM growth through acting on these other targets; however, this possibility is unlikely since we showed that NC9 requires TG2 in order to suppress colony growth of GBM cells (FIG. 2). There are several other possible explanations for this observation. First, it is possible that VA5 may not be as stable as the other inhibitors inside the cell. Also, VA5 could be affecting TG2 differently, but this difference could well be below the detection limit of the methods we use. As an example of this possibility, the open conformation of VA5-bound TG2 could be different than the VA4-bound TG2, but the electrophoretic mobility of the drug-TG2 complex could be very similar (FIG. 12). This would suggest that classifying TG2 conformations into distinct "open" and "closed" forms is likely an oversimplification. Lastly, VA5 could have other targets than TG2 and its effect on these targets could be counteracting its effect on TG2. The fact that VA5 actually promoted colony growth in U87 (FIG. 4A) and TS543 lines (FIG. 5A), instead of just failing to retard growth, is supportive of this possibility.

Materials and Methods for Examples 1-3

All reagents and solvents for reactions were used as received unless otherwise stated.

Lentiviral vectors. Lentiviral knockdown vectors were prepared and used as previously described (Gundemir, S. et al., PLoS ONE 4(7):e6123, 2009; Barde, I. et al., Curr. Protoc. Neurosci. Chapter 4, Unit 4.21, 1-23, 2010).

Monolayer cell cultures. U87, U251, 1321N, T98G and C6 cells were cultured in Minimum Essential Medium (MEM) (Irvine Scientific) supplemented with 5% fetal bovine serum (Invitrogen); SH-SY5Y cells were cultured in RPMI medium supplemented with 10% fetal bovine serum. All media were supplemented with 2 mM L-glutamine (Invitrogen), 100 μg/ml streptomycin (Invitrogen, Life Technologies, Inc.), 100 units/ml penicillin (Invitrogen), and non-essential amino acids (Invitrogen). Cells were grown in a humidified atmosphere containing 5% $CO_2$ at (Colak, G. et al., Neurobiol. Dis. 45(3):1042-50, 2012).

Neurosphere cultures. TS543, TS565 and TS676, which represent the mesenchymal, proneural and classical glioblastoma subtypes respectively, based on transcriptomic and genomic analysis, were obtained from C. Brennan through the Monoclonal Antibody Core Facility at Memorial Sloan Kettering Cancer Center (Brennan, C. et al., PLoS One 4(11):e7752, 2009; Pyonteck, S. M. et al., Nature Med. 19(10):1264-72, 2013; Rohle, D. et al., Science 340(6132): 626-30, 2013) and maintained in NeuroCult™ NS-A Proliferation Kit (Human) (Stem Cell Technologies) according to manufacturer's instructions. (NeuroCult Medium was supplemented with 20 ng/mL FGF, 50 ng/mL EGF and 0.0002% Heparin). To prevent neurosphere attachment to the bottom of the cell culture plates, Poly 2-hydroxyethyl methacrylate (PHM) was used. 6-well plates were coated with 1 mL/well of 1% PHM in ethanol (w/v). The plates were air dried in a sterile environment overnight and washed once with PBS and they were kept in the fridge in a sterile environment until use. For passaging, neurospheres were triturated according to instructions and 5,000 cells were seeded in each well in 2 mL medium. For treatments with TG2 inhibitors, cells were inoculated in medium containing 25 µM TG2 inhibitor or DMSO control. 200 µL of medium containing the 25 µM TG2 inhibitor or DMSO was added every other day. At the end of 2 weeks, 20-50 random microscopic images were captured for each group. The average volume of each sphere image was determined using Image J by a person blinded for neurosphere lines and treatments and volumes were calculated from the area data and used for comparison.

Immunoblotting. Cells were rinsed in ice-cold phosphate-buffered saline (PBS) and collected in lysis buffer, containing 0.5% NP-40, 150 mM NaCl, 10 mM Tris-Cl (pH 7.4), 1 mM EGTA, 1 mM EDTA, 1 mM phenylmethylsulphonyl fluoride, 1 µM okadaic acid, and 10 µg/mL each of aprotinin, leupeptin, and pepstatin. Samples were sonicated on ice and centrifuged at 16,000 g for 10 min. Protein concentrations of supernatants were then determined by the bicinchoninic acid assay with bovine serum albumin (BSA) as a standard and samples were diluted to a final concentration of 1 mg/mL with 2× reducing stop buffer (0.25 M Tris-HCl, pH 6.8, 5 mM EDTA, 5 mM EGTA, 25 mM dithiothreitol, 2% SDS, 10% glycerol, and bromophenol blue as the tracking dye). Samples (20 or 40 µg of protein) were resolved on 10% SDS-polyacrylamide gels, and transferred to nitrocellulose. Blots were blocked in 5% nonfat dry milk in TBST (20 mM Tris-HCl, pH 7.6, 137 mM NaCl, 0.05% Tween 20) for 1 h at room temperature. The blots were then incubated overnight with the primary antibody. The antibodies used were: EGFR, phospho-EGFR, rabbit monoclonal antibodies from Cell Signaling Technology, TG2 mouse monoclonal antibody (CUB7402) from Life Technologies, and a mouse monoclonal α-tubulin antibody from Thermo Scientific. The membranes were then washed three times with TBST and incubated with HRP-conjugated secondary antibody for 1 h at room temperature. The membranes were rinsed three times for 30 min with TBST, followed by four quick rinses with distilled water, and developed with enhanced chemiluminescence (Gundemir, S. et al., Biochim. Biophys. Acta. 1833(1):1-10, 2013).

Agarose colony formation assay. Agarose colony formation assay was conducted as described (Horman, S. R. et al., J. Biomol. Screen 18(10):1298-308, 2013; Zhang, K. et al., Tumour Biol. 35(3):2537-48, 2014) using 6-well plates and 5,000 cells in each well. 10 µM NC9 or DMSO was added to every layer at the start of the experiments. 2 mL liquid MEM containing 10 µM NC9 or DMSO was used to cover the agarose and it was changed 3 times a week. Colony growth was monitored every day and at the end of 10-15 days, the colonies were fixed with 4% paraformaldehyde, stained with 0.005% crystal violet, washed with PBS twice and 40 random pictures were taken from each treatment group. A person blinded for the treatments measured the area of the colonies using ImageJ program and the volumes were calculated from the area data under the assumption that the colonies are perfect spheres. The volumes were used to compare the effect of NC9 on colony growth.

In situ transglutaminase assay. In situ transamidating activity measurement was conducted as described previously (Gundemir, S. and Johnson, G. V., PLoS ONE 4(7): e6123, 2009) with slight modifications. Briefly, 24 h after transfection of HEK 293A cells, normal growth media was changed to fresh growth media with 5% FBS containing given amount of ionomycin (0-1.5 µM) and 0.1 mM 5-(biotinamido)pentylamine (BAP) (Pierce). 3 h later, cells were collected in media, pelleted, washed once with PBS and resuspended in homogenization buffer (50 mM Tris-Cl, pH: 7.5, 150 mM NaCl, 1 mM EDTA), sonicated on ice. In a high protein binding 96-well plate (Falcon), 10 µg of protein was loaded in a total of 50 µL homogenization buffer and the plate was incubated at 4° C. overnight. The next day, 200 µL of blocking buffer (5% BSA, 0.01% Tween 20 in borate saline [100 mM boric acid, 20 mM Na-borate and 0.76 mM NaCl]) was added to each sample and the plate was incubated at 37° C. for 1 h. Each well was then rinsed 3 times with rinsing buffer (1% BSA, 0.01% Tween 20 in borate saline) and incubated with 1 µg/µL Horseradish peroxidase conjugated neutravidin (Pierce) in a total of 100 µL rinsing buffer at room temperature for 1 h. The samples were washed 4 times with rinsing buffer, and peroxidase reaction was conducted in the dark in 200 µL of OPD buffer (50 mL of 0.1 M $Na_2HPO_4$, 50 mM citric acid, 1 tablet o-phenylenediamine (Sigma Aldrich), 0.0006% $H_2O_2$). After 20 minutes, the reaction was stopped by addition of 50 µL of 1 M sulfuric acid and read at 493 nm wavelength.

High protein binding plates were coated with N,N-dimethyl casein (100 µL of 15 µg/µL solution in 100 mM Tris-Cl, pH: 7.4 and 5 mM EDTA) overnight at 4° C. The next day, the wells were blocked by 5% BSA in 50 mM Tris-Cl, pH 7.4 containing 5 mM EDTA at room temperature for 2 h; followed by 3 washes with 50 mM Tris-Cl, pH 7.4. The reaction was carried out in 50 mM Tris-Cl, pH 7.4 solution containing 5 ng guinea pig TG2/well, 0.1 mM 5-(biotinamido)pentylamine (BAP), 10 mM $CaCl_2$, 1 mM dithiothreitol. The reaction was carried out at 37° C. for 1 h. At the end of the reaction, the plates were washed with 50 mM Tris-Cl, pH 7.4 three times. 100 µL of extravidin-HRP solution (1:2500 diluted extravidin-HRP in 3% BSA in 100 mM Tris-Cl, pH 7.4 and 5 mM EDTA) was added to each well and the plates were incubated overnight at 4° C. The next day, the plates were washed with 50 mM Tris-Cl, pH 7.4 four times. The reaction was conducted in 100 µL/well OPD buffer (50 mM $Na_2HPO_4$, 50 mM citric acid, 1 tablet o-phenylenediamine (Sigma Aldrich), 0.0006% $H_2O_2$) for 2-20 min. The reaction was stopped by the addition of 50 µL 2.5 M sulphuric acid and the absorbance was read at 450 nm.

EdU Incorporation Assay. After treatment of cells seeded in PolyD-Lys coated coverslips, half of the media was replaced with 10 µM EdU in 10% FBS MEM. After 90 min, cells were fixed with 4% PFA and permeabilized with 0.5% Triton X-100. Detection of EdU was performed as directed in the Click-iT EdU Alexa 647 kit (Life Technologies). 1:2000 Hoechst dilution was used to stain nuclei. Randomized pictures were taken for each group and a person blinded for the treatments counted the EdU and Hoechst positive cells.

Native PAGE. Native gel electrophoresis experiments were performed using a method similar to those described previously (Begg, G. E. et al., Proc. Natl. Acad. Sci. U.S.A. 103: 19683-19688, 2006; Pinkas, D. M. et al., PLoS Biol. 5: e327, 2007). Briefly, TG2 or inhibited TG2 (2.5 µM) was incubated for 1.5 h at room temperature in pre-incubation buffer (50 mM Tris, 5 mM DTT, 0.5 mM EDTA) at pH 7.0 with or without 100 µM GTP/1.0 mM MgCl$_2$ or 5.0 mM CaCl$_2$. Laemmli native loading buffer was added (1:1) and 1.5 µg of TG2 was loaded onto a 4-20% Tris-HCl ReadyGel (Bio-Rad) using Tris-glycine as the running buffer with 100 µM GTP/1.0 mM MgCl$_2$. For 90 min, 120 V was applied at 4° C. The gel was stained with 0.5% Coomassie brilliant blue R-250 in 40% methanol/10% acetic acid and destained in 10% methanol/10% acetic acid.

Q-RTPCR. After RNA isolation, cDNA was synthesized using the verso cDNA kit (ThermoFisher) with oligo-dT primers following the manufacturer's instructions. Quantitative real time PCR was carried out using SYBR green mix (Agilent Technologies) along with primers against total human TG2 or GAPDH (for normalization) as previously described (Cao, L. et al., Oncogene 31(20):2521-34, 2012).

BODIPY FL GTP-γ-S binding assay. GTP binding was performed using a similar method as reported previously (McEwen, D. P. et al., Anal. Biochem. 291: 109-117, 2001). For all experiments, GTP binding was assayed using 1 µM of the fluorescent, non-hydrolysable GTP analogue BODIPY GTP-γ-S (Invitrogen), whose fluorescence increases when bound by protein. TG2 (9 µg) was incubated with BODIPY GTP-γ-S at 25° C. for 10 min in 100 mM MOPS (pH=7.0) and 5 mM MgCl$_2$ followed by addition of H$_2$O, inhibitor alone or inhibitor plus 0.5 mM CaCl$_2$. The concentrations of inhibitors used were 120 µM for NC9, 40 µM for VA4 and 40 µM for VA5. After 45 min incubation, fluorescence was then measured on a microplate reader (ex: 490 nm, em: 520 nm).

Kinetics. Kinetic runs were performed at 25° C. in 100 mM MOPS buffer (pH 7.0) containing 3 mM CaCl$_2$ and 50 µM EDTA. For kinetic runs, 54 µM of the chromogenic substrate Cbz-Glu(γ-p-nitrophenyl ester)Gly was used, corresponding to 3.75×K$_M$, in the presence of 1-60 µM and 1-35 µM of inhibitor VA4 or VA5, respectively. Stock solutions of the substrate and inhibitors were prepared in DMF such that the final concentration of this co-solvent was constant at 10% v/v. Reactions were initiated with the addition of enzyme with an activity of approximately 0.05 U/mL. Kinetic evaluation was carried out by the method of Stone and Hofsteenge (Stone, S. R. and Hofsteenge, J., Biochem. J. 230: 497-502, 1985). Monoexponential time-dependent inactivation was observed for all of the inhibitors studied herein. Observed first-order rate constants of inactivation were determined from non-linear regression, to a monoexponential model. These rate constants were in turn fit to equation 1 by non-linear regression, providing the kinetic parameters $$k_{inact} \text{ and } K_I: k_{obs} = \frac{k_{inact}[I]}{[I] + K_I\left(1 + \frac{[S]}{K_M}\right)}.$$

Example 4. Characterization of TG2 Expression in Human ECS Cells

The metastatic cascade, from primary tumor to metastasis, is a complex process involving multiple pathways and signaling cascades. Cells that complete the metastatic cascade migrate away from the primary tumor through the blood to a distant site and there form a secondary tumor. The epithelial-mesenchymal transition (EMT) EMT is a property of tumor stem cells that confers an ability to migrate and invade surrounding tissue and is associated with enhanced cancer cell migration and stem cell self-renewal. EMT regulators, including Snail, Twist, and Slug, are increased in expression in EMT and control expression of genes associated with the EMT phenotype (Wang, Y. et al., Curr. Cancer Drug Targets 13:963-972, 2013).

We report herein studies to investigate the role of TG2 in regulating EMT in ECS cells. Our studies show that TG2 knockdown or treatment with TG2 inhibitor resulted in a reduced EMT marker expression, and reduced cell migration and invasion. TG2 has several activities, but the most prominent are its transamidase and GTP binding activity; analysis of a series of TG2 mutants revealed that TG2 GTP binding activity, but not the transamidase activity, was required for expression of EMT markers (Twist, Snail, Slug, vimentin, fibronectin, N-cadherin and HIF-1a), and increased ECS cell invasion and migration. This coupled with reduced expression of E-cadherin. Additional studies indicated that NFκB signaling, which has been implicated as mediating TG2 impact on EMT in breast cancer cells, was not involved in TG2 regulation of EMT in skin cancer. Our studies suggest that TG2 is required for maintenance of ECS cell EMT, invasion and migration, and suggests that inhibiting TG2 GTP binding/G-protein related activity may reduce skin cancer tumor survival.

Figure 15:
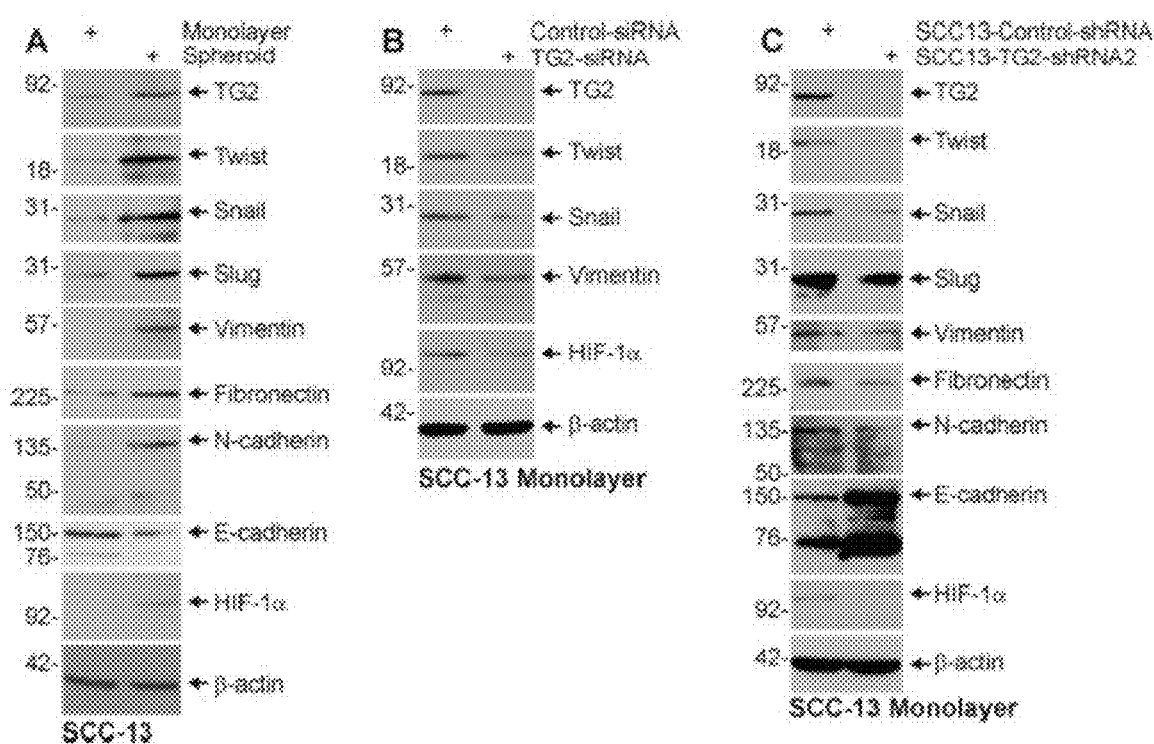
FIG. 15 shows TG2 and EMT marker expression is enriched in ECS cells, and TG2 is required for EMT. In (A) it is shown that ECS cells have elevated TG2 and mesenchymal markers. SCC-13 cells (40,000 per well) were grown in spheroid medium in attached (monolayer) and non-attached (spheroid, ECS cells). Cells were harvested after 10 days (d) and lysates were prepared for electrophoresis and detection of the indicated epitopes. In (B), SCC-13 cells were electroporated with control- or TG2-siRNA and cultured in spheroid medium as monolayer cultures. After 72 hours (h) extracts were prepared to assay TG2 and EMT markers. In (C), SCC13-Control-shRNA and SCC13-TG2-shRNA2 cells were grown in spheroid media for 10 d, harvested and lysates prepared for immune-detection of TG2 and EMT markers. Similar results were observed in three separate experiments.

First, we examined whether ECS cells express EMT markers. Non-stem cancer cells and ECS cells, derived from the SCC-13 cancer cell line, were analyzed for expression of EMT markers. FIG. 15A shows that a host of EMT transcriptional regulators, including Twist, Snail and Slug, were increased in ECS cells (spheroid) as compared to non-stem cancer cells (monolayer). This was associated with increased levels of vimentin, fibronectin and N-cadherin, which are mesenchymal proteins, and reduced expression of E-cadherin, an epithelial marker. HIF-1α, an additional marker frequently associated with EMT, was also elevated.

Figure 16:
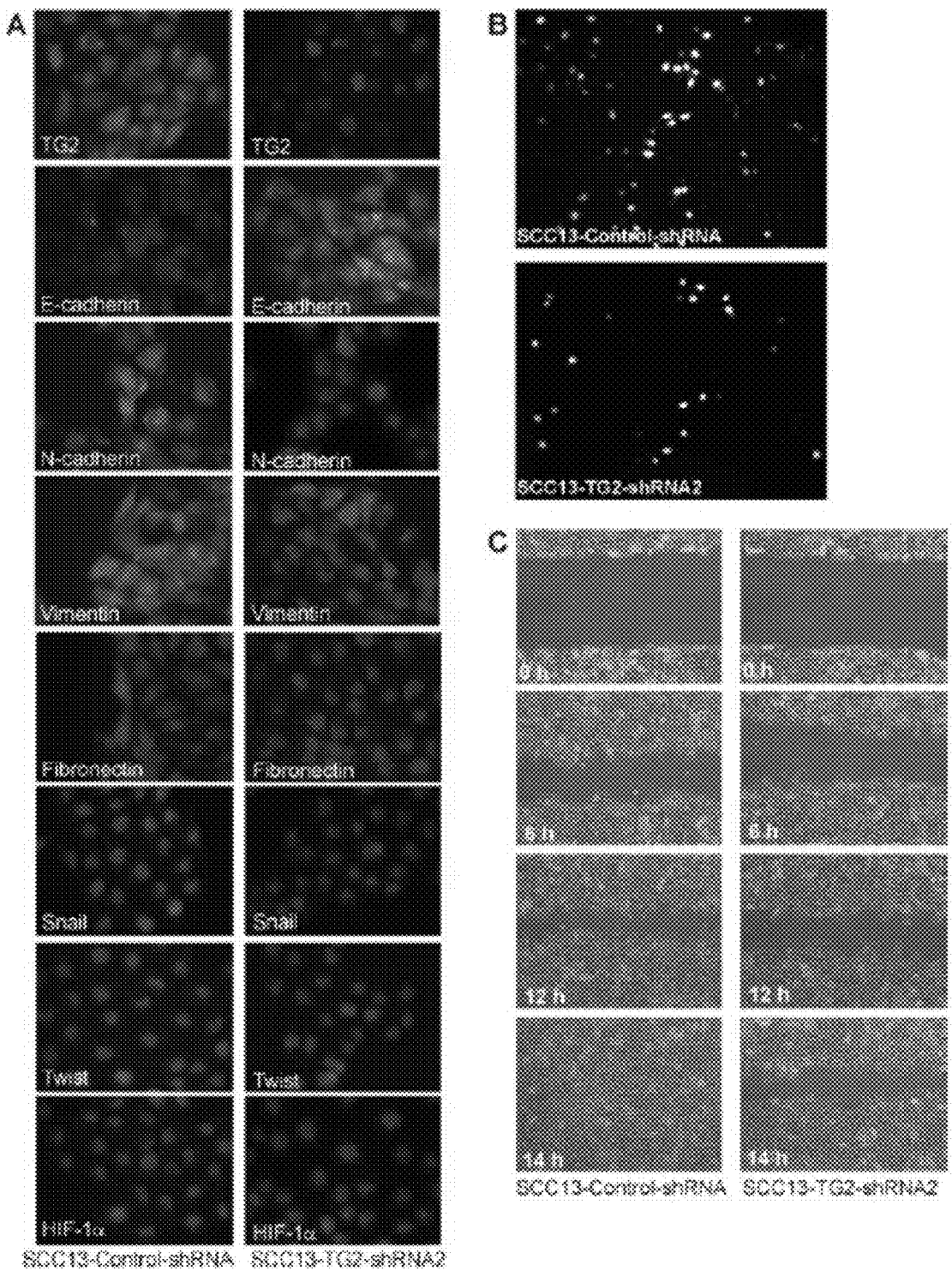
FIG. 16 shows TG2 is required for EMT marker expression and invasion/migration. In (A). SCC13-Control-shRNA and SCC13-TG2-shRNA2 cells were grown in spheroid medium as spheroids in non-attached culture for 8 d, and then plated as monolayers in 12 well plates (100,000 cells/well). After overnight attachment, the cells were fixed, permeabilized and incubated with antibodies specific for the indicated epitopes. In (B), SCC13-Control-shRNA and SCC13-TG2-shRNA2 cells were seeded on the upper chamber atop a matrigel-coated membrane in 1 mL of growth medium in a Millicell chamber. After migration, the membrane was removed, rinsed, fixed and DAPI stained. Nuclei were counted on the underside of the membrane using an inverted fluorescent microscope. In (C), SCC13-Control-shRNA and SCC13-TG2-shRNA2 cells (2 million) were plated on 100 mm dishes in spheroid medium in monolayer conditions. The confluent monolayers were scratched with a 10-µL pipette tip to create a wound and the released cells were removed. Images were taken at 0-14 h after the initial scratch. Similar results were observed in three experiments.

We next examined whether TG2 is required to maintain EMT marker expression. SCC-13 cell-derived ECS cells were grown in the presence of control- or TG2-siRNA, to reduce TG2, and the impact on EMT marker level was measured. FIG. 15B shows that loss of TG2 was associated with reduced expression of Twist, Snail, vimentin and HIF-1α. To further assess the role of TG2, we utilized SCC13-Control-shRNA and SCC13-TG2-shRNA2 cell lines. These lines were produced by infection of SCC-13 cells with lentiviruses encoding control- or TG2-specific shRNA. FIG. 15C shows that SCC13-TG2-shRNA2 cells expressed markedly reduced levels of TG2 and that this was associated with reduced expression of EMT associated transcription factors and target proteins, and increased expression of E-cadherin. To confirm this, we grew SCC3-Control-shRNA and SCC13-TG2-shRNA2 cells as monolayer cultures for immunostain detection of EMT markers. As shown in FIG. 16A, TG2 levels were reduced in TG2-shRNA expressing cells, and this was associated with the anticipated changes in epithelial and mesenchymal marker expression. Our results show that TG2 is required for expression of EMT markers.

Tumor cells that express EMT markers have been shown to display enhanced migration and invasion ability. We therefore examined the impact of TG2 reduction on these responses. To measure invasion, control-shRNA and TG2-shRNA cells were monitored for ability to move through matrigel. FIG. 16B shows that loss of TG2 reduced movement through matrigel by 50%. Further, this was associated with a reduction in cell migration in a monolayer culture wound closure assay. The control cells closed the wound completely within 14 h, while TG2 knockdown reduced closure rate (FIG. 16C).

Figure 17:
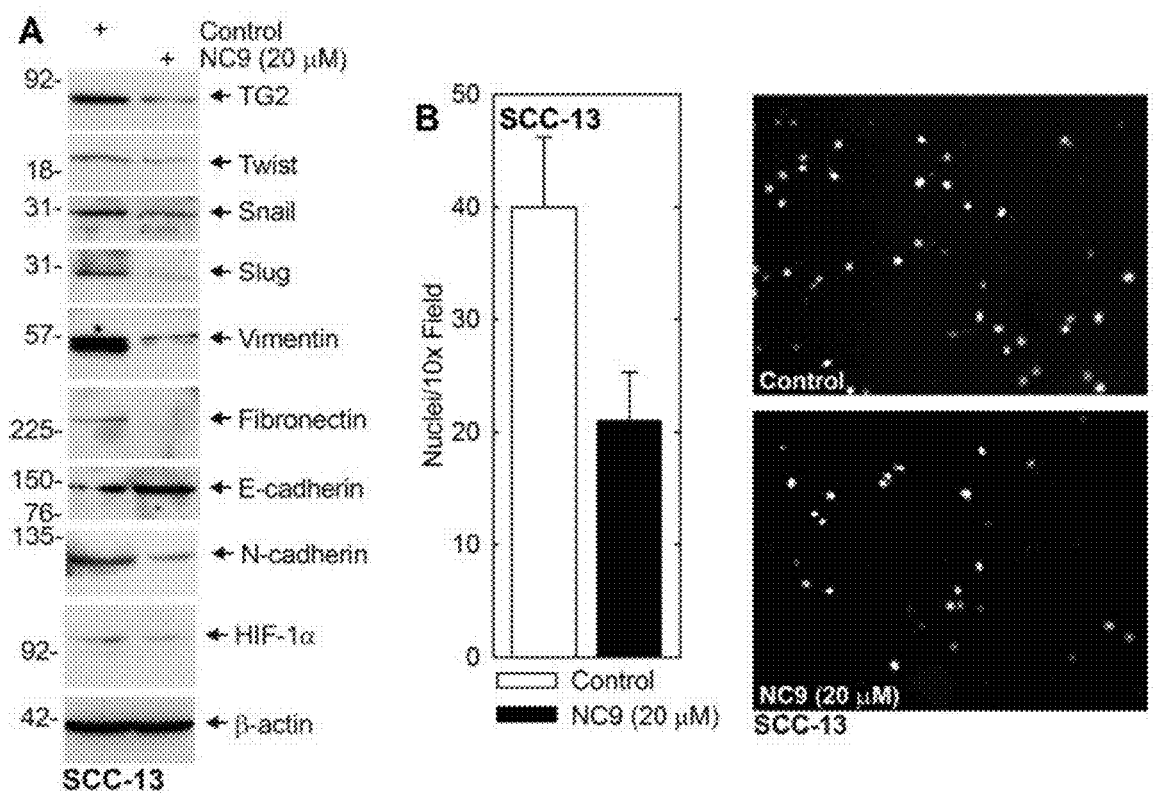
FIG. 17 shows NC9 reduces EMT protein expression and invasion/migration. In (A), SCC-13 cells (500,000) were plated in monolayer culture in spheroid medium in 100 mm dishes. Fresh spheroid medium containing 0 or 20 µM NC9 was added at time zero and again at 24 h. After 48 h lysates were collected for electrophoresis and immunoblot. In (B), SCC-13 cells were pretreated with 0 or 20 µM NC9 for 2 h and then harvested and plated (25,000 cells) in the upper chamber in 1 mL of medium, above a matrigel-coated membrane, in a Millicell chamber. After 30 h. the inside of membrane was harvested and the nuclei of migrated cells on the bottom of the membrane were counted using an inverted fluorescent microscope. The values are mean±SEM, n=3 (p, 0.05). In (C), SCC-13 (2 million) cells were plated in spheroid medium in 100 mm dishes and grown as monolayer cultures. Confluent monolayers were then scratched with a 10-µL pipette tip and wound width was monitored for 0-18 h. Similar results were observed in each of three experiments.
Figure 17:
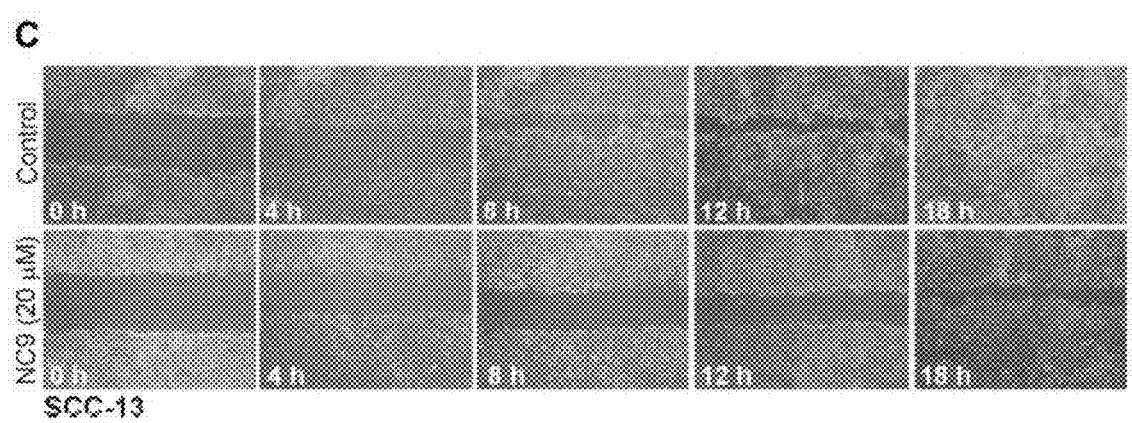

Next we asked whether pharmacologic inhibition of TG2 suppresses EMT, using the TG2-specific inhibitor NC9. SCC-13 cells were treated with 0 or 20 µM NC9. FIG. 17A shows that NC9 treatment reduced EMT transcription factor (Twist, Snail, Slug) and EMT marker (vimentin, fibronectin, N-cadherin, HIF-1α) levels. Consistent with these changes, the level of the epithelial marker, E-cadherin, was elevated. FIGS. 17B and 17C show that pharmacologic inhibition of TG2 activity also reduced EMT biological response. Invasion (FIG. 17B) and cell migration (FIG. 17C) were also reduced. Thus, a TG2 inhibitor reduced EMT marker expression and EMT functional responses.

Example 5. Identification of TG2 Functional Domain Required for EMT

Figure 18:
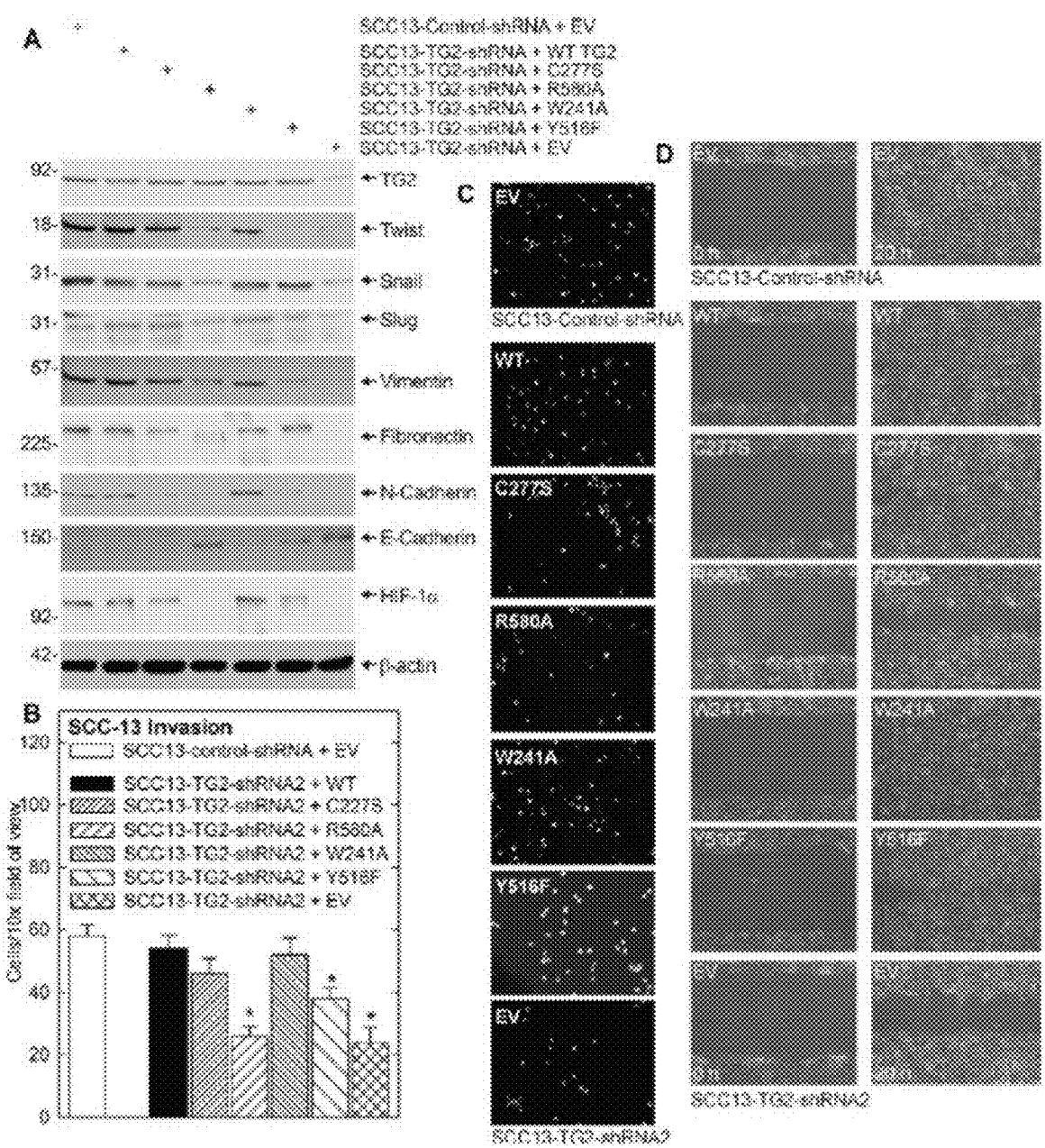
FIG. 18 shows TG2 GTP binding/G-protein function is necessary for EMT. In (A), TG2 impact on EMT marker expression is shown. SSC13-Control-shRNA or SCC13-TG2-shRNA2 cells were electroporated with 3 µg of empty vector (EV) or vector encoding the indicated TG2 proteins. The cells were then grown as monolayer cultures in spheroid medium for three days. The cells were then harvested and extracts prepared for electrophoresis and immunoblot detection of the indicated epitopes. Similar results were observed in three experiments. In (B), SCC13-TG2-shRNA2 cells were electroporated with plasmids encoding wild-type TG2, mutant TG2, or empty vector and grown in spheroid medium as monolayers. At 48 h post-electroporation, SCC13-Control-shRNA and SCC13-TG2-shRNA2 cells were harvested and seeded in the upper chamber above a matrigel-coated membrane in 1 mL of spheroid medium containing 1% serum in a Millicell chamber. The lower chamber included spheroid medium containing 10% serum. Nuclei of migrated cells were stained and counted on the lower surface of the membrane using an inverted fluorescent microscope. The values are mean±SEM, n=3 (p<0.01). In (C), images of DAPI-stained membrane are shown. In (D), SCC3-Control-shRNA and SCC13-TG2-shRNA2 cells were electroporated with empty vector (EV) or vector encoding the indicated TG2 proteins and grown in spheroid medium as monolayers. After 24 h, 2 million cells were plated in spheroid media on 100 mm dishes in monolayer conditions. The confluent monolayer cultures were then scratched with a 10-µL pipette tip and width of the wound was monitored at 0-18 h to assess closure. Similar results were observed in each of three experiments.

We next performed studies to identify the functional domains and activities required for TG2 regulation of EMT. As discussed above, TG2 is a multifunctional enzyme that serves as a scaffolding protein, as a transamidase, as a kinase, and as a GTP binding protein. The two best studied functions are the transamidase and GTP binding/G-protein related activities. Transamidase activity is observed in the presence of elevated intracellular calcium, while GTP binding-related signaling is favored by low calcium conditions. To identify the TG2 activity required for EMT, we measured the ability of wild-type and mutant TG2 to restore EMT in SCC13-TG2-shRNA2 cells, which have reduced TG2 expression (FIG. 18A). SCC13-TG2-shRNA2 cells displayed reduced expression of EMT markers including Twist, Snail, Slug, vimentin, fibronectin, N-cadherin and HIF-1α, and increased expression of the epithelial maker, E-cadherin, as compared to SCC3-Control-shRNA cells. Expression of wild-type TG2, or the TG2-C277S or TG2-W241A mutants, restored marker expression in SCC13-TG2-shRNA2 cells (FIG. 18A). TG2-C277S and TG2-W241A mutants are known to lack transamidase activity (Kumar, A. et al., Breast Cancer Res. 14:R4, 2012; Gundemir, S. et al., Biochim. Biophys Acta 1823:406-419, 2012; Gundemir, S. and Johnson, G. V., PLoS One 4:e6123, 2009; Gundemir, S. et al., Biochim. Biophys Acta 1833:1-10, 2013). In contrast, TG2-R580A, which lacks G-protein activity (Gundemir, S. et al., Biochim. Biophys Acta 1823:406-419, 2012; Gundemir, S. and Johnson, G. V., PLoS One 4:e6123, 2009; Gundemir, S. et al., Biochim. Biophys Acta 1833:1-10, 2013), and TG2-Y516F, which retains only partial G-protein activity (Gundemir, S. and Johnson, G. V., PLoS One 4:e6123, 2009), did not efficiently restore marker expression. These findings suggest that the TG2 GTP binding function is required for EMT.

We next assayed the ability of the TG2 mutants to restore EMT functional responses such as invasion and migration. FIGS. 18B and 18C show that wild-type TG2, TG2-C277S and TG2-W241A restored the ability of SCC13-TG2-shRNA2 cells to invade matrigel, but TG2-R580A and Y516F were less active. FIG. 18D shows a similar finding for cell migration, in that the TG2-R580A and Y517F mutant were only partially able to restore SCC13-TG2-shRNA2 cell migration. These findings suggest that TG2 GTP binding/G-protein related activity is required for EMT-related migration and invasion by skin cancer cells.

Figure 19:
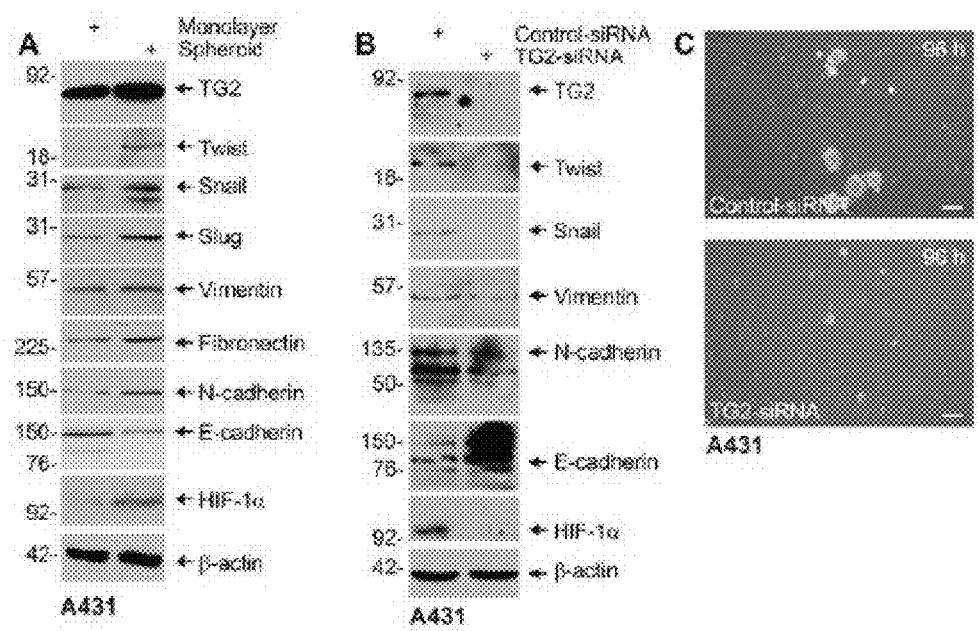
FIG. 19 shows TG2, EMT markers and EMT response in A431 cells. In (A), it is shown that A431-derived ECS cells have elevated TG2 and mesenchymal markers. A431 cells (40,000 cells/well) were grown in spheroid media in monolayer conditions or as non-attached spheroids (ECS cells) for 10 d. Cells were harvested and lysates prepared for immunoblot. In (B), A431 cells were electroporated with 3 µg of control- or TG2-siRNA and at 72 h extracts were prepared to assay TG2 and EMT marker level. In (C), A431-derived ECS cells were electroporated with 3 µg of the indicated siRNA and then grown as spheroids for 96 h. Similar results were observed in three separate experiments. In (D), A431 cells (500,000 cells/well) were plated in monolayer culture in spheroid media in 100 mm dishes. The following day, at time zero, 0 or 20 µM NC9 was added with fresh addition of medium and NC9 at 24 h. At 48 h the cells were harvested and extracts prepared for immunoblot. In (E), A431 cells were pretreated in 0 or 20 µM NC9 for 2 h and then harvested and 25,000 cells were seeded in the upper chamber above a matrigel-coated membrane in 1 mL of growth medium containing 1% FCS in a Millicell chamber. The lower chamber was filled with growth medium containing 10% FCS. After 30 h, the membrane was removed, washed and stained with DAPI, and an inverted fluorescent microscope was used to count the nuclei of migrated cells. In (F), A431 (40,000) cells were plated in spheroid media in non-attached conditions. On day 8, spheroids were treated with 0 or 20 µM NC9 and images were taken after 48 h to monitor spheroid fragmentation. In (G), A431 (2 million) cells were plated in spheroid media on 100 mm dishes and grown as monolayers. Confluent monolayers were then scratched with a 10-µL pipette tip, rinsed, and width of the wound was monitored for 0-14 h. Similar results were observed in each of three experiments.
Figure 19:
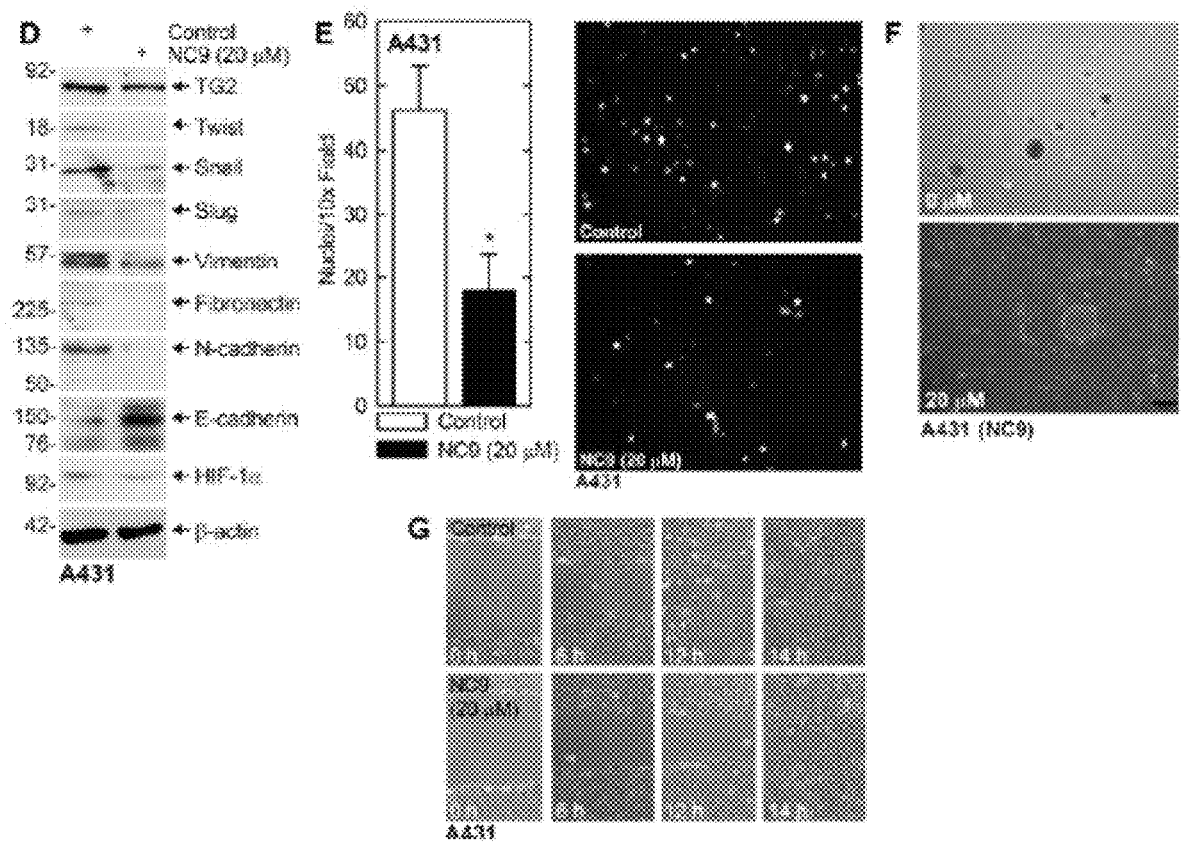

Next we characterized the role of TG2 in regulating EMT in A431 cells. As the number of available epidermis-derived squamous cell carcinoma cell lines is limited, we decided to compare our findings with A431 cells. A431 cells are squamous cell carcinoma cells established from human vulvar skin. A431 cells were grown as monolayer (non-stem cancer cells) and spheroids (ECS cells) and after 10 days the cells were harvested and assayed for expression of TG2 and EMT makers. FIG. 19A shows that TG2 levels were elevated in ECS cells and that this was associated with increased levels of mesenchymal markers, including Twist, Snail, Slug, vimentin, fibronectin, N-cadherin and HIF-1α. In contrast, E-cadherin levels were reduced.

We next examined the impact of TG2 knockdown on EMT marker expression. FIG. 19B shows that mesenchymal markers were globally reduced and E-cadherin level was increased. As a biological endpoint of EMT, we examined the impact of TG2 knockdown on spheroid formation and found that TG2 loss led to reduced spheroid formation (FIG. 19C). We next examined the impact of NC9 treatment on EMT and found a reduction in EMT markers expression associated with an increase in epithelial (E-cadherin) marker level (FIG. 19D). This loss of EMT marker expression was associated with reduced matrigel invasion (FIG. 19E), reduced spheroid formation (FIG. 19F) and reduced cell migration (FIG. 19G).

Example 6. Characterization of the Role of NFKB

Figure 20:
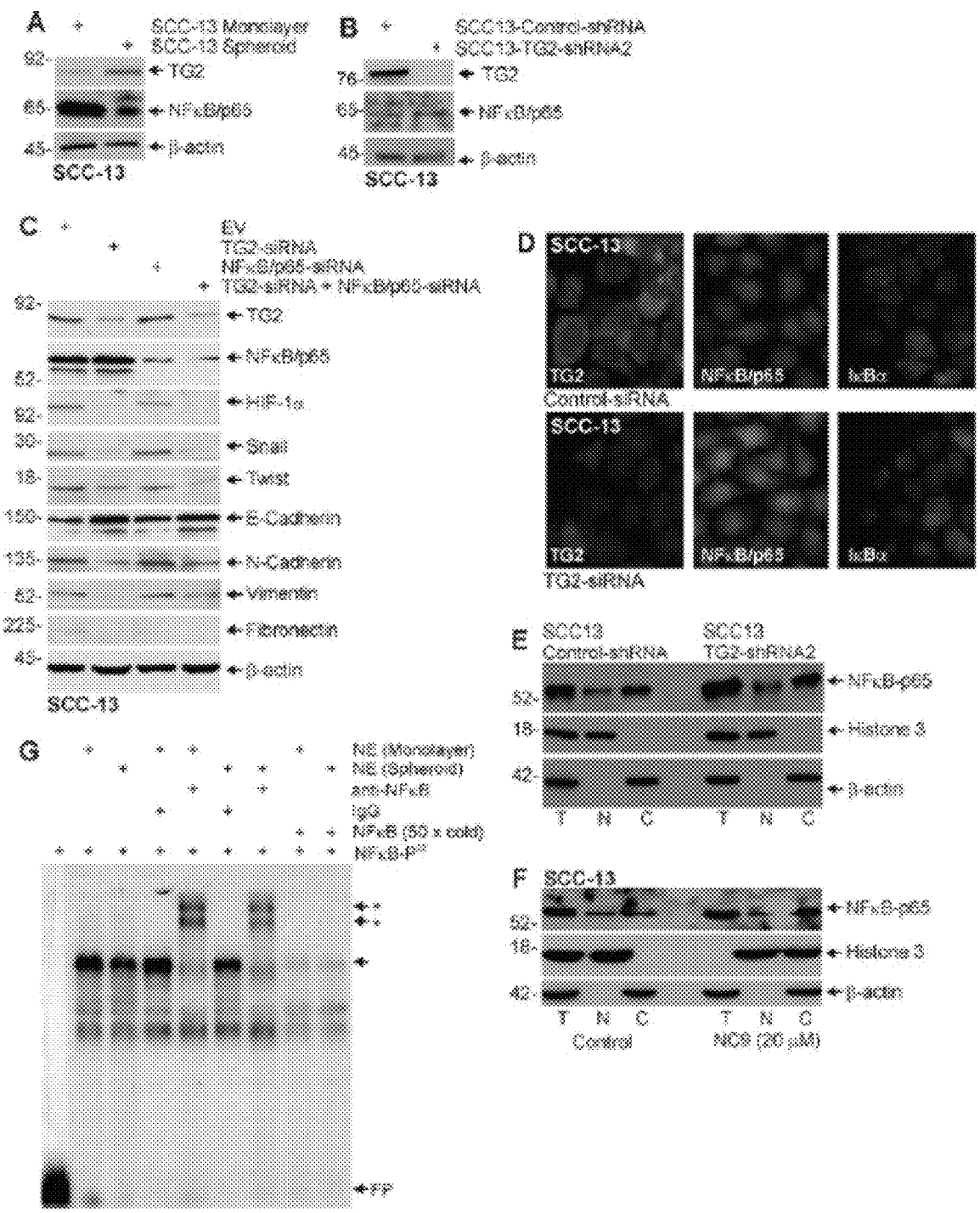
FIG. 20 shows NFκB expression is not required for EMT. In (A), it is shown that ECS cells have reduced NFκB-p65 levels. SCC-13 cells (40,000) were grown in spheroid medium in attached (monolayer) and non-attached (spheroid, ECS cells) conditions. Lysates were prepared after 10 d in culture for electrophoresis and detection of indicated epitopes. In (B). SCC3-Control-shRNA and SCC13-TG2-shRNA2 cells were grown in spheroid medium as monolayers. After 10 d in culture, lysates were collected for detection of TG2 and NFκB-p65. In (C), SCC-13 cells were electroporated with control-, NFκB-p65- or TG2-siRNA and then cultured as monolayers in spheroid medium. After 72 h extracts were prepared to assay TG2, NFκB-p65 and EMT markers. In (D), SCC-13 cells were electroporated with empty vector Control- or TG2-siRNA and plated in monolayer culture. The following day cells were fixed, permeabilized and incubated with antibodies specific for the indicated epitopes. Similar results were observed in each of three experiments. In (E), an equal number of cell equivalents of total (T), nuclear (N), and cytosolic (C) extract, prepared from SCC13-Control-shRNA and SCC13-TG2- shRNA2 (TG2 knockdown) cells, was electrophoresed for immunoblot detection of NFκB, histone 3 (nuclear marker) and β-actin (cytoplasmic marker). Similar results were observed in three separate experiments. In (F), total (T), nuclear (N), and cytosolic (C) extract was prepared from 8 day spheroids (ECS cells) treated with 0 or 20 μM NC9 for 48 h. An equal number of cell equivalents of total, nuclear and cytosol extract was electrophoresed for immunoblot detection with the indicated antibodies. Similar results were observed in three separate experiments. In (G), nuclear extract (NE), prepared from non-stem cancer cells (monolayer) or ECS cells (spheroids), was incubated with $^{32}$P-NFκB probe and electrophoresed on a non-denaturing 6% acrylamide gel. Various groups were incubated with IgG, anti-NFkB or a 50-fold (50×cold) molar excess of radioinert NFkB probe prior to electrophoresis. FP indicates free $^{32}$P-NFκB probe, the arrow indicates the gel mobility shift and the arrows with asterisks indicate the anti-dependent supershifted bands.

Previous studies in breast cancer, ovarian cancer, and epidermoid carcinoma have indicated that NFκB signaling mediates TG2 impact on EMT. We therefore assessed the role of NFκB in skin cancer cells. As shown in FIG. 20A, the increase in TG2 level observed in ECS cells (spheroids) was associated with reduced NFκB level. In addition, NFκB level was increased in TG2 knockdown cells (FIG. 20B). Thus, increased NFκB was not associated with increased TG2.

We next assessed the impact of NFκB knockdown on TG2 control of EMT marker expression. FIG. 20C shows that TG2 was required for increased expression of EMT markers (HIF-1α, snail, twist, N-cadherin, vimentin and fibronectin) and reduced expression of the E-cadherin epithelial marker; however, knockdown of NFκB expression did not interfere with TG2 regulation of these endpoints.

We next examined the effect of TG2 knockdown on NFκB and IκBα localization. The fluorescence images in FIG. 20D suggest that TG2 knockdown with TG2-siRNA did not alter the intracellular localization of NFκB or IκBα. This was confirmed by subcellular fractionation assay (FIG. 20E) which compared NFκB level in SCC13-TG2-Control and SCC13-TG2-shRNA2 (TG2 knockdown) cells. We also monitored NFκB subcellular distribution following treatment with NC9, the TG2 inhibitor. FIG. 20F shows that cytoplasmic/nuclear distribution of NFκB was not altered by NC9. Finally, we monitored the impact of TG2 expression on NFκB binding to a canonical NFκB-response element. Increased NFκB binding to the response element is a direct measure of NFκB activity (Kumar, A. et al., Breast Cancer Res. 14:R4, 2012). FIG. 20G shows that overall binding was reduced in nuclear (N) extract prepared from ECS cells (spheroids) as compared to non-stem cancer cells (monolayer), and that NFκB binding, as indicated by gel supershift assay, was also slightly reduced in ECS cell extracts. These findings indicate that NFkB binding was slightly reduced in ECS cells, which are TG2-enriched (FIG. 15A).

We next monitored the role of NFκB on biological endpoints of EMT. FIGS. 21A and 21B show that TG2 knockdown reduced migration through matrigel, but NFκB knockdown had no impact. Likewise, TG2 knockdown reduced wound closure, but NFκB knockdown did not. These findings suggest that NFκB does not mediate the pro-EMT actions of TG2 in epidermal squamous cell carcinoma.

In summary, we have characterized a population of ECS cells derived from epidermal squamous cell carcinoma and shown that these cells, which display enhanced migration and invasion, possess elevated levels of TG2. Moreover, these cells were enriched in expression of transcription factors associated with EMT (Snail, Slug, and Twist, HIF-1α) as well as mesenchymal structural proteins including vimentin, fibronectin and N-cadherin. Consistent with a shift to mesenchymal phenotype, E-cadherin, an epithelial marker, was reduced in level. Additional studies showed that TG2 knockdown resulted in a marked reduction in EMT marker expression and that this was associated with reduced ability of the cells to migrate to close a scratch wound and reduced movement in matrigel invasion assays. We also examined the impact of treatment with a TG2 inhibitor, NC9. NC9 is an irreversible active site inhibitor of TG2, that locks the enzyme in an open conformation (Caron, N. S. et al., PLoS One, 7:e44159, 2012; Al-Jallad, H. F. et al., PLos One: 6:e5893, 2011; Colak. G. et al., PLoS One 6:e16665, 2011; Clouthie, C. M. et al., Angew. Chem. Int. Ed. Engl. 51:12464-12468, 2012). NC9 treatment of ECS cells resulted in decreased levels of Snail, Slug and Twist. These transcription factors suppress E-cadherin expression and their decline in level is associated with increased levels of E-cadherin. NC9 inhibition of TG2 also reduced expression of vimentin, fibronectin and N-cadherin, and these changes were associated with reduced cell migration and reduced invasion through matrigel. Overall, our results have shown that TG2 is required for EMT in ECS cells.

We also examined the role of T02 in A431 squamous cell carcinoma cells derived from the vulva epithelium. TG2 was elevated in A431-derived ECS cells, as were EMT markers, and knockdown of TG2, with TG2-siRNA, reduced EMT marker expression and spheroid formation. Studies with NC9 indicated that NC9 inhibited A431 spheroid formation, EMT, migration and invasion. These studies indicated that TG2 is also required for EMT and migration and invasion in A431 cells. Based on these findings, we conclude that TG2 is essential for EMT, migration and invasion, and is likely to contribute to metastasis in squamous cell carcinoma.

As discussed above, TG2 is a multifunctional enzyme that can act as a transamidase, GTP binding protein, protein disulfide isomerase, protein kinase, protein scaffold, and DNA hydrolase, the two most studied functions being the transamidase and GTP binding functions. To identify the TG2 activity responsible for induction of EMT, we studied the ability of TG2 mutants to restore EMT in SCC13-TG2-shRNA2 cells, which express low levels of TG2 and do not express elevated levels of EMT markers or display EMT-related biological responses. These studies showed that wild-type TG2 restored EMT marker expression and the ability of the cells to migrate on plastic and invade matrigel. TG2 mutants that retain GTP binding activity (TG2-C277S and TG2-W241A) also restored EMT. In contrast, TG2-R580A, which lacks GTP binding function, did not restore EMT. This evidence suggested that the GTP binding function is essential for TG2 induction of the EMT phenotype in ECS cells. Recent reports have also suggested that the TG2 is important for maintenance of stem cell survival in breast and ovarian cancer cells.

To gain further insight into the mechanism of TG2 mediated EMT, we examined the role of NFκB. NFκB has been implicated as mediating EMT in breast, ovarian, and pancreatic cancer, however, NFκB may have a unique role in epidermal squamous cell carcinoma. Here we have shown that TG2 levels were elevated and NFκB levels were reduced in ECS cells as compared to non-stem cancer cells, and that TG2 knockdown was associated with increased NFκB level. In addition, TG2 knockdown, or inhibition of TG2 by treatment with NC9, did not alter the nuclear/cytoplasmic distribution of NFκB. We further showed that elevated levels of TG2 in spheroid culture resulted in a slight reduction in NFκB binding to the NFκB response element, as measured by gel mobility supershift assay. These molecular assays strongly suggested that NFκB does not mediate the action of TG2 in epidermal cancer stem cells. Moreover, knockdown of NFκB-p65 in TG2 positive cells did not result in a reduction in Snail. Slug and Twist, or mesenchymal marker proteins expression, and concurrent knockdown of TG2 and NFκB did not reduce EMT marker protein levels beyond that of TG2 knockdown alone. These findings suggested that NFκB is not an intermediary in TG2-stimulated EMT in ECS cells, in contrast to reports of the required role of NFκB in mediating TG2 induction of cell survival and EMT in breast cancer cells, ovarian cancer, and epidermoid carcinoma.

Materials and Methods for Examples 4-6

Reagents. Cells were maintained as monolayer cultures in growth medium including DMEM (Invitrogen, Frederick, Md.) supplemented with 4.5 mg/ml D-glucose, 200 mM L-glutamine, 100 mg/ml sodium pyruvate, and 5% fetal calf serum. Heat-inactivated fetal calf serum (FCS, F4135) and anti-β-actin (A5441) were purchased from Sigma (St. Louis, Mo.). Cell lysis Buffer (9803) was purchased from Cell Signaling Technology (Danvers, Mass.). Anti-TG2 (2187378) was purchased from EMD Millipore (Bedford, Mass.). Antibodies for HIF-1α (ab113642), Twist (ab49254) and Slug (ab27568) were purchased from Abcam. Antibodies for vimentin (5741) and Snail (3895) were purchased from Cell Signaling Technologies. NFκB-p65 antibody (sc-109) was purchased from Santa Cruz (Santa Cruz, Calif.). Anti-E-cadherin was purchased from Epitomics (Ab40772). N-cadherin (610920) and fibronectin (610077) antibodies were purchased from BD Biosciences (San Jose, Calif.). Peroxidase-conjugated anti-mouse IgG (NXA931) and anti-rabbit IgG (NA934V) were obtained from GE Healthcare (Buckinghamshire, UK). Alexa Fluor 555 goat anti-mouse IgG (A21424) and Alexa Fluor 488 goat-anti-rabbit IgG (A11034) were purchased from Invitrogen. DAPI (D9542) was purchased from Sigma (St. Louis, Mo.). NC9 synthesis was as described previously (Keillor, J. et al., Can. J. Chem. 86:271-276, 2008; Caron, N. S. et al., PLoS One 7:e44159, 2012). TG2-(sc-37514) and control-siRNA (sc-37007) were purchased from Santa Cruz (Dallas, Tex.). Matrigel (354234) and BD Biocoat cell inserts (353097) were purchased from BD Biosciences.

Immunoblot. Equivalent amounts of protein were electrophoresed on denaturing and reducing 10% polyacrylamide gels and transferred to nitrocellulose membrane. The membrane was blocked by 5% nonfat dry milk for 1 hour (h) and incubated with primary antibody (diluted 1:1000) in 5% nonfat dry milk. Blots were rinsed and then incubated with secondary antibody (diluted 1:5000) for 2 h. Secondary antibody binding was visualized using ECL Prime chemiluminescence detection technology (Amersham).

TG2-shRNA lentivirus production. TG2-shRNA encoding lentivirus was produced using 293T packaging cells maintained in Dulbecco's modified Eagle's medium containing 1 mM L-glutamine, 1 mM sodium pyruvate and 10% fetal calf serum. Cells were plated in 100 mm dishes at 50% confluence 24 h prior to transfection. The media was removed, and the cells washed with Hank's Balanced Salt Solution and transferred to serum-free growth medium 24 h before transfection with 1 µg of pCMV-VSVG, 0.5 µg pCMV-dr8.91 and 0.5 µg TG2-shRNA encoding plasmid. pCMV-VSVG (8454) and pCMV-dr8.91 were purchased from Addgene and kindly provided by Dr. C Y Lin. The lentivirus plasmids, pLKO.1-NT-Puro-shRNA (Control) (SHC016) and pLKO.1-Puro-hTGM2-shRNA (TRCN-0000272760) were from Sigma-Aldrich (St. Louis, Mo.). At 3 h post-transfection, fresh medium containing 10% FCS was added. After an additional 72 h the conditioned-medium was collected, centrifuged for 15 min at 1,500 RPM, filtered through a 22 µm filter and pipetted into aliquots for storage at −80° C.

Stable TG2 knockdown cell lines. SCC-13 cells ($1\times10^5$) were plated in 24 well cluster plates and allowed to attach overnight, followed by incubation with 1 ml of pLKO.1-Puro-hTGM2-shRNA lentivirus in serum-free growth media containing 8 µg/ml polybrene at 37° C. for 5 h. The media was then supplemented with 5% fetal calf serum followed by selection for two weeks with 0.25 µg/ml puromycin. The resulting cells were infected a second time with the same virus and reselected with puromycin to produce the SCC13-TG2-shRNA2 cell line. TG2 knockdown was confirmed by anti-TG2 immunoblot. A control cell line, SCC13-Control-shRNA, was produced by double infection with pLKO.1-Puro-NT-shRNA lentivirus, which encodes control-shRNA, using an identical protocol.

Spheroid formation assay. Cells, maintained as monolayer cultures in growth medium consisting of DMEM (Invitrogen, Frederick, Md.) supplemented with 4.5 mg/ml D-glucose, 200 mM L-glutamine, 100 mg/ml sodium pyruvate, and 5% fetal calf serum, were harvested, collected by centrifugation, and resuspended in spheroid medium comprising DMEM/F12 (1:1) (DMT-10-090-CV, Mediatech Inc., Manassas, Va.) supplemented with 2% B27 serum-free supplement (17504-044, Invitrogen, Frederick, Md.), 20 ng/ml EGF (E4269, Sigma, St. Louis, Mo.), 0.4% bovine serum albumin (B4287, Sigma) and 4 µg/ml insulin (19278 Sigma, St. Louis, Mo.). The cells (40,000) were plated in 9.6 $cm^2$ wells in Costar six well ultra-low attachment cluster dishes (4371, Corning, Tewksbury, Mass.). Spheroid size and number was monitored with time in culture as previously described (Adhikary, G. et al., PLoS One 8:e84324, 2013).

Electroporation of nucleic acids. Cells were maintained in monolayer culture in growth medium. Near-confluent cultures were harvested the day prior to electroporation and plated in 60 mm dishes in growth medium. After 24 h, when 50% confluent, the cells were re-trypsinized, centrifuged at 200×g, and replated. The next morning $1\times10^6$ cells were harvested, washed with sterile phosphate-buffered saline, suspended in 100 µl of keratinocyte nucleofection reagent containing 3 µg of plasmid or siRNA and electroporated using the Amaxa Electroporator on the T-018 setting (Adhikary, G. et al., J. Invest. Dermatol. 130(8):2017-30, 2010). Immediately after electroporation, the cells were resuspended in pre-warmed medium and plated. When siRNA was used, the cells were harvested at 72 h post-electroporation and re-electroporated a second time. This double electroporation assured sustained target knockdown.

Invasion assay. Matrigel was diluted in 0.01 M Tris-HCl/0.7% NaCl, filter sterilized and 0.1 ml was used to coat individual BD BioCoat inserts (Millicell-PCF, 0.4 µm, 12 mm, PIHP01250). Cells (25,000) were plated in 100 µl in growth medium, supplemented with 1% FCS, in the upper chamber. The lower chamber contained growth medium supplemented with 10% FCS. After migration, the membranes were harvested and excess cells were removed from the upper membrane surface. The membrane was fixed in 4% paraformaldehyde, stained with 1 µg/m DAPI, and the underside of the membrane was photographed with an inverted fluorescent microscope and the number of cells counted.

Migration assay. SCC13-Control-shRNA or SCC13-TG2-shRNA2 cells ($2\times10^6$) were plated in 10 cm dishes and grown as monolayer cultures in spheroid medium until confluent. A 10 µl pipette tip was used to prepare areas void of cells and the dishes were washed to remove the dislodged cells. Images were collected, at 0-18 h after the scratch using the 10× objective, and the width of the opening was measured as a function of time as an index of cell migration potential.

Gel mobility shift assay. For gel mobility shift assay, 3 µg of nuclear extract was incubated for 30 min at room temperature in a 20 µl volume containing 20 mM HEPES, pH 7.5, 10% glycerol, 50 mM KCl, 2 mM $MgCl_2$, 0.5 mM EDTA, 0.5 mM DTT, 1 mg/ml poly(dI:dC), 0.1 mg/ml bovine serum albumin, and 40,000 cpm radioactive double-stranded $^{32}$P-NFκB binding site oligonucleotide (5' AGTT-GAGGGACTTTCCCAGGC). For competition studies, a 50-fold molar excess of non-radioactive competitor NFκB oligonucleotide was added to the DNA binding reaction. For gel mobility supershift assay, 2 µg of normal rabbit IgG (sc-3888) or rabbit anti-NFκB (sc-109), purchased from Santa Cruz Biotechnology, was added to the reaction mixture and incubated 1 h at 25° C. The $^{32}$P-labeled probe was then added and the incubation was continued for an additional 30 min at 25° C. Protein-DNA complexes were resolved by electrophoresis on a 6% polyacrylamide non-denaturing gel (Han, B. et al., PLoS One 7:e36941, 2012).

Cell fractionation. Cell fractionation was performed using the NE-PER Nuclear and Cytoplasmic Extraction Kit (78440) and Halt protease inhibitor (78440) obtained from Thermo-Scientific (Waltham, Mass.). Four million cells were trypsinized, washed in phosphate-buffered saline and pelleted. The pellet was resuspended in 200 µl of ice cold CER I buffer and maintained for 10 min on ice. Ice-cold CER II buffer (50 µl) was added, the sample was vortexed and maintained on ice for 1 min prior to centrifugation. The supernatant (cytosol) was then collected as a total volume of 250 µl and stored at −80° C. The nuclear pellet was suspended, by repeated vortexing, in 50 µl of ice cold NER buffer over 40 min. The sample was then centrifuged for 10 min and the nuclear extract was stored at −80° C. until use. For analysis, 0.56 million cell equivalents of nuclear (35 µl) or cytosolic (7 µl) extract was electrophoresed for immunoblot detection of NFκB, histone H3 and β-actin.

Example 7. Characterization of TG2 in ECS Cell Survival and Spheroid Formation

Cancer stem cells (CSCs) are thought to be responsible for rapid tumor growth, metastasis and enhanced tumor survival following drug treatment. We report herein studies that identify TG2 as a potential target for anticancer stem cell therapy in human squamous cell carcinoma. TG2 was determined to be highly elevated in epidermal cancer stem cells (ECS cells) and TG2 knockdown or suppression of TG2 function with inhibitors reduced ECS cell survival, spheroid formation, matrigel invasion and migration. The reduction in survival was associated with activation of apoptosis. Mechanistic studies, using TG2 mutants revealed that the GTP-binding activity was required for maintenance of ECS cell growth and survival, and that the action of TG2 in ECS cells was not mediated by NFκB signaling. Our studies suggest that TG2 has an important role in maintaining cancer stem cell survival, invasive and metastatic behavior, and is an important therapeutic target to reduce survival of cancer stem cells in epidermal squamous cell carcinoma.

Previously, it was shown that ECS cells, which comprise less than 0.2% of the total cancer cell population, can be isolated from bulk SCC-13 cancer cells by growth as spheroids in non-attached conditions (Adhikary, G. et al., PLoS One 8:e84324, 2013). We found that ECS cells (spheroids) were highly enriched for expression of TG2 as compared to non-stem cell (monolayer) cultures (FIG. 22A), and that this expression was associated with expression of stem cell markers, including Oct4, Nanog and Sox2 (FIG. 22A). To determine whether TG2 has a role in ECS cell survival/maintenance and spheroid formation, we treated SCC-13 cells with control- or TG2-siRNA to knockdown TG2 (FIG. 22B) and monitored ability to form spheroids. Markedly fewer spheroids were formed by TG2 knockdown cells (FIG. 22C). Moreover, loss of spheroid formation, following TG2 knockdown, was associated with accumulation of single cells (FIG. 22D).

To confirm this finding, we prepared TG2-negative cell lines by infection of SCC-13 cells with TG2-shRNA encoding lentivirus. FIG. 22E confirms that the SCC13-TG2-shRNA2 cells, which had reduced TG2 expression (FIG. 22F), formed spheroids less efficiently than SCC13-control-shRNA cells. Most SCC13-TG2-shRNA2 cells remained as single cells (FIG. 22G). However, some spheroid formation was observed in SCC13-TG2-shRNA2 cultures, and we wondered whether this was due to TG2 re-expression. To test this, we grew SCC13-TG2-shRNA2 cells as non-attached spheroids for 10 days (d) and then isolated spheroids and single cells for preparation of extracts. FIG. 22H reveals that the few spheroids that did form expressed TG2, further suggesting that TG2 is required for spheroid formation.

We next studied the impact of TG2 inhibitor on spheroid formation. Spheroids were grown for 8 days and then treated with NC9, an irreversible inhibitor of TG2 transamidase (TGase, crosslinking) activity (Keillor, J. et al., Can. J. Chem. 86:271-6, 2008). NC9 treatment reduced spheroid number (FIG. 23A) which was associated with accumulation of spheroid fragments and single cells (FIG. 23B). A key issue is whether the NC9 treatment reduced cell viability. As shown in FIG. 23C, as assessed by ability to exclude trypan blue, NC9 caused a concentration-dependent reduction in viable cell number. FIG. 23D shows that the reduction in TG2 activity was not associated with reduced TG2 level. This indicates that TG2 knockdown (FIG. 22) or inhibition of activity (FIG. 23) reduced ECS cell survival.

To confirm that NC9 inhibits TG2 transamidase (TGase) activity, we loaded cells with fluorescein cadaverine (FC), a known transglutaminase substrate, added 0 or 20 μM NC9, activated TG2 TGase activity by treatment with calcium ionophore and monitored for intracellular incorporation of the fluorescent label. This experiment shows that TG2 activity was reduced by NC9 treatment (FIG. 23E). To gain some insight regarding the mechanism, we monitored for cleavage of procaspase 3. FIG. 23F shows that the response to NC9 included cleavage of procaspase 3 and that this cleavage was initiated within 1 h after NC9 addition.

We next assessed whether NC9 can prevent spheroid formation initiated from single cells. We seeded SCC-13 single cells in spheroid growth conditions and after 12 hours (h) added NC9, and monitored spheroid number over fourteen days. We did not replenish the medium or add fresh NC9 during this time course. Spheroid number increased in all groups until day eight, but then selectively declined in the NC9 treated groups (FIG. 24A). This was associated with morphological survival of the spheroids until 8 d and progressive destruction from 8 to 14 d (FIG. 24B) indicating that spheroids could form in the presence of NC9, but that fully formed spheroids underwent NC9-associated destruction. This is consistent with NC9-related destruction of mature spheroids shown in FIG. 23. In addition, the findings shown in FIG. 24 suggest that a single treatment with NC9 produced long-lasting effects on ECS cell survival and spheroid formation.

We next monitored the impact of another transglutaminase inhibitor, fluorescein cadaverine (FC), on spheroid formation. FC acts as a competitive substrate inhibitor of transglutaminase that prevents TG2 interaction with intracellular targets (Sturniolo, M. T. et al., Oncogene 24:2963-72, 2005; Sturniolo, M. T. et al., J. Biol. Chem. 278:48066-73, 2003). Spheroids were grown for 8 d and then treated with FC. FC treatment reduced spheroid number and promoted accumulation of spheroid fragments and dissociated single cells (FIGS. 24C and D).

We recently demonstrated that epidermal cancer-derived ECS cells migrate more efficiently than non-stem cancer cells (Adhikary, G. et al., PLoS One 8:e84324, 2013). To determine whether this requires TG2, we monitored the ability of TG2 knockdown cells to invade Matrigel and close a scratch wound. FIGS. 24E-F shows that TG2 loss reduced cell migration through Matrigel. FIG. 24G shows that ability of cells to close a scratch wound was also reduced in the absence of TG2 (FIG. 24G). Moreover, FIG. 24H shows that pretreating the cells with NC9 reduced matrigel invasion. These results show that TG2 was required for ECS cell migration.

The two most important enzymatic functions of TG2 are the TGase and GTP binding activities (Gundemir, S. et al., Biochim. Biophys. Acta 1823:406-19, 2012). We therefore examined which activity is required for ECS cell spheroid formation. To accomplish this, we measured the ability of wild-type and mutant TG2 to restore SCC13-TG2-shRNA2 cell spheroid formation. Plasmids encoding wild-type and mutant TG2 forms were delivered by electroporation. The mutants included C277S (no TGase activity, partial GTP binding activity), R580A (wild-type TGase activity, no GTP binding activity), W241A (no TGase activity, wild-type GTP binding activity) and Y516F (partial TGase activity, partial GTP binding activity) (FIG. 25A) (Gundemir, S. et al., PLoS One: 4:e6123, 2009). FIG. 25B shows that each electroporated mutant was expressed at a comparable level. We also show (FIG. 25C) that each mutant localized in a pattern which resembles that of wild-type endogenous TG2 (SCC13-Control-shRNA, EV) and that SCC13-TG2-shRNA2 cells expressed reduced levels of TG2. These results shows that TG2 GTP binding function was required for activity.

We next assessed the ability of wild-type and mutant TG2 to drive spheroid formation. The time course in FIG. 25D shows that SCC13-TG2-shRNA2 cells (TG2 knockdown) formed 80% fewer spheroids than empty vector (EV)-electroporated SCC13-Control-shRNA cells when measured at 5 days. We next examined the ability of wild-type TG2 and TG2 mutants to restore SCC13-TG2-shRNA2 cell spheroid formation (FIG. 25D). The general trend was the same at all times. Considering the 5 d time point, expression of wild-type TG2 restored spheroid number to approximately 80% of control. Mutants C277S and W241A, which retain partial and full GTP binding function, respectively, also largely restored spheroid formation. In contrast, Y516F, which retains partial GTP binding activity, slightly restored spheroid formation, and R580A, which lacks GTP binding function, did not restore spheroid formation. The fact that C277S and W241A, which lack TGase activity, restored spheroid formation, suggests that TGase activity was not required.

We also examined the impact of wild-type TG2 and mutants on cell migration and wound closure. SCC13-TG2-shRNA2 cells (TG2 knockdown) had reduced efficiency of wound closure compared to SCC13-Control-shRNA cells which expressed normal endogenous levels of TG2 (FIG. 26A). Mutants C277S and W241A, which retain partial and full GTP binding function, respectively, largely restored wound closure. Y516F, which retains partial GTP binding activity, was also effective, but R580A, which lacks GTP binding function, was largely ineffective (FIG. 26A). The fact that C277S and W241A, which lack TGase activity, enhanced closure, suggests that TGase activity was not required. FIG. 26B shows the wound images at the 20 h time point for a representative experiment. FIG. 26C shows that these cell lines showed no difference in cell number over three days of growth, suggesting that differences in cell proliferation rate cannot explain the marked difference in wound closure and invasions rates.

We wanted to compare these findings in another squamous cell carcinoma cell type. We chose A431 cells, as we have previously shown that spheroid-forming ECS cells comprise 0.03% of this cell population (Adhikary, G. et al., PLoS One 8:e84324, 2013). These cells are derived from human vulvar skin. FIG. 27A reveals that TG2 level was substantially elevated in A431-derived ECS cells.

We next examined the impact of TG2 knockdown or treatment with NC9 on spheroid formation. Electroporation of A431 ECS cells with TG2-siRNA reduced TG2 level (FIG. 27B). As shown in FIG. 27C, TG2 loss reduced A431 cell spheroid formation by seventy percent. Moreover, the ability of A431 ECS cells to invade Matrigel was reduced by 50% in the presence of NC9, as was ability to close a scratch wound (FIGS. 27E-F). Inhibitor data is shown in FIG. 27G, also showing that GTP binding was required for ECS cell function. These results show that TG2 was also required for survival and migration of A431 ECS cells.

Experiments displayed in FIGS. 24E-F show that TG2 was required for ECS cell invasion through matrigel. Previous studies have implicated NFκB as a mediator of TG2-dependent EMT-related processes in several cancer cell types. We therefore examined whether NFκB plays a role in mediating these processes in SCC-13 cells. ECS cells were electroporated with control- or NFκB-siRNA before plating on matrigel. FIGS. 28A-B show that NFκB knockdown did not reduce ECS cell invasion, and FIG. 28C confirmed the knockdown.

We next determined whether NFκB knockdown attenuates TG2 stimulation of invasion. SCC13-TG2-shRNA2 cells were electroporated with plasmid encoding wild-type TG2 in the presence or absence of NFκB-siRNA. FIGS. 28D-E show that expression of TG2 enhanced invasion, and that TG2-simulated invasion was not reduced by NFκB knockdown. FIG. 28F confirms the elevation of TG2 and the knockdown of NFκB. We also examined the impact of NFκB knockdown on ECS cell migration. FIG. 28G shows that NFκB knockdown did not alter the rate of ECS cell wound repair (migration). Interestingly, recent studies have suggested that in some cancer cell types TG2 activates NFκB to promote cancer cell survival, in contrast to our findings that knockdown of TG2 does not impair TG2 regulation of invasion or migration (FIG. 28) or spheroid formation or EMT (not shown). NFκB has been described as having a unique role in epidermal cells where it actually inhibits cell proliferation (Zhang, J. Y. et al., Genes Dev. 18:17-22, 2004), and this difference in properties may explain the lack of a role for NFκB as a TG2 mediator in ECS cells.

We also assessed the likelihood that other transglutaminase forms may be involved in the regulation. Transformed keratinocytes express relatively low levels of TG1 and FXIIIa. FIG. 28H shows that ECS cells (spheroids) expressed elevated levels of TG; however, there was no change in FXIIIa or TG1 levels. FIG. 28I shows that knockdown of TG2 in ECS cells was associated with a slight increase in TG1 and FXIIIa level. The fact that these enzymes changed minimally in level in ECS cells as compared to non-stem cancer cells, and were minimally impacted by TG2 knockdown, suggests they did not play a role in the observed loss of ECS cell properties observed following TG2 loss.

In summary, we have characterized putative epidermal cancer stem cells established from epidermal squamous cell carcinoma cells. These ECS cells can be selected by growth in non-attached conditions (Adhikary, G. et al., PLoS One 8:e84324, 2013). Under these conditions, <0.2% of the cells form spheroids and express a host of epidermal and embryonic stem cell markers. When injected into immune compromised mice, these cells form large, rapidly growing, aggressive, invasive and highly-vascularized tumors. This is in contrast to the small and non-vascularized tumors that form upon injection of cell population comprised largely of non-stem cells. Moreover, injection of as few as one-hundred ECS cells can drive formation of large vascularized tumors. These cells also display enhanced mobility and invasion of Matrigel. The fact that these cells are readily able to form aggressive tumors, as compared to non-stem cells, confirms that they are important targets for cancer prevention and therapy. TG2 is important in several epithelial cancers, and we examined expression of TG2 in skin cancer. Our studies show that TG2 levels were markedly elevated in ECS cells as compared to bulk cultures of cancer cells. Moreover, knockdown of TG2 using siRNA or by creating stable TG2 knockdown cell lines resulted in a marked reduction in ECS cell survival and spheroid formation. Inhibition of TG2 resulted in destruction of pre-established ECS cell spheroids and suppression of spheroid growth. Moreover, TG2 knockdown cells displayed a reduced ability to form spheroids.

We have also examined the impact of TG2 inhibitors on ECS cell survival and spheroid formation. Treating ECS cells with NC9 inhibited spheroid formation and also promoted destruction of pre-existing spheroids, and this was associated with inhibition of TGase activity. Our studies strongly suggest that NC9 inhibits both GTP binding and transamidation activity and show that NC9 causes ECS cell apoptosis and reduced viability. Overall, these observations suggest that inhibiting TG2 disrupts multiple ECS cell processes. In particular, TG2 appears to be required for ECS cell spheroid formation, survival, migration and invasion. Survival, migration and invasion are properties known to be required for tumor cell extravasation during metastasis, suggesting that TG2 may be required for in vivo metastasis.

Materials and Methods for Example 7

Antibodies and reagents. Dulbecco's modified Eagle's medium (11960-077), sodium pyruvate (11360-070), L-Glutamine (25030-164) and 0.25% trypsin-EDTA (25200-056)

were purchased from Gibco (Grand Island, N.Y.). Heat-inactivated fetal calf serum (FCS, F4135), anti-β-actin (A5441) and A23187 ionophore (C7522), trypan blue (T8154) were purchased from Sigma (St. Louis, Mo.). Cell lysis Buffer (9803) was purchased from Cell Signaling Technology (Danvers, Mass.). Anti-TG2 (MAB3839) was purchased from EMD Milipore (Bedford, Mass.). Antibody for Sox2 (ab15830-100) was purchased from Abcam. Antibodies for caspase-3 (9665) and Nanog (4839), and NFκB-p65 siRNA (6261) were purchased from Cell Signaling Technologies. Anti-Oct4 (611203) was purchased from BD Transduction Laboratories (San Jose, Calif.). Peroxidase-conjugated anti-mouse IgG (NXA931) and anti-rabbitIgG (NA934V) were obtained from GE Healthcare (Buckinghamshire, UK). Production of NC9 was described previously (Keillor, J. et al., Can. J. Chem. 86: 271-6, 2008). TG2-(sc-37514) and control-siRNA (sc-37007) were purchased from Santa Cruz (Dallas, Tex.). Anti-TG1 (SC-166467) and anti-NFκB-p65 (sc-109) were purchased from Santa Cruz (Dallas, Tex.). Anti-FXIIIa (ab79759) was purchased from Abcam. Fluorescein cadaverine (FC) was purchased from Life Technologies. BD Biocoat cell inserts (353097) and Matrigel (354234) were purchased from BD Biosciences. Proteins were detected by immunoblot as described (Efimova, T. et al., J. Biol. Chem. 273:24387-95, 1998; Efimova, T. et al., J. Biol. Chem. 277: 31753-60, 2002).

Plasmids. Plasmids encoding wild-type TG2 and TG2 (C277S) cloned in EC1214 vector were provided by Dr. Kapil Mehta. Plasmids encoding TG2(R580A), TG2 (Y526F0), TG2(W241A), cloned in pcDNA3.1 were provided by Dr. Gail Johnson (Gundemir, S. et al., Biochim. Biophys. Acta 1823:406-19, 2012; Gundemir, S. et al., PLoS One 4:e6123, 2009; Ruan, Q. et al., Int. J. Clin. Exp. Med. 1:248-59, 2008).

Lentivirus production. Lentiviruses were packaged using 293T cells which were maintained in DMEM containing 1 mM sodium pyruvate, 1 mM L-glutamine and 10% fetal calf serum (FCS). The cells were harvested and plated in 100 mm dishes at 60% confluence 24 hours prior to transfection. The serum-containing medium was removed and the cultures washed with Hank's Balanced Salt Solution prior to co-transfection with 1 μg pCMV-VSVG, 0.5 μg pCMV-dr8.91 and 0.5 μg shRNA encoding plasmid in serum-free medium. pCMV-VSVG (8454) and pCMV-dr8.91 were purchased from Addgene and kindly provided by Dr. C Y Lin. After 3 hours the medium was supplemented with 10% FCS and after an additional 72 hours the medium was collected, centrifuged at 1500 rpm for 15 min, forced through a 22 μm filter, aliquoted at 1 ml/tube and stored frozen at −80° C. The lentivirus plasmids, pLKO.1-Puro-NT-shRNA (Control) and pLKO.1-Puro-hTGM2-shRNA (TRCN-0000272760), were purchased from Sigma-Aldrich (St. Louis, Mo.).

Production of TG2 knockdown stable cell lines. SCC-13 cells ($1\times10^5$) were allowed to attach overnight in 24 well cluster plates and then infected with TG2-shRNA encoding lentivirus in serum-free growth media for 5 hours at 37° C. The serum-free growth media contained 8 μg/ml polybrene. The medium was then replaced with 5% fetal calf serum supplemented growth media and near-confluent cells were harvested, plated at low density in 100 mm dishes and selected for two weeks in the presence of 0.25 μg/ml puromycin. These cells were then infected a second time with the same virus and reselected. The resulting cells were a non-clonal population of cells we call SCC13-TG2-shRNA2. A control population of cells (SCC13-Control-shRNA) was derived by double infection with control-shRNA (scrambled) encoding lentivirus using an identical protocol.

Spheroid formation assay. Spheroid formation assays were exactly as outlined previously (Adhikary, G. et al., PLoS ONE 8:e84324, 2013), except that the spheroids were grown in six well ultra-low attachment Costar cluster dishes (4371, Corning, Tewksbury, Mass.).

Electroporation of nucleic acids. Cells were electroporated exactly as outlined previously (Adhikary, G. et al., J. Invest. Dermatol., 130(8):2017-30, 2010). In applications using siRNA, the cells were harvested 72 hours post-electroporation and electroporated a second time following the same protocol (double-electroporation). This resulted in sustained knockdown of the target transcript.

Insitu TG2 activity assay. Cells (40,000) were plated in 24-well attachment dishes in spheroid media and grown until 50% confluent. Fluorescein cadaverine (FC) was added in 2 mL of serum-free medium at a final concentration of 20 μM and incubated for 4 hours. The wells were washed twice with serum-free spheroid medium, and then 2 mL of fresh serum-free medium was added containing 0-20 μM NC9. After 30 min, the wells were supplemented with 10 μM A23187. Cells were incubated for an additional 90 min and then washed three times with $Ca^{++}/Mg^{++}$-free HBSS, fixed with formalin, and washed with phosphate-buffered saline and imaged to detect fluorescein.

Trypan Blue viability assay. SCC-13 cells were grown as spheroids in six well cluster dishes in spheroid medium for 8 days and then treated with 0-20 μM NC9. At 0, 24, 48, and 72 hours post-NC9 treatment, spheroids were counted, and all cells in the well were collected to prepare a single cell suspension in Hank's Balanced Salt Solution. Trypan Blue solution (0.5 mL, 0.4%) was added to a 15 mL conical tube with 0.3 mL of Hank's Balanced Salt Solution and 0.2 ml of cell suspension. After 10 min, 8 μL of the mixture was transferred to a hemocytometer to count viable and total cell number.

Invasion assay. Matrigel (BD Biolabs) was diluted into 2 mL of 0.01 M Tris-HC/0.7% NaCl to a final concentration of 300 μg/mL, filter sterilized and 0.1 mL was added per BD BioCoat cell insert. After 2 hours, near-confluent SCC13-TG2-shRNA2 and SCC13-Control-shRNA cells were harvested and 25,000 cells were plated in 100 μL of growth media containing 1% FCS atop the Matrigel layer. Growth medium containing 10% FCS was added to the bottom chamber followed by an overnight incubation at 37° C. The following day a cotton swab was used to remove cells from the upper side of the membrane, the membrane was rinsed with phosphate-buffered saline, fixed with 4% paraformaldehyde for 10 min, washed again, and stained with 1 μg/mL DAPI for 10 min. The underside of the membrane was viewed with an inverted fluorescent microscope and nuclei were counted.

Example 8. Further Characterization of Transamidase Site-Targeted Compounds and their Effects on Cancer Stem Cell Survival As discussed above, we surprisingly observed that transamidase site-specific inhibitors reduced ECS cell survival, migration, invasion and/or tumor formation. To test further whether covalent transamidation site-specific inhibitors act by suppressing TG2 transamidation (crosslinking) activity and also locking TG2 into the extended (open) conformation which disorganizes/inactivates the GTP binding site, we've examined further the impact of irreversible (NC9, VA4, VA5) and reversible (Cp4d) TG2 transamidase site specific inhibitors on TG2 transamidase activity, TG2 structure, and TG2 GTP binding activity (irreversible inhibitors (NC9, AV4 and AV5) specifically react with Cys-277 in the TG2 transamidation site (Keillor, J. et al., Can. J. Chem. 86:271-6 (2008)), and Cp4d competitively suppresses substrate access to the transamidation site (Keillor, J. W. et al., Bioorg. Chem. 57:186-97(2014))).

In this example we show that compounds NC9, VA4 and VA5, which react exclusively at the TG2 transamidase site, inhibit both transamidase and GTP-binding activities. Transamidase activity is inhibited by direct inhibitor binding at the transamidase site, and GTP binding is blocked because inhibitor interaction at the transamidase site locks the protein in the extended/open conformation thereby disorganizing/inactivating the GTP binding site. These findings suggest that transamidase site specific inhibitors may inhibit GTP binding/signaling by driving a conformation change that disorganizes the TG2 GTP binding to reduce TG2-dependent signaling, leading to reduced cancer stem cell survival. This site may therefore represent a good target for anti-cancer agents.

To test whether TG2 inhibitors that specifically bind to the transamidase site can produce a conformational change that results in indirect inhibition of TG2 GTP binding to inhibit GTP-dependent TG2 survival signaling, we studied the impact of irreversible (NC9, VA4, VA5) and reversible (Cp4d) TG2 transamidase site-specific inhibitors on TG2 structure, transamidase activity, and GTP binding (FIG. 29A). We monitored the impact of each inhibitor on intracellular TG2 structure using FLIM (Fluorescence Lifetime Imaging Microscopy). FLIM is a quantitative method of assessing fluorescence lifetime that measures energy transfer between donor and accept probes Fluorescence lifetime is measured in nanoseconds and a short lifetime correlates with close contact between probes (FIG. 29B). An advantage of this method is that fluorescent lifetimes are independent of probe concentration. In the present experiments, we expressed in cells a TG2 fusion protein in which the donor probe (mCER) is fused to the N-terminus and the acceptor probe (YFP) at the C-terminus (FIG. 29B). mCER and YFP comprise an ideal donor/acceptor pair; the donor probe is excited by laser illumination and energy transfer to the acceptor is monitored. The fluorescent lifetime is shorter when TG2 is in the closed conformation which brings mCER and YFP close together. SCC-13 cells were electroporated with empty vector, mCER-TG2 or mCER-TG2-YFP. The anti-TG2 protein blot shown in FIG. 29C confirms that each TG2 fusion protein was expressed, and FIG. 29D reveals that the subcellular distribution (cytoplasmic, nuclear and membrane) of each protein mimicked that of endogenous TG2 (Eckert, R. L. et al., Physiol. Rev. 94:383-417 (2014)).

To confirm that the constructs responded in the expected manner, SCC-13 cells were electroporated with mCer-TG2 or mCer-TG2-YAP and after 24 h incubated with 0 (control) or 10 µM A23187 for 24 h. A23187, a calcium ionophore, causes an increase in intracellular calcium which causes TG2 to shift to the extended conformation. The cell images in FIG. 29E display the signal intensity and lifetime fluorescence values. The blue and green graphs show the lifetime distribution for control and 10 µM A23187-treated mCer-TG2-YFP expressing cells. These plots reveal that calcium ionophore (A23187) treatment caused the lifetime to increase from 2.94 to nearly 3.1 ns. The maximal lifetime, determined using the mCer-TG2 construct (absence of YFP acceptor) was 3.15 ns (orange distribution) (FIG. 29E). An identical lifetime for the mCer-TG2 protein was observed in untreated cells (not shown), indicating the calcium treatment did not non-specifically impact the donor probe. The bar graph (FIG. 29E) quantifies the findings from multiple experiments. These plots show that lifetime was markedly increased when mCer-TG2-YFP expressing cells were treated with A23187, indicating that calcium treatment caused TG2 to adopt an open conformation.

We next examined the impact of inhibitors that covalently bind to the TG2 transamidation site on TG2 conformation. These compounds covalently and irreversibly attach to Cys-277 in the transamidase site catalytic triad which includes Cys-277, His-335 and Asp-358 (Keillor, J. W. et al., Trends Pharmacol. Sci. 36:32-40, 2015; Keillor, J. W. et al., Adv. Enzymol. Relat. Areas Mol. Biol. 78:415-47, 2011). Cells expressing mCer-TG2-YFP were treated with increasing concentrations of each compound. FIG. 30A/B/C shows that the lifetime was markedly increased in mCer-TG2-YFP expressing cells treated with NC9, VA4 or VA5, showing that these agents shifted TG2 from a closed to open conformation. We also monitored the impact of Cp4d, a reversible TG2 inhibitor that competes with the acyl donor substrate for binding at the transamidase site (Keillor, J. W. et al., Trends Pharmacol. Sci. 36:32-40, 2015; Pardin, C. et al., Chem. Biol. Drug Des. 72:189-96, 2008. Cells expressing mCer-TG2 or mCer-TG2-YFP were treated with increasing concentrations of Cp4d. We found a consistent, but not significant, decrease in fluorescent lifetime following treatment with Cp4d (FIG. 31A), indicating that Cp4d caused a slight reduction in lifetime suggesting that Cp4d either did not influence or slightly closed TG2 structure. As expected, these agents did not alter the lifetime of the control probe (orange distributions) (FIG. 30A/B/C and FIG. 31A). These findings show that NC9, VA4, VA5 and Cp4d can alter TG2 conformation.

We next examined the impact of these agents on TG2 functional activity (GTP binding/signaling activity). We first assessed the impact on transamidation (crosslinking) activity. Cells were preloaded with fluorescein cadaverine (FC), a fluorescein-labeled TG2 transamidase site substrate (Jans, R. et al., J. Invest. Dermatol.128:517-29, 2008; Oliverio, S. et al., Mol. Cell. Biol. 17:6040-8, 1997), and then treated with 0 or 20 µM NC9, VA4, VA5 or Cp4d (FIG. 29A) for 30 min followed by treatment with A23187, a calcium ionophore, for 90 min. In this assay, compounds that inhibit TG2 transamidation activity reduced calcium-activated TG2 crosslinking of FC resulting in reduced cell-retained fluorescence (Sturniolo, M. T. et al., Oncogene 24:2963-72, 2005; Sturniolo, M. T. et al., J. Biol. Chem. 278:48066-73, 2003). The control cells appeared green due to transglutaminase-catalyzed covalent crosslinking of FC to cellular proteins, and this incorporation was drastically reduced in inhibitor-treated cells (FIG. 31B), confirming that these agents inhibited TG2 transamidase activity.

We next assessed whether these transamidase site inhibitors alter TG2 GTP binding. Cells were incubated with 0 or 5 µM of each inhibitor for 24 h. Extracts were then prepared and TG2 binding to GTP-agarose beads was measured by immunoblot (Gundemir, S. et al., PLoS ONE 4(7):e6123, 2009; Gundemir, S. et al., Biochimica et Biophysica Acta. 1823(2):406-419, 2012). The lanes contain cell equivalents of extract so that the TG2 GTP-bound fraction can be compared to the total amount of TG2 (FIG. 31C). These studies indicate that essentially all TG2 is in a GTP-bound state in non-treated cells, and that inhibitor treatment reduces the quantity to near-zero. This demonstrates that these inhibitors reduce TG2 GTP-binding activity.

The results shown in FIGS. 30 and 31 indicate that NC9, VA4, VA5 and Cp4d can shift TG2 to an open conformation in cells. However, it could be argued that this was an indirect effect. To confirm that these agents directly interacted with TG2, we examined their effect on purified recombinant TG2. TG2 conformation can be measured by native gel electrophoresis where closed-conformation TG2 migrates more rapidly than the extended form (Pinkas, D. M. et al., PLoS Biol. 5: e327, 2007; Gundemir, S. et al., PLoS ONE 4(7): e6123, 2009). We pre-incubated recombinant TG2 for 1 h with inhibitor and then incubated for an additional hour following addition of 1 mM MgCl2 and 0 or 500 μM GTP. The samples were then electrophoresed on native gels to measure TG2 conformation. FIG. 31D shows that purified recombinant TG2 was largely in the extended conformation (lane 1) and that GTP addition shifted some to the closed state (Lane 2). Lanes 3 through 8 indicate that pre-incubation with NC9, VA4 or VA5 shifted TG2 from the closed to extended conformation and that this was not reversed by GTP addition. Lanes 9 and 10 indicate that Cp4d was less able to shift TG2 to an extended conformation (FIG. 31D).

We next examined the impact of simultaneous incubation with inhibitor and 500 μM GTP on inhibitor ability to shift TG2 to the extended conformation. These studies (FIG. 31E) show that the inhibitors did not produce a shift to open form under these conditions, arguing that the presence of GTP maintained the protein in the closed state and prevented inhibitor access to the transamidase site.

As discussed above, epidermal cancer stem cells (ECS cells) display a specific malignant phenotype that includes spheroid forming capacity, and enhanced invasion and migration. Moreover, TG2 has a major role in maintaining and enhancing this phenotype, a role that requires functional GTP binding. We therefore tested the effect of each inhibitor on ECS cell biology. FIG. 31F/G shows that NC9, VA4, VA5 and Cp4d inhibited spheroid formation (a measure of cancer stem cell survival) and matrigel invasion (a measure of invasive potential) and FIG. 31H shows that these agents inhibited cell migration leading to reduced closure of a scratch wound (a measure of migration potential).

To determine whether these agents can act in a similar manner in other epidermis-derived cell lines, we studied their impact on TG2 structure, TG2 transamidase and GTP binding activity, and ability to suppress survival of ECS cells derived from the HaCaT cell line. HaCaT cells are an immortalized, but not malignant, human epidermal cell line (Boukamp, P. et al., J. Cell. Biol. 106:761-71 (1988)). To examine inhibitor impact on TG2 structure, HaCaT cells were electroporated with mCer-TG2 or mCer-TG2-YAP and then treated with inhibitor. FIG. 32A shows that treatment with NC9, VA4 or VA5 increased fluorescence lifetime, indicating that inhibitor treatment shifted TG2 from the closed to the extended conformation. In contrast, and as noted in SCC-13 cells, Cp4d produced a minimal change in TG2 structure.

We next examined inhibitor impact on TG2 transamidase and GTP binding activity. NC9, VA4, VA5 and Cp4d suppressed TG2 transamidase activity (as measured by suppression of FC incorporation) (FIG. 32B) and also reduced TG2 GTP binding (FIG. 32C).

We next examined the effect of each compound on biological endpoints. FIGS. 32D and E show that NC9, VA4, VA5 and Cp4d suppressed ECS cell spheroid formation and invasion through matrigel, indicating that these agents reduced ECS cell survival and invasive potential.

To understand the molecular changes that occur at the TG2 GTP binding site during an inhibitor-induced shift from the closed to open conformation, we performed in silico structure analysis. FIG. 32F shows that the α- and β-phosphates of GDP hydrogen bond with residues R476, R478 and R580 of closed-conformation TG2, and that the guanine base of GDP is cradled in a hydrophobic pocket bracketed by the TG2 M483 and F174 residues. Binding is further stabilized by a hydrogen bond between the Oγ of S482 and the guanine exocyclic amino group. When TG2 is in the extended conformation, the hydrogen bonding network that recognizes the α- and β-phosphates of GDP is altered such that R476 and R478 are no longer in position to contact the GDP β-phosphate. Moreover, the hydrophobic pocket is no longer intact because the first β-barrel domain has moved away from the catalytic core, and M483 has shifted such that it clashes, sterically, with N1, C6, and O6 of the guanine base.

Since most of the residues that comprise the GTP/GDP-binding pocket in closed TG2 reside in the TG2 first β-barrel domain, it is instructive to examine whether this domain remains competent to bind GTP/GDP in the TG2 open conformation. We therefore attempted to dock GDP to a model of the TG2 open conformation. This analysis showed that in open/extended TG2, the TG2 residues that engage in hydrogen bonding with GDP are oriented such that they do not appropriately contact GDP. The most severe perturbations occur in the hydrophobic pocket that envelops the guanine base. In closed conformation TG2, M483 and F174 form the face of this pocket. The position of M483 is stabilized by interactions with L584 and E585, which are in turn buttressed by interactions with K176. Similarly, F174 engages in aromatic stacking with the guanine base which is in part stabilized by van der Waals interactions with Y583. In contrast, two major changes occur in the guanine-binding pocket in the TG2 open form. First, the conformational shift that opens TG2 moves F174 approximately 45 Å from the guanine-binding pocket. Second, M483 shifts such that it sterically clashes with the GDP guanine base. These changes may result in reduced GDP binding capacity of extended conformation TG2.

In conclusion, our results show that, surprisingly, transamidase site-specific inhibitors can alter GTP binding through a conformational change in TG2, leading to suppression of epidermal cancer stem cell survival as TG2-dependent stimulation of cancer stem cell survival requires GTP binding activity. Binding of irreversible inhibitors (NC9, AV4, AV5) at the transamidase catalytic site cysteine (Cys-277) caused intracellular TG2 to shift from a closed to an open conformation, and also suppressed TG2 GTP binding. These agents also suppressed ECS cell survival, invasion and migration. Moreover, although the substrate competitive inhibitor, Cp4d, had a minimal impact on TG2 conformation, it also suppressed TG2 GTP binding and suppressed ECS cell survival, suggesting that is also produced a TG2 conformation change, even though this change was not readily detected in our assay system because Cp4d did not irreversibly interact with site Cys-277 which permits TG2 to continue to undergo open/closed conformation state changes.

Materials and Methods for Example 8

Antibodies and reagents. Dulbecco's modified Eagle's medium (11960-077), sodium pyruvate (11360-070), L-Glutamine (25030-164), and 0.25% trypsin-EDTA (25200-056) were purchased from Gibco (Grand Island, N.Y.). Heat-inactivated FCS (F4135), anti-β-actin (A5441), A23187 ionophore were purchased from Sigma (St. Louis, Mo.) (C7522). Anti-green fluorescent protein was purchase from Abcam (Cambridge, UK) (ab290). Cell lysis buffer (9803)

was purchased from Cell Signaling Technology. Anti-TG2 (MAB3839) was purchased from EMD Millipore (Bedford, Mass.). Production of VA4, VA5, NC9, and Cp4d was as described previously (Keillor, J. et al., Can. J. Chem. 86:271-276, 2008). Fluorescein cadaverine (FC) was purchased from Life Technologies (Thermo Fisher Scientific, Waltham, Mass.). BD Biocoat cell inserts (353097) and Matrigel (354234) were purchased from BD Biosciences (San Jose, Calif.). Proteins were detected by immunoblot.

Electroporation. Plasmids encoding mCer-TG2 or mCer-TG2-YFP(linker), referred to in Example 8 as mCer-TG2-YFP, cloned in EC1214 vector were provided by Dr. Ray Truant (University of Ottawa, Ontario, Canada) (Caron, N. S. et al., PLoS ONE 7: e44159, 2012). Cells were electroporated using the Amaxa electroporator and the VPD-1002 nucleofection kit (Amaxa, Cologne, Germany). For electroporation, cells were harvested with trypsin and replated one day before use. On the day of electroporation, one million cells were harvested with trypsin, washed with 1 ml of sterile phosphate-buffered saline (pH 7.5), and suspended in 100 µl of nucleofection solution. The cell suspension, which included 3 µg of plasmid, was mixed by gentle up and down pipetting and electroporated using the T-018 settings. Warm medium (500 µl) was added and the suspension was transferred to a 60 mm cell culture plate containing 1.5 ml of medium. Expression of plasmid was confirmed with immunofluorescence microscopy and immunoblot. In all cases, maximal expression was observed by at 48 to 96 h.

In situ TG2 transamidase activity assay. Cells (40,000) were plated in 24-well attachment dishes in spheroid media and grown until 50% confluent. FC was added in 2 ml of serum-free medium at a final concentration of 20 µM and incubated for 4 h. The wells were washed twice with serum-free spheroid medium, and then 2 ml of fresh serum-free medium was added containing vehicle (DMSO) or 20 µM of NC9, VA4, VA5 or Cp4d. After 30 min, the wells were supplemented with 10 NM A23187, a calcium ionophore. Cells were incubated for an additional 90 minutes and then washed three times with $Ca^{++}/Mg^{++}$-free HBSS, fixed with formalin, washed with PBS, and imaged to detect covalent fluorescein cadaverine incorporation (Eckert, R. L. et al., Amino Acids 36:739-46, 2009; Jans, R. et al., J. Invest. Dermatol. 128:517-29, 2008).

Fluorescence lifetime imaging. Fluorescence lifetime images were acquired using FLIM system (Alba 5 from ISS). The excitation was from pulsed laser diode 443 nm coupled with scanning mirrors module (ISS) through multiband dichroic filter 443/532/635 nm (Semrock) to microscope (Olympus IX71S) with objective 20× 0.45 NA (UPlan Olympus). Emission was observed through bandpass filter 480/35 nm (Chroma Technology) and detected by a photomultiplier H7422-40 (Hamamatsu). FLIM data were acquired using time-domain modality (SPC-830 TCSPC module from Becker and Hickl GmbH). Images were acquired using an image size of 256×256 pixels and a pixel dwell time of 1 ms. To account for intensity heterogeneity within single intensity images, two to five consecutive scans were acquired and summed to build FLIM intensity image for lifetime analysis. Image frame sizes were varied to accommodate multiple cells expressing mCer-TG2 or mCer-TG2-YFP (Caron, N. S. et al., PLoS ONE 7: e44159, 2012) (from about 400×400 µm$^2$ to about 100×100 µm$^2$). mCer-TG2-YFP is referred to as mCer-TG2-YFP in Example 8. FLIM data were analyzed using VistaVision Suite software (Vista v.213 from ISS). Lifetime images were generated by fitting data using single exponential intensity decay model. Intensity threshold for lifetime analysis was set of at least 3-fold above the intensity of dim cells and fitting procedure was performed for binned pixels at level of 3 (7×7 pixels). Lifetime distribution within image is represented with histogram showing pixel frequency of specific lifetime. The average lifetime values with standard deviations were calculated based on all processed pixels in lifetime image. FRET values were calculated according to the formula $ET=1-(\tau DA/\tau D)$, where $\tau D$ is the lifetime of donor (mCer-TG2) and $\tau DA$ is the lifetime of donor-acceptor pair (mCer-TG2—YFP).

TG2 GTP binding assay. The GTP binding/GTP-agarose pull-down assay was performed as previously described (Gundemir, S. et al., PLoS ONE 4(7):e6123, 2009; Gundemir, S. et al., Biochimica et Biophysica Acta. 1823(2): 406-419, 2012). Cells were incubated for 24 h in spheroid media containing 0 or 5 µM VA4, VA5, NC9 or Cp4d. After trypsinization, the cells were rinsed in ice-cold PBS, pelleted, and resuspended in GTP-binding buffer containing 20 mM Tris-HCl pH=7.5, 5 mM MgCl2, 2 mM PMSF, 20 µg/ml leupeptin, 20 µg/ml pepstatin, 10 µg/ml aprotinin plus 150 mM NaCl and 0.1% Triton-X. The cells were sonicated for 15 s, centrifuged at 13,000 g for 10 min at 4° C., and the supernatant collected. A fraction of the supernatant was set aside for electrophoresis to detect total TG2 level. Supernatant protein (100 µg) was incubated with 100 µl of GTP-agarose beads (Sigma-Aldrich), pre-equilibrated in GTP-binding buffer), in a total of 500 µl of GTP-binding buffer for 30 min at 4° C. The beads were centrifuged at 10,000 g for 2 min and the supernatant retained. The beads were then again washed three times with 1 ml of GTP-binding buffer and the retained supernatant incubated with the beads for another 30 min. The beads were washed and incubated with the retained supernatant overnight at 4° C. Beads were washed seven times with GTP-binding buffer, and bound protein was eluted by boiling in 100 µl of 2×Laemmli buffer. The samples (50 µg protein equivalents, 50 µl) were then electrophoresed for anti-TG2 immunoblot. Total supernatant (50 µg protein) was electrophoresed in a parallel lane.

Inhibitor modulation of recombinant TG2 conformation. Recombinant TG2 protein was prepared in the Center for Biomolecular Therapeutics by Dr. Eric Toth (University of Maryland School of Medicine). TG2 protein (3.3 µM, 8 µg per 30 µl reaction) was pre-incubated with 0 or 500 µM NC9, VA4, VA5 or Cp4d for 1 h in 75 mM imidazole, 0.5 mM EDTA, 5 mM DTT, pH 7.2 prior to addition of 500 µM GTP/1 mM $MgCl_2$ and further incubation for 1 h at 25 C (Pinkas, D. M. et al., PLoS Biol 5:e327, 2007). In some experiments, inhibitor and GTP were added simultaneously. Laemmli native loading buffer was added, and 6 µg of protein was electrophoresed on a native 4% to 6% acrylamide gel and electrophoresed at 125 V for 45 min at 4° C. using Tris-glycine running buffer (Pinkas, D. M. et al., PLoS Biol 5:e327, 2007; Begg, G. E. et al., Proc. Natl. Acad. Sci. USA 103:19683-8, 2006). The gel was subsequently fixed in 40% methanol/10% acetic acid for 30 min, stained 30 minutes with 0.25% Coomassie R-250, destained overnight with 10% methanol/10% acetic acid and photographed.

Spheroid formation assay. Spheroid formation assays were as reported previously (Adhikary, G. et al., PLoS One 8:e84324, 2013), except that the spheroids were grown in 6-well ultralow attachment Costar cluster dishes (Corning). SCC-13 or HaCaT cells were grown as spheroids in 6-well cluster dishes in spheroid medium (Adhikary, G. et al., PLoS One 8:e84324, 2013; Fisher, M. L. et al., Oncotarget 6:20525-39, 2015) for 8 days and then treated with 0 to 20 μM NC9, VA4, VA5 or Cp4d for 0, 24, 48 and 72 h and spheroids were counted.

Invasion assay. Matrigel (BD Biolabs) was diluted into 2 ml of 0.01 M Tris-HC/0.7% NaCl to a final concentration of 300 μg/ml, filter sterilized, and 0.1 ml was added per BD BioCoat cell insert (8 microns pore size, surface area 0.3 cm2). After 2 h, near-confluent SCC-13 cells were harvested and 25,000 cells were plated in 100 μl of growth media containing 1% FCS atop the Matrigel layer. Growth medium containing 10% FCS was added to the bottom chamber followed by an overnight incubation at 37° C. The following day a cotton swab was used to remove cells from the upper side of the membrane, the membrane was rinsed with PBS, fixed with 4% paraformaldehyde, washed again, and stained with 1 μg/ml DAPI for 10 min. The underside of the membrane was viewed with an inverted fluorescent microscope, and nuclei were counted (Adhikary, G. et al., PLoS One 8:e84324, 2013).

Migration assay. Cells (2 million) were plated in 10 cm dishes and grown as monolayer cultures in spheroid medium until confluent. A 10 μl pipette tip was used to prepare areas void of cells and the dishes were washed to remove the dislodged cells. The ability of the cells to close the scratch wounds was monitored at 0-18 h after the scratch using the 10× objective, and the width of the opening was measured as a function of time as an index of cell migration (Adhikary, G. et al., PLoS One 8:e84324, 2013).

Example 9. Transglutaminase Interacts with A6/B4-Integrin to Stimulate Hippo-Dependent ΔNP63A Stabilization Leading to Enhanced Epidermal Cancer Stem Cell Survival We investigated the mechanisms by which TG2 mediates epidermal squamous cell carcinoma cancer stem cell survival. In this example we show that TG2 is constitutively expressed in ECS cells where it interacts with α6/β4 integrin to stimulate FAK and Src signaling leading to phosphoinositide 3 kinase (PI3K) activation of phosphoinositide dependent kinase 1 (PDK1). PDK1 inhibits Hippo signaling leading to enhanced nuclear accumulation of YAP1 which interacts with and stabilizes ΔNp63α to enhance ECS cell spheroid formation, invasion and migration. These findings suggest that constitutive TG2 expression may result in stabilization of ΔNp63α leading to enhanced maintenance of cancer stem cell properties.

ΔNp63α is an important member of the p63 family of proteins that regulate epithelial cell differentiation, stem cell status and fate. Studies in murine models have identified ΔNp63α as a key controller of differentiation in epidermis. The function of p63 in epithelial development was first observed in p63 knockout mice that die shortly after birth due to defects in the epidermal barrier. Restoration of TAp63α in p63 null mice restores some epithelialization, whereas reintroduction of ΔNp63α enhances epithelialization (Candi, E. et al., Cell Death Differ. 13:1037-47, 2006). Another study showed that TAp63 expression is required for initiation of epithelial stratification and the inhibition of terminal differentiation in mouse embryogenesis (Koster, M. I. et al., Genes Dev. 18:126-31, 2004), while ΔNp63α counteracts TAp63 action to promote epidermal differentiation (Koster, M. I. et al., Genes Dev. 18:126-31, 2004). Thus, ΔNp63α, which is the primary p63 variant expressed in squamous epithelial tissues (Yang, A. et al., Mol. Cell 2:305-16, 1998), is a key controller of normal epidermal development.

ΔNp63α overexpression is a frequent event in some human cancers, including squamous cell carcinoma. Although its function has been studied, the role of ΔNp63α in tumors is not yet well understood. Moreover, knowledge of the mechanisms that control ΔNp63α function and expression is limited. In the present example we show that TG2 and ΔNp63α are constitutively enriched in ECS cells as compared to non-stem epidermal cancer cells, that both proteins are required for ECS cell survival, migration and invasion, and that TG2 controls ΔNp63α level. Our findings suggest that TG2 may associate with the ΔNp63α-integrins to increase FAK/Src signaling and PI3K/PDK1 activity, and that PDK1, in turn, may suppress Hippo signaling leading to enhanced YAP1 and ΔNp63α accumulation and enhanced ECS cell survival.

We examined the role of ΔNp63α as a downstream mediator of TG2 action. We note that ECS cells are enriched in both TG2 and ΔNp63α as compared to non-stem cancer (monolayer) cells (FIG. 33A), suggesting a role for each protein in mediating ECS cell survival. To understand the role of these proteins, we studied their role in ECS cell spheroid formation. FIG. 33B shows that TG2 knockdown was associated with reduced ΔNp63α expression and reduced ECS cell spheroid formation. ΔNp63α knockdown also reduced spheroid formation, but this was not associated with loss of TG2 (FIG. 33C). These findings suggest that TG2 maintains ΔNp63α level to drive ECS cell spheroid formation. To elucidate the relationship between TG2 and ΔNp63α, TG2 knockdown cells were assayed for ability to form spheroids following restoration of TG2 or ΔNp63α. FIG. 33D confirms that TG2 level was reduced in SCC13-TG2-shRNA2 cells, demonstrates that this was associated with reduced ΔNp63α levels, and shows that vector-mediated expression of TG2 restored ΔNp63α level. Consistent with the idea that ΔNp63α is downstream of TG2, vector-mediated expression of ΔNp63α did not restore TG2 expression (FIG. 33D). FIG. 33E shows the biological effect of manipulating TG2 and ΔNp63α, and demonstrates that restoring expression of TG2 or ΔNp63α enhanced spheroid formation to a level approaching that observed in control (wild-type TG2 level) cells. FIG. 33F shows that there are subtle differences in the properties of the spheroids, with TG2-restored cells forming compact spheroids versus the less compact spheroids formed following restoration of ΔNp63α. These findings suggest that both proteins can drive spheroid formation, but that they have subtly different roles. FIGS. 33G and H show that TG2 knockdown cells also displayed reduced matrigel invasion and migration, and that restoration of ΔNp63α partially restored these properties. The results show that TG2 may stimulate integrin signaling to increase ΔNp63α level.

To identify the TG2 activated signaling events that maintain ΔNp63α level, we compared non-stem cancer cell and ECS cell integrin signaling. FIG. 34A shows TG2 level is elevated in ECS cells and that this is associated with increased α6/β4 level and increased focal adhesion kinase (FAK) and src kinase activities, suggesting that the integrin/FAK/src cascade is selectively activated in ECS cells. This is consistent with immunoprecipitation experiment showing that TG2 associates with β4-integrin (FIG. 34B). We next examined the impact of TG2 knockdown in integrin-related signaling. FIG. 34C shows that TG2 knockdown reduced β4-integrin level, and FAK and src kinase activity, and that this was associated with reduced ΔNp63α level. FIGS. 34D/E/F show that knockdown of β4-integrin, FAK or src reduced ΔNp63α level. Together, these findings strongly suggest that TG2 can maintain ΔNp63α level via a mechanism that requires activity in this cascade. We next examined the impact of TG2, α6-integrin, β4-integrin, FAK and src knockdown on ECS cell biological responses. FIGS. 34G/H/I show that loss of these regulators reduced spheroid formation, matrigel invasion and migration. To further confirm that FAK kinase is involved in TG2 regulation of ΔNp63α, we electroporated SCC-13 cells with empty vector (EV) or ΔNp63α expression vector, plated the cells for growth as spheroids and then added 10 µM PF-573288, a FAK kinase inhibitor, and monitored spheroid number at 6 d. FIG. 34J shows that PF-573228 treatment markedly reduced spheroid formation which was partially reversed by ΔNp63α expression. FIG. 34K confirms that PF-573228 reduced FAK kinase activity and that this was associated with reduced ΔNp63α level. FIG. 34L shows that treatment with src kinase inhibitor (PP2) also suppressed spheroid formation.

Hippo is a cell survival cascade that controls organ size during development (Harvey, K. F. et al., Nat. Rev. Cancer 13:246-57, 2013). When an organ reaches a proper size, cell-cell contact activates hippo signaling to halt cell growth (Harvey, K. F. et al., Nat. Rev. Cancer 13:246-57, 2013). The signal to halt proliferation involves activation of LATS1 kinase which phosphorylates YAP1 causing it to relocate to the cytoplasm where it undergoes proteasome-associated degradation. YAP1 is a transcriptional adaptor protein that interacts with TEAD transcription factors in the nucleus to drive cell proliferation (Harvey, K. F. et al., Nat. Rev. Cancer 13:246-57, 2013). LATS1 activity is reduced in many tumor types leading to nuclear YAP1 accumulation to drive tumor formation (Harvey, K. F. et al., Nat. Rev. Cancer 13:246-57, 2013). Integrin/FAK/src signaling has been reported to enhance PI3K/PDK1 signaling to inhibit LATS1 activity and enhance cell proliferation (Fan, R. et al., Proc. Natl. Acad. Sci. USA 110:2569-74, 2013; Kim, N. G. et al., J. Cell Biol. 210:503-15, 2015). In addition, YAP1 has been reported to interact with ΔNp63α in airway epithelial cells and HaCaT cells (Zhao, R. et al., Dev. Cell 30:151-65, 2014; Tomlinson, V. et al., Cell Death Dis. 1:e29, 2010).

We therefore tested whether TG2, α6/β4-integrins, FAK and src regulate PI3K/PDK1 and LATS1 activity. Consistent with a potential role for this cascade in ECS cells, PI3K and PDK1 activities were increased, while LATS1 activity was reduced in ECS cells (FIG. 35A) as compared to non-stem cancer cells. FIGS. 35B/C/D/E show that knockdown of TG2, α6/β4-integrin, FAK or src reduced PI3K/PDK1 activity and increased LATS1 activity, suggesting a role for TG2/integrin/FAK/src signaling in control of PI3K/PDK1 and LATS1. As noted above, LATS1 phosphorylates YAP1 causing it to localize in the cytoplasm as an inactive form that is degraded (Harvey, K. F. et al., Nat. Rev. Cancer 13:246-57, 2013). We anticipated that TG2 knockdown would increase LATS1 activity to enhance YAP1 phosphorylation and mobilization to the cytoplasm. FIG. 35F shows that TG2 loss resulted in a marked reduction in YAP1 level which was associated with an apparent reduction in YAP phosphorylation. These results suggest that cytoplasmic YAP1-P may be rapidly degraded in these cells as a mechanism of YAP1 inactivation. This reduction in YAP1 level in TG2-knockdown cells was confirmed by immunostaining. SCC-13 cells were electroporated with control- or TG2-siRNA, plated at 40% confluence and after 24 h stained to detect YAP1. FIG. 35G shows that YAP1 was present in both the nucleus and cytoplasm on control cells and that the YAP1 levels were reduced in TG2-siRNA treated cells.

We next assessed the mechanism whereby TG2 and YAP1 increase ΔNp63α level. As shown in FIG. 35H, TG2 knockdown did not reduce ΔNp63α mRNA, suggesting that TG2/YAP1 do not regulate ΔNp63α via transcriptional or RNA stability mechanisms. We next determined whether YAP1 may stabilize ΔNp63α against proteasomal degradation. Such a mechanism implies formation of aYAP1/ΔNp63α-containing complex. To assess this, we monitored YAP1ΔNp63α interaction. FIG. 35I shows that immunoprecipitation of YAP1 or ΔNp63α resulted in co-precipitation of the other protein. We next determined whether YAP1 loss leads to proteasome degradation of ΔNp63α. To test this we treated cells with control- or YAP1-siRNA in the presence or absence of the proteasome inhibitor, lactacystin. FIG. 35J shows that YAP1-siRNA reduced YAP1 and ΔNp63α level and that the ΔNp63α reduction was partially reversed by lactacystin treatment.

The above studies suggested that TG2 regulates YAP1 level to regulate ΔNp63α and predicted that YAP1 knockdown should reduce ΔNp63α level and ECS cell biological response. FIG. 35K shows that YAP1 knockdown was associated with reduced ΔNp63α expression and FIGS. 35L/M/N show that this was associated with reduced spheroid formation, matrigel invasion and migration. We next examined whether constitutively active YAP1, YAP (S127A), expression in TG2 knockdown cells can restore ΔNp63α expression and the biological responses. FIG. 36A shows that YAP1 and ΔNp63α levels were reduced in SCC13-TG2-shRNA2 cells, and that vector-mediated YAP (S127A) expression restored ΔNp63α level and spheroid formation, matrigel invasion and migration (FIGS. 36B/C/D). These findings indicate a role for YAP1 in maintaining ΔNp63α level and thereby driving the ECS cell survival.

To assess whether this cascade functions in vivo in tumors, we injected 200,000 ECS cells per each front flank in NSG mice and then initiated treatment with 20 mg/kg body weight NC9, a TG2 inhibitor (Keillor, J. et al., Can. J. Chem. 86:271-276, 2008; Keillor, J, W. et al., Trends Pharmacol. Sci. 36:32-40, 2015). FIGS. 36E/F show that NC9 treatment markedly suppressed tumor formation. Extracts were prepared from representative tumors to assess the impact of NC9 on the TG2 level and integrin and Hippo signaling. FIG. 36G shows that NC9 treatment reduced integrin-04 level, and FAK and Src activity, and increased LATS1-P and YAP-P, indicating that the HIPPO signaling cascade was activated in two separate tumors.

To assess whether this signaling pathway functions in other epidermis-derived cells, we used HaCaT cells, an immortal but non-transformed line isolated from epidermis (Boukamp, P. et al., J. Cell Biol. 106:761-71, 1988). HaCaT cells were grown as monolayer or spheroid cultures and signaling kinase activity was monitored. FIG. 37A shows that TG2 and ΔNp63α levels were elevated in HaCaT-derived ECS cells (spheroid cultures), and that this was associated with increased integrin level, and FAK and src signaling activity. In addition, TG2 knockdown reduced ΔNp63α level and FAK and src signaling (FIG. 37B), and knockdown of α6/β4-integrin, FAK or src also reduced ΔNp63α (FIGS. 37C/D/E). These findings suggest that TG2 control of ΔNp63α level occurs via a similar signaling mechanism as observed in SCC-13 cells.

We also confirmed that TG2/integrin and YAP1/ΔNp63α interaction occurs in HaCaT cells (FIGS. 37F/G). Since YAP1 and ΔNp63α interact, a key determination is whether YAP1 controls ΔNp63α level. FIG. 37H shows that YAP1 knockdown reduced ΔNp63α, but not TG2, level. We next studied the impact of these proteins on HaCaT cell phenotype. FIG. 37I shows that HaCaT cell spheroid formation is dependent upon TG2, ΔNp63α and YAP1. Finally, FIGS.

37J/K/L show that restoration of ΔNp63α in TG2 knockdown cells can restore spheroid formation.

In summary, we have identified a signaling cascade that mediates TG2-dependent ECS cell survival (FIG. 36H). Immunoprecipitation studies identified a TG2/β6/β4-integrin complex in ECS cells and showed that TG2 can impact integrin level. The elevated TG2 expression detected in ECS cells was associated with enhanced α6/β4 integrin level. Consistent with a role for TG2 in maintaining integrin expression, reduced integrin levels are observed in TG2 knockdown cultures, and in TG2 inhibitor-treated tumors, suggesting that TG2 may act to maintain integrin level. Moreover, TG2 interaction with and maintenance of integrin level is associated with increased integrin signaling. In particular, FAK and Src kinase activity are elevated in TG2-positive cells and reduced in TG2 knockdown cultures, suggesting that TG2 may interact with integrins to enhance FAK/Src signaling, a finding also reported in pancreatic cancer cells (Verma, A. et al., Cancer Res. 66:10525-33, 2006). TG2 interaction with integrins has been noted in other cell types as well.

We've shown also that TG2, FAK or Src knockdown, or treatment with pharmacologic inhibitors of these targets, increased PI3K/PDK1 activity in ECS cell cultures, suggesting that FAK/Src signaling may trigger PI3K/PDK1 activation. A recent study indicates that PDK1. LATS1 activity was reduced in TG2-expressing cells and increased following TG2 knockdown or pharmacologic inhibition. Moreover, inhibition of TG2, integrin, FAK, Src, PI3K or PDK1 function increased LATS1 activity (FIG. 36H). Thus, our studies suggest that TG2-dependent integrin/FAK/Src signaling may enhance PI3K/PDK1 signaling to inhibit LATS1 kinase activity. PDK1 inhibition of LATS1, as observed in our study, has also been observed in breast cancer cells (Kim, N. G. et al., J. Cell Biol. 210:503-15, 2015).

YAP1 and TAZ LATS1 reduced cell proliferation by phosphorylating the pro-proliferation/survival/transcription adaptor proteins, YAP1 and TAZ, resulting in their movement to the cytoplasm and subsequent degradation (Harvey, K. F. et al., Nat. Rev. Cancer 13:246-57, 2013). In contrast, non-phosphorylated YAP1 and TAZ interact with TEAD transcription factors in the nucleus to stimulate cell survival and proliferation. Activation of YAP1 and TAZ is widespread in cancer (Harvey, K. F. et al., Nat. Rev. Cancer 13:246-57, 2013; Moroishi, T. et al., Nat. Rev. Cancer 15:73-9, 2015) and YAP1 activity is associated with enhanced stem cell survival in epidermis and other tissues (Ramos, A. et al., Trends Cell Biol. 22:339-46, 2012). Moreover, induced expression of YAP1 and TAZ triggers transition of epithelial cells to a metastatic state and confers stem cell characteristics (Moroishi, T. et al., Nat. Rev. Cancer 15:73-9, 2015). We demonstrated that TG2 and YAP1/TAZ levels were elevated in ECS cells and that maintenance of YAP1 and TAZ level required TG2.

Our studies have also shown that ΔNp63α level was elevated in ECS cells and was required for maintenance of ECS cell survival, spheroid formation, invasion and migration, revealing an important and unexpected link between TG2, YAP1 and ΔNp63α. TG2, YAP1 and ΔNp63α were elevated in ECS cells as compared to non-stem cancer cells and TG2 knockdown was associated with loss of ΔNp63α. In contrast, ΔNp63α did not regulate TG2 level, implying that ΔNp63α is downstream of TG2. Moreover, forced expression of ΔNp63α partially reversed the reduction in ECS cell spheroid formation, invasion and migration associated with TG2 knockdown, suggesting it might mediate TG2 biological activity.

Our studies also demonstrate that YAP1 may act through ΔNp63α to mediate TG2 biological responses. Indeed, expression of constitutively active YAP1, YAP(S127A), can restore ΔNp63α level, and spheroid formation, invasion and migration in TG2-deficient cells. Our studies further suggest that YAP1 may control ΔNp63α level. We showed that the reduction in ΔNp63α level observed in TG2 deficient cells was not associated with a change in the level of ΔNp63α-encoding mRNA. Instead, TG2-stimulated signaling appeared to control ΔNp63α protein level. YAP1 appears to be a key mediator, as YAP1 knockdown reduced ΔNp63α level. The reduction in ΔNp63α observed in TG2- or YAP1-knockdown cells was proteasome-dependent, as it is reversed by lactacystin treatment. These findings suggest that formation of a YAP1/ΔNp63α complex may protect ΔNp63α from degradation.

Tumor xenograft experiments have shown that treatment with NC9, an irreversible TG2 inhibitor (Keillor, J. et al., Can. J. Chem. 86:271-276 2008), reduced tumor formation, and previously it was demonstrated that NC9 blocked ECS cell spheroid formation, EMT, invasion and migration (Fisher, M. L. et al., Mol. Cancer Res. 13:1083-94, 2015; Fisher, M. L. et al., Oncotarget 6:20525-39, 2015). Characterization of tumor extract from several tumors indicated that NC9 inhibition of TG2 reduces β4-integrin level, and FAK, Src and PI3K/PDK1 activity, and increases LATS1 kinase activity and YAP1-P formation leading to enhanced ΔNp63α degradation. TG2 may associate with the α6/β4-integrins to increase FAK/Src signaling and this may lead to PI3K/PDK1 activation; PDK1, in turn, may suppress LATS1 (Hippo) signaling leading to enhanced nuclear accumulation of YAP1 which forms a complex with and stabilizes ΔNp63α to enhance ECS cell survival (FIG. 36H). This pathway may help explain how TG2, via maintenance of the ΔNp63α stem cell survival factor, functions to maintain ECS cell survival, matrigel invasion, migration and tumor formation, and indicate that drugs designed to inhibit TG2 could be suitable for treating squamous cell carcinoma.

Materials and Methods for Example 9

Antibodies and reagents. Sodium pyruvate (11360-070), DMEM (11960-077), 0.25% trypsin-EDTA (25200-056) and L-Glutamine (25030-164) were purchased from Gibco (Grand Island, N.Y.). Heat inactivated fetal calf serum (FCS, F4135) and anti-β-actin (A5441) antibody was purchased from Sigma (St. Louis, Mo.). Cell lysis Buffer (9803) was purchased from Cell Signaling Technology (Danvers, Mass.). TG2 (2187378) was purchased from EMD Milipore (Bedford, Mass.). Antibodies for Src (ab47411) and Src-P (ab321012) were purchased from Abcam. Antibodies for ERK1/2 (9102) ERK1/2-P (9101), Bcl-2 (2872), YAP (4912), YAP-P (13008), JNK1/2 (9252), JNK1/2-P (9251), FAK-P (3283) and Sox2 (ab15830-100) were purchased from Cell Signaling Technologies. p63 (sc-8431), integrin-04 (sc-9090) and integrin-α6 (sc-374057) were purchased from Santa Cruz. Ezh2 (554002), FAK (610087) and Oct4 (611203) antibodies were purchased from BD Transduction Laboratories. Peroxidase-conjugated anti mouse IgG (NXA931) and anti-rabbit igG (NA934V) were obtained from GE healthcare (Buckinghamshire, UK). Alexaflour 555 (A21424) and Alexaflour 488 (A11034) were purchased from Invitrogen. DAPI (D9542) was purchased from Sigma. Paraformaldehyde (15713) was purchased from Electron Microscopy Sciences (Hatfield, Pa.). Production of NC9 was previously described (Keillor, J. et al., Can. J. Chem. 86:271-276, 2008). TG2-(sc-37514), p63-(sc-36161), FAK-(sc-29310), integrin α6-(sc-43129), integrin β4-(sc-35678) and control-siRNA (sc-37007) were purchased from Santa Cruz (Dallas, Tex.). YAP1-siRNA (S102662954) was purchased from Qiagen (Valencia, Calif.). Matrigel (354234) and BD Biocoat cell inserts (353097) were purchased from BD Biosciences.

Immunoblot. Equivalent amounts of protein were electrophoresed on denaturing and reducing 10% polyacrylamide gels and transferred to nitrocellulose membrane. The membrane was blocked by 5% nonfat dry milk for one hour and incubated with 1:1000 primary antibody in 5% nonfat dry milk. Blots were rinsed in TBS-T and then incubated with secondary antibodies (1:5000) for 2 h. Secondary antibody binding was visualized using ECL Prime (Amersham) chemiluminescence detection technology.

Lentivirus production. Lentivirus was produced using 293T cells maintained in DMEM with 1 mM L-glutamine, 1 mM sodium pyruvate and 10% fetal calf serum. 293T cells were harvested and plated in 100 mm dishes at 50% confluence 24 h prior to transfection. Media was removed and plates were washed with Hank's Balanced Salt Solution before serum free media was added containing 1 mg pCMVVSVG, 5 mg pCMV-dr8.91 and 5 mg shRNA encoding plasmid for co-transfection. After 3 h 10% FCS was added, and at 72 h after transfection the medium was collected, centrifuged for 15 min at 1500 rpm, sterile filtered (22 micron, and stored at −80° C. in aliquots.

Production of TG2 knockdown stable cell lines. SCC-13 cells ($1 \times 10^5$) were plated in 24 well cluster plates and allowed to attach overnight. The cells were then infected with 1 ml of medium containing lentivirus encoding TG2-specific shRNA. The infection was performed in serum-free growth media containing 8 µg/ml polybrene at 37 C for 5 h. The media was then changed to growth media supplemented with 5% fetal calf serum. Cells were then plated in 100 µM dishes and grown in the presence of 0.25 µg puromycin per ml for two weeks. The TG2 knockdown cells were then infected a second time with the same virus at a 1:1 dilution in serum free media with 8 µg/ml polybrene. The virus was left on for 72 h and cells were subsequently selected for two weeks with puromycin at 0.25 µg/ml. TG2 knockdown was confirmed by anti-TG2 immunoblot. These cells are referred to as SCC13-TG2-shRNA2 in this example. A control cell line was produced by double infection with control-shRNA encoding lentivirus using an identical protocol as above. These cells are referred to as SCC13-Control-shRNA in this example.

Spheroid formation assay. Cancer cells were maintained under attached conditions in growth media containing DMEM (Invitrogen, Frederick, Md.) supplemented with 4.5 mg/ml D-glucose, 200 mM Lglutamine, 100 mg/ml sodium pyruvate, and 5% fetal calf serum. Near-confluent monolayer cultures were dissociated with 0.25% trypsin, followed by serum-dependent trypsin inactivation. Cells were collected by centrifugation, and resuspended in spheroid media, consisting of DMEM/F12 (1:1) (DMT-10-090-CV, Mediatech INC, Manassas, Va.) containing 2% B27 serum-free supplement (17504-044, Invitrogen, Frederick, Md.), 20 ng/ml EGF (E4269, Sigma, St. Louis), 0.4% bovine serum albumin (B4287, Sigma) and 4 µg/ml insulin (19278 Sigma, St. Louis, Mo.), and plated at 40,000 cells per 9.6 cm² well in six well ultra-low attachment Costar cluster dishes (4371, Corning, Tewksbury, Mass.). Parallel cultures were plated in spheroid media on conventional plastic dishes for growth as monolayer cultures.

Electroporation of nucleic acids. Cancer cells (150,000) were plated on 60 mm plates in growth medium. After 24 h, when approximately 50% confluent, the cells were collected using 0.25% trypsin, centrifuged at 200×g, washed with sterile PBS (pH 7.5), suspended in 100 µl of keratinocyte nucleofection reagent VPD-1002 (Walkersville, Md.), and electroporated. The cell suspension, containing either 3 µg of siRNA or 2 µg of plasmid DNA, was gently mixed and electroporated using the T-018 setting on the AMAXA Electroporator. Immediately after electroporation, pre-warmed spheroid media was added and the suspension was transferred to a 60 mm cell culture plate and media adjusted to a final volume of 4 ml with spheroid media. When siRNA was used, but no plasmid DNA, the cells were electroporated a second time, following the same protocol, 72 h after the initial electroporation.

Invasion Assay. Matrigel (BD Biolabs) was diluted in 0.01 M Tris-HCL/0.7% NaCl and filter sterilized. 0.1 ml was used to cover BD BioCoat cell inserts (Adhikary, G. et al., PLoS One 8:e84324, 2013). After 2 h, cells were harvested and 25,000 cells were plated in 100 ml of growth media with 1% FCS on top of the Matrigel. Growth media with 10% FCS was added to the lower chamber and the cells were incubated overnight at 37° C. The following day, excess cells from the top side of the membrane were removed with a cotton swab, and the membrane was rinsed in PBS, fixed with 4% paraformaldehyde for 10 minutes, washed and stained in 1 µg/ml DAPI for 10 minutes. The underside of the membrane was photographed with an inverted fluorescent microscope to count the number of nuclei.

Wound closure assay. SCC13-Control-shRNA or SCC-13-TG2-shRNA2 cells (2 million) were plated on 10 cm dishes in spheroid media under monolayer conditions. Once confluent, a 10 µl pipette was used to create uniform wounds. The dishes were washed with PBS to remove free cells, and fresh spheroid medium was added. Images were taken at 10× to measure how wound closure from 0-24 h.

Tumor xenograft growth assay. Spheroid-selected (ECS) cells were trypsinized to prepare single cell suspensions, resuspended in phosphate buffered saline containing 30% Matrigel and 100,000 cells, in 100 µl, was injected subcutaneously into the two front flanks of NOD scid IL2 receptor gamma chain knockout mice (NSG mice) using a 26.5 gauge needle. Five mice were used per data point (Adhikary, G. et al., PLoS One 8:e84324, 2013). Tumor growth was monitored by measuring tumor diameter and calculating tumor volume=$4/3\pi \times (diameter/2)^3$ (Streit, M. et al., Am. J. Pathol. 155:441-52, 1999). Tumor samples were harvested to prepare extracts for immunoblot and sections for immunostaining. These studies were approved by the institutional boards and followed accepted national and international practices for the treatment and welfare of animals. NC9 was dissolved at 300 mM in dimethyl sulfoxide and stored in small aliquots at −20° C. For animal experiments, NC9 was delivered in Captisol, a non-toxic delivery vehicle (McCabe, M. T. et al., Nature 492:108-12, 2012). Briefly, 40% Captisol (RC-0C7-020, CyDex Pharmaceuticals, Lawrence, Kans.) was prepared in sterile water by stirring overnight at 25° C. followed by filter sterilization. The 40% captisol solution was diluted 1:1 in sterile water and supplemented with 0.5 ml of 1 N acetic acid to make 20% captisol. NC9 was prepared as a 2 mg/ml stock by mixing 7.17 µl of 300 mM NC9 with 742.83 µl of 20% captisol. NC9 was delivered by intraperitoneal injection, three times per week on alternate days, of 200 µl of the 2 mg/ml stock (20 mg/kg body weight).

Example 10. Kinetic Parameters of Irreversible Inhibitors of TG2

Kinetic parameters of selected irreversible inhibitors are shown in Table 4. Kinetic parameters were determined as described above.

TABLE 4

| Compound | $K_i$ (µM) | $k_{inact}$ (min$^{-1}$) | $k_{inact}/K_i$ (µM$^{-1}$ min$^{-1}$) |
|---|---|---|---|
| VA1[a] | n.d. | n.d. | 0.053 (±2.41 × 10$^{-3}$) |
| VA2[a] | n.d. | n.d. | 0.047 (±1.70 × 10$^{-3}$) |
| VA3 | 23.5 (±3.07) | 1.45 (±0.12) | 0.062 (±0.013) |
| VA4 | 5.12 (±1.11) | 0.745 (±0.092) | 0.146 (±0.049) |
| AA14[b] | n.d. | n.d. | n.d. |
| AA15[b] | n.d. | n.d. | n.d. |
| AA16 | 8.97 (±1.44) | 0.803 (±0.084) | 0.089 (±0.023) |
| NMI18 | 3.85 (±0.69) | 0.492 (±0.043) | 0.128 (±0.034) |
| NMI17 | 2.57 (±0.48) | 0.386 (±0.032) | 0.150 (±0.040) |
| NMI14 | 4.66 (±0.30) | 0.610 (±0.021) | 0.131 (±0.013) |
| NMI16 | 4.78 (±0.74) | 0.544 (±0.040) | 0.114 (±0.026) |
| MAI23 | 5.60 (±0.98) | 0.919 (±0.083) | 0.164 (±0.044) |
| NMI26 | 4.13 (±0.43) | 0.692 (±0.031) | 0.168 (±0.024) |
| NMI27 | 3.42 (±0.61) | 0.498 (±0.032) | 0.146 (±0.035) |
| VA5 | 4.20 (±0.98) | 0.694 (±0.086) | 0.165 (±0.059) |
| AA9 | 3.33 (±0.36) | 0.901 (±0.052) | 0.271 (±0.044) |
| AA10 | 5.04 (±0.85) | 1.21 (±0.12) | 0.240 (±0.064) |

[a] no saturation observed in hyperbolic plot, efficiency obtained from initial slope.
[b] no time-dependant inhibition observed;
n.d. = not determined

Example 11. Further Characterization of NC9, VA4, VA5 and CP4D Compounds in Cellular Assays The NC9, VA4, VA5 and CP4d compounds were tested using the spheroid formation, matrigel invasion, and migration assays described herein. Compounds were tested in skin squamous cell carcinoma cells (SCC-13), epidermis derived immortalized keratinocytes (HaCaT), epidermoid carcinoma (A431) and head and neck (TU159, HNSCC3) cancer cell lines. Results are shown in FIGS. 38-42. The results show that the indicated compounds inhibit spheroid formation, matrigel invasion and migration in the cells.

Example 12. Design, Synthesis and Characterization of Additional TG2 Inhibitors First, analogs of NC9 and VA4 were synthesized and tested. The number of rotatable bonds was reduced by systematically decreasing the length of the diamine spacer between the Cbz-Lys(Acr) and the dansyl functional group of NC9. The mono-dansylated alkyl amines 105-107 in Scheme 4 (below) were synthesized and coupled to the activated carboxylic acid of 101 in Scheme 4 to give inhibitors 109-111, and a piperazine linker (108) was also coupled to 101 to produce the more rigid inhibitor VA4. Kinetic parameters of irreversible inhibitors with varying backbone spacers (109-111 and VA4) are given in Table 5. Kinetic parameters were determined as described below.

TABLE 5

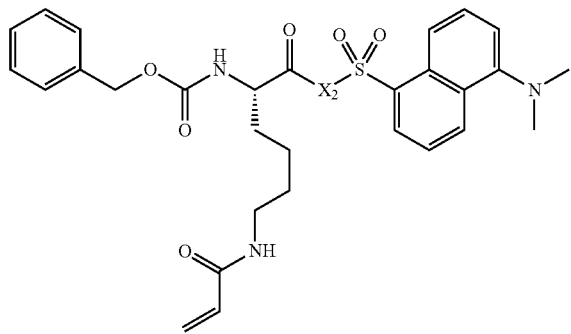

TABLE 5-continued

| Inhibitor | $X_2$ group | $K_I$ (µM) | $k_{inact}$ (min$^{-1}$) | $k_{inact}/K_I$ (10$^3$M$^{-1}$ min$^{-1}$) |
|---|---|---|---|---|
| 109[a] | HN—(CH$_2$)$_4$—NH | 27.1 ± 11.9 | 2.19 ± 0.94 | 80.8 ± 4.7 |
| 110[a] | HN—(CH$_2$)$_3$—NH | 30.5 ± 9.4 | 0.85 ± 0.25 | 27.6 ± 1.7 |
| 111 | HN—(CH$_2$)$_2$—NH | 23.5 ± 3.1 | 1.45 ± 0.12 | 61.5 ± 9.6 |
| VA4 | piperazine | 12.9 ± 2.6 | 1.40 ± 0.13 | 107 ± 23.8 |

As shown in Table 5, reducing the spacer length from eight atoms in NC9 to four atoms in compound 109 resulted in little change with respect to the kinetic parameters measured. Interestingly, reducing the spacer to three methylene groups (110) resulted in a marked reduction in efficiency, mainly due to a significant drop in the inactivation rate constant. Decreasing the spacer length to two methylene units (111) restored inhibitor efficiency to the values seen for the compound NC9. Maintaining the distance associated with a two-methylene spacer but in the form of the more rigid piperazine (VA4) gave the best inhibition parameters in the series. In addition to exceeding the overall inhibition efficiency of NC9, inhibitor VA4 also showed a greater than two-fold reduction in the inhibition binding constant, suggestive of more favorable interactions with the binding pocket of human TG2 compared to inhibitors with more flexible spacers.

Next, using VA4 as a new parent compound, additional inhibitors were prepared that contained the dansyl piperazine but whose side chains bearing the acrylamide warhead varied in length. Compounds 112-114 were synthesized from commercially available starting materials using modified literature procedures (Wityak, J. et al., ACS Med. Chem. Lett. (2012), 3 (12): 1024-1028; de Macedo, P. et al., Bioorg. Med. Chem. (2001), 10 (2): 355-360) and were coupled to the mono-dansyl piperazine to afford irreversible inhibitors 115-117 (Scheme 5). Kinetic parameters of these derivatives having varied side chain length are shown in Table 6. Kinetic parameters were determined as described below.

TABLE 6

| Compound | (CH$_2$)$_n$ | $K_I$ (µM) | $k_{inact}$ (min$^{-1}$) | $k_{inact}/K_I$ (10$^3$M$^{-1}$ min$^{-1}$) |
|---|---|---|---|---|
| 115 | n = 1 | n.d. | n.d. | n.d. |
| 116 | n = 2 | n.d. | n.d. | n.d. |
| 117[a] | n = 3 | 47.7 ± 37.8 | 1.18 ± 0.93 | 24.7 ± 2.2 |
| VA4 | n = 4 | 12.9 ± 2.6 | 1.40 ± 0.13 | 107 ± 23.8 | n.d = not determined

Time-dependent inhibition of human TG2 within a reasonable inhibitor concentration range was only observed for compound 117 and consequently we were unable to determine the kinetic parameters for 115 and 116. As another means of comparison, we tested high concentrations of inhibitors 115-117 in our colorimetric assay and measured relative observed rate constants ($k_{obs}$) from the time-dependent curves. Results are shown in FIG. 43. As can be seen in FIG. 43, the results are consistent with previous studies performed on the Cbz-Phe-X and Cbz-X-Gly scaffolds (Marrano, C. et al., Bioorg. Med. Chem. (2001), 9 (7): 1923-1928). It is possible that both the Cbz and dansyl functional groups present favorable contacts with the extended binding pocket and thus help to position the acrylamide warhead for attack by Cys277 at the base of the active site tunnel. A sidechain of one or two methylene units is apparently not long enough to position the acrylamide group for nucleophilic attack, and therefore no significant enzyme inactivation was observed. Extending the side chain to three methylene units resulted in the reappearance of enzyme inhibition albeit only modestly in comparison to NC9 and VA4. It is evident from the data presented in Table 6 and FIG. 43 that the side chain length is a critical component of this inhibitor scaffold for successful inhibition of human TG2.

Having established the advantages of a piperazine linker and a four-methylene side chain, we moved our attention to modification of the dansyl group. We began by synthesizing derivatives that maintained the sulfonamide connection, while replacing the dansyl group with various aromatic and aliphatic functional groups. First, the piperazine sulfonamide intermediates 119-127 were synthesized using standard techniques, followed by peptide coupling with carboxylic acid (indicated as "1" in scheme 6) to give final compounds 128-136 (Scheme 6).

Compound 128 differs from VA4 only by the lack of the dimethyl amino group on the naphthalene ring. Interestingly, the inhibition constants for both 128 and VA4 were very comparable (Table 7); however, the rate constant of inactivation of 128 was more than three-fold less than that of VA4, resulting in a lower overall inhibition efficiency for 128. Changing the orientation of the naphthyl moiety in compound 129 gave a modest gain in inhibition efficiency and reducing the size of the aromatic ring from naphthyl to phenyl in compound 130 resulted in similar inhibition kinetics to those of 128. The introduction of the more flexible phenylacetyl group in compound 131 resulted in a reduction of inhibition efficiency to values comparable with 129. Comparing the kinetic data for compounds 128-131 suggests that the binding pocket is relatively indiscriminate and will accept moderate to large hydrophobic groups.

The importance of the aromaticity of these substituents was then investigated by synthesizing and evaluating non-aromatic compounds 132-134. Based on the kinetic data shown in Table 7, aromaticity is not necessary to achieve modest inhibition efficiency; the cyclohexyl (132), isopropyl (133), ethyl (134) and methyl (135) sulfonamides all gave comparable inhibition values to those of the aromatic derivatives. Interestingly, the methyl sulfonamide (135) had the best inhibition kinetics of the series of sulfonamides presented in Table 7, while the electron-rich thiophene sulfonamide derivative (136) showed poor inhibition kinetics.

TABLE 7

Kinetic parameters of piperazine sulfonamide derivatives.

| Inhibitor | $R_{10}$ group | $K_I$ (μM) | $k_{inact}$ (min$^{-1}$) | $k_{inact}/K_I$ (10$^3$M$^{-1}$ min$^{-1}$) |
|---|---|---|---|---|
| 128 | 1-naphthyl | 10.4 ± 1.8 | 0.39 ± 0.03 | 37.2 ± 7.1 |
| 129 | 2-naphthyl | 6.7 ± 1.1 | 0.38 ± 0.03 | 57.3 ± 10.6 |
| 130 | phenyl | 8.8 ± 1.5 | 0.47 ± 0.04 | 53.3 ± 9.8 |
| 131 | benzyl | 14.7 ± 3.2 | 0.47 ± 0.06 | 34.9 ± 8.7 |
| 132 | cyclohexyl | 11.0 ± 1.1 | 0.69 ± 0.03 | 62.9 ± 7.1 |
| 133 | isopropyl | 9.1 ± 1.6 | 0.50 ± 0.03 | 54.7 ± 10.4 |
| 134 | ethyl | 36.0 ± 3.6 | 1.42 ± 0.09 | 39.4 ± 4.5 |
| 135 | methyl | 6.4 ± 1.8 | 0.50 ± 0.05 | 78.4 ± 23.7 |

TABLE 7-continued

Kinetic parameters of piperazine sulfonamide derivatives.

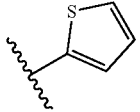

| Inhibitor | $R_{10}$ group | $K_I$ (μM) | $k_{inact}$ (min$^{-1}$) | $k_{inact}/K_I$ (10$^3$M$^{-1}$ min$^{-1}$) |
|---|---|---|---|---|
| 136 | thiophene | 40.1 ± 6.0 | 1.48 ± 0.13 | 36.8 ± 6.4 |

The final series of derivatives that were investigated were also constructed from a Cbz-Lys(Acr)-pip-X scaffold, but the C-terminal sulfonamide group was replaced with a carboxamide functional group. Piperazine amide intermediates 138-146 were prepared from the Boc-protected piperazine (137). Various acid chlorides or activated carboxylic acids were also coupled to 137 to afford the desired Boc-piperazine intermediates. Removal of the Boc group, followed by peptide coupling with acrylamide (indicated as 1 in Scheme 7) gave the desired final compounds 147-155 (Scheme 7).

Kinetic parameters of piperazine amide derivatives are shown in Table 8.

TABLE 8

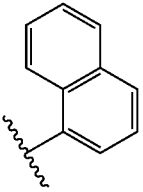 [SMILES: *c1cccc2ccccc12]

| Inhibitor | $R_{11}$ group | $K_I$ (μM) | $k_{inact}$ (min$^{-1}$) | $k_{inact}/K_I$ (10$^3$M$^{-1}$ min$^{-1}$) |
|---|---|---|---|---|
| 147 (AA9) | 1-naphthyl | 8.9 ± 1.0 | 0.90 ± 0.05 | 101 ± 12.8 |
| 148 (AA10) | 2-naphthyl | 13.4 ± 2.3 | 1.21 ± 0.13 | 90.3 ± 18.0 |
| 149 | phenyl | 36.6 ± 4.8 | 4.77 ± 0.46 | 130 ± 21.2 |

TABLE 8-continued

[Structure: benzyl carbamate-protected amino acid with piperazine amide and acrylamide side chain, bearing R₁₁ group]

| Inhibitor | R₁₁ group | $K_I$ (μM) | $k_{inact}$ (min⁻¹) | $k_{inact}/K_I$ (10³M⁻¹ min⁻¹) |
|---|---|---|---|---|
| 150 | benzyl | 20.0 ± 5.8 | 2.26 ± 0.37 | 113 ± 37.5 |
| 151 | isopropyl | 52.1 ± 6.7 | 2.06 ± 0.18 | 36.9 ± 6.1 |
| 152 | 2-pyridyl | 32.1 ± 5.4 | 2.93 ± 0.29 | 91.3 ± 17.9 |
| 153 | 3-pyridyl | 23.4 ± 2.2 | 1.44 ± 0.07 | 61.4 ± 6.4 |
| 154 | 4-pyridyl | 38.7 ± 5.7 | 1.43 ± 0.13 | 37.0 ± 6.4 |
| VA5 | 7-hydroxycoumarin-3-yl | 11.2 ± 2.6 | 0.69 ± 0.09 | 62.1 ± 16.4 |

Direct comparison of the 1-naphthyl (147; also referred to herein as AA9), 2-naphthyl (148; also referred to herein as AA10) (Mironov, G. G. et al., Nat. Chem. Biol. (2016), 12 (11): 918-922), phenyl (149) and benzyl (150) amide derivatives in Table 8 to their corresponding sulfonamide derivatives in Table 7 suggests that the presence of an amide functional group in lieu of the sulfonamide is beneficial for inhibition of human TG2. All four of these aromatic derivatives (147-150) showed at least a two-fold increase in overall inhibition efficiency compared to their sulfonamide counterparts. Surprisingly, this trend did not hold for the acetyl derivative (151), which had an overall inhibition efficiency almost three times less than that of the methyl sulfonamide derivative (135).

The introduction of an N-heterocycle in the form of three different pyridine isomers showed an interesting trend in inhibition efficiencies as the nitrogen is moved around the aromatic ring relative to the amide bond (Table 8). The picolinamide derivative (152) showed the best overall efficiency, followed by the nicotinamide derivative (153) and then the isonicotinamide derivative (154). All three of the N-heterocycles had inferior inhibition efficiencies compared to the non-polar phenyl compound (149), suggesting a polar substituent is not necessary but is tolerated by human TG2. Finally, the coumarin derivative VA5 (also referred to herein as compound 155) was intended for use as a cellular fluorescent probe visible in the blue region. The inhibition kinetic parameters of this compound were comparable to those of VA4.

Overall, upon consideration of both affinity and efficiency, we found that VA4 and compound 147 (also referred to herein as AA9), were among the best lead compounds from the sulfonamide and amide piperazinyl linked derivatives.

Next, VA4 and AA9 were tested further for their ability to abolish GTP binding. GTP binding was assessed using a fluorescent non-hydrolysable GTP analogue (GTPγS FL BODIPY) whose fluorescence increases when bound to a GTP-binding protein as described above. According to this evaluation, human TG2 (hTG2) showed significant loss in GTP binding ability after incubation with our inhibitors (FIG. 44). Therefore, in addition to their ability to inactivate TGase transamidation function by covalently modifying the active site Cys277 residue, VA4 and AA9 can also abolish GTP binding nearly completely. Our studies thus show that the inhibitors can abolish both acyl transferase and GTP binding activities in vitro by covalent attachment to Cys277, which subsequently results in locking hTG2 in an open conformation.

Example 13. Isozyme Selectivity Screening

Selectivity of certain irreversible inhibitors over other members of the transglutaminase family was assessed. Specifically, two efficient irreversible inhibitors, VA4 and NC9, were tested against four therapeutically relevant isoforms of human transglutaminase: FXIIIa, hTG3, hTG1 and hTG6. Inhibitors were tested using a continuous colorimetric assay (Leblanc, A. et al., Biochemistry (2001), 40 (28): 8335-8342) for hTG1 and hTG6 and a commercially available continuous fluorescent assay that utilizes a peptidic FRET quenched substrate (Oertel, K. et al., Anal. Biochem. (2007), 367 (2): 152-158; Király, R. et al., Amino Acids (2016), 48 (1): 31-40) for the other transglutaminases, FXIIIa and hTG3. The rate constant of enzyme inactivation ($k_{obs}$) for a specific concentration of inhibitor was obtained using Kitz and Wilson conditions (Kitz, R. et al., J. Biol. Chem. (1962), 237: 3245-49). Inhibitor concentrations were adjusted to account for competition with substrates in each enzymatic reaction. In general, our potent irreversible inhibitors showed excellent selectivity towards human TG2 (hTG2) over the other isozymes (Table 9). Both inhibitors demonstrated superior selectivity towards hTG2 over hTG3a by about 390-fold. VA4 was 48-fold less reactive with hTG1, 80-fold less reactive with FXIIIa and no inhibition was observed with hTG6 compared to inhibition of hTG2. In addition, VA4 illustrated a lower reactivity towards other transglutaminase isozymes compared to NC9. The subsequent in vitro selectivity over homologous transglutaminases suggests that the irreversible inhibitors may possess in vivo selectivity as well.

taining 3.0 mM $CaCl_2$ and 50 μM EDTA. Enzymatic inhibition assays were run under Kitz & Wilson conditions (Kitz, R. et al., J. Biol. Chem. (1962), 237: 3245-49) established for each transglutaminase isoform by varying the concentration of substrate to be 112 μM, 112 μM, and 436 μM of AL5 for hTG1, hTG2, and hTG6, respectively. A stock solution of AL5 was prepared in DMSO such that the final concentration of this co-solvent was constant at 2.5% v/v. Stock solutions of the inhibitors were made in the buffer system previously described. The reaction was initiated with the addition of 40-60 mU/mL of the respective enzyme (0.10 μM hTG1, 0.25 μM hTG2 or 0.32 μM hTG6). Product formation was monitored at 405 nm in a polystyrene 96-well microplate using a BioTek Synergy 4 plate reader. Mono-exponential time-dependent inactivation was observed for all the inhibitors studied. Observed first-order rate constants of inactivation ($k_{obs}$) were determined from non-linear regression fit to a mono-exponential model (Equation 1) of the observed absorbance of the enzymatic hydrolysis product, p-nitrophenolate (pNP). These rate constants ($k_{obs}$) were in turn fit to a saturation kinetics model (Equation 2), by non-linear regression, providing the kinetic parameters $k_{inact}$ and $K_I$, as previously described by Stone and Hofsteenge (Stone, S. R. et al., Biochem. J. (1985), 230 (2): 497-502). A double reciprocal plot of equation 2 was applied when the observed rate constant of inactivation ($k_{obs}$) did not demonstrate saturation at high inhibitor concentrations, or when solubility issues were encountered. Experiments were done in triplicate and variation between repeats was less than 30%.

$$f(pNP) = [pNP]_0 + (\text{Plateau} - [pNP]_0)(1 - e^{(k_{obs})}) \quad (1)$$

$$k_{obs} = \frac{k_{inact}[I]}{[I] + K_I\left(1 + \frac{[S]}{K_M}\right)} \quad (2)$$

Inhibition irreversibility. VA4 was incubated with hTG2 and the reaction solution was filtered over a 10-kDa molecular weight cut-off membrane, after which the residual enzyme solution was diluted and subjected to an activity assay as described previously. In comparison to a positive control of uninhibited hTG2, the inhibited enzyme exhibited no recovered activity (data not shown). Furthermore, we have previously demonstrated by mass spectrometry that incubation with acrylamide inhibitor VA4 results in the

TABLE 9

Selectivity of VA4 and NC9 against transglutaminase (TGase) isoforms.

| | $k_{obs}$ ($10^{-3}$ min$^{-1}$) | | | | |
|---|---|---|---|---|---|
| Compound | TG2 | TG1 | TG3a | TG6 | FXIIIa |
| NC9 | 390 ± 49 | 78.9 ± 5.9 | 1.01 ± 0.09 | 6.16 ± 0.14 | 5.91 ± 1.59 |
| VA4 | 394 ± 37 | 8.27 ± 0.76 | 0.65 ± 0.21 | n.d. | 4.08 ± 0.77 | n.d. = not determined

Materials and Methods for Examples 12-13

In Vitro Assays. Colorimetric transamidase activity assay. The activities of hTG1, hTG2 and hTG6 were measured via a colorimetric assay using the chromogenic substrate Cbz-Glu(γ-p-nitrophenyl ester)Gly (AL5). The assay was conducted at 25° C. in 100 mM MOPS buffer (pH 6.5) conincorporation of one equivalent of inhibitor (Mironov, G. G. et al., Nat. Chem. Biol. (2016), 12 (11): 918-922).

Fluorescence isopeptidase activity assay. The isopeptidase activity of pre-activated TG3a and FXIIIa (purchased from Zedira) was measured via a fluorescence-based assay (Király, R. et al., Amino Acids (2016), 48 (1): 31-40) using the commercially available peptidic FRET quenched probe A101 from Zedira. Briefly, the final concentration in the reaction mixture contained 50 mM Tris (pH 7.0), 10 mM CaCl$_2$, 100 mM NaCl, 2.8 mM TCEP, 50 µM A101 and 14 mM H-Gly-OMe. The reaction was monitored at 25° C. using a BioTek Synergy 4 plate reader (Ex/Em: 318/413 nm). Enzymatic inhibition assays were run under Kitz and Wilson conditions (Kitz, R. et al., J. Biol. Chem. (1962), 237: 3245-49) which was established for TG3a and FXIIa at a substrate (A101) concentration of 50 µM using enzyme concentrations of 0.17 µM and 0.11 µM for TG3a and FXIIIa, respectively.

In vitro GTP binding assay. GTP binding was measured using a method similar to that reported previously (McEwen, D. P. et al., Anal. Biochem. (2001), 291 (1): 109-117). For all experiments, GTP binding was measured using 3 µM of the fluorescent, non-hydrolysable GTP analogue BODIPY GTP-γ-S (Invitrogen), whose fluorescence increases when bound by protein. hTG2 (8-10 µg) was incubated at 25° C. for 30 minutes with or without irreversible inhibitor (2×K$_I$) with 3.0 mM CaCl$_2$ in 100 mM MOPS (pH=6.54). The buffer was then exchanged to 100 mM MOPS (pH=7.0), 1 mM EGTA and 5 mM MgCl$_2$ to remove calcium using a 10-kDa molecular weight cut off membrane. The fluorescent GTP analog was then added to give a final concentration of 3.0 µM and fluorescence was then measured on a microplate reader after 10 minutes of incubation (Ex/Em: 490/520 nm).

Synthesis Methods and Characterization

Synthesis of VA4 and VA5. The synthesis of a common scaffold bearing an acrylamide warhead is shown in Scheme 1. The synthetic route for the preparation of VA4 is shown in Scheme 2. The synthetic route for the preparation of VA5 is shown in Scheme 3.

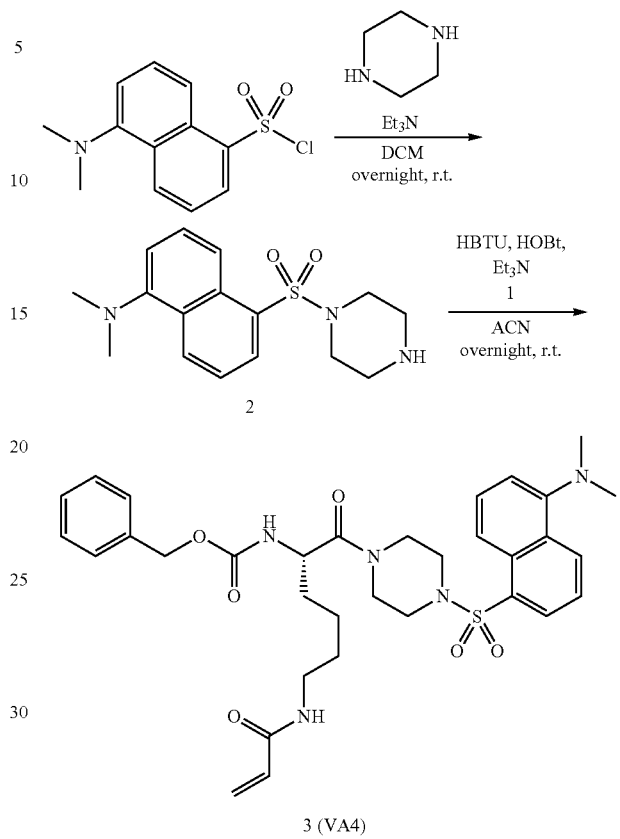

Scheme 2. Synthesis of VA4.

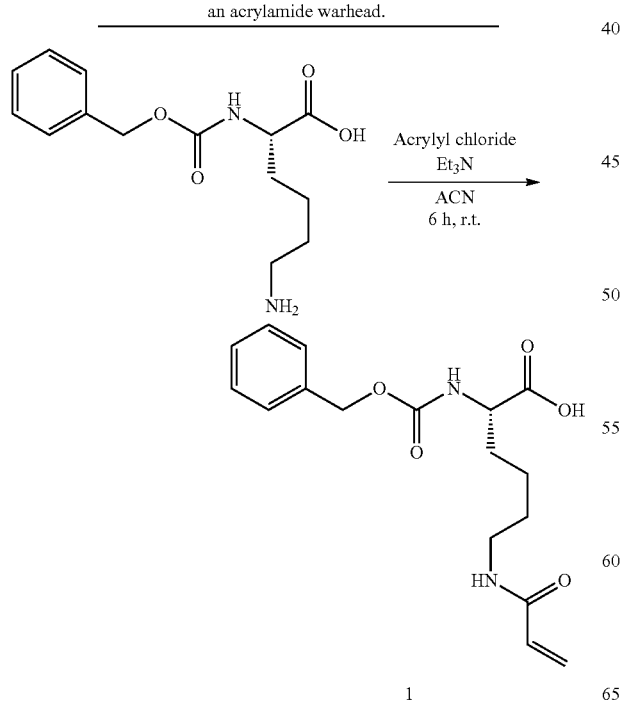

Scheme 1. Synthesis of a common scaffold bearing an acrylamide warhead.

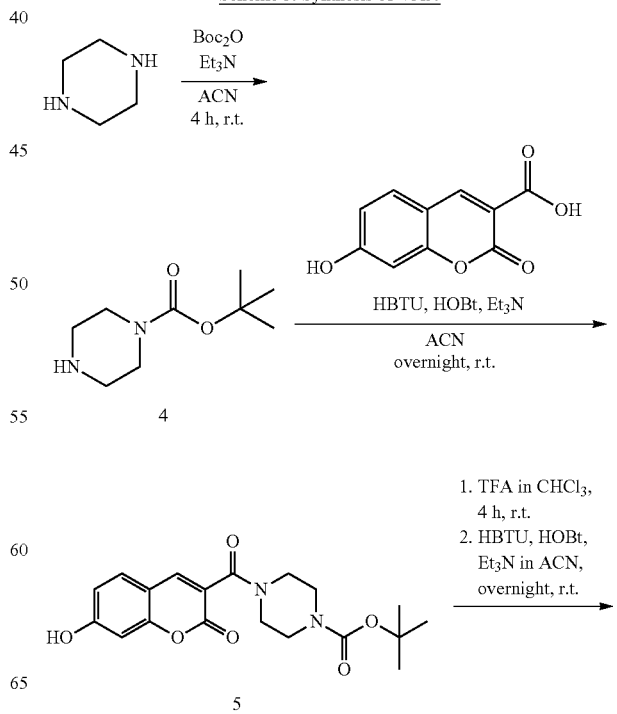

Scheme 3. Synthesis of VA5.

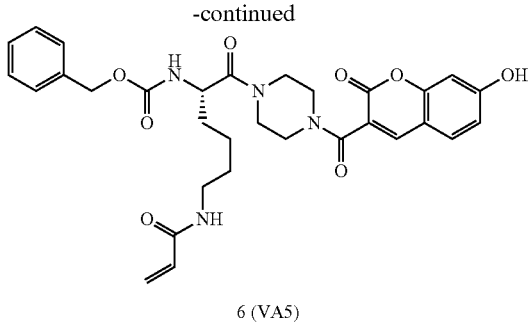

6 (VA5)

α-N-Carbobenzyloxy-ε-N-acryloyl-L-lysine (1): Cbz-Lys-OH (0.500 g, 1.78 mmol) was dissolved in acetonitrile (50 mL). The solution was cooled to 0° C. After the addition of Et$_3$N (2.50 mL, 1.87 mmol), acryloyl chloride (0.86 mL, 10.68 mmol) was added dropwise. The mixture was allowed to warm to room temperature overnight with stirring. The reaction mixture was then evaporated under reduced pressure and the residue was dissolved in water (40 mL). The pH was adjusted to around 1.5 with 1 M HCl (15-20 mL) and the product was extracted with ethyl acetate (3×30 mL). The organic layer was dried over MgSO$_4$, filtered and concentrated under reduced pressure to give crude product (confirmed by MS ESI positive mode) as a colorless oil which was used in the next step without further purification.

N,N-dimethyl-5-(piperazin-1-ylsulfonyl)naphthalen-1-amine (2): In a 100-mL round-bottomed flask, dansyl chloride (0.500 g, 1.9 mmol) was added to 30 mL of DCM, along with Et$_3$N (0.26 mL, 1.90 mmol). Piperazine (2.70 mL, 19.0 mmol) was added dropwise and the reaction was stirred overnight. Saturated sodium bicarbonate was added to the reaction mixture and the aqueous layer was washed with dichloromethane. The aqueous layer was then acidified and extracted with ethyl acetate. The organic layer was washed with brine, dried over MgSO$_4$, filtered and evaporated under reduced pressure. The residue was purified by flash chromatography (96:4 DCM:MeOH) to yield a light green oil in 85% isolated yield.

$^1$H-NMR (400 MHz, CDCl$_3$) δ 8.53 (d, 1H, J=8.48), 8.41 (d, 1H, J=8.76), 8.17 (d, 1H, J=7.12), 7.50 (m, 2H), 7.15 (d, 1H, J=7.36), 3.12 (m, 4H), 2.86 (m, 6H), 2.83 (m, 3H), 1.59 (bs, 1H).

$^{13}$C-NMR (75 MHz, CDCl$_3$) δ 151.7, 132.6, 130.6, 130.6, 130.5, 130.1, 128.0, 123.1, 119.6, 115.2, 46.5, 45.5, 45.4.

HRMS (ESI) calculated for C$_{16}$H$_{22}$N$_3$O$_2$S [M+H]$^+$: 320.1433, Found: 320.1373.

(S)-benzyl(6-acrylamido-1-(4-((5-(dimethylamino)naphthalen-1-yl)sulfonyl)piperazin-1-yl)-1-oxohexan-2-yl)carbamate (3 or VA4): 1 (0.663 g, 1.99 mmol) and 2 (0.762 g, 2.39 mmol) were combined with HOBt (0.375 g, 2.39 mmol), HBTU (0.906 g, 2.39 mmol) and Et$_3$N (0.35 mL, 2.39 mmol) in a 100 mL round-bottomed flask containing 40 mL of ACN. The resulting mixture was stirred at 25° C. overnight after which solvents were evaporated. The resulting residue was dissolved in CHCl$_3$ and this solution was washed successively with saturated Na$_2$CO$_3$ and 0.1 M HCl, dried over MgSO$_4$ and evaporated under reduced pressure. The residue was purified by flash chromatography (97:3 DCM:MeOH) to yield a dark yellow oil in 25% isolated yield.

$^1$H-NMR (400 MHz, CDCl$_3$) δ 8.55 (d, 1H, J=8.48), 8.30 (d, 1H, J=8.68), 8.17 (d, 1H, J=7.36), 7.51 (m, 2H), 7.26 (m, 5H), 7.15 (d, 1H, J=7.52), 6.20 (m, 1H), 6.02 (m, 1H), 5.91 (m, 1H), 5.69 (d, 1H, J=8.36), 5.55 (d, 1H, J=10.2), 4.99 (s, 2H), 4.49 (m, 1H), 3.78 (m, 1H), 3.56 (m, 1H), 3.43 (m, 2H), 3.30 (m, 2H), 3.21 (m, 2H), 3.03 (m, 2H), 2.85 (s, 6H), 1.52 (m, 4H), 1.28 (m, 2H).

$^{13}$C-NMR (75 MHz, CDCl$_3$) δ 207.1, 170.3, 165.6, 156.1, 151.9, 136.1, 132.2, 131.2, 130.7, 130.8, 130.3, 130.1, 128.5, 128.4, 128.2, 128.0, 126.3, 123.2, 119.2, 115.4, 67.0, 53.5, 50.1, 45.6, 45.4, 45.2, 45.2, 41.7, 38.9, 32.7, 30.9, 28.8, 22.2.

HRMS (ESI) calculated for C$_{33}$H$_{42}$N$_5$O$_6$SNa [M+Na]$^+$: 658.2675, Found: 658.2657.

Tert-butyl piperazine-1-carboxylate (4): To the mixture of piperazine (1.00 g, 11.6 mmol), acetonitrile (30 mL) and Et$_3$N (2.41 mL, 17.3 mmol) was added Boc anhydride (1.01 g, 4.65 mmol) drop wise and further stirred at room temperature (rt) for 4 h. The reaction mixture was concentrated under reduced pressure. Ethyl acetate (50 mL) was added in reaction mixture and separated solid was filtered off. Filtrate was washed with water (20 mL×3), dried over MgSO$_4$, filtered and evaporated under reduced pressure to give crude product (confirmed by MS ESI positive mode) as colorless oil which was used in the next step without further purification.

Tert-butyl 4-(7-hydroxy-2-oxo-2H-chromene-3-carbonyl)piperazine-1-carboxylate (5): To a solution of 7-hydroxycoumarin-3-carboxylic acid (500 mg, 2.43 mmol) in acetonitrile (ACN) (40 mL) were added Et$_3$N (0.85 mL, 6.08 mmol), HBTU (1.11 g, 2.92 mmol) and HOBt (395 mg, 2.92 mmol), followed by a solution of 1 (451 mg, 2.43 mmol) in ACN (10 mL). The resulting mixture was stirred at room temperature overnight after which solvents were evaporated. The resulting residue was dissolved in CHCl$_3$ and this solution was washed successively with saturated Na$_2$CO$_3$ and 0.1 M HCl, dried over MgSO$_4$ and evaporated under reduced pressure to give the crude compound. Compound 5 was purified by flash chromatography (96:4 DCM:MeOH) to yield an off-white sticky solid in 60% isolated yield.

$^1$H-NMR (400 MHz, CD$_3$D) δ 8.02 (s, 1H), 7.55 (d, 1H), 6.85 (d, 1H), 6.75 (s, 1H), 3.71 (m, 2H), 3.50 (m, 6H), 1.47 (s, 9H).

$^{13}$C-NMR (100 MHz, CD$_3$OD) δ 166.7, 164.4, 160.5, 157.7, 156.2, 145.6, 131.7, 120.4, 115.2, 112.5, 103.4, 81.7, 48.2, 43.2, 28.6.

HRMS (ESI) calculated for C$_{19}$H$_{22}$N$_2$O$_6$ [M–H]$^-$: 373.1400, Found: 373.1403.

(S)-Benzyl(6-acrylamido-1-(4-(7-hydroxy-2-oxo-2H-chromene-3-carbonyl)piperazin-1-yl)-1-oxohexan-2-yl)carbamate (6 or VA5): TFA (2.77 mL, 36.0 mmol) was added to a solution of 5 (267 mg, 0.898 mmol) in CHCl$_3$ (10 mL). The resulting mixture was stirred at room temperature for 4 h after which solvents were evaporated. A white solid was precipitated from the resulting oil upon addition of Et$_2$O, and used in the next step without further purification. A solution of the TFA salt in ACN (10 mL) was added to a solution of 1 (218 mg, 0.988 mmol), HBTU (189 mg, 0.988 mmol), HOBt (134 mg, 0.988 mmol) and Et$_3$N (0.26 mL, 1.89 mmol) in ACN (20 mL). The resulting mixture was stirred at room temperature overnight after which solvents were evaporated under reduced pressure. The crude was dissolved in CHCl$_3$ and this organic phase was washed successively with saturated Na$_2$CO$_3$ and 0.1 M HCl, dried over MgSO$_4$ and evaporated under reduced pressure to give the crude product. Compound 6 was purified by flash chromatography (96:4 DCM:MeOH) to obtain a sticky beige solid in 23% yield.

$^1$H-NMR (400 MHz, CDCl$_3$) δ 8.01 (s, 1H), 7.66 (bs, 1H), 7.57 (d, 1H), 7.29 (m, 5H), 6.93 (bs, 1H), 6.85 (dd, J=8.5 Hz, J=2.25 Hz, 1H), 6.77 (d, 1H), 6.19 (m, 1H), 6.07 (m, 1H), 5.52 (m, 1H), 5.04 (s, 2H), 4.44 (m, 1H), 3.49 (m, 6H), 3.14 (m, 2H), 1.62 (m, 2H), 1.47 (m, 2H), 1.35 (m, 2H).

$^{13}$C-NMR (75 MHz, CDCl$_3$) δ 172.9, 170.9, 164.9, 163.1, 158.5, 156.4, 155.1, 144.1, 137.5, 132.3, 130.9, 128.8, 128.5, 128.1, 125.3, 119.7, 114.3, 111.1, 102.5, 65.9, 50.9, 45.5, 45.1, 42.2, 41.8, 38.7, 31.4, 29.2, 23.2.

HRMS (ESI) calculated for C$_{31}$H$_{34}$N$_4$O$_8$Na [M+Na]$^+$: 613.2282, Found: 613.2274.

(S)-benzyl-6-acrylamido-1-oxo-1-(4-(phenylsulfo-nyl)piperazin-1-yl)hexan-2-ylcarbamate (NM-I-14)

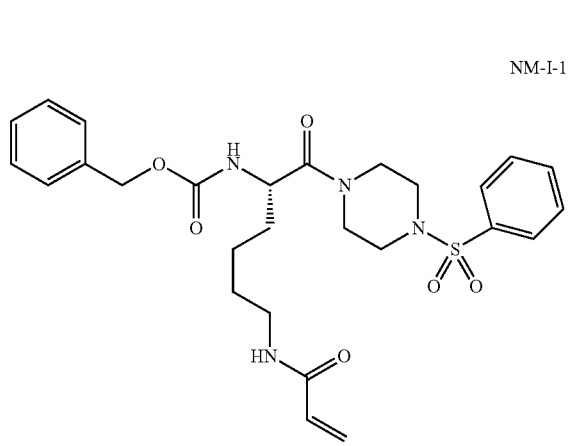

NM-I-14

Synthesis was modified from Bioorg. Med. Chem. 10: 355-360, 2002. Acrylamide Cbz-Lys-OH (250 mg, 0.748 mmol), EDC-HCl (172 mg, 0.897 mmol), HOBt (101 mg, 0.748 mmol) and DIPEA (0.32 mL, 0.897 mmol) were dissolved in 10 mL of acetonitrile and stirred at room temperature for 30 min. Compound sulfonamide (202 mg, 0.897 mmol) was added and the solution was left stirring at room temperature for 20 hours. The acetonitrile was evaporated under reduced pressure and the residue was dissolved in chloroform. The chloroform was washed with water (1×10 mL), saturated sodium bicarbonate solution (2×10 mL), 1M hydrochloric acid (1×10 mL) and brine (2×10 mL), dried with magnesium sulfate, filtered and concentrated under reduced pressure to afford the crude product as an oil. The crude product was purified by flash chromatography over silica gel (elution with gradient CHCl$_3$, CHCl$_3$:MeOH (1%), CHCl$_3$:MeOH(2%)) to afford 82 mg (20%) of the desired product as a white foam.

$^1$H NMR (400 MHz, CDCl$_3$) δ 7.77-7.72 (m, 2H), 7.65-7.60 (m, 1H), 7.58-7.52 (m, 2H), 7.36-7.29 (m, 5H), 6.26 (dd, J=17.0, 1.5 Hz, 1H), 6.05 (dd, J=16.9, 10.3 Hz, 1H), 5.68 (s, 1H), 5.64-5.58 (m, 2H), 5.05 (s, 2H), 4.54 (td, J=8.5, 4.2 Hz, 1H), 3.92 (d, J=13.4 Hz, 1H), 3.65 (s, 1H), 3.53 (d, J=18.2 Hz, 2H), 3.28 (qd, J=18.4, 16.0, 9.3 Hz, 4H), 2.88 (dd, J=21.5, 10.4 Hz, 2H), 1.67-1.47 (m, 3H), 1.36 (q, J=7.3 Hz, 2H).

$^{13}$C NMR (101 MHz, CDCl$_3$) δ 170.4, 165.7, 156.3, 136.3, 135.5, 133.4, 130.9, 129.5, 128.7, 128.4, 128.1, 127.8, 126.5, 67.1, 50.3, 46.2, 45.9, 45.1, 41.6, 39.1, 32.9, 28.9, 22.3; mass spectrum (ESI-TOF), m/z (relative intensity) 565 (100, [M+Na]$^+$); HRMS (ESI-TOF) m/z [M+Na]$^+$ calcd for C$_{27}$H$_{34}$N$_4$NaO$_6$S 565.2097; found 565.2094.

(S)-benzyl-6-acrylamido-1-oxo-1-(4-(phenylsulfo-nylmethyl)piperazin-1-yl)hexan-2-ylcarbamate (NM-I-16)

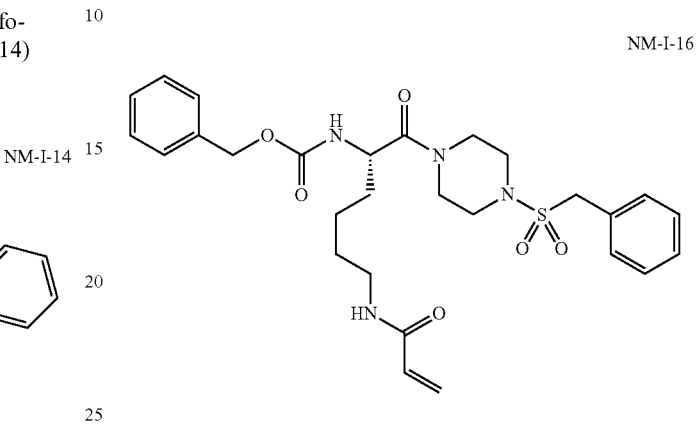

NM-I-16

Synthesis was modified from Bioorg. Med. Chem. 10: 355-360, 2002. Acrylamide Cbz-Lys-OH (250 mg, 0.748 mmol), EDC-HCl (172 mg, 0.897 mmol), HOBt (101 mg, 0.748 mmol) and DIPEA (0.32 mL, 0.897 mmol) were dissolved in 10 mL of acetonitrile and stirred at room temperature for 30 min. The sulfonamide (216 mg, 0.897 mmol) was added and the solution was left stirring at room temperature for 20 hours. The acetonitrile was evaporated under reduced pressure and the residue was dissolved in chloroform. The chloroform was washed with, water (1×10 mL), saturated sodium bicarbonate solution (2×10 mL), 1M hydrochloric acid (1×10 mL) and brine (2×10 mL), dried with magnesium sulfate, filtered and concentrated under reduced pressure to afford the crude product as an oil. The crude product purified by flash chromatography over silica gel (elution with gradient CHCl$_3$, CHCl$_3$:MeOH(1%), CHCl$_3$:MeOH(2%)) to afford 96 mg (23%) of the desired product as a white foam.

$^1$H NMR (400 MHz, CDCl$_3$) δ 7.41-7.29 (m, 10H), 6.25 (dd, J=17.0, 1.5 Hz, 1H), 6.07 (dd, J=17.0, 10.2 Hz, 1H), 5.86 (t, J=5.9 Hz, 1H), 5.74 (d, J=8.4 Hz, 1H), 5.60 (dd, J=10.3, 1.5 Hz, 1H), 5.08 (d, J=1.3 Hz, 2H), 4.55 (td, J=8.4, 4.4 Hz, 1H), 4.23 (s, 2H), 3.72-3.66 (m, 1H), 3.53-3.45 (m, 1H), 3.44-3.24 (m, 4H), 3.20-3.11 (m, 2H), 3.01 (dtt, J=20.5, 8.7, 3.7 Hz, 2H), 1.63 (ddd, J=12.0, 5.7, 2.8 Hz, 1H), 1.57-1.50 (m, 3H), 1.37 (q, J=7.5 Hz, 2H).

$^{13}$C NMR (101 MHz, CDCl$_3$) δ 170.5, 165.7, 156.25, 136.3, 130.9, 130.8, 129.2, 129.0, 128.7, 128.5, 128.4, 128.1, 126.4, 67.1, 57.5, 50.3, 46.1, 45.8, 42.3, 39.0, 32.8, 28.9, 22.3; mass spectrum (ESI-TOF), m/z (relative intensity) 579 (100, [M+Na]$^+$); HRMS (ESI-TOF) m/z [M+Na]$^+$ calcd for C$_{28}$H$_{36}$N$_4$NaO$_6$S 579.2253; found 579.2299.

(S)-benzyl 6-acrylamido-1-(4-(naphthalen-2-ylsulfonyl)piperazin-1-yl)-1-oxohexan-2-ylcarbamate (NM-I-17)

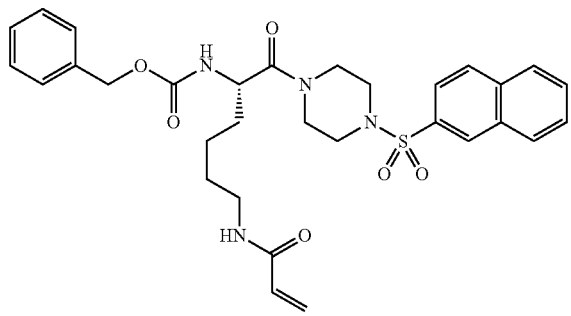

NM-I-17

Synthesis was modified from *Bioorg. Med. Chem.* 10: 355-360, 2002. Acrylamide Cbz-Lys-OH (250 mg, 0.748 mmol), EDC-HCl (172 mg, 0.897 mmol), HOBt (101 mg, 0.748 mmol) and DIPEA (0.32 mL, 0.897 mmol) were dissolved in 10 mL of acetonitrile and stirred at room temperature for 30 min. The sulfonamide (246 mg, 0.897 mmol) was added and the solution was left stirring at room temperature for 20 hours. The acetonitrile was evaporated under reduced pressure and the residue was dissolved in chloroform. The chloroform was washed with water (1×10 mL), saturated sodium bicarbonate solution (2×10 mL), 1M hydrochloric acid (1×10 mL) and brine (2×10 mL), dried with magnesium sulfate, filtered and concentrated under reduced pressure to afford the crude product as an oil. The crude product was purified by flash chromatography over silica gel (elution with gradient DCM, DCM:MeOH(1%), DCM:MeOH(2%)) to afford 102 mg (24%) of the desired product as a white foam.

$^1$H NMR (400 MHz, CDCl$_3$) δ 8.33 (d, J=1.7 Hz, 1H), 7.99 (d, J=8.2 Hz, 2H), 7.92 (d, J=7.6 Hz, 1H), 7.72 (dd, J=8.7, 1.8 Hz, 1H), 7.65 (pd, J=6.9, 1.5 Hz, 2H), 7.35-7.27 (m, 5H), 6.24 (dd, J=17.0, 1.5 Hz, 1H), 6.03 (dd, J=17.0, 10.3 Hz, 1H), 5.70 (t, J=5.8 Hz, 1H), 5.59 (dd, J=10.2, 1.5 Hz, 2H), 4.99 (d, J=1.8 Hz, 2H), 4.51 (td, J=8.4, 4.2 Hz, 1H), 3.95-3.85 (m, 1H), 3.68-3.61 (m, 1H), 3.52 (dt, J=13.8, 10.3 Hz, 2H), 3.24 (qd, J=13.5, 6.6 Hz, 4H), 3.05-2.81 (m, 2H), 1.63-1.42 (m, 4H), 1.43-1.15 (m, 2H);

$^{13}$C NMR (101 MHz, CDCl$_3$) δ 170.4, 165.7, 156.2, 136.3, 135.2, 132.6, 132.3, 130.9, 129.7, 129.4, 129.3, 129.3, 128.7, 128.3, 128.1, 128.1, 127.9, 126.5, 122.8, 67.1, 50.3, 46.3, 45.9, 45.2, 41.7, 39.1, 32.9, 28.9, 22.3; mass spectrum (ESI-TOF), m/z (relative intensity) 615 (100, [M+Na]$^+$); HRMS (ESI-TOF) m/z [M+Na]$^+$ calcd for C$_{31}$H$_{36}$N$_4$NaO$_6$S 615.2249; found 615.2253.

(S)-benzyl 6-acrylamido-1-(4-(naphthalen-1-ylsulfonyl)piperazin-1-yl)-1-oxohexan-2-ylcarbamate (NM-I-18)

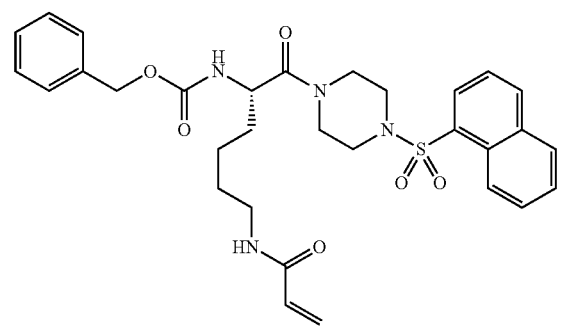

NM-I-18

Synthesis was modified from Bioorg. Med. Chem. 10: 355-360, 2002. Acrylamide Cbz-Lys-OH (250 mg, 0.748 mmol), EDC-HCl (172 mg, 0.897 mmol), HOBt (101 mg, 0.748 mmol) and DIPEA (0.32 mL, 0.897 mmol) were dissolved in 10 mL of acetonitrile and stirred at room temperature for 30 min. The sulfonamide (246 mg, 0.897 mmol) was added and the solution was left stirring at room temperature for 20 hours. The acetonitrile was evaporated under reduced pressure and the residue was dissolved in chloroform. The chloroform was washed with water (1×10 mL), saturated sodium bicarbonate solution (2×10 mL), 1M hydrochloric acid (1×10 mL) and brine (2×10 mL), dried with magnesium sulfate, filtered and concentrated under reduced pressure to afford the crude product as an oil. The crude product purified by flash chromatography over silica gel (elution with gradient DCM, DCM:MeOH(1%), DCM:MeOH(2%)) to afford 100 mg (23%) of the desired product as a white foam.

$^1$H NMR (400 MHz, CDCl3) δ 8.70 (d, J=8.7 Hz, 1H), 8.22 (dd, J=7.4, 1.2 Hz, 1H), 8.10 (d, J=8.2 Hz, 1H), 7.97-7.91 (m, 1H), 7.71-7.53 (m, 3H), 7.39-7.27 (m, 5H), 6.24 (dd, J=17.0, 1.5 Hz, 1H), 6.04 (dd, J=17.0, 10.2 Hz, 1H), 5.74 (broad s, 1H), 5.67-5.56 (m, 2H), 5.03 (s, 2H), 4.51 (td, J=8.4, 4.3 Hz, 1H), 3.87-3.79 (m, 1H), 3.58 (d, J=5.1 Hz, 1H), 3.47 (dt, J=12.9, 9.3 Hz, 2H), 3.39-3.19 (m, 4H), 3.13-3.00 (m, 2H), 1.65-1.46 (m, 4H), 1.38-1.23 (m, 2H).

13C NMR (101 MHz, CDCl3) δ 170.4, 165.7, 156.2, 136.3, 135.1, 134.6, 132.2, 131.0, 130.9, 129.2, 128.9, 128.7, 128.5, 128.4, 128.1, 127.2, 126.5, 124.9, 124.3, 67.1, 50.3, 45.8, 45.4, 45.3, 41.8, 39.1, 32.9, 28.9, 22.3; mass spectrum (ESI-TOF), m/z (relative intensity) 615 (100, [M+Na]$^+$); HRMS (ESI-TOF) m/z [M+Na]$^+$ calcd for C$_{31}$H$_{36}$N$_4$NaO$_6$S 615.2253; found 615.2232.

(S)-benzyl 6-acrylamido-1-(4-(methylsulfonyl)piper-azin-1-yl)-1-oxohexan-2-ylcarbamate (MA-I-23)

(S)-benzyl-6-acrylamido-1-(4-(isopropylsulfonyl)piperazin-1-yl)-1-oxohexan-2-ylcarbamate (NM-I-26)

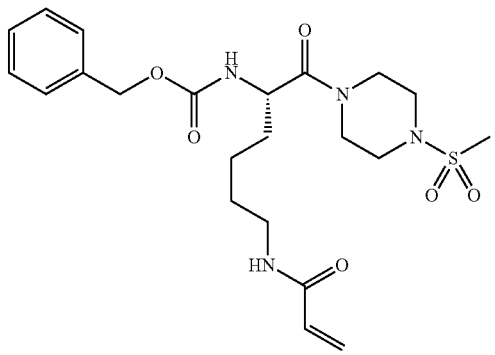

MA-I-23

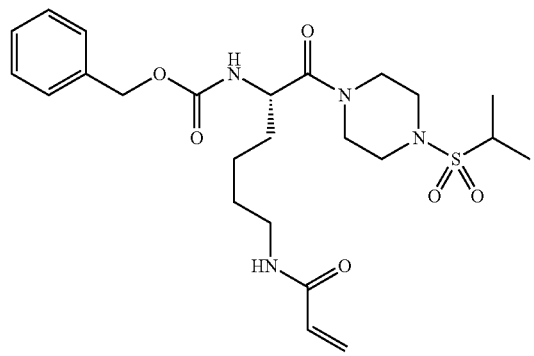

NM-I-26

Acrylamide Cbz-Lys-OH (250 mg, 0.748 mmol) was dissolved in 11 mL of acetonitrile. Afterwards, EDC-HCl (172 mg, 0.897 mmol), DIPEA (0.31 mL, 1.79 mmol) and HOBt (101.5 mL, 0.748 mmol) were added to the solution which was then stirred at room temperature for 20 mins. Methylsulfonyl piperazine (147.3 mg, 0.897 mmol) was then added to the solution slowly, the latter which then was left to stir overnight at room temperature. The solution was then with water (2×15 mL), with a saturated sodium bicarbonate solution (2×15 mL) and with brine (1×10 mL) before being dried with magnesium sulfate, filtered, and concentrated under reduced pressure to give the crude product, a yellow oil. The crude product was purified by flash chromatography over silica gel (elution with gradient DCM, DCM:MeOH(0.5%), DCM:MeOH(1%), DCM:MeOH(2%)) to give 92.8 mg (26%) of the product as a white foam.

$^1$H NMR (400 MHz, CDCl$_3$) δ 3.24-3.15 (m, 4H), 2.99-2.92 (m, 4H), 2.77 (s, 3H); $^{13}$C NMR (101 MHz, CDCl$_3$) δ 46.9, 45.7, 34.2. $^1$H NMR (400 MHz, CDCl$_3$) δ 7.38-7.30 (m, 5H), 6.25 (dd, J=17.0, 1.5 Hz, 1H), 6.06 (dd, J=17.0, 10.2 Hz, 1H), 5.78 (bs, 1H), 5.71 (d, J=8.3 Hz, 1H), 5.62 (dd, J=10.2, 1.5 Hz, 1H), 5.08 (d, J=2.3 Hz, 2H). 4.62 (td, J=8.3, J=4.6 Hz, 1H), 3.89-3.82 (m, 1H). 3.73-3.66 (m, 1H), 3.63-3.55 (m, 2H), 3.37-3.24 (m, 4H), 3.23-3.10 (m, 2H), 2.80 (s, 3H), 1.77-1.66 (m, 2H), 1.64-1.50 (m, 3H), 1.39 (p, J=7.5 Hz, 2H);

$^{13}$C NMR (101 MHz, CDCl$_3$) δ 170.7, 165.8, 156.3, 136.3, 130.0, 128.7, 128.4, 128.2, 126.5, 67.2, 50.4, 45.0, 45.6, 45.4, 41.9, 38.9, 35.1, 32.8, 29.1, 22.3. Mass spectrum (ESI-TOF), m/z (relative intensity) 503 (100, [M+Na]$^+$); HRMS (ESI-TOF) m/z [M+Na]$^+$ calcd for C$_{22}$H$_{32}$N$_4$NaO$_6$S 503.1940; found 503.1947.

Synthesis was modified from Bioorg. Med. Chem 10: 355-360, 2002. Acrylamide Cbz-Lys-OH (250 mg, 0.748 mmol), EDC-HCl (172 mg, 0.897 mmol), HOBt (101 mg, 0.748 mmol) and DIPEA (0.32 mL, 0.897 mmol) were dissolved in 10 mL of acetonitrile and stirred at room temperature for 30 min. The sulfonamide (173 mg, 0.897 mmol) was added and the solution was left stirring at room temperature for 20 hours. The acetonitrile was evaporated under reduced pressure and the residue was dissolved in chloroform. The chloroform was washed with, water (1×10 mL), saturated sodium bicarbonate solution (2×10 mL), 1M hydrochloric acid (1×10 mL) and brine (2×10 mL), dried with magnesium sulfate, filtered and concentrated under reduced pressure to afford the crude product as an oil. The crude product was purified by flash chromatography over silica gel (elution with gradient DCM, DCM:MeOH(1%), DCM:MeOH(2%)) to afford 115 mg (29%) of the desired product as a white foam.

$^1$H NMR (400 MHz, CDCl$_3$) δ 7.40-7.29 (m, 5H), 6.26 (dd, J=17.0, 1.5 Hz, 1H), 6.07 (dd, J=17.0, 10.2 Hz, 1H), 5.80 (s, 1H), 5.73 (d, J=8.4 Hz, 1H), 5.61 (dd, J=10.3, 1.5 Hz, 1H), 5.09 (s, 2H), 3.87-3.78 (m, 1H), 3.61 (s, 1H), 3.57-3.22 (m, 8H), 3.18 (p, J=6.8 Hz, 1H), 1.76 (s, 1H), 1.71-1.66 (m, 1H), 1.62-1.54 (m, 3H), 1.43-1.36 (m, 1H), 1.35 (s, 3H), 1.33 (s, 3H).

$^{13}$C NMR (101 MHz, CDCl$_3$) δ 170.6, 165.7, 156.3, 136.3, 130.9, 128.7, 128.4, 128.2, 126.5, 67.2, 53.8, 50.4, 46.5, 46.3, 46.2, 42.8, 39.1, 32.9, 29.0, 22.3, 16.9; mass spectrum (ESI-TOF), m/z (relative intensity) 531 (100, [M+Na]$^+$); HRMS (ESI-TOF) m/z [M+Na]$^+$ calcd for C$_{24}$H$_{36}$N$_4$NaO$_6$S 561.2253; found 531.2241.

101

(S)-benzyl-6-acrylamido-1-(4-(cyclohexylsulfonyl)piperazin-1-yl)-1-oxohexan-2-ylcarbamate (NM-I-27)

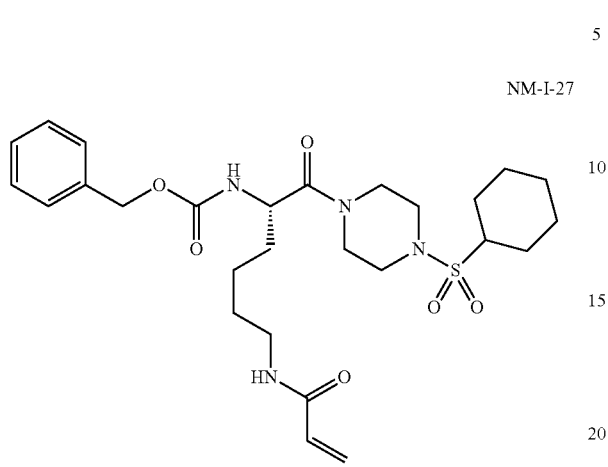

Synthesis was modified from Bioorg. Med. Chem. 10: 355-360, 2002. Acrylamide Cbz-Lys-OH (250 mg, 0.748 mmol), EDC-HCl (172 mg, 0.897 mmol), HOBt (101 mg, 0.748 mmol) and DIPEA (0.32 mL, 0.897 mmol) were dissolved in 10 mL of acetonitrile and stirred at room temperature for 30 min. The sulfonamide (209 mg, 0.897 mmol) was added and the solution was left stirring at room temperature for 20 hours. The acetonitrile was evaporated under reduced pressure and the residue was dissolved in chloroform. The chloroform was washed with water (1×10 mL), saturated sodium bicarbonate solution (2×10 mL), 1M hydrochloric acid (1×10 mL) and brine (2×10 mL), dried with magnesium sulfate, filtered and concentrated under reduced pressure to afford the crude product as an oil. The crude product was purified by flash chromatography over silica gel (elution with gradient DCM, DCM:MeOH(1%), DCM:MeOH(2%)) to afford 88 mg (21%) of the desired product as a white foam.

$^1$H NMR (400 MHz, CDCl$_3$ δ 7.42-7.28 (m, 5H), 6.26 (dd, J=17.0, 1.5 Hz, 1H), 6.07 (dd, J=17.0, 10.2 Hz, 1H), 5.80 (bs, 1H), 5.73 (d, J=8.4 Hz, 1H), 5.61 (dd, J=10.3, 1.5 Hz, 1H), 5.09 (s, 2H), 4.61 (td, J=8.4, 4.5 Hz, 1H), 3.81 (bs, 1H), 3.61 (bs, 1H), 3.57-3.36 (m, 4H), 3.36-3.26 (m, 4H), 3.18 (p, J=6.8 Hz, 1H), 1.88-1.64 (m, 2H), 1.58 (dt, J=13.4, 7.2 Hz, 3H), 1.39 (t, J=7.4 Hz, 2H), 1.34 (d, J=6.8 Hz, 6H).

$^{13}$C NMR (101 MHz, CDCl$_3$) δ 170.6, 165.7, 156.3, 136.3, 130.9, 128.7, 128.4, 128.2, 126.5, 67.2, 53.8, 50.4, 46.5, 46.3, 46.2, 42.6, 39.1, 32.9, 29.0, 22.3, 16.8; mass spectrum (ESI-TOF), m/z (relative intensity) 571 (100, [M+Na]$^+$); HRMS (ESI-TOF) m/z [M+Na]$^+$ calcd for C$_{27}$H4N$_4$NaO$_6$S 571.2566; found 571.2544.

Synthesis of hTG2 inhibitors with varying spacer length is shown in Scheme 4.

Scheme 4. Synthesis of hTG2 inhibitors with varing spacer length. (a) EDC—HCl, HOBt, triethylamine, acetonitrile, rt, 16 h.

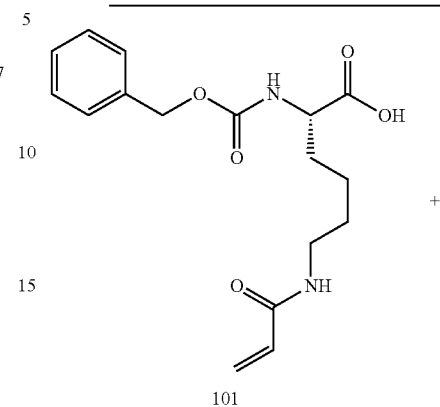

101

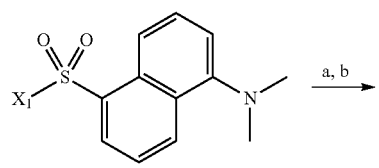

105 X$_1$ = H$_2$N—(CH$_2$)$_4$—NH
106 X$_1$ = H$_2$N—(CH$_2$)$_3$—NH
107 X$_1$ = H$_2$N—(CH$_2$)$_2$—NH
108 X$_1$ = piperazine

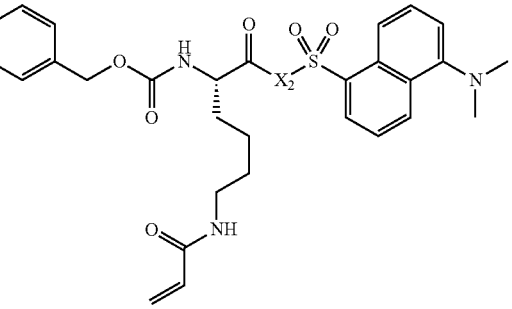

109 X$_2$ = HN—(CH$_2$)$_4$—NH
110 X$_2$ = HN—(CH$_2$)$_3$—NH
111 X$_2$ = HN—(CH$_2$)$_3$—NH
VA4 X$_2$ = piperazine Synthesis of irreversible hTG2 inhibitors 115-117 is shown in Scheme 5.

Scheme 5. Synthesis of irreversible hTG2 inhibitors 115-117.
(a) EDC—HCl, HOBt, triethylamine, acetonitrile, rt, 16 h.

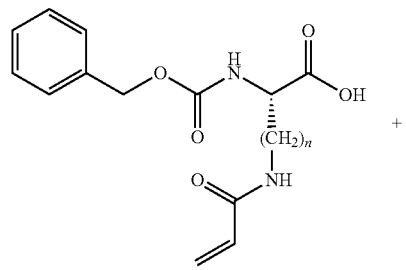

112 n = 1
113 n = 2
114 n = 3

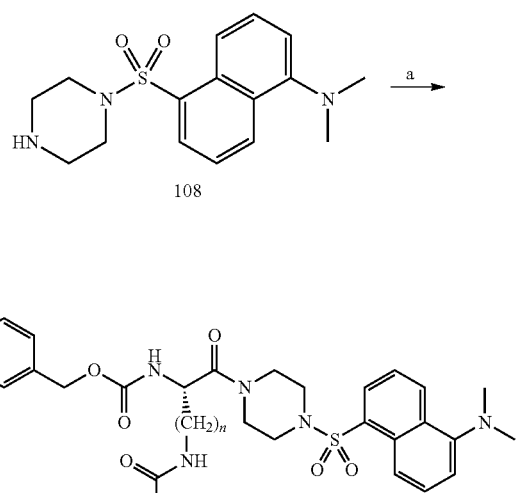

115 n = 1
116 n = 2
117 n = 3

Synthesis of sulfonamide-containing hTG2 inhibitors is shown in Scheme 6.

Scheme 6. Synthesis of sulfonamide-containing hTG2 inhibitors.
(a) triethylamine, DCM, rt, 16 h; (b) EDC—HCl, HOBt, triethylamine, acetonitrile, 16 h.

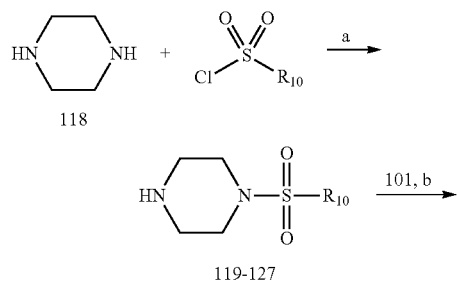

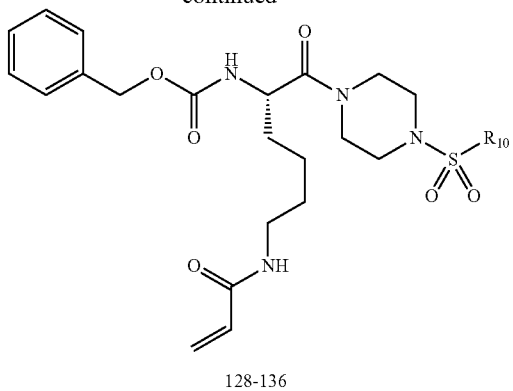

128-136

Synthesis of carboxamide hTG2 inhibitors is shown in Scheme 7.

Scheme 7. Synthesis of carboxamide hTG2 inhibitors.
(a) EDC—HCl, NCS, acetonirile, rt, 16 h; (b) triethylamine, acetonitrile, rt, 4 h; (c) triethylamine, DCM, rt, 4 h.

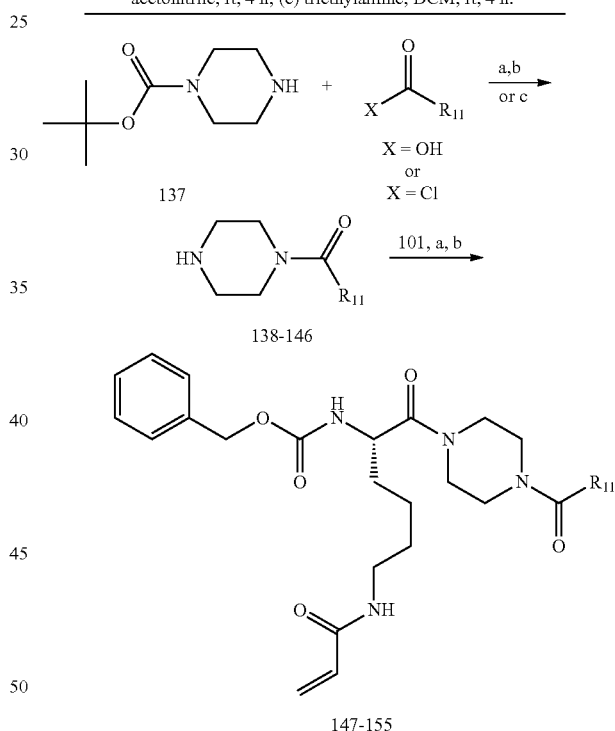

147-155

General procedure for the synthesis of Cbz-Lys(Acr)-OH compounds 112-114: The commercially available Cbz-protected amino acid (1 equiv) was dissolved in THF:1M NaOH (1:1 v/v) and cooled to 0° C. Sodium hydroxide (1 equiv) and acryloyl chloride (1.2 equiv) were slowly added concurrently. The solution was stirred for 10 min and quenched by the addition of saturated NaCl solution. The mixture was acidified to pH 1 with 1 M HCl and extracted three times with ethyl acetate or dichloromethane. The organic extracts were combined and washed with brine, dried with $MgSO_4$, filtered and concentrated to afford clear, colorless oils.

(S)-3-acrylamido-2-(((benzyloxy)carbonyl)amino)propanoic acid (112): Collected 240 mg (72%) as a clear, colorless oil. $^1$H NMR (400 MHz, $CD_3OD$) δ 7.37-7.27 (m, 5H), 6.22-6.20 (m, 2H), 5.67-5.64 (m, 1H), 5.09-5.08 (m, 2H), 4.38-4.35 (m, 1H), 3.77-3.73 (m, 1H), 3.59-3.54 (m, 1H), $^{13}$C NMR (100 MHz, CD$_3$OD) δ 173.4, 168.8, 158.5, 138.1, 131.7, 129.4, 129.0, 128.8, 127.1, 67.7, 55.5, 41.7; HRMS (ESI-TOF) m/z [M+Na]$^+$ calcd for C$_{14}$H$_{16}$N$_2$O$_5$Na 315.0957; found 315.0945.

(S)-4-acrylamido-2-(((benzyloxy)carbonyl)amino)butanoic acid (113): Collected 165 mg (64%) as a clear, colorless oil. $^1$H NMR (400 MHz, CDCl$_3$) δ 9.44 (br s, 1H), 7.26-7.19 (m, 5H), 7.08-7.03 (m, 1H), 6.18-6.13 (d, J=16.9 Hz, 1H), 6.06-6.00 (dd, J=16.9 Hz, J=10.4 Hz, 1H), 5.98-5.95 (m, 1H), 5.54-5.52 (d, J=10.4 Hz, 1H), 4.99 (s, 2H), 4.28-4.24 (m, 1H), 3.57-3.51 (m, 1H), 3.07-3.02 (m, 1H), 2.05-1.97 (m, 1H), 1.80-1.71 (m, 1H), $^{13}$C NMR (100 MHz, CDCl$_3$) δ 174.2, 167.2, 156.8, 136.1, 130.4, 128.7, 128.3, 128.1, 127.5, 67.3, 51.7, 36.2, 32.7, 29.3; HRMS (ESI-TOF) m/z [M+Na]$^+$ calcd for C$_{15}$H$_{18}$N$_2$O$_5$Na 329.1113; found 329.1103.

(S)-5-acrylamido-2-(((benzyloxy)carbonyl)amino)pentanoic acid (114): Collected 254 mg (67%) as a clear colorless oil. $^1$H NMR (400 MHz, CD$_3$OD) δ 7.34-7.27 (m, 5H), 6.22-6.19 (m, 2H), 5.64-5.61 (m, 1H), 2.08 (s, 2H), 4.19-4.15 (m, 1H), 3.28-3.24 (t, J=6.8 Hz, 2H), 1.93-1.83 (m, 1H), 1.74-1.57 (m, 3H), $^{13}$C NMR (100 MHz, CD$_3$OD) δ 175.6, 168.1, 158.6, 138.1, 131.9, 129.4, 128.9, 128.7, 126.6, 67.6, 55.1, 39.9, 30.1, 26.8; HRMS (ESI-TOF) m/z [M+Na]$^+$ calcd for C$_{16}$H$_{20}$N$_2$O$_5$Na 343.1270; found 343.1272.

General procedure for the synthesis of mono-dansylated amine intermediates (105-108): The commercially available diamine (6.0 equiv) was dissolved in cooled DCM followed by addition of dansyl chloride (1.0 equiv). The solution was allowed to warm to room temperature and left stirring for 30 min. The solution was washed three times with saturated NaHCO$_3$ solution and the organic phase was washed with brine, dried with MgSO$_4$, filtered and evaporated under reduced pressure to provide a green/yellow oil. The crude product was purified by flash chromatography over silica gel (elution with gradient of 1-4% MeOH in CH$_2$Cl$_2$) to afford the desired products as yellow/green oils.

General procedure for the synthesis of intermediates 119-127 (de Macedo, P. et al., Bioorg. Med. Chem. (2001), 10 (2): 355-360): Commercially available piperazine (10 equiv) was dissolved in DCM and cooled to 0° C. The sulfonyl chloride (1 equiv) was dissolved in dichloromethane and added slowly via dropping funnel, typically resulting in an opaque solution. The mixture was stirred at 0° C. for 30 min and then at room temperature for 1 h. Dilution in DCM followed by addition of saturated NaHCO$_3$ solution gave a clear, colorless solution. The DCM was separated, washed with brine, dried with MgSO$_4$, filtered and concentrated under reduced pressure to afford typically white or yellow solids.

General procedure for the synthesis of intermediates 140, 142 starting from acid chlorides: Boc-piperazine (137) (Gobbo, P. et al., Synlett (2015), 26 (09): 1169-1174) (1 equiv) was dissolved in ACN. Triethylamine (2.5 equiv) and the acid chloride (3 equiv) were added dropwise resulting in an opaque solution. The solution was stirred at room temperature for either 1 h or overnight. The solution was concentrated under reduced pressure and the residue was dissolved in DCM. The solution was washed with water, saturated NaHCO$_3$ solution and brine, dried with MgSO$_4$, filtered and concentrated under reduced pressure to afford typically a white or yellow solid. The desired products were used without further purification.

General procedure for the synthesis of intermediates 138, 139, 141-145 starting from carboxylic acids: The carboxylic acid (1 equiv) was dissolved in ACN. EDC.HCl (1 equiv) and NHS (1 equiv) were added and the solution was stirred for 16 h to form the activated ester. N,N-diisopropylethylamine (1 equiv), and Boc-piperazine (137) (1 equiv) were added and the solution was stirred at room temperature for 4 h. The ACN was evaporated under reduced pressure and the residue was dissolved in DCM. The DCM solution was washed with water, saturated NaHCO$_3$ solution and brine and subsequently dried with anhydrous MgSO$_4$. The suspension was filtered and the filtrate was concentrated under reduced pressure to afford typically a white or yellow solid. The desired products were used without further purification.

General Procedure A. Coupling using EDC/NHS to afford irreversible inhibitors 149-154: Compound 101 (1 equiv) (Marrano, C. et al., Bioorg. Med. Chem. (2001), 9 (7): 1923-1928) was dissolved in ACN and EDC.HCl (1 equiv) and NHS (1 equiv) were added. The solution was stirred at room temperature for 16 h. The solution was diluted with ethyl acetate and washed with water, saturated NaHCO$_3$ solution and brine. The ethyl acetate solution was dried with MgSO$_4$, filtered and concentrated to afford the crude NHS ester typically as a white solid. The NHS ester was carried forward without further purification. Crude NHS ester (1.05 equiv) was dissolved in 10 mL ACN. Triethylamine (1 equiv) and the desired amine intermediate (1 equiv) were added and the reaction was left to stir at room temperature for 3 h or kept overnight. The solution was diluted with ethyl acetate, washed with saturated NaHCO$_3$ solution and brine, dried with MgSO$_4$, filtered and concentrated to afford typically white sticky foams.

General Procedure B. Coupling using EDC/HOBt to afford irreversible inhibitors 109-111, VA4, 115-117, 128-136: Compound 101 (1 equiv) was added to a solution of EDC.HCl (1.2 equiv), HOBt (1.2 equiv) and N,N-diisopropylethylamine (1.2 equiv) in ACN and stirred at room temperature for 30 min. The amine intermediate (1.2 equiv) was added and the solution was left stirring at room temperature for 20 h. The ACN was evaporated under reduced pressure and the residue was dissolved in CHCl$_3$. The CHCl$_3$ was washed with water, saturated NaHCO$_3$ solution, 1M HCl and brine. The organic phase was dried with MgSO$_4$, filtered and concentrated under reduced pressure to afford the crude product, typically as an oil. The crude products were purified by flash chromatography over silica gel (elution with a gradient of 0-3% MeOH in CH$_2$Cl$_2$) to afford the desired products mostly as sticky foams.

(S)-benzyl (6-acrylamido-1-((4-(5-(dimethylamino)naphthalene-1-sulfonamido)butyl)amino)-1-oxohexan-2-yl)carbamate (109): Compound 109 was prepared from N-(4-aminobutyl)-5-(dimethylamino)naphthalene-1-sulfonamide and compound 101 using General Procedure B to collect 101 mg (26%) of product as light green crystals. mp 54-56° C.; $^1$H NMR (400 MHz, CDCl$_3$) δ 8.51 (d, J=8.4 Hz, 1H), 8.31 (d, J=8.6 Hz, 1H), 8.18 (d, J=7.3 Hz, 1H), 7.49-7.45 (m, 2H), 7.27 (m, 5H), 7.14 (d, J=7.5 Hz, 1H), 6.68 (brs, 1H), 6.28 (brs, 1H), 6.23 (d, J=16.8 Hz, 1H), 6.07 (m, 1H), 5.98 (brs, 1H), 5.88 (brs, 1H), 5.52 (d, J=10.3 Hz, 1H), 5.03 (s, 2H), 4.10 (m, 1H), 3.25 (m, 2H), 3.10 (m, 2H), 2.85 (s, 6H), 2.81 (m, 2H), 1.78 (m, 1H), 1.64 (m, 1H), 1.50 (m, 2H), 1.40 (m, 6H), 1.23 (m, 1H), $^{13}$C NMR (100 MHz, CDCl$_3$) δ 172.3, 166.3, 156.6, 152.0, 136.4, 135.1, 131.0, 130.5, 130.0, 129.8, 129.6, 128.5, 126.7, 123.4, 119.2, 115.4, 67.2, 55.1, 45.6, 43.0, 39.0, 32.2, 29.0, 26.9, 26.6, 22.6; HRMS (ESI-QTOF) m/z [M+Na]$^+$ calcd for C$_{33}$H$_{43}$N$_5$O$_6$SNa 660.2833; found 660.2842.

(S)-benzyl (6-acrylamido-1-((3-(5-(dimethylamino)naphthalene-1-sulfonamido)propyl)amino)-1-oxohexan-2-yl)carbamate (110): Compound 110 was prepared from N-(3-aminopropyl)-5-(dimethylamino)naphthalene-1-sulfonamide and compound 101 using General Procedure B to afford 158 mg (36%) of the product as light green crystals. mp 65-67° C.; $^1$H NMR (400 MHz, CDCl$_3$) δ 8.46-8.43 (d J=8.5 Hz, 1H), 8.26-8.24 (d, J=8.6 Hz, 1H), 8.14-8.12 (dd, J=7.3 Hz, J=1.2 Hz, 1H), 7.49-7.41 (m, 2H), 7.27-7.21 (m, 5H), 7.10-7.08 (d, J=7.5 Hz, 1H), 6.61-6.59 (m, 1H), 6.18-6.13 (d, J=16.9 Hz, 1H), 6.02-5.95 (dd, J=16.9 Hz, 10.2 Hz, 1H), 5.94-5.89 (m, 1H), 5.58-5.56 (d, J=7.5 Hz, 1H), 5.49-5.46 (d, J=10.2 Hz, 1H), 5.04-4.95 (m, 2H), 4.03-3.98 (m, 1H), 3.29-3.13 (m, 4H), 2.86-2.77 (m, 8H), 1.75-1.65 (m, 1H), 1.57-1.39 (m, 5H), 1.32-1.21 (m, 2H); $^{13}$C NMR (100 MHz, CDCl$_3$) δ 172.5, 166.0, 151.9, 136.2, 135.2, 130.7, 130.3, 129.9, 129.6, 129.2, 128.5, 128.3, 128.2, 128.1, 128.0, 126.6, 123.2, 119.0, 115.2, 67.0, 54.9, 45.4, 40.3, 38.6, 36.3, 31.7, 29.6, 28.9, 22.3; HRMS (ESI-QTOF) m/z [M+Na]$^+$ calcd for C$_{32}$H$_{41}$N$_5$O$_6$SNa 646.2675; found 646.2657.

(S)-benzyl (6-acrylamido-1-((2-(5-(dimethylamino)naphthalene-1-sulfonamido)ethyl)amino)-1-oxohexan-2-yl)carbamate (111): Compound 111 was prepared from N-(2-aminoethyl)-5-(dimethylamino)naphthalene-1-sulfonamide and compound 101 using General Procedure B to collect 89 mg (21%) of the product as a yellow/green sticky foam. $^1$H NMR (400 MHz, CDCl$_3$) δ 8.50 (d, J=8.5 Hz, 1H), 8.27 (d, J=8.6 Hz, 1H), 8.15 (d, J=7.1 Hz, 1H), 7.46 (m, 2H), 7.26 (m, 5H), 7.11 (d, J=7.4 Hz, 1H), 6.55 (m, 1H), 6.50 (m, 1H), 6.21-6.16 (dd, J=16.9 Hz, 1.5 Hz, 1H), 6.10-6.03 (dd, J=10.0 Hz, 16.9 Hz, 1H), 5.95 (d, J=7.4 Hz, 1H), 5.49-5.46 (dd, J=10.0 Hz, 1.5 Hz, 1H), 5.04-5.01 (m, 2H), 4.09 (m, 1H), 3.25 (m, 4H), 2.96 (m, 2H), 2.83 (s, 6H), 1.75 (m, 1H), 1.64 (m, 1H), 1.47 (m, 2H), 1.34 (m, 2H); $^{13}$C NMR (100 MHz, CDCl$_3$) δ 172.9, 166.3, 156.6, 136.3, 135.0, 130.9, 130.6, 129.7, 129.5, 128.7, 128.5, 128.4, 128.3, 126.7, 123.5, 119.2, 115.6, 67.3, 55.1, 45.6, 42.9, 39.5, 38.9, 32.0, 29.0, 22.6; HRMS (ESI-QTOF) m/z [M+Na]$^+$ calcd for C$_{31}$H$_{39}$N$_5$O$_6$SNa 632.2519; found 632.2526.

(S)-benzyl (3-acrylamido-1-(4-((5-(dimethylamino)naphthalen-1-yl)sulfonyl)piperazin-1-yl)-1-oxopropan-2-yl)carbamate (115): Compound 115 was prepared from N,N-dimethyl-5-(piperazin-1-ylsulfonyl)naphthalen-1-amine and acrylamide 112 using General Procedure B to afford 58 mg (32%) of the final compound as a yellow/green sticky foam. $^1$H NMR (400 MHz, CDCl$_3$) δ 8.83-8.71 (m, 1H), 8.49-8.41 (m, 1H), 8.24-8.23 (d, J=7.2 Hz, 1H), 7.66-7.54 (m, 2H), 7.36-7.26 (m, 6H), 6.27-6.15 (m, 2H), 6.04-5.95 (m, 1H), 5.88-5.84 (m, 1H), 5.61-5.59 (d, J=10.2 Hz, 1H), 5.04 (s, 2H), 4.76-4.70 (m, 1H), 3.73-3.56 (m, 5H), 3.38-3.15 (m, 5H), 2.99 (s, 6H); $^{13}$C NMR (100 MHz, CDCl$_3$) δ 168.3, 166.30, 156.3, 152.0, 136.1, 132.4, 131.2, 130.9, 130.3, 130.2, 128.6, 128.5, 128.4, 128.2, 127.2, 123.3, 119.4, 115.5, 67.3, 50.8, 45.6, 45.5, 45.3, 45.1, 42.6, 41.9; HRMS (ESI-QTOF) m/z [M+Na]$^+$ calcd for C$_{30}$H$_{35}$N$_5$O$_6$SNa 616.2206; found 616.2194.

(S)-benzyl (4-acrylamido-1-(4-((5-(dimethylamino)naphthalen-1-yl)sulfonyl)piperazin-1-yl)-1-oxobutan-2-yl)carbamate (116): Compound 116 was prepared from N,N-dimethyl-5-(piperazin-1-ylsulfonyl)naphthalen-1-amine and acrylamide 113 using General Procedure B to afford 117 mg (26%) of the final compound as a yellow/green sticky foam. $^1$H NMR (400 MHz, CDCl$_3$) δ 8.59-8.57 (d, J=8.5 Hz, 1H), 8.32-8.29 (d, J=8.7 Hz, 1H), 8.20-8.18 (m, J=7.2 Hz, 1H), 7.56-7.52 (m, 2H), 7.19-7.18 (d, J=7.5 Hz, 1H), 6.62-6.57 (m, 1H), 6.25-6.21 (d, J=16.5 Hz, 1H), 6.11-6.05 (dd, J=16.5 Hz, 10.2 Hz, 1H), 5.90-5.88 (d, J=7.8 Hz, 1H), 5.63-5.61 (d, J=10.2 Hz, 1H), 5.06 (s, 2H), 4.59-4.49 (m, 1H), 3.75-3.67 (m, 2H), 3.58-3.50 (m, 1H), 3.41-3.33 (m, 2H), 3.28-3.10 (m, 4H), 3.01-2.92 (m, 1H), 2.88 (s, 6H), 1.97-1.87 (m, 1H), 1.56-1.45 (m, 1H); $^{13}$C NMR (100 MHz, CDCl$_3$) δ 170.0, 165.8, 156.9, 152.0, 136.1, 132.3, 131.3, 130.9, 130.3, 130.2, 128.7, 128.5, 128.4, 128.1, 126.7, 123.3, 119.3, 115.6, 67.3, 48.5, 45.6, 45.5, 45.2, 45.1, 41.8, 35.6, 33.2; HRMS (ESI-QTOF) m/z [M+H]$^+$ calcd for C$_{31}$H$_{38}$N$_5$O$_6$S 608.2543; found 608.2549.

(S)-benzyl (5-acrylamido-1-(4-((5-(dimethylamino)naphthalen-1-yl)sulfonyl)piperazin-1-yl)-1-oxopentan-2-yl)carbamate (117): Compound 117 was prepared from N,N-dimethyl-5-(piperazin-1-ylsulfonyl)naphthalen-1-amine and acrylamide 114 using General Procedure B to afford 39 mg (23%) of the final compound as a yellow/green solid. mp 69-70° C.; $^1$H NMR (400 MHz, CDCl3) δ 8.53-8.51 (d, J=8.5 Hz, 1H), 8.27-8.24 (d, J=8.5 Hz, 1H), 8.14-8.12 (dd, J=7.3, 1.0 Hz, 1H), 7.49-7.45 (m, 2H), 7.28-7.21 (m, 5H), 7.13-7.11 (d, J=7.2 Hz, 1H), 6.19-6.15 (dd, J=17.0, 1.3 Hz, 1H), 6.01-5.94 (dd, J=17.0, 10.2 Hz, 1H), 5.89-5.84 (m, 1H), 5.60-5.57 (d, J=8.4 Hz, 1H), 5.55-5.52 (dd, J=10.2, 1.3 Hz, 1H), 4.97 (s, 2H), 4.55-4.50 (m, 1H), 3.51-3.37 (m, 3H), 3.32-3.18 (m, 4H), 3.11-2.98 (m, 3H), 2.82 (s, 6H), 1.58-1.42 (m, 4H); $^{13}$C NMR (100 MHz, CDCl$_3$) δ 170.3, 165.7, 156.3, 152.0, 136.2, 132.4, 131.3, 131.0, 130.9, 130.4, 130.2, 128.7, 128.5, 128.3, 128.2, 126.7, 123.3, 119.4, 115.5, 67.2, 50.2, 45.7, 45.5, 45.3, 41.9, 39.0, 31.2, 24.9; HRMS (ESI-QTOF) m/z [M+Na]$^+$ calcd for C$_{32}$H$_{41}$N$_5$O$_6$SNa 646.2675; found 646.2657.

(S)-benzyl 6-acrylamido-1-(4-(naphthalen-1-ylsulfonyl)piperazin-1-yl)-1-oxohexan-2-yl-carbamate (128): Compound 128 was prepared from 1-(naphthalen-1-ylsulfonyl)piperazine (119) and compound 101 using General Procedure B to afford 100 mg (23%) of the desired product as a white foam. mp 59-61° C.; $^1$H NMR (400 MHz, CDCl$_3$) δ 8.70 (d, J=8.7 Hz, 1H), 8.22 (dd, J=7.4, J=1.2 Hz, 1H), 8.10 (d, J=8.2 Hz, 1H), 7.97-7.91 (m, 1H), 7.71-7.53 (m, 3H), 7.39-7.27 (m, 5H), 6.24 (dd, J=17.0, 1.5 Hz, 1H), 6.04 (dd, J=17.0, 10.2 Hz, 1H), 5.74 (br s, 1H), 5.67-5.56 (m, 2H), 5.03 (s, 2H), 4.51 (td, J=8.4, 4.3 Hz, 1H), 3.87-3.79 (m, 1H), 3.58 (d, J=5.1 Hz, 1H), 3.47 (dt, J=12.9, 9.3 Hz, 2H), 3.39-3.19 (m, 4H), 3.13-3.00 (m, 2H), 1.65-1.46 (m, 4H), 1.38-1.23 (m, 2H); $^{13}$C NMR (100 MHz, CDCl$_3$) δ 170.4, 165.7, 156.2, 136.3, 135.1, 134.6, 132.2, 131.0, 130.9, 129.2, 128.9, 128.7, 128.5, 128.4, 128.1, 127.2, 126.5, 124.9, 124.3, 67.1, 50.3, 45.8, 45.4, 45.3, 41.8, 39.1, 32.9, 28.9, 22.3; HRMS (ESI-QTOF) m/z [M+Na]$^+$ calcd for C$_{31}$H$_{36}$N$_4$O$_6$SNa 615.2253; found 615.2232.

(S)-benzyl (6-acrylamido-1-(4-(naphthalen-2-ylsulfonyl)piperazin-1-yl)-1-oxohexan-2-yl)-carbamate (129): Compound 129 was prepared from 1-(naphthalen-2-ylsulfonyl)piperazine (120) and compound 101 using General Procedure B to collect 102 mg (24%) of the desired product as a white foam. mp 65-66° C.; $^1$H NMR (400 MHz, CDCl$_3$) δ 8.33 (d, J=1.7 Hz, 1H), 7.99 (d, J=8.2 Hz, 2H), 7.92 (d, J=7.6 Hz, 1H), 7.72 (dd, J=8.7, 1.8 Hz, 1H), 7.65 (dd, J=6.9, 1.5 Hz, 2H), 7.35-7.27 (m, 5H), 6.24 (dd, J=17.0, 1.5 Hz, 1H), 6.03 (dd, J=17.0, 10.3 Hz, 1H), 5.70 (t, J=5.8 Hz, 1H), 5.59 (dd, J=10.2, 1.5 Hz, 2H), 4.99 (d, J=1.8 Hz, 2H), 4.51 (td, J=8.4, 4.2 Hz, 1H), 3.95-3.85 (m, 1H), 3.68-3.61 (m, 1H), 3.52 (dt, J=13.8, 10.3 Hz, 2H), 3.24 (qd, J=13.5, 6.6 Hz, 4H), 3.05-2.81 (m, 4H), 1.63-1.42 (m, 4H), 1.43-1.15 (m, 2H); $^{13}$C NMR (100 MHz, CDCl$_3$) δ 170.4, 165.7, 156.2, 136.3, 135.2, 132.6, 132.3, 130.9, 129.7, 129.4, 129.3, 129.3, 128.7, 128.3, 128.1, 128.1, 127.9, 126.5, 122.8, 67.1, 50.3, 46.3, 45.9, 45.2, 41.7, 39.1, 32.9, 28.9, 22.3; HRMS (ESI-QTOF) m/z [M+Na]$^+$ calcd for C$_{31}$H$_{36}$N$_4$O$_6$SNa 615.2249; found 615.2253.

(S)-benzyl (6-acrylamido-1-oxo-1-(4-(phenylsulfonyl)piperazin-1-yl)hexan-2-yl)carbamate (130): Compound 130 was prepared from 1-(phenylsulfonyl)piperazine (121) and compound 101 using General Procedure B to collect 82 mg (20%) of the desired product as a sticky, white foam. $^1$H NMR (400 MHz, CDCl$_3$) δ 7.77-7.72 (m, 2H), 7.65-7.60 (m, 1H), 7.58-7.52 (m, 2H), 7.36-7.29 (m, 5H), 6.26 (dd, J=17.0, 1.5 Hz, 1H), 6.05 (dd, J=16.9, 10.3 Hz, 1H), 5.68 (s, 1H), 5.64-5.58 (m, 2H), 5.05 (s, 2H), 4.54 (td, J=8.5, 4.2 Hz, 1H), 3.92 (d, J=13.4 Hz, 1H), 3.65 (s, 1H), 3.53 (d, J=18.2 Hz, 2H), 3.28 (qd, J=18.4, 16.0, J=9.3 Hz, 4H), 2.88 (dd, J=21.5, 10.4 Hz, 2H), 1.67-1.47 (m, 3H), 1.36 (q, J=7.3 Hz, 2H), $^{13}$C NMR (100 MHz, CDCl$_3$) δ 170.4, 165.7, 156.3, 136.3, 135.5, 133.4, 130.9, 129.5, 128.7, 128.4, 128.1, 127.8, 126.5, 67.1, 50.3, 46.2, 45.9, 45.1, 41.6, 39.1, 32.9, 28.9, 22.3; HRMS (ESI-QTOF), m/z [M+Na]$^+$ calcd for C$_{27}$H$_{34}$N$_4$O$_6$SNa 565.2097; found 565.2094.

(S)-benzyl (6-acrylamido-1-(4-(benzylsulfonyl)piperazin-1-yl)-1-oxohexan-2-yl)carbamate (131): Compound 131 was prepared from 1-(benzylsulfonyl)piperazine (122) and compound 101 using General Procedure B to collect 96 mg (23%) of the desired product as a white foam. mp 50-52° C.; $^1$H NMR (400 MHz, CDCl$_3$) δ 7.41-7.29 (m, 10H), 6.25 (dd, J=17.0, 1.5 Hz, 1H), 6.07 (dd, J=17.0, 10.2 Hz, 1H), 5.86 (t, J=5.9 Hz, 1H), 5.74 (d, J=8.4 Hz, 1H), 5.60 (dd, J=10.3, 1.5 Hz, 1H), 5.08 (d, J=1.3 Hz, 2H), 4.55 (td, J=8.4, 4.4 Hz, 1H), 4.23 (s, 2H), 3.72-3.66 (m, 1H), 3.53-3.45 (m, 1H), 3.44-3.24 (m, 4H), 3.20-3.11 (m, 2H), 3.01 (dtt, J=20.5, 8.7, 3.7 Hz, 2H), 1.63 (ddd, J=12.0, 5.7, 2.8 Hz, 1H), 1.57-1.50 (m, 3H), 1.37 (q, J=7.5 Hz, 2H), $^{13}$C NMR (100 MHz, CDCl$_3$) δ 170.5, 165.7, 156.25, 136.3, 130.9, 130.8, 129.2, 129.0, 128.7, 128.5, 128.4, 128.1, 126.4, 67.1, 57.5, 50.3, 46.1, 45.8, 42.3, 39.0, 32.8, 28.9, 22.3; HRMS (ESI-QTOF) m/z [M+Na]$^+$ calcd for C$_{28}$H$_{36}$N$_4$O$_6$SNa 579.2253; found 579.2299.

(S)-benzyl (6-acrylamido-1-(4-(cyclohexylsulfonyl)piperazin-1-yl)-1-oxohexan-2-yl)carbamate (132): Compound 132 was prepared from 1-(cyclohexylsulfonyl)piperazine (23) and compound 101 using General Procedure B to collect 88 mg (21%) of the desired product as a sticky, white foam. $^1$H NMR (400 MHz, CDCl$_3$) δ 7.39-7.30 (m, 5H), 6.27 (dd, J=17.0, 1.5 Hz, 1H), 6.07 (dd, J=17.0, 10.3 Hz, 1H), 5.75 (br s, 1H), 5.71 (d, J=8.5 Hz, 1H), 5.62 (dd, J=10.3, 1.5 Hz, 1H), 5.09 (s, 2H), 4.62 (td, J=8.4, 4.4 Hz, 1H), 3.81 (br s, 1H), 3.61 (br s, 1H), 3.56-3.40 (m, 4H), 3.35-3.24 (m, 2H), 2.94-2.87 (m, 1H), 2.10 (d, J=13.0 Hz, 2H), 1.89 (d, J=13.3 Hz, 2H), 1.73-1.67 (m, 2H), 1.61-1.33 (m, 7H), 1.31-1.16 (m, 3H), $^{13}$C NMR (100 MHz, CDCl$_3$) δ 170.6, 165.7, 156.3, 136.3, 130.9, 128.7, 128.4, 128.2, 126.5, 67.2, 61.9, 50.4, 46.5, 46.3, 46.2, 42.8, 39.1, 33.0, 29.0, 26.7, 25.3, 25.2, 22.3; HRMS (ESI-QTOF) m/z [M+Na]$^+$ calcd for C$_{27}$H$_{40}$N$_4$O$_6$SNa 571.2566; found 571.2544.

(S)-benzyl(6-acrylamido-1-(4-(isopropylsulfonyl)piperazin-1-yl)-1-oxohexan-2-yl)carbamate (133): Compound 133 was prepared from 1-(isopropylsulfonyl)piperazine (124) and compound 101 using General Procedure B to collect 115 mg (29%) of the desired product as white crystals. mp 48-49° C.; $^1$H NMR (400 MHz, CDCl$_3$) δ 7.40-7.29 (m, 5H), 6.26 (dd, J=17.0, 1.5 Hz, 1H), 6.07 (dd, J=17.0, 10.2 Hz, 1H), 5.80 (s, 1H), 5.73 (d, J=8.4 Hz, 1H), 5.61 (dd, J=10.3, 1.5 Hz, 1H), 5.09 (s, 2H), 3.87-3.78 (m, 1H), 3.61 (s, 1H), 3.57-3.22 (m, 8H), 3.18 (p, J=6.8 Hz, 1H), 1.76 (s, 1H), 1.71-1.66 (m, 1H), 1.62-1.54 (m, 3H), 1.43-1.36 (m, 1H), 1.35 (s, 3H), 1.33 (s, 3H), $^{13}$C NMR (100 MHz, CDCl$_3$) δ 170.6, 165.7, 156.3, 136.3, 130.9, 128.7, 128.4, 128.2, 126.5, 67.2, 53.8, 50.4, 46.5, 46.3, 46.2, 42.8, 39.1, 32.9, 29.0, 22.3, 16.9; HRMS (ESI-QTOF) m/z [M+Na]$^+$ calcd for C$_{24}$H$_{36}$N$_4$O$_6$SNa 561.2253; found 531.2241.

(S)-benzyl (6-acrylamido-1-(4-(ethylsulfonyl)piperazin-1-yl)-1-oxohexan-2-yl)carbamate (134): Compound 134 was prepared from 1-(ethylsulfonyl)piperazine (25) and compound 101 using General Procedure B to collect 102 mg (22%) of the desired product as a clear, colorless oil. $^1$H NMR (400 MHz, CDCl$_3$) δ 7.41-7.30 (m, 5H), 6.26 (dd, J=17.0, 1.5 Hz, 1H), 6.06 (dd, J=17.0, 10.2 Hz, 1H), 5.74 (br s, 1H), 5.70 (d, J=8.4 Hz, 1H), 5.62 (dd, J=10.2, 1.5 Hz, 1H), 5.09 (d, J=1.8 Hz, 2H), 4.62 (td, J=8.4, 4.5 Hz, 1H), 3.86 (br s, 1H), 3.66 (br s, 1H), 3.60-3.54 (m, 2H), 3.44-3.17 (m, 6H), 2.96 (q, J=7.4 Hz, 2H), 1.79-1.65 (m, 1H), 1.66-1.50 (m, 3H), 1.45-1.33 (m, 5H); $^{13}$C NMR (100 MHz, CDCl$_3$) δ 170.8, 168.4, 165.9, 156.4, 151.7, 149.9, 136.4, 135.0, 131.1, 128.7, 128.2, 126.3, 69.1, 68.0, 67.1, 59.7, 53.2, 50.5, 46.0, 45.8, 45.6, 44.5, 42.3, 39.0, 32.7, 29.1, 23.7, 22.4, 20.4, 7.9; HRMS (ESI-QTOF) m/z [M+Na]+ calcd for C$_{23}$H$_{34}$N$_4$O$_6$NaS 517.2097; found 517.2140.

(S)-benzyl(6-acrylamido-1-(4-(methylsulfonyl)piperazin-1-yl)-1-oxohexan-2-yl)carbamate (135): Compound 135 was prepared from 1-(methylsulfonyl)piperazine (126) and compound 101 using General Procedure B to collect 93 mg (26%). $^1$H NMR (400 MHz, CDCl$_3$) δ 7.38-7.30 (m, 5H), 6.25 (dd, J=17.0, 1.5 Hz, 1H), 6.06 (dd, J=17.0, 10.2 Hz, 1H), 5.78 (bs, 1H), 5.71 (d, J=8.3 Hz, 1H), 5.62 (dd, J=10.2, 1.5 Hz, 1H), 5.08 (d, J=2.3 Hz, 2H), 4.62 (td, J=8.3, J=4.6 Hz, 1H), 3.89-3.82 (m, 1H), 3.73-3.66 (m, 1H), 3.63-3.55 (m, 2H), 3.37-3.24 (m, 4H), 3.23-3.10 (m, 2H), 2.80 (s, 3H), 1.77-1.66 (m, 2H), 1.64-1.50 (m, 3H), 1.39 (p, J=7.5 Hz, 2H); $^{13}$C NMR (100 MHz, CDCl$_3$) δ 170.7, 165.8, 156.3, 136.3, 130.0, 128.7, 128.4, 128.2, 126.5, 67.2, 50.4, 45.0, 45.6, 45.4, 41.9, 38.9, 35.1, 32.8, 29.1, 22.3; HRMS (ESI-QTOF) m/z [M+Na]$^+$ calcd for C$_{22}$H$_{32}$N$_4$NaO$_6$S 503.1940; found 503.1947.

(S)-benzyl(6-acrylamido-1-oxo-1-(4-(thiophen-2-ylsulfonyl)piperazin-1-yl)hexan-2-yl)carbamate (136): Compound 136 was prepared from 1-(thiophen-2ylsulfonyl)piperazine (127) and compound 101 using General Procedure B to collect 39 mg (8%) of the desired product as a clear oil; $^1$H NMR (400 MHz, CDCl$_3$) δ 7.64-7.63 (dd, J=5.0, 1.2 Hz, 1H), 7.53-7.52 (dd, J=3.7, 1.1 Hz, 1H), 7.36-7.28 (m, 5H), 7.16-7.13 (dd, J=5.0, 3.8 Hz, 1H), 6.26-6.22 (dd, J=17.0, 1.5 Hz, 1H), 6.09-6.02 (dd, J=17.0, 10.2 Hz, 1H), 5.96 (s, 1H), 5.76-5.74 (d, J=8.4 Hz, 1H), 5.60-5.58 (dd, J=10.2, 1.4 Hz, 1H) 5.04 (s, 2H), 4.57-4.52 (m, 1H), 3.93-3.89 (m, 1H), 3.70-3.67 (m, 1H), 3.57-3.46 (m, 2H), 3.33-3.17 (m, 4H), 2.96-2.85 (m, 2H), 1.96 (s, 1H), 1.67-1.58 (m, 1H), 1.54-1.44 (m, 3H), 1.37-1.30 (m, 2H); $^{13}$C NMR (100 MHz, CDCl$_3$) δ 170.5, 165.8, 156.3, 136.2, 135.5, 133.0, 132.9, 130.9, 128.6, 128.3, 128.1, 128.0, 126.4, 67.1, 50.3, 46.2, 45.8, 44.9, 41.4, 39.0, 32.8, 29.7, 28.9, 22.3; HRMS (ESI-QTOF) m/z [M+Na]$^+$ calcd for C$_{25}$H$_{32}$N$_4$O$_6$NaS$_2$ 571.1661; found 571.1626.

(S)-benzyl (1-(4-(1-naphthoyl)piperazin-1-yl)-6-acrylamido-1-oxohexan-2-yl)carbamate (147/AA9): Compound 147 was prepared from Boc-deprotected 138 and compound 101 using General Procedure B to collect 254 mg (41%) of the desired product as a white sticky foam. $^1$H NMR (500 MHz, (CD$_3$)$_2$SO) at 120° C.) δ 7.99-7.96 (m, 2H), 7.84-7.81 (m, 2H), 7.59-7.54 (m, 3H), 7.46-7.44 (m, 2H), 7.35-7.26 (m, 4H), 6.74-6.72 (d, J=7.5 Hz, 1H), 6.21-6.16 (dd, J=17.1, 10.3 Hz, 1H), 6.05-6.01 (dd, J=17.1, 2.1 Hz, 1H), 5.51-5.48

(dd, J=10.3, 2.1 Hz, 1H), 5.04 (s, 1H), 4.46-4.41 (m, 1H), 3.63-3.38 (m, 8H), 3.16-3.12 (q, J=6.85 Hz, 2 Hz), 1.71-1.56 (m, 2H), 1.51-1.44 (m, 2H), 1.39-1.29 (m, 2H), $^{13}$C NMR (100 MHz, (CD$_3$)$_2$SO) δ169.9, 167.8, 164.1, 155.0, 136.5, 133.5, 132.6, 131.7, 128.7, 128.2, 127.6, 127.5, 126.9, 126.8, 126.2, 125.6, 124.5, 123.9, 123.2, 123.1, 65.0, 50.3, 42.7, 37.8, 30.8, 28.2, 21.9; HRMS (ESI-QTOF) m/z [M+Na]$^+$ calcd for C$_{32}$H$_{36}$N$_4$O$_5$Na 579.2584; found 579.2574.

General procedure for Boc-deprotection of intermediates 138-146: Boc-piperizine intermediate (1 equiv) was dissolved in CHCl$_3$ with 10% v/v trifluoroacetic acid. The solution was stirred at room temperature and monitored via TLC (5% CH$_3$OH:DCM with 0.5% triethylamine). Starting material was no longer detected after approximately 2 h and the CHCl$_3$ was concentrated under reduced pressure. The residue was triturated with diethyl ether and the TFA salt was dissolved in 5 mL of ACN containing one equivalent of trimethylamine and carried forward without further purification.

(S)-benzyl(1-(4-(2-naphthoyl)piperazin-1-yl)-6-acrylamido-1-oxohexan-2-yl)carbamate (148/AA10): Compound 148 was prepared from Boc-deprotected 139 and compound 101 using General Procedure B to collect 195 mg (36%) of the desired product as a white sticky foam. $^1$H NMR (300 MHz, (CD$_3$)$_2$SO at 120° C.) δ 7.99-7.92 (m, 4H), 7.74 (br s, 1H), 7.60-7.48 (m, 3H), 7.33-7.23 (m, 5H), 7.06 (br s, 1H), 6.22-6.13 (dd, J=17.2, 10.1 Hz, 1H), 6.06-5.99 (dd, J=17.2, 2.4 Hz, 1H), 5.67 (s, 1H), 5.52-5.47 (dd, J=10.1, 2.4 Hz, 1H), 5.02 (s, 2H), 4.46-4.38 (m, 1H), 3.63-3.46 (m, 8H), 3.14-3.07 (m, 2H), 1.65-1.53 (m, 2H), 1.49-1.39 (m, 2H), 1.36-1.25 (m, 2H), δ $^{13}$C NMR (75 MHz, (CD$_3$)$_2$SO) 170.9, 169.8, 165.1, 137.6, 133.7, 133.6, 132.8, 132.6, 128.7, 128.6, 128.5, 128.1, 128.0, 127.5, 127.1, 126.9, 124.8, 124.6, 66.0, 55.1, 51.2, 38.8, 31.7, 29.3, 23.1; HRMS (ESI-QTOF) m/z [M+Na]$^+$ calcd for C$_{32}$H$_{36}$N$_4$O$_5$Na 579.2584; found 579.2557.

(S)-benzyl 5-acrylamido-1-(4-benzoylpiperazin-1-yl)-1-oxopentan-2-yl)carbamate (149): Compound 149 was prepared from Boc-deprotected 140 and compound 101 using General Procedure A to collect 151 mg (31%) of the desired product as a white, sticky foam. $^1$H NMR (300 MHz, (CD$_3$)$_2$SO at 80° C.) δ 7.73-7.65 (br s, 1H), 7.44-7.22 (m, 10H), 7.05-6.98 (br s, 1H), 6.17-6.09 (dd, J=17.1, 10.0 Hz, 1H), 6.01-5.95 (dd, J=17.1, 2.3 Hz, 1H), 5.47-5.44 (dd, J=10.0, 2.3 Hz, 1H), 4.97 (s, 2H), 4.41-4.36 (m, 1H), 3.55-3.36 (m, 8H), 3.09-3.02 (m, 2H), 1.61-1.49 (m, 2H), 1.44-1.33 (m, 2H), 1.32-1.20 (m, 2H), $^{13}$C NMR (75 MHz, (CD$_3$)$_2$SO at 80° C.) δ 170.1, 168.9, 164.2, 136.7, 135.4, 131.7, 129.1, 127.9, 127.8, 127.2, 127.1, 126.4, 123.7, 65.1, 50.3, 37.9, 30.8, 28.3, 22.2; HRMS (ESI-QTOF) m/z [M+Na]$^+$ calcd for C$_{28}$H$_{34}$N$_4$O$_5$Na 529.2427; found 529.2433.

(S)-benzyl (6-acrylamido-1-oxo-1-(4-(2-phenylacetyl)piperazin-1-yl)hexan-2-yl)carbamate (150): Compound 150 was prepared from Boc-deprotected 141 and compound 101 using General Procedure A to collect 36 mg (21%) of the desired product as a whit solid. mp 48-49° C.; $^1$H NMR (400 MHz, CDCl$_3$) δ 7.41-7.29 (m, 7H), 7.24 (d, J=7.1 Hz, 3H), 6.25 (dd, J=17.0, 1.5 Hz, 1H), 6.06 (dd, J=17.0, 10.2 Hz, 1H), 5.78 (br s, 1H), 5.70 (d, J=8.4 Hz, 1H), 5.60 (dd, J=10.5, 3.4 Hz, 1H), 5.07 (s, 2H), 4.73-4.44 (m, 1H), 3.75 (s, 2H), 3.65 (br s, 1H), 3.60-3.40 (m, 5H), 3.37-3.20 (m, 3H), 1.65 (br s, 1H), 1.62-1.46 (m, 2H), 1.42-1.28 (m, 2H); $^{13}$C NMR (100 MHz, CDCl$_3$) δ 171.0, 170.2, 166.0, 156.6, 136.7, 135.0, 131.3, 129.4, 129.0, 128.9, 128.7, 128.5, 127.6, 126, 67.5, 50.7, 46.5, 46.1, 45.7, 42.4, 41.7, 41.5, 39.4, 33.3, 29.3, 22.6; HRMS (ESI-QTOF) m/z [M+Na]$^+$ calcd for C$_{29}$H$_{36}$N$_4$O$_5$Na 543.2583; found 543.2587.

(S)-benzyl(1-(4-acetylpiperazin-1-yl)-5-acrylamido-1-oxopentan-2-yl)carbamate (151): Compound 151 was prepared from Boc-deprotected 142 and compound 101 using General Procedure A to collect 36 mg (21%) of the desired product as a clear oil. $^1$H NMR (400 MHz, CDCl$_3$) δ 7.37-7.28 (m, 5H), 6.27-6.22 (d, J=17.0, 1H), 6.10-6.03 (dd, J=10.2, 17.0 Hz, 1H), 5.99 (s, 1H), 5.83-5.81 (d, J=8.3 Hz, 1H), 5.61-5.58 (d, J=10.2 Hz, 1H), 5.07 (s, 2H), 4.62 (s, 1H), 3.78-3.69 (m, 2H), 3.63-3.43 (m, 6H), 3.36-3.30 (m, 2H), 2.10 (s, 3H), 1.68 (s, 1H), 1.61-1.54 (m, 3H), 1.42-1.31 (m, 2H); $^{13}$C NMR (100 MHz, CDCl$_3$) δ 170.7, 170.5, 169.3, 169.2, 165.7, 156.2, 136.2, 130.9, 128.5, 128.2, 128.0, 126.3, 67.0, 50.3, 46.2, 45.8, 45.5, 45.2, 41.9, 41.3, 41.0, 39.0, 38.8, 32.8, 32.7, 28.9, 22.2, 21.3; HRMS (ESI-TOF) m/z [M+Na]+ calcd for C$_{23}$H$_{32}$N$_4$O$_5$Na 467.2270; found 467.2300.

(S)-benzyl(6-acrylamido-1-oxo-1-(4-picolinoylpiperazin-1-yl)hexan-2-yl)carbamate (152): Compound 152 was prepared from Boc-deprotected 143 and compound 101 using General Procedure A to collect 17 mg (10%) of the desired product as a colorless oil. $^1$H NMR (300 MHz, (CD$_3$)$_2$SO at 80° C.) δ 8.60 (d, J=4.6 Hz, 1H), 7.93 (td, J=7.7, 1.8 Hz, 1H), 7.76 (br s, 1H), 7.61 (d, J=7.8 Hz, 1H), 7.48 (ddd, J=7.6, 4.8, 1.2 Hz, 1H), 7.38-7.31 (m, 5H), 7.08 (br s, 1H), 6.20 (dd, J=17.1, 10.0 Hz, 1H), 6.04 (dd, J=17.1, 2.4 Hz, 1H), 5.52 (dd, J=10.0, 2.4 Hz, 1H), 5.04 (s, 2H), 4.55-4.29 (m, 1H), 3.57 (br s, 8H), 3.18-3.08 (m, 2H), 1.68-1.58 (m, 2H), 1.53-1.40 (m, 2H), 1.40-1.23 (m, 1H), $^{13}$C NMR (75 MHz, (CD$_3$)$_2$SO at 80° C.) δ 170.1, 166.5, 164.2, 153.4, 147.9, 136.8, 136.7, 131.7, 127.8, 127.2, 127.1, 124.2, 123.8, 122.8, 65.2, 50.4, 37.9, 30.0, 28.4, 22.2; HRMS (ESI-QTOF) m/z [M+Na]$^+$ calcd for C$_{27}$H$_{33}$N$_5$NaO$_5$ 530.2379; found 530.2347.

(S)-benzyl (6-acrylamido-1-(4-nicotinoylpiperazin-1-yl)-1-oxohexan-2-yl)carbamate (153): Compound 153 was prepared from Boc-deprotected 144 and compound 101 using General Procedure A to collect 25 mg (14%) of the desired product as a clear, colorless oil. $^1$H NMR (300 MHz, (CD$_3$)$_2$SO at 120° C.) δ 8.70-8.60 (m, 1H), 7.86-7.77 (m, 1H), 7.46 (dd, J=7.9, 4.8 Hz, 1H), 7.41-7.22 (m, 5H), 6.79 (bs, 1H), 6.20 (dd, J=17.2, 10.1 Hz, 1H), 6.04 (dd, J=17.2, 2.4 Hz, 1H), 5.51 (dd, J=10.1, 2.4 Hz, 1H), 5.06 (s, 2H), 4.51-4.42 (m, 1H), 3.62-3.54 (m, 4H), 3.53.48 (d, 4H), 3.15 (q, J=6.5 Hz, 2H), 1.71-1.58 (m, J=14.3, 7.6 Hz, 2H), 1.52-1.44 (m, J=6.8 Hz, 2H), 1.40-1.32 (m, J=8.4, 7.8 Hz, 1H), $^{13}$C NMR (75 MHz, (CD$_3$)$_2$SO at 120° C.) δ 169.9, 166.6, 164.2, 155.0, 149.7, 147.0, 136.5, 133.9, 131.7, 131.0, 127.5, 126.9, 126.82, 123.1, 122.6, 65.1, 50.2, 43.7, 37.8, 30.8, 28.2, 21.9; HRMS (ESI-QTOF) m/z [M+Na]$^+$ calcd for C$_{27}$H$_{33}$N$_5$O$_5$Na 530.2379; found 530.2396.

(S)-benzyl-(6-acrylamido-1-(4-isonicotinoylpiperazin-1-yl)-1-oxohexan-2-yl)carbamate (154): Compound 154 was prepared from Boc-deprotected 145 and compound 101 using General Procedure A to collect 40 mg (22%) of the desired product as a clear, colorless oil. $^1$H NMR (300 MHz, (CD$_3$)$_2$SO at 80° C.) δ 8.68 (d, J=6.0 Hz, 2H), 7.76 (br s, 1H), 7.38 (d, J=5.9 Hz, 2H), 7.36-7.27 (m, 5H), 7.07 (bs, 1H), 6.20 (dd, J=17.2, 10.0 Hz, 1H), 6.04 (dd, J=17.2, 2.5 Hz, 1H), 5.52 (dd, J=10.0, 2.5 Hz, 1H), 5.04 (s, 2H), 4.43 (td, J=8.0, 5.3 Hz, 1H), 3.73-3.34 (m, 8H), 3.12 (q, J=6.5 Hz, 2H), 1.70-1.54 (m, 2H), 1.49-1.40 (m, 2H), 1.38-1.27 (m, 2H), $^{13}$C NMR (75 MHz, (CD$_3$)$_2$SO at 80° C.) δ 170.1, 166.7, 164.2, 155.3, 149.6, 142.8, 136.7, 131.7, 127.8, 127.3, 127.1, 123.8, 120.7, 65.2, 50.3, 37.9, 30.8, 28.4, 22.2; HRMS (ESI-QTOF) m/z [M+Na]$^+$ calcd for C$_{27}$H$_{33}$N$_5$NaO$_5$ 530.2379; found 530.2370.

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A compound of Formula I:

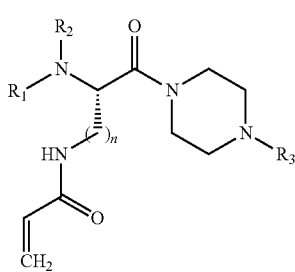

Formula I or a pharmaceutically acceptable salt thereof, wherein:
   R$_1$ is —C(O)—R$^a$;
   R$_2$ is H or C$_{1-6}$ alkyl, wherein C$_{1-6}$ alkyl is optionally substituted with one or more substituents independently selected from the group consisting of C(O)NH$_2$, C(O)OH, C(O)OC$_{1-6}$ alkyl, NH$_2$, NHC$_{1-6}$ alkyl, N(C$_{1-6}$ alkyl)$_2$, OH, and OC(O)NH$_2$;
   R$_3$ is —C(O)—R$^c$ or —S(O)$_2$—R$^b$;
   R$^a$ is —CH$_2$CH$_2$-phenyl, —OCH$_2$-phenyl, —OCH$_2$-naphthalen-2-yl, —OCH$_2$-pyridin-3-yl, —OCH$_2$-quinolin-3-yl, phenyl, naphthalen-2-yl, or pyridin-3-yl;
   R$^b$ is phenyl, naphthalen-1-yl, 5-(dimethylamino)naphthalen-1-yl, naphthalen-2-yl, 7-hydroxy-2H-chromen-2-on-3-yl, or 7-methoxy-2H-chromen-2-on-3-yl; and
   n is 1, 2, 3, or 4.

2. The compound of claim 1, or a pharmaceutically acceptable salt thereof, wherein R$_1$ is —C(O)OCH$_2$-phenyl.

3. The compound of claim 1, or a pharmaceutically acceptable salt thereof, wherein R$_2$ is H or CH$_3$.

4. The compound of claim 1, or a pharmaceutically acceptable salt thereof, wherein n is 4.

5. The compound of claim 1, wherein the compound is selected from the group consisting of:

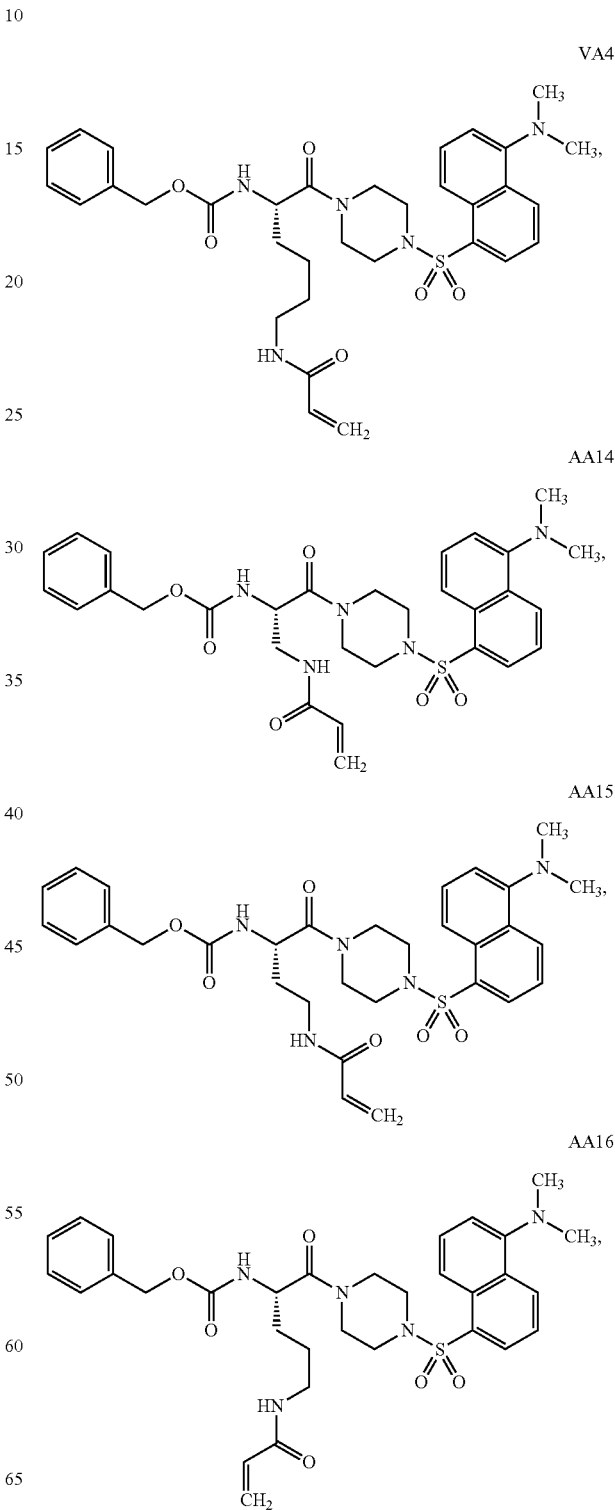

NMI18
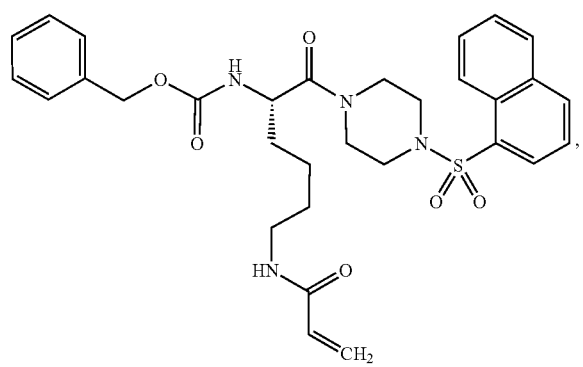
AA9
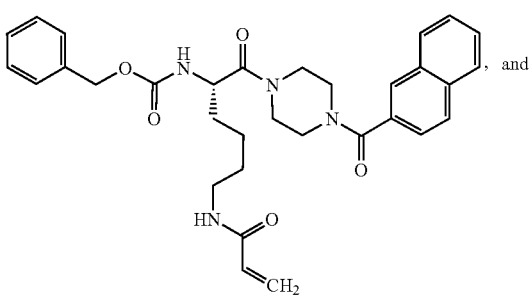
NMI17
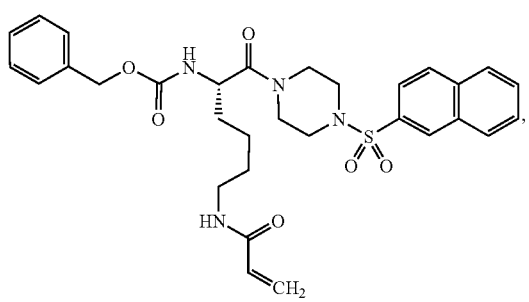
AA10
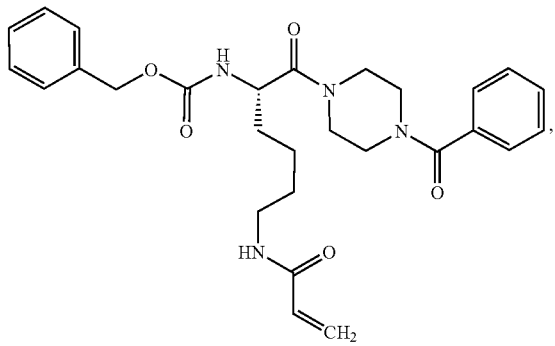
, and
NMI14
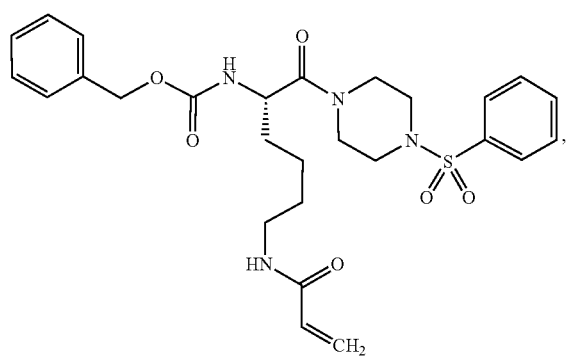
Compound 149
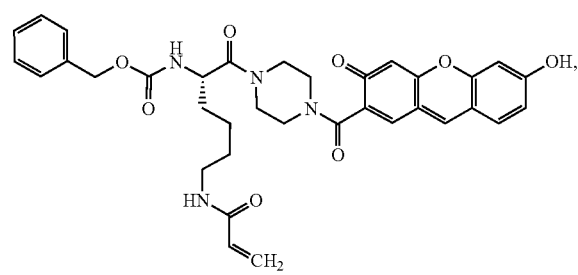
VA5
or a pharmaceutically acceptable salt thereof.

6. The compound of claim 1, wherein the compound is selected from the group consisting of:

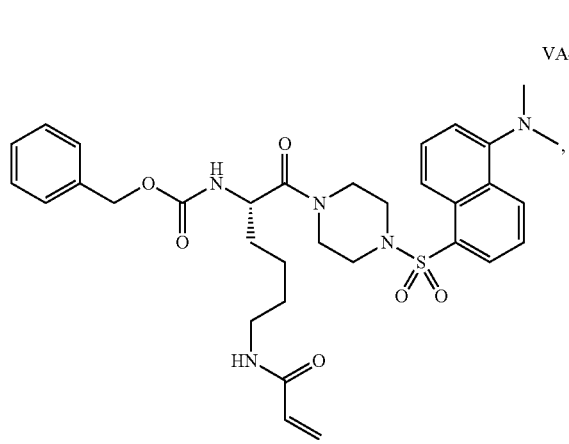
VA4

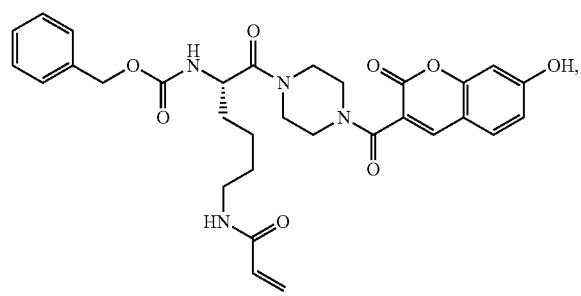
VA5

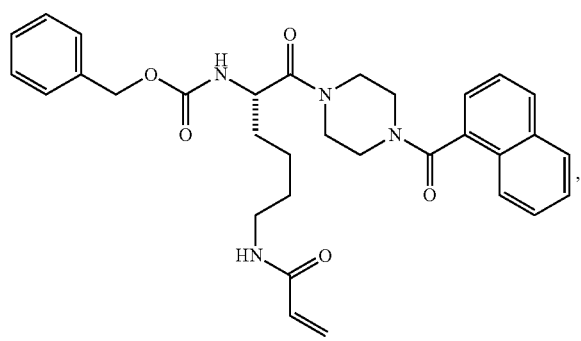
AA9

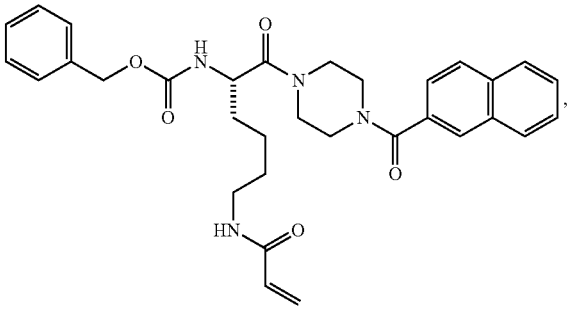
AA10 or a pharmaceutically acceptable salt thereof.

7. A pharmaceutical composition comprising a compound of claim 1, or a pharmaceutically acceptable salt thereof, and a pharmaceutically acceptable carrier.

8. A method for inhibiting tissue transglutaminase 2 activity in a cell, comprising contacting the cell with the compound of claim 1, or a pharmaceutically acceptable salt thereof.

9. The method of claim 8, wherein the inhibition is of a tissue transglutaminase 2 activity selected from the group consisting of guanosine triphosphatase activity, guanosine triphosphate binding activity, and transamidation activity of transglutaminase 2, or a combination thereof.

10. The method of claim 8, wherein contacting the cell with the compound holds tissue transglutaminase 2 in an open conformation.

11. A method for inhibiting tissue transglutaminase 2 activity in a subject, comprising administering to the subject in need thereof a therapeutically effective amount of the compound of claim 1, or a pharmaceutically acceptable salt thereof.

12. The method of claim 11, wherein the inhibition is of a tissue transglutaminase 2 activity selected from the group consisting of guanosine triphosphatase activity, guanosine triphosphate binding activity, and transamidation activity of transglutaminase 2, or a combination thereof.

* * * * *